US008426042B2

(12) United States Patent
Takada et al.

(10) Patent No.: US 8,426,042 B2
(45) Date of Patent: Apr. 23, 2013

(54) MATERIAL FOR ORGANIC ELECTROLUMINESCENCE DEVICE, AND ORGANIC ELECTROLUMINESCENCE DEVICE

(75) Inventors: Saki Takada, Kanagawa (JP); Tetsuro Otsuka, Kanagawa (JP); Takeshi Murakami, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 13/499,505

(22) PCT Filed: Sep. 24, 2010

(86) PCT No.: PCT/JP2010/066605

§ 371 (c)(1), (2), (4) Date: Mar. 30, 2012

(87) PCT Pub. No.: WO2011/040343

PCT Pub. Date: Apr. 7, 2011

(65) Prior Publication Data

US 2012/0181528 A1 Jul. 19, 2012

(30) Foreign Application Priority Data

Sep. 30, 2009 (JP) ................................ 2009-228690
Mar. 30, 2010 (JP) ................................ 2010-079925
Sep. 3, 2010 (JP) ................................ 2010-198384

(51) Int. Cl.
*H01L 51/54* (2006.01)

(52) U.S. Cl.
USPC ...... 428/690; 428/917; 252/301.16; 313/504; 313/506; 257/40; 257/89; 257/102; 257/E51.044

(58) Field of Classification Search ........................ None
See application file for complete search history.

(56) References Cited

U.S. PATENT DOCUMENTS

| | | | | |
|---|---|---|---|---|
| 2003/0218418 | A9 * | 11/2003 | Sato et al. | 313/504 |
| 2004/0137267 | A1 | 7/2004 | Igarashi et al. | |
| 2006/0012292 | A1 * | 1/2006 | Kitamura et al. | 313/504 |
| 2008/0265762 | A1 * | 10/2008 | Furugori et al. | 313/504 |
| 2008/0297033 | A1 | 12/2008 | Knowles et al. | |

FOREIGN PATENT DOCUMENTS

| | | | |
|---|---|---|---|
| JP | 2004-221065 | A | 8/2004 |
| JP | 2005-347004 | A | 12/2005 |
| JP | 2006-290988 | A | 10/2006 |
| WO | 2005/112520 | A1 | 11/2005 |

OTHER PUBLICATIONS

International Search Report (PCT/ISA/210) issued by the International Searching Authority in corresponding International Application No. PCT/JP2010/066605 on Nov. 30, 2010.

Written Opinion (PCT/ISA/237) of the International Searching Authority, issued in corresponding International Application No. PCT/JP2010/066605 on Nov. 30, 2010.

* cited by examiner

*Primary Examiner* — Michael H Wilson
(74) *Attorney, Agent, or Firm* — Morgan, Lewis & Bockius, LLP

(57) ABSTRACT

A material for an organic electroluminescence device containing at least phosphorescent metal complex A and phosphorescent metal complex B, metal complex A and metal complex B are both organic metal complexes containing a metal having an atomic weight of 40 or more and a ligand, metal complex A has a specific structure, and metal complex B has the same structure with metal complex A except that one or more atoms directly bonding to ligand structures are substituted with atoms belonging to the same group of the atoms and having a greater atomic weight, and ratio of the content of metal complex B to the content of metal complex A is 0.005% by mass or more and 2% by mass or less.

19 Claims, 5 Drawing Sheets

MATERIAL FOR ORGANIC ELECTROLUMINESCENCE DEVICE, AND ORGANIC ELECTROLUMINESCENCE DEVICE

TECHNICAL FIELD

The present invention relates to materials for an organic electroluminescence device, and an electroluminescence device.

BACKGROUND ART

Since organic electroluminescence devices (hereinafter also referred to as "devices" or "organic EL devices") are capable of obtaining high luminance light emission by low voltage driving, they are actively researched and developed in recent years. An organic electroluminescence device generally includes a pair of electrodes and at least one organic layer including a light-emitting layer between the pair of electrodes, and electrons injected from the cathode and holes injected from the anode are recombined in the organic layer including a light-emitting layer, and generated energy of exciton is used for emission of light.

In recent years, efficiency of devices has been advanced by the use of phosphorescent materials. For example, an organic electroluminescence device excellent in light emission efficiency and durability of device by using iridium complex or platinum complex as the phosphorescent materials is proposed.

Further, doping type devices using a light-emitting layer obtained by doping a light-emitting material in a host material are widely adopted.

For example, iridium complexes containing a condensed azole ligand which are highly durable and capable of blue light emission are disclosed in Patent Document 1.

It has been conventionally considered that when materials for use in organic EL devices such as light-emitting materials contain impurities, durability of devices is banefully influenced. Accordingly, techniques capable of reducing impurities in the materials and increasing the purity of the materials are proposed.

For example, for the purpose of the improvement of durability of a device, a luminescence device is disclosed in Patent Document 2, in which at least one organic compound layer contains a metal-coordinated compound and the content of the decomposed product or the raw material of the metal-coordinated compound in the organic compound layer is 0.5% by mass or less.

RELATED ART

Patent Documents

Patent Document 1: U.S. Patent Publication 2008/0,297,033

Patent Document 2: JP-A-2005-347004

SUMMARY OF THE INVENTION

Problems that the Invention is to Solve

A luminescence device having high blue purity and excellent durability is disclosed in Patent Document 1, however, as described on page 55 of Patent Document 1, the metal complexes disclosed in Patent Document 1 are susceptible to visible light, and they have to be handled under light-shielding condition from synthesis to isolation and they are easily oxidized. Accordingly, manufacturing process is complicated and inferior in productivity, and the improvement has been desired.

Further, techniques for increasing the purity of light-emitting materials are disclosed in Patent Document 2 mainly for the purpose of the improvement of a device. However, stability of the light-emitting materials under visible light and efficiency of the electroluminescence device at the time when the device is driven at high luminance are not examined in Patent Document 2.

An object of the invention is to provide a material that can be used for an organic EL device, can be stably preserved under visible light, and can exhibit excellent efficiency when the device is driven at high luminance, and another object is to provide an organic electroluminescence device using the same material.

Means for Solving The Problems

As a result of earnest examinations, the present inventors have found that storage stability under visible light and the effect of excellent in efficiency at the time when a device is driven in high luminance can be obtained by a method of mixing a specific phosphorescent metal complex A and a separately synthesized phosphorescent metal complex B, or by a method of synthesizing metal complex A so that metal complex B is also formed at the time of the synthesis of a metal complex A to obtain a material for an organic electroluminescence device containing the metal complex A and the metal complex B in a content ratio of a specific range, thus the invention has been attained.

That is, the above problems can be solved by the following means.

[1] A material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure with the phosphorescent metal complex A except that, in at least one substituent of $R^1$ and $R^2$ in the formula (1), one or more atoms directly bonding to $Q^1$ or $Q^2$ are substituted with an atom belonging to the same group as in the one or more atoms and having a greater atomic weight than the one or more atoms, and a ratio of the content of the phosphorescent metal complex B to a content of the phosphorescent metal complex A is 0.005% by mass or more and 2% by mass or less:

(1)

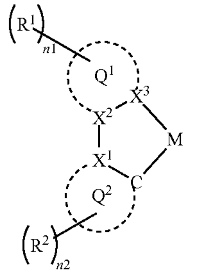

wherein each of $R^1$ and $R^2$ independently represents a substituent; when a plurality of $R^1$'s are present, the $R^1$'s may be the same with or different from each other, when a plurality of $R^2$'s are present, the $R^2$'s may be the same with or different from each other, and the $R^1$'s and the $R^2$'s may be bonded to each other to form a ring; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

[2] The material for an organic electroluminescence device as claimed in [1], wherein the metal complex A has at least one fluorine atom as at least one of $R^1$ and $R^2$ in formula (1), and the at least one fluorine atom of the metal complex A is replaced with at least one halogen atom other than the fluorine atom in the metal complex B.

3. The material for an organic electroluminescence device as claimed in [2], wherein the halogen atom other than the fluorine atom in the metal complex B is a chlorine atom.

4. The material for an organic electroluminescence device as claimed in any of [1] to [3], wherein both of $R^1$ and $R^2$ are fluorine atoms.

5. The material for an organic electroluminescence device as claimed in any of [1] to [4], wherein the metal complex A comprises a partial structure represented by the following formula (2):

(2)

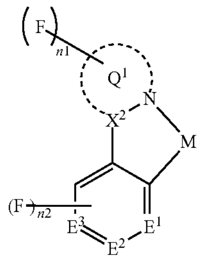

wherein M represents a metal having an atomic weight of 40 or more; $X^2$ represents a carbon atom or a nitrogen atom; $Q^1$ represents a 5- or 6-membered aromatic heterocyclic ring; each of $E^1$, $E^2$ and $E^3$ independently represents a carbon atom or a nitrogen atom, provided that all of $E^1$, $E^2$ and $E^3$ do not represent a nitrogen atom; each of n1 and n2 independently represents an integer of 0 to 4, but there is no case where the sum of n1 and n2 is 0; and the bidentate ligand including ring $Q^1$ and the ring containing $E^1$, $E^2$ and $E^3$ may form a tridentate or higher multidentate ligand by bonding to other ligands.

6. The material for an organic electroluminescence device as claimed in any of [1] to [5], wherein the metal complex A comprising a partial structure represented by the following formula (3):

(3)

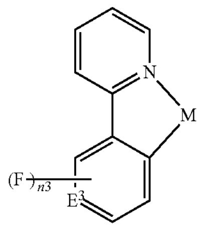

wherein M represents a metal having an atomic weight of 40 or more; $E^3$ represents a carbon atom or a nitrogen atom; n3 represents an integer of 1 to 4; and the bidentate ligand including pyridine and the ring containing $E^3$ may form a tridentate or higher multidentate ligand by bonding to other ligands.

7. The material for an organic electroluminescence device as claimed in any of [1] to [6], wherein $E^3$ represents a carbon atom.

8. The material for an organic electroluminescence device as claimed in any of [1] to [7], wherein M represents Pt.

9. The material for an organic electroluminescence device as claimed in [1], wherein the formula (1) is represented by the following formula (C-2):

formula(C-2)

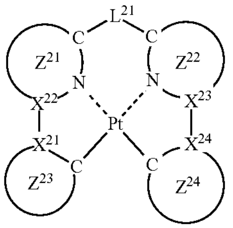

wherein $L^{21}$ represents a single bond or a divalent linking group; each of $Z^{21}$ and $Z^{22}$ independently represents a 5- or 6-membered nitrogen-containing aromatic heterocyclic ring; each of $Z^{23}$ and $Z^{24}$ independently represents a benzene ring or a 5- or 6-membered aromatic heterocyclic ring; each of $Z^{21}$ and $Z^{23}$ may independently have 1 to 4 substituents, and these substituents may be bonded to each other to form a ring, provided that at least one of $Z^{21}$ and $Z^{23}$ has one or more substituents; each of $Z^{22}$ and $Z^{24}$ may have a substituent and these substituents may be bonded to each other to form a ring; and each of $X^{21}$, $X^{22}$, $X^{23}$ and $X^{24}$ independently represents a carbon atom or a nitrogen atom.

10. The material for an organic electroluminescence device as claimed in any of [1] to [7], wherein M represents Ir.

11. The material for an organic electroluminescence device as claimed in [1], wherein the formula (1) is represented by the following formula (A10):

(A10)

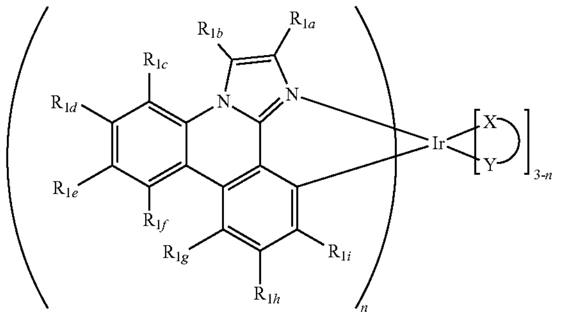

wherein each of $R_{1a}$ to $R_{1i}$; independently represents a hydrogen atom or a substituent; X—Y represents a mono-anionic bidentate ligand; and n represents an integer of 1 to 3.

12. The material for an organic electroluminescence device as claimed in [1], wherein the formula (1) is represented by the following formula (P-1):

(P-1)

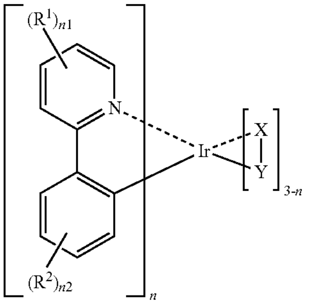

wherein each of $R^1$ and $R^2$ independently represents a substituent, and when a plurality of $R^1$ and $R^2$ are present, these $R^1$ and $R^2$ may be the same with or different from each other; each of n1 and n2 independently represents an integer of 0 to 4, but there is no case where the sum of n1 and n2 is 0; X—Y represents a mono-anionic bidentate ligand; and n represents an integer of 1 to 3.

13. An organic electroluminescence device comprising a substrate having thereon a pair of electrodes and at least one organic layer comprising a light-emitting layer comprising a light-emitting material between the pair of electrodes, wherein at least any layer of the organic layers comprising the material for an organic electroluminescence device as claimed in any of [1] to [12].

14. The organic electroluminescence device as claimed in [13], wherein the light-emitting layer comprises the material for an organic electroluminescence device as claimed in any of [1] to [12].

15. A composition of a material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure with phosphorescent the metal complex A except that, in at least one substituent of $R^1$ and $R^2$ in the formula (1), one or more atoms directly bonding to $Q^1$ or $Q^2$ are substituted with atoms belonging to the same group of the one or more atoms and having a greater atomic weight than the one or more atoms, and ratio of the content of the phosphorescent metal complex B to the content of phosphorescent the metal complex A is 0.005% by mass or more and 2% by mass or less:

(1)

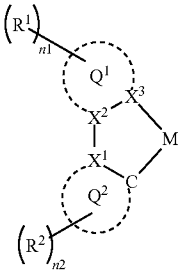

wherein each of $R^1$'s and $R^2$'s independently represents a substituent, when a plurality of $R^1$'s and a plurality of $R^2$'s are present, the plurality of $R^1$ and $R^2$ may be the same with or different from each other, and the plurality of $R^1$ and $R^2$ may be bonded to each other to form a ring; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

16. A light-emitting layer which comprises a material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure with the phosphorescent metal complex A except that, in at least one substituent of $R^1$ and $R^2$ in the formula (1), one or more atoms directly bonding to $Q^1$ or $Q^2$ are substituted with atoms belonging to the same group of the one or more atoms and having a greater atomic weight than one or more atoms, and ratio of the content of the phosphorescent metal complex B to the content of the phosphorescent metal complex A is 0.005% by mass or more and 2% by mass or less:

(1)

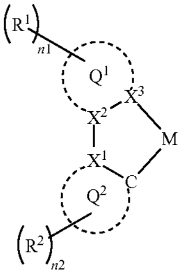

wherein each of $R^1$'s and $R^2$'s independently represents a substituent, and when a plurality of $R^1$'s and a plurality of $R^2$'s are present, the plurality of $R^1$ and $R^2$ may be the same with or different from each other; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

17. A light emission apparatus using the organic electroluminescence device as claimed in [13] or [14].

18. A display apparatus using the organic electroluminescence device as claimed in [13] or [14].

19. An illumination apparatus using the organic electroluminescence device as claimed in [13] or [14].

Advantage of The Invention

According to the invention, a material which can be used for an organic EL device, can be stably preserved under visible light, and can exhibit excellent efficiency when the device is driven in high luminance, and an organic electroluminescence device using the same material can be provided.

MODE FOR CARRYING OUT THE INVENTION

Figure 1:
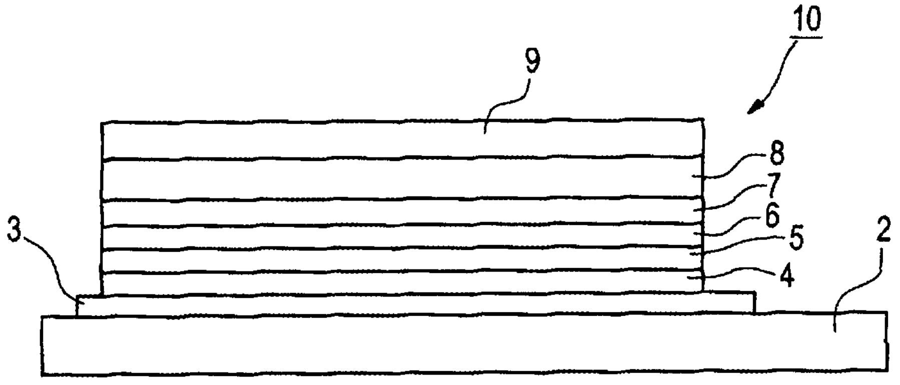
FIG. 1 is a schematic drawing showing an example (a first embodiment) of layer structure of the organic EL device according to the invention.

The material for an organic electroluminescence device in the invention is a material for an organic electroluminescence device containing at least phosphorescent metal complex A and phosphorescent metal complex B, wherein phosphorescent metal complex A contains a partial structure represented by the following formula (1), and phosphorescent metal complex B has the same structure with phosphorescent metal complex A except that, in at least one substituent of $R^1$ and $R^2$ in the formula (1), one or more atoms directly bonding to $Q^1$ or $Q^2$ are substituted with an atom belonging to the same group as in the one or more atoms and having a greater atomic weight than the one or more atoms, and a ratio of the content of the phosphorescent metal complex B to the content of the phosphorescent metal complex A is 0.005% by mass or more and 2% by mass or less:

(1)

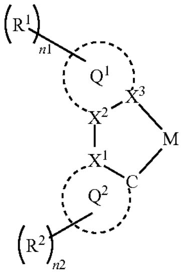

In formula (1), each of $R^1$ and $R^2$ independently represents a substituent, when plural $R^1$'s are present, the $R^1$'s may be the same with or different from each other, and when a plurality of $R^2$'s are present, the $R^2$'s may be the same with or different from each other, and the $R^1$'s and the $R^2$'s may be bonded to each other to form a ring; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

As described above, in patent document 2, the content of the decomposed product or the raw material of the metal complex is the smaller, the better, and the content is prescribed not to exceed a definite amount, but in the invention, specific phosphorescent metal complex A and another phosphorescent metal complex B are used in a content ratio of a specific range. That is, the invention and patent document 2 are based on absolutely different technical concepts. Further, when a device using the material of the invention is driven at extremely high luminance, what is called a roll-off phenomenon accompanied by lowering of efficiency is reduced and high efficiency is maintained.

The phosphorescent metal complex having a partial structure represented by formula (1) in the invention is also referred to as a specific phosphorescent metal complex.

Incidentally, a hydrogen atom in the description of each formula in the specification of the invention also includes an isotope (a deuterium atom and the like), and an atom further constituting a substituent means to also include the isotope thereof.

[Phosphorescent Metal Complex] (Phosphorescent Metal Complex A)

The material for an organic electroluminescence device in the invention contains at least phosphorescent metal complex A and phosphorescent metal complex B. Metal complex A contains a partial structure represented by the following formula (1) having at least one substituent in at least one ligand, and metal complex B has the same structure with metal complex A except that, in at least one substituent of $R^1$ and $R^2$ in the formula (1), one or more atoms directly bonding to $Q^1$ or $Q^2$ are substituted with atoms belonging to the same group of the atoms and having a greater atomic weight.

(1)

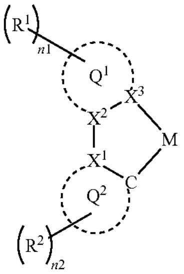

In formula (1), each of $R^1$ and $R^2$ independently represents a substituent. When plural $R^1$'s are present, the $R^1$'s may be the same with or different from each other, when plural $R^2$'s are present, $R^2$'s may be the same with or different from each other, The $R^1$'s and the $R^2$'s may be bonded to each other to form a ring. M represents a metal having an atomic weight of 40 or more. Each of $X^1$, $X^2$ and $X^3$ independently represents a carbon atom or a nitrogen atom, provided that all of $X^1$, $X^2$ and $X^3$ do not represent a nitrogen atom. $Q^1$ represents a 5- or 6-membered aromatic heterocyclic ring, and $Q^2$ represents a 5- or 6-membered aromatic hydrocarbon ring or aromatic heterocyclic ring. Each of n1 and n2 independently represents an integer of 0 to 4, but there is no case where the sum of n1 and n2 is 0. The bidentate ligand including $Q^1$ and $Q^2$ may form a tridentate or higher multidentate ligand by bonding to other ligands. $Q^1$ and $Q^2$ may be linked via a linking group to form a ring. The lines for bonding $X^2$ to $X^3$ and $X^1$ to the carbon atom are shown as a single line but bonding may be any kind, i.e., may be a single bond or may be a double bond.

In formula (1), each of $R^1$ and $R^2$ independently represents a substituent. When plural $R^1$'s are present, the $R^1$'s may be the same with or different from each other. When plural $R^2$'s are present, the $R^2$'s may be the same with or different from each other. The $R^1$'s and the $R^2$'s may be bonded to each other to form a ring. The substituent is preferably selected from among the following substituent group A.

(Substituent group A)

Substituent group A include an alkyl group (preferably having 1 to 30 carbon atoms, more preferably 1 to 20 carbon atoms, and especially preferably 1 to 10 carbon atoms, e.g., methyl, ethyl, isopropyl, tert-butyl, n-octyl, n-decyl, n-hexadecyl, cyclopropyl, cyclopentyl, cyclohexyl and the like are exemplified), an alkenyl group (preferably having 2 to 30 carbon atoms, more preferably 2 to 20 carbon atoms, and especially preferably 2 to 10 carbon atoms, e.g., vinyl, allyl, 2-butenyl, 3-pentenyl and the like are exemplified), an alkynyl group (preferably having 2 to 30 carbon atoms, more preferably 2 to 20 carbon atoms, and especially preferably 2 to 10 carbon atoms, e.g., propargyl, 3-pentynyl and the like are exemplified), an aryl group (preferably having 6 to 30 carbon atoms, more preferably 6 to 20 carbon atoms, and especially preferably 6 to 12 carbon atoms, e.g., phenyl, p-methylphenyl, naphthyl, anthranyl and the like are exemplified), an amino group (preferably having 0 to 30 carbon atoms, more preferably 0 to 20 carbon atoms, and especially preferably 0 to 10 carbon atoms, e.g., amino, methylamino, dimethylamino, diethylamino, dibenzylamino, diphenylamino, ditolylamino and the like are exemplified), an alkoxy group (preferably having 1 to 30 carbon atoms, more preferably 1 to 20 carbon atoms, and especially preferably 1 to 10 carbon atoms, e.g., methoxy, ethoxy, butoxy, 2-ethylhexyloxy and the like are exemplified), an aryloxy group (preferably having 6 to 30 carbon atoms, more preferably 6 to 20 carbon atoms, and especially preferably 6 to 12 carbon atoms, e.g., phenyloxy, 1-naphthyloxy, 2-naphthyloxy and the like are exemplified), a heterocyclic oxy group (preferably having 1 to 30 carbon atoms, more preferably 1 to 20 carbon atoms, and especially preferably 1 to 12 carbon atoms, e.g., pyridyloxy, pyrazyloxy, pyrimidyloxy, quinolyloxy and the like are exemplified), an acyl group (preferably having 2 to 30 carbon atoms, more preferably 2 to 20 carbon atoms, and especially preferably 2 to 12 carbon atoms, e.g., acetyl, benzoyl, formyl, pivaloyl and the like are exemplified), an alkoxycarbonyl group (preferably having 2 to 30 carbon atoms, more preferably 2 to 20 carbon atoms, and especially preferably 2 to 12 carbon atoms, e.g., methoxycarbonyl, ethoxycarbonyl and the like are exemplified), an aryloxycarbonyl group (preferably having 7 to 30 carbon atoms, more preferably 7 to 20 carbon atoms, and especially preferably 7 to 12 carbon atoms, e.g., phenyloxycarbonyl and the like are exemplified), an acyloxy group (preferably having 2 to 30 carbon atoms, more preferably 2 to 20 carbon atoms, and especially preferably 2 to 10 carbon atoms, e.g., acetoxy, benzoyloxy and the like are exemplified), an acylamino group (preferably having 2 to 30 carbon atoms, more preferably 2 to 20 carbon atoms, and especially preferably 2 to 10 carbon atoms, e.g., acetylamino, benzoylamino and the like are exemplified), an alkoxycarbonylamino group (preferably having 2 to 30 carbon atoms, more preferably 2 to 20 carbon atoms, and especially preferably 2 to 12 carbon atoms, e.g., methoxycarbonylamino and the like are exemplified), an aryloxycarbonylamino group (preferably having 7 to 30 carbon atoms, more preferably 7 to 20 carbon atoms, and especially preferably 7 to 12 carbon atoms, e.g., phenyloxycarbonylamino and the like are exemplified), a sulfonylamino group (preferably having 1 to 30 carbon atoms, more preferably 1 to 20 carbon atoms, and especially preferably 1 to 12 carbon atoms, e.g., methanesulfonylamino, benzenesulfonylamino and the like are exemplified), a sulfamoyl group (preferably having 0 to 30 carbon atoms, more preferably 0 to 20 carbon atoms, and especially preferably 0 to 12 carbon atoms, e.g., sulfamoyl, methylsulfamoyl, dimethylsulfamoyl, phenylsulfamoyl and the like are exemplified), a carbamoyl group (preferably having 1 to 30 carbon atoms, more preferably 1 to 20 carbon atoms, and especially preferably 1 to 12 carbon atoms, e.g., carbamoyl, methylcarbamoyl, diethylcarbamoyl, phenylcarbamoyl and the like are exemplified), an alkylthio group (preferably having 1 to 30 carbon atoms, more preferably 1 to 20 carbon atoms, and especially preferably 1 to 12 carbon atoms, e.g., methylthio, ethylthio and the like are exemplified), an arylthio group (preferably having 6 to 30 carbon atoms, more preferably 6 to 20 carbon atoms, and especially preferably 6 to 12 carbon atoms, e.g., phenylthio and the like are exemplified), a heterocyclic thio group (preferably having 1 to 30 carbon atoms, more preferably 1 to 20 carbon atoms, and especially preferably 1 to 12 carbon atoms, e.g., pyridylthio, 2-benzimidazolylthio, 2-benzoxazolylthio, 2-benzothiazolylthio and the like are exemplified), a sulfonyl group (preferably having 1 to 30 carbon atoms, more preferably 1 to 20 carbon atoms, and especially preferably 1 to 12 carbon atoms, e.g., mesyl, tosyl and the like are exemplified), a sulfinyl group (preferably having 1 to 30 carbon atoms, more preferably 1 to 20 carbon atoms, and especially preferably 1 to 12 carbon atoms, e.g., methanesulfinyl, benzenesulfinyl and the like are exemplified), a ureido group (preferably having 1 to 30 carbon atoms, more preferably 1 to 20 carbon atoms, and especially preferably 1 to 12 carbon atoms, e.g., ureido, methylureido, phenylureido and the like are exemplified), a phosphoric amide group (preferably having 1 to 30 carbon atoms, more preferably 1 to 20 carbon atoms, and especially preferably 1 to 12 carbon atoms, e.g., diethylphosphoric amide, phenylphosphoric amide and the like are exemplified), a hydroxyl group, a mercapto group, a halogen atom (e.g., a fluorine atom, a chlorine atom, a bromine atom, and an iodine atom), a cyano group, a sulfo group, a carboxyl group, a nitro group, a hydroxamic acid group, a sulfino group, a hydrazino group, an imino group, a heterocyclic group (also including an aromatic heterocyclic group, and preferably having 1 to 30 carbon atoms, and more preferably 1 to 12 carbon atoms, the examples of the hetero atoms include e.g., a nitrogen atom, an oxygen atom, a sulfur atom, a phosphorus atom, a silicon atom, a selenium atom, and a tellurium atom, and specifically pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, a silolyl group and the like are exemplified), a silyl group (preferably having 3 to 40 carbon atoms, more preferably 3 to 30 carbon atoms, and especially preferably 3 to 24 carbon atoms, e.g., trimethylsilyl, triphenylsilyl and the like are exemplified), a silyloxy group (preferably having 3 to 40 carbon atoms, more preferably 3 to 30 carbon atoms, and especially preferably 3 to 24 carbon atoms, e.g., trimethylsilyloxy, triphenylsilyloxy and the like are exemplified), and a phosphoryl group (e.g., a diphenylphosphoryl group, a dimethylphosphoryl group and the like are exemplified).

These substituents may further be substituted, and as further substituents, the groups selected from the above substituent group A can be exemplified.

In formula (1), each of $R^1$ and $R^2$ preferably represents a halogen atom, a hydrocarbon substituent (preferably a substituted or unsubstituted alkyl group, cycloalkyl group, or aryl group), a cyano group, $OR_{2a}$, $SR_{2a}$, $NR_{28}R_{2b}$, $BR_{2a}R_{2b}$, or $SiR_{2a}R_{2b}R_{2c}$, and more preferably a halogen atom, an alkyl group having 1 to 6 carbon atoms, an aryl group having 6 to 10 carbon atoms, a fluoroalkyl group, a cyano group, or $OR_{2a}$. As the substituents that the hydrocarbon substituent may have, those described in the above substituent group A are exemplified, and preferred ranges are also the same with those of $R^1$ and $R^2$. Each of $R_{2a}$, $R_{2b}$ and $R_{2c}$ independently represents a hydrocarbon substituent, or a hydrocarbon substituent substituted with a hetero atom. The examples of the hetero atoms include oxygen, nitrogen, phosphorus, sulfur, selenium and arsenic atoms, preferably oxygen, sulfur and nitrogen atom atoms, and more preferably a nitrogen atom. The preferred range of $R_{2a}$, $R_{2b}$ and $R_{2c}$ is the same with the case where each of $R^1$ and $R^2$ represents a hydrocarbon substituent.

When two or more $R^1$ and $R^2$ are present, two of $R^1$ and $R^2$ may be bonded to each other to form a saturated or unsaturated aromatic ring or non-aromatic ring.

In formula (1), each of $R^1$ and $R^2$ especially preferably represents a halogen atom for capable of controlling light emission wavelength without reducing durability and a fluorine atom is most preferred. $R^1$ and $R^2$ may be substituted anywhere of an aromatic hydrocarbon ring or an aromatic heterocyclic ring represented by $Q^1$ or $Q^2$, which is the mother structure of metal complex A, without any restriction, and almost the same effect can be obtained.

It is especially preferred in formula (1) that both $R^1$ and $R^2$ represent fluorine atoms.

In the invention, "number of carbon atoms" of the substituent such as an alkyl group also include a case where the alkyl group may be substituted with any other substituent(s), which means to include the number of carbon atoms of the other substituent(s).

In formula (1), M represents a metal having an atomic weight of 40 or more, and preferably a non-radiative metal. The metal is more preferably Re, Ru, Os, Rh, Ir, Pd, Pt, Cu or Au, still more preferably Os, Ir or Pt, especially preferably Ir or Pt, and most preferably Pt in view of high light emission efficiency and high stability of a complex.

In formula (1), each of $X^1$, $X^2$ and $X^3$ independently represents a carbon atom or a nitrogen atom, provided that all of $X^1$, $X^2$ and $X^3$ do not represent a nitrogen atom.

$X^1$ preferably represents a carbon atom.

$X^2$ preferably represents a carbon atom.

$X^3$ is an atom having a bonding hand to a metal, and for the reason of maintaining chemical stability of a complex, $X^3$ is preferably a nitrogen atom.

In formula (1), $Q^1$ represents a 5- or 6-membered aromatic heterocyclic ring. Specifically as $Q^1$, pyridine, pyrazine, pyrimidine, pyridazine, pyrrole, imidazole, pyrazole, oxazole, thiazole, isoxazole, isothiazole, triazole, tetrazole, and structures of condensation of these rings with other rings are exemplified, preferably pyridine, pyrazine, pyrimidine, imidazole, pyrazole, and structures of condensation of these rings with other rings, and more preferably pyridine, imidazole, pyrazole, and structures of condensation of these rings with other rings. As the structures condensed with other rings, indolizine, purine, pteridine, β-carboline, naphthyridine, quinoxaline, acridine, phenanthroline, phenazine, and imidazopyridine are exemplified.

In formula (1), $Q^2$ represents a 5- or 6-membered aromatic hydrocarbon ring or aromatic heterocyclic ring. Specifically as $Q^2$, benzene, pyridine, pyrazine, pyrimidine, pyridazine, pyrrole, imidazole, pyrazole, oxazole, thiazole, isoxazole, isothiazole, triazole, tetrazole, and structures of condensation of these rings with other rings are exemplified, preferably benzene, pyridine, pyrazine, pyrimidine, imidazole, pyrazole, and structures of condensation of these rings with other rings, and more preferably benzene, pyridine, imidazole, pyrazole, and structures of condensation of these rings with other rings. As the structures condensed with other rings, indolizine, purine, pteridine, β-carboline, naphthyridine, quinoxaline, acridine, phenanthroline, phenazine, and imidazopyridine are exemplified.

In formula (1), $Q^1$ and $Q^2$ may be linked by a linking group (preferably an arylene group, and more preferably a phenylene group) to form a ring. Since the ring is conjugated, it can be considered to be the same with $Q^1$ and $Q^2$, and in the substituent bonding to the ring, atoms directly bonding to the ring which are substituted with atoms having a greater atomic weight are also included as metal complex B in the invention.

That is, in formula (1), in the invention, $Q^1$ and $Q^2$ may form a condensed ring as a whole through $X^1$-$X^2$. As such examples, formulae (A1) to (A4) described later are exemplified.

In formula (1), each of n1 and n2 independently represents an integer of 0 to 4, but there is no case where the sum of n1 and n2 is 0. n1 is preferably 0 or 1, and more preferably 0. n2 is preferably 1 to 3, and more preferably 1 or 2. Formula (1) is preferably represented by the following formula (2).

(2)

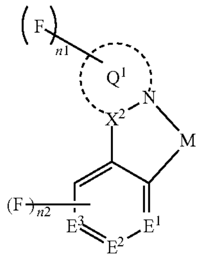

In formula (2), M represents a metal having an atomic weight of 40 or more, and $X^2$ represents a carbon atom or a nitrogen atom. $Q^1$ represents a 5- or 6-membered aromatic heterocyclic ring. Each of $E^1$, $E^2$ and $E^3$ independently represents a carbon atom or a nitrogen atom, provided that all of $E^1$, $E^2$ and $E^3$ do not represent a nitrogen atom. Each of n1 and n2 independently represents an integer of 0 to 4, but there is no case where the sum of n1 and n2 is 0.

In formula (2), the preferred ranges of M, $X^2$, $Q^1$, n1 and n2 are respectively the same with the preferred ranges of M, $X^2$, $Q^1$, n1 and n2 in formula (1).

In formula (2), two or more of $E^1$, $E^2$ and $E^3$ preferably represent a carbon atom, and more preferably $E^1$ and $E^2$ represent a carbon atom. $E^3$ represents a carbon atom or a nitrogen atom, but from the viewpoint of obtaining light emission of shorter wavelength, $E^3$ preferably represents a nitrogen atom. Further, in view of chemical stability of the compound and durability of the device, it is also preferred for $E^3$ to represent a carbon atom.

Formula (2) is preferably represented by the following formula (3).

(3)

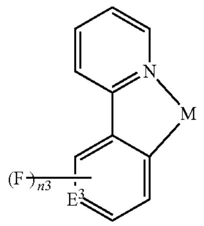

In formula (3), M represents a metal having an atomic weight of 40 or more, and $E^3$ represents a carbon atom or a nitrogen atom. n3 represents an integer of 1 to 4

In formula (3), the preferred range of M is the same with the preferred range of M in formula (1). n3 is preferably 1 or 2.

A metal complex of the case where M in formula (1) is Pt will be described below.

A metal complex of the case where M in formula (1) is Pt is preferably represented by the following formula (C-1).

(C-1)

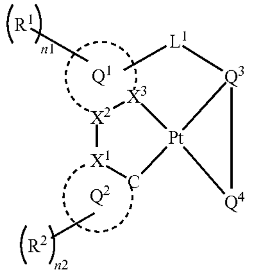

In formula (C-1), each of $R^1$'s and $R^2$'s independently represents a substituent. When plural $R^1$'s are present, the $R^1$'s may be the same or different from each other. When plural $R^2$'s are present, the $R^2$'s may be the same with or different from each other, and the $R^1$ and the $R^2$ may be bonded to each other to form a ring. Each of $X^1$, $X^2$ and $X^3$ independently represents a carbon atom or a nitrogen atom, provided that all of $X^1$, $X^2$ and $X^3$ do not represent a nitrogen atom. $Q^1$ represents a 5- or 6-membered aromatic heterocyclic ring, and $Q^2$ represents a 5- or 6-membered aromatic hydrocarbon ring or aromatic heterocyclic ring. Each of $Q^3$ and $Q^4$ independently represents a ligand to coordinate to Pt. Each of $Q^3$ and $Q^4$ may have a substituent, and the substituents may be bonded to each other to form a ring. Each of n1 and n2 independently represents an integer of 0 to 4, but there is no case where the sum of n1 and n2 is 0. $L^1$ represents a single bond or a divalent linking group.

Formula (C-1) is described below. Each of $Q^1$, $Q^2$, $Q^3$ and $Q^4$ independently represents a ligand to coordinate to Pt. At this time, bonding of $Q^1$, $Q^2$, $Q^3$ and $Q^4$ to Pt may be any bonding via a covalent bond, an ionic bond or a coordinate bond. As the atoms in $Q^1$, $Q^2$, $Q^3$ and $Q^4$ to be bonded to Pt, a carbon atom, a nitrogen atom, an oxygen atom, a sulfur atom and a phosphorus atom are preferred, and it is preferred that at least one atom of the atoms in $Q^1$, $Q^2$, $Q^3$ and $Q^4$ to be bonded to Pt is a carbon atom, more preferably two atoms are carbon atoms, and especially preferably two are carbon atoms and two are nitrogen atoms.

$X^1$ preferably represents a carbon atom.

$X^2$ preferably represents a carbon atom.

$X^3$ is an atom having a bonding hand to a metal, and for the reason of maintaining chemical stability of a complex, $X^3$ is preferably a nitrogen atom.

$Q^3$ and $Q^4$ to be bonded to Pt via a carbon atom may be an anionic ligand, a neutral ligand, or may be a cyclic ligand or an acyclic ligand. The examples of anionic ligands include a vinyl ligand, an aromatic hydrocarbon cyclic ligand (e.g., a benzene ligand, a naphthalene ligand, an anthracene ligand, a phenanthrene ligand, etc.), a heterocyclic ligand (e.g., a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, and a condensed ring containing any of these ligands (e.g., a quinoline ligand and a benzothiazole ligand)). As the neutral ligand, a carbene ligand is exemplified.

$Q^3$ and $Q^4$ to be bonded to Pt via a nitrogen atom may be a neutral ligand or an anionic ligand. The examples of neutral ligands include a nitrogen-containing aromatic heterocyclic ligand (e.g., a pyridine ligand, a pyrazine ligand, a pyrimidine ligand, a pyridazine ligand, a triazine ligand, an imidazole ligand, a pyrazole ligand, a triazole ligand, an oxazole ligand, a thiazole ligand, and a condensed ring containing any of these ligands (e.g., a quinoline ligand and a benzimidazole ligand)), an amine ligand, a nitrile ligand, and an imine ligand. As the anionic ligands, an amino ligand, an imino ligand, and a nitrogen-containing aromatic heterocyclic ligand (e.g., a pyrrole ligand, an imidazole ligand, a triazole ligand, and a condensed ring containing any of these ligands (e.g., an indole ligand and a benzimidazole ligand)) are exemplified.

$Q^3$ and $Q^4$ to be bonded to Pt via an oxygen atom may be a neutral ligand or an anionic ligand. As the neutral ligands, an ether ligand, a ketone ligand, an ester ligand, an amide ligand, an oxygen-containing heterocyclic ligand (e.g., a furan ligand, an oxazole ligand, and a condensed ring containing any of these ligands (e.g., a benzoxazole ligand, etc.)) are exemplified. As the anionic ligands, an alkoxy ligand, an aryloxy ligand, a heteroaryloxy ligand, an acyloxy ligand, and a silyloxy ligand are exemplified.

$Q^3$ and $Q^4$ to be bonded to Pt via a sulfur atom may be a neutral ligand or an anionic ligand. As the neutral ligands, a thioether ligand, a thioketone ligand, a thioester ligand, a thioamide ligand, a sulfur-containing heterocyclic ligand (e.g., a thiophene ligand, a thiazole ligand, and a condensed ring containing any of these ligands (e.g., a benzothiazole ligand, etc.)) are exemplified. As the anionic ligands, an alkylmercapto ligand, an arylmercapto ligand, and a heteroarylmercapto ligand are exemplified.

$Q^3$ and $Q^4$ to be bonded to Pt via a phosphorus atom may be a neutral ligand or an anionic ligand. As the neutral ligands, a phosphine ligand, a phosphate ligand, a phosphite ligand, and a phosphorus-containing heterocyclic ligand (e.g., a phosphinine ligand) are exemplified. As the anionic ligands, a phosphino ligand, a phosphinyl ligand, and a phosphoryl ligand are exemplified.

Each of $Q^3$ and $Q^4$ may have a substituent, and the above-described substituent group A is arbitrarily applicable as the substituents. Substituents may be linked to each other (when $Q^3$ and $Q^4$ are linked, it becomes a Pt complex of a cyclic tetradentate ligand).

Each of $Q^3$ and $Q^4$ preferably represents an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, an acyloxy ligand, an alkyloxy ligand, an aryloxy ligand, a heteroaryloxy ligand, or a silyloxy ligand, more preferably an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, an acyloxy ligand, or an aryloxy ligand, and still more preferably an aromatic hydrocarbon cyclic ligand to be bonded to Pt via a carbon atom, an aromatic heterocyclic ligand to be bonded to Pt via a carbon atom, a nitrogen-containing aromatic heterocyclic ligand to be bonded to Pt via a nitrogen atom, or an acyloxy ligand.

As $Q^1$, pyridine, pyrazine, pyrimidine, pyridazine, pyrrole, imidazole, pyrazole, oxazole, thiazole, isoxazole, isothiazole, triazole, tetrazole, and structures of condensation of these rings with other rings are exemplified, preferably pyridine, pyrazine, pyrimidine, imidazole, pyrazole, and structures of condensation of these rings with other rings, and more preferably pyridine, imidazole, pyrazole, and structures of condensation of these rings with other rings are exemplified. As the structures condensed with other rings, indolizine, purine, pteridine, β-carboline, naphthyridine, quinoxaline, acridine, phenanthroline, phenazine, and imidazopyridine are exemplified.

As $Q^2$, benzene, pyridine, pyrazine, pyrimidine, pyridazine, pyrrole, imidazole, pyrazole, oxazole, thiazole, isoxazole, isothiazole, triazole, tetrazole, and structures of condensation of these rings with other rings are exemplified, preferably benzene, pyridine, pyrazine, pyrimidine, imidazole, pyrazole, and structures of condensation of these rings with other rings, and more preferably benzene, pyridine, imidazole, pyrazole, and structures of condensation of these rings with other rings are exemplified. As the structures condensed with other rings, indolizine, purine, pteridine, β-carboline, naphthyridine, quinoxaline, acridine, phenanthroline, phenazine, and imidazopyridine are exemplified.

In formula (C-1), the substituents represented by each of $R^1$ and $R^2$ are the same with the substituents represented by $R^1$ and $R^2$ in formula (1), and preferred range is also the same.

It is preferred for any one or more of $Q^1$, $Q^2$, $Q^3$ and $Q^4$ to have a fluorine substituent. The number of the fluorine substituent is not particularly restricted, but from the viewpoint of controlling layer separation, three or less per one ligand is preferred. In view of chemical stabilization, fluorine substituent is preferably substituted on an aromatic hydrocarbon cyclic ligand, a heterocyclic ligand, and a condensed ring containing any of these ligands of $Q^1$, $Q^2$, $Q^3$ and $Q^4$.

$L^1$ represents a single bond or a divalent linking group. The examples of the divalent linking groups represented by $L^1$ include an alkylene group (e.g., methylene, ethylene, propylene and the like), an arylene group (e.g., phenylene, naphthalenediyl), a heteroarylene group (e.g., pyridinediyl, thiophenediyl and the like), an imino group (—NR—), (e.g., a phenylimino group and the like), an oxy group (—O—), a thio group (—S—), a phosphinidene group (—PR—) (e.g., a phenylphosphinidene group and the like), a silylene group (—SiRR'—) (e.g., a dimethylsilylene group, a diphenylsilylene group and the like), and a combination of these groups. These linking groups may further have a substituent. Substituents selected from the above substituent group A are exemplified as the substituent and preferred range is the same with the preferred range of $R^1$ and $R^2$.

From the viewpoint of stability of complex and light-emitting quantum yield, $L^1$ preferably represents a single bond, an alkylene group, an arylene group, a heteroarylene group, an imino group, an oxy group, a thio group, or a silylene group, more preferably a single bond, an alkylene group, an arylene group, or an imino group, still more preferably a single bond, an alkylene group, or an arylene group, still further preferably a single bond, a methylene group or a phenylene group, still yet preferably a single bond or a di-substituted methylene group, still more yet preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, and especially preferably a single bond, a dimethylmethylene group, diphenylmethylene group, or a cyclohexanediyl group.

In formula (C-1), each of n1 and n2 independently represents an integer of 0 to 4, but there is no case where the sum of n1 and n2 is 0. n1 preferably represents 0 or 1, and more preferably 0. n2 preferably represents 1 to 3, and more preferably 1 or 2.

The platinum complex represented by formula (C-1) is more preferably represented by the following formula (C-2).

formula(C-2)

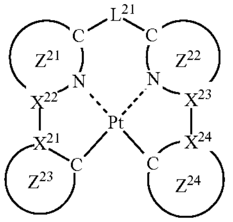

In formula (C-2), $L^{21}$ represents a single bond or a divalent linking group. Each of $Z^{21}$ and $Z^{22}$ independently represents a 5- or 6-membered nitrogen-containing heterocyclic ring. Each of $Z^{23}$ and $Z^{24}$ independently represents a benzene ring or a 5- or 6-membered aromatic heterocyclic ring. Each of $Z^{21}$ and $Z^{23}$ may independently have 1 to 4 substituents, and these substituents may be bonded to each other to form a ring, provided that at least either $Z^{21}$ or $Z^{23}$ has one or more substituents. Each of $Z^{22}$ and $Z^{24}$ may independently have a substituent, and these substituents may be bonded to each other to form a ring. Each of $X^{21}$, $X^{22}$, $X^{23}$ and $X^{24}$ independently represents a carbon atom or a nitrogen atom.

Formula (C-2) is described below. $L^{21}$ has the same meaning with the meaning of $L^1$ in formula (C-1) and the preferred range is also the same. Each of $X^{21}$, $X^{22}$, $X^{23}$ and $X^{24}$ has the same meaning with the meaning of $X^1$ and $X^2$ in formula (C-1) and the preferred range is also the same.

Each of $Z^{21}$ and $Z^{22}$ independently represents a 5- or 6-membered nitrogen-containing heterocyclic ring. As the nitrogen-containing heterocyclic rings represented by $Z^{21}$ and $Z^{22}$, a pyridine ring, a pyrimidine ring, a pyrazine ring, a triazine ring, an imidazole ring, a pyrazole ring, a quinoline ring, an isoquinoline ring, an oxazole ring, a thiazole ring, a triazole ring, an oxadiazole ring, and a thiadiazole ring are exemplified. From the viewpoint of complex stability, control of light emission wavelength and light-emitting quantum yield, the rings represented by $Z^{21}$ and $Z^{22}$ are preferably a pyridine ring, a pyrazine ring, an imidazole ring, and a pyrazole ring, more preferably a pyridine ring, an imidazole ring, and a pyrazole ring, still more preferably a pyridine ring and a pyrazole ring, and especially preferably a pyridine ring.

The 5- or 6-membered nitrogen-containing aromatic heterocyclic ring represented by $Z^{22}$ may have a substituent. The above substituent group A is applicable as the substituent on a carbon atom and the following substituent group B is applicable as the substituent on a nitrogen atom.

(Substituent group B)

Substituent group B includes an alkyl group (preferably having 1 to 30 carbon atoms, more preferably 1 to 20 carbon atoms, and especially preferably 1 to 10 carbon atoms, e.g., methyl, ethyl, isopropyl, tert-butyl, n-octyl, n-decyl, n-hexadecyl, cyclopropyl, cyclopentyl, cyclohexyl, trifluoromethyl, and pentafluoroethyl are exemplified), an alkenyl group (preferably having 2 to 30 carbon atoms, more preferably 2 to 20 carbon atoms, and especially preferably 2 to 10 carbon atoms, e.g., vinyl, allyl, 2-butenyl, and 3-pentenyl are exemplified), an alkynyl group (preferably having 2 to 30 carbon atoms, more preferably 2 to 20 carbon atoms, and especially preferably 2 to 10 carbon atoms, e.g., propargyl and 3-pentynyl are exemplified), an aryl group (preferably having 6 to 30 carbon atoms, more preferably 6 to 20 carbon atoms, and especially preferably 6 to 12 carbon atoms, e.g., phenyl, p-methylphenyl, naphthyl, anthranyl, pentafluorophenyl are exemplified), an acyl group (preferably having 1 to 30 carbon atoms, more preferably 1 to 20 carbon atoms, and especially preferably 1 to 12 carbon atoms, e.g., acetyl, benzoyl, formyl, and pivaloyl are exemplified), an alkoxycarbonyl group (preferably having 2 to 30 carbon atoms, more preferably 2 to 20 carbon atoms, and especially preferably 2 to 12 carbon atoms, e.g., methoxycarbonyl and ethoxycarbonyl are exemplified), an aryloxycarbonyl group (preferably having 7 to 30 carbon atoms, more preferably 7 to 20 carbon atoms, and especially preferably 7 to 12 carbon atoms, e.g., phenyloxycarbonyl is exemplified), an acyloxy group (preferably having 2 to 30 carbon atoms, more preferably 2 to 20 carbon atoms, and especially preferably 2 to 10 carbon atoms, e.g., acetoxy and benzoyloxy are exemplified), a sulfamoyl group (preferably having 0 to 30 carbon atoms, more preferably 0 to 20 carbon atoms, and especially preferably 0 to 12 carbon atoms, e.g., sulfamoyl, methylsulfamoyl, dimethylsulfamoyl, and phenylsulfamoyl are exemplified), a carbamoyl group (preferably having 1 to 30 carbon atoms, more preferably 1 to 20 carbon atoms, and especially preferably 1 to 12 carbon atoms, e.g., carbamoyl, methylcarbamoyl, diethylcarbamoyl, and phenylcarbamoyl are exemplified), a heterocyclic group (preferably having 1 to 30 carbon atoms, and more preferably 1 to 12 carbon atoms, and the examples of the hetero atoms include e.g., a nitrogen atom, an oxygen atom and a sulfur atom, specifically imidazolyl, pyridyl, quinolyl, furyl, thienyl, piperidyl, morpholino, benzoxazolyl, benzimidazolyl, benzothiazolyl, a carbazolyl group, and an azepinyl group are exemplified).

As the substituent on a carbon atom, an alkyl group, a polyfluoroalkyl group, an aryl group, an aromatic heterocyclic group, a dialkylamino group, a diarylamino group, an alkoxy group, a cyano group or a halogen atom is preferred. The substituent is arbitrarily selected for controlling light emission wavelength and electric potential. For shortening the wavelength, an electron donating group, a fluorine atom, or an aromatic cyclic group is preferred and, for example, an alkyl group, a dialkylamino group, an alkoxy group, a fluorine atom, an aryl group or an aromatic heterocyclic group is selected. For lengthening the wavelength, an electron withdrawing group is preferred and, for example, a cyano group or a polyfluoroalkyl group is selected.

As the substituent on a nitrogen atom, an alkyl group, an aryl group, or an aromatic heterocyclic group is preferred, and from the aspect of the stability of complex, an alkyl group or an aryl group is preferred. These substituents may be linked to each other to form a condensed ring. As the rings to be formed, a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring are exemplified.

Each of $Z^{23}$ and $Z^{24}$ independently represents a benzene ring or a 5- or 6-membered aromatic heterocyclic ring. As the nitrogen-containing aromatic heterocyclic ring represented by $Z^{23}$ and $Z^{24}$, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring are exemplified. From the viewpoint of complex stability, control of light emission wavelength and light-emitting quantum yield, the rings represented by $Z^{23}$ and $Z^{24}$ are preferably a benzene ring, a pyridine ring, a pyrazine ring, an imidazole ring, a pyrazole ring, and a thiophene ring, more preferably a benzene ring, a pyridine ring and a pyrazole ring, and still more preferably a benzene ring and a pyridine ring.

The benzene ring or 5- or 6-membered nitrogen-containing aromatic heterocyclic ring represented by $Z^{24}$ may have a substituent. The above substituent group A is applicable as the substituent on a carbon atom and the above substituent group B is applicable as the substituent on a nitrogen atom.

As the substituent on a carbon atom, an alkyl group, a polyfluoroalkyl group, an aryl group, an aromatic heterocyclic group, a dialkylamino group, a diarylamino group, an alkoxy group, a cyano group or a halogen atom is preferred. The substituent is arbitrarily selected for controlling light emission wavelength and electric potential. For lengthening the wavelength, an electron donating group or an aromatic cyclic group is preferred and, for example, an alkyl group, a dialkylamino group, an alkoxy group, an aryl group or an aromatic heterocyclic group is selected. For shortening the wavelength, an electron withdrawing group is preferred and, for example, a fluorine group, a cyano group or a polyfluoroalkyl group is selected.

As the substituent on a nitrogen atom, an alkyl group, an aryl group, or an aromatic heterocyclic group is preferred, and from the aspect of the stability of complex, an alkyl group or an aryl group is preferred. These substituents may be linked to each other to form a condensed ring. As the rings to be formed, a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring are exemplified.

In formula (C-2), as the substituents that $Z^{21}$ and $Z^{23}$ may have, the substituents selected from substituent group A are exemplified, and the preferred range is the same with the preferred range $R^1$ and $R^2$ in formula (1). The preferred range of the number of substituents is also the same as in formula (1).

It is preferred that either one of $Z^{21}$ and $Z^{23}$ has a fluorine substituent. The number of the fluorine substituent is not particularly restricted, but from the viewpoint of controlling layer separation, three or less per one ring is preferred.

The preferred range of the substituents that $Z^{22}$ and $Z^{24}$ may have is the same with the range of $Z^{21}$ and $Z^{23}$.

Of the platinum complexes represented by formula (C-2), one of more preferred embodiments is a platinum complex represented by the following formula (C-3).

(C-3)

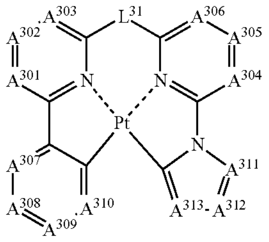

In formula (C-3), each of $A^{301}$ to $A^{313}$ independently represents C—R or a nitrogen atom. R represents a hydrogen atom or a substituent. $L^{31}$ represents a single bond or a divalent linking group.

Formula (C-3) is described below. $L^{31}$ has the same meaning with the meaning of $L^{21}$ in formula (C-2) and the preferred range is also the same. Each of $A^{301}$ to $A^{306}$ independently represents C—R or a nitrogen atom. R represents a hydrogen atom or a substituent. As the substituent represented by R, those enumerated above as substituent group A can be applied.

Each of $A^{301}$ to $A^{306}$ preferably represents C—R, and R's may be linked to each other to form a ring. When each of $A^{301}$ to $A^{306}$ represents C—R, each R of $A^{302}$ and $A^{305}$ preferably represents a hydrogen atom, an alkyl group, an aryl group, an amino group, an alkoxy group, an aryloxy group, a fluorine group, or a cyano group, more preferably a hydrogen atom, an alkyl group, an aryl group, an amino group, or a fluorine group, and especially preferably a hydrogen atom, a methyl group, a phenyl group, a xylyl group, or a fluorine group. The alkyl group and aryl group may further have a substituent, and an alkyl group, an aryl group, a cyano group, an amino group, a halogen atom, and a fluoroalkyl group are exemplified as the examples of the substituents, preferably an alkyl group having 1 to 6 carbon atoms, a cyano group, an amino group, a halogen atom, and a fluoroalkyl group (preferably a trifluoromethyl group), and more preferably an alkyl group having 1 to 6 carbon atoms and a halogen atom (preferably a fluorine atom). When each of $A^{302}$ and $A^{305}$ represents C—R, each R of $A^{302}$ and $A^{305}$ preferably represents an aryl group from the point of the improvement of durability of the device, and preferably represents a hydrogen atom, an alkyl group, an amino group, an alkoxy group, a fluorine group, or a cyano group from the point of capable of obtaining a short light emission wavelength.

Each R of $A^{301}$, $A^{303}$, $A^{304}$ and $A^{306}$ preferably represents a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, and especially preferably a hydrogen atom, but it is preferred that one or more R's represent a fluorine atom.

Each of $A^{307}$, $A^{308}$, $A^{309}$ and $A^{310}$ independently represents C—R or a nitrogen atom. R represents a hydrogen atom or a substituent. Those enumerated above as substituent group A can be applied to the substituent represented by R. When each of $A^{307}$, $A^{308}$, $A^{309}$ and $A^{310}$ represents C—R, each R preferably represents a hydrogen atom, an alkyl group, a polyfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a polyfluoroalkyl group, an aryl group, a dialkylamino group, a cyano group, or a fluorine atom, and still more preferably a hydrogen atom, an alkyl group, a trifluoromethyl group, or a fluorine atom. If possible, substituents may be linked to each other to form a condensed ring structure. When light emission wavelength is shifted to the shorter wavelength side, it is preferred that $A^{308}$ represents a nitrogen atom.

When $A^{307}$, $A^{308}$, $A^{309}$ and $A^{310}$ are selected as described above, as the 6-membered ring formed by two carbon atoms and $A^{307}$, $A^{308}$, $A^{309}$ and $A^{310}$, a benzene ring, a pyridine ring, a pyrazine ring, a pyrimidine ring, a pyridazine ring, and a triazine ring are exemplified, preferably a benzene ring, a pyridine ring, a pyrazine ring, a pyrimidine ring, and a pyridazine ring, and especially preferably a benzene ring and a pyridine ring. By the 6-membered ring being a pyridine ring, a pyrazine ring, a pyrimidine ring, or a pyridazine ring (especially preferably a pyridine ring), as compared with a benzene ring, acidity of the hydrogen atom present at the position for forming a metal-carbon bond is improved, and so advantageous in that a metal complex can be more easily formed.

Each of $A^{311}$, $A^{312}$ and $A^{313}$ independently represents C—R or a nitrogen atom. R represents a hydrogen atom or a substituent. Those enumerated above as substituent group A can be applied to the substituents represented by R. When each of $A^{311}$, $A^{312}$ and $A^{313}$ represents C—R, each R preferably represents a hydrogen atom, an alkyl group, a polyfluoroalkyl group, an aryl group, an aromatic heterocyclic group, a dialkylamino group, a diarylamino group, an alkyloxy group, a cyano group, or a halogen atom, more preferably a hydrogen atom, an alkyl group, a polyfluoroalkyl group, an aryl group, a dialkylamino group, a cyano group, or a fluorine atom, and still more preferably a hydrogen atom, an alkyl group, a trifluoromethyl group, or a fluorine atom. If possible, substituents may be linked to each other to form a condensed ring structure. It is preferred that at least one of $A^{311}$, $A^{312}$ and $A^{313}$ represents a nitrogen atom, and it is especially preferred for $A^{311}$ to represent a nitrogen atom.

Of the platinum complexes represented by formula (C-2), one of more preferred embodiments is a platinum complex represented by the following formula (C-4).

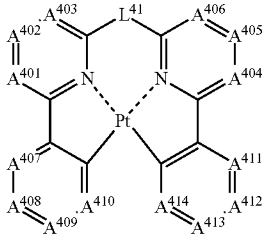

In formula (C-4), each of $A^{401}$ to $A^{414}$ independently represents C—R or a nitrogen atom. R represents a hydrogen atom or a substituent. $L^{41}$ represents a single bond or a divalent linking group.

Formula (C-4) is described below.

Each of $A^{401}$ to $A^{414}$ independently represents C—R or a nitrogen atom. R represents a hydrogen atom or a substituent, and the preferred range is the same with R in formula (C-3), but it is preferred that one or more of R's represent a fluorine atom. $A^{401}$ to $A^{406}$ and $L^{41}$ respectively have the same meanings with those of $A^{301}$ to $A^{306}$ and $L^{31}$ in formula (C-3) and preferred ranges are also the same.

As $A^{407}$ to $A^{414}$, in each of $A^{407}$ to $A^{410}$ and $A^{411}$ to $A^{414}$, the number of nitrogen atom is preferably 0 to 2, and more preferably 0 or 1. When light emission wavelength is shifted to the shorter wavelength side, it is preferred that $A^{408}$ or $A^{412}$ represents a nitrogen atom, and it is more preferred both $A^{408}$ and $A^{412}$ represent a nitrogen atom.

When each of $A^{407}$ to $A^{414}$ represents C—R, each R of $A^{408}$ and $A^{412}$ preferably represents a hydrogen atom, an alkyl group, a polyfluoroalkyl group, an aryl group, an amino group, an alkoxy group, an aryloxy group, a fluorine group, or a cyano group, more preferably a hydrogen atom, a polyfluoroalkyl group, an alkyl group, an aryl group, a fluorine group, or a cyano group, and especially preferably a hydrogen atom, a polyfluoroalkyl group, a fluorine group, or a cyano group. Each R of $A^{407}$, $A^{409}$, $A^{411}$ and $A^{413}$ preferably represents a hydrogen atom, an alkyl group, a polyfluoroalkyl group, an aryl group, an amino group, an alkoxy group, an aryloxy group, a fluorine group, or a cyano group, more preferably a hydrogen atom, a polyfluoroalkyl group, a fluorine group, or a cyano group, and especially preferably a hydrogen atom or a fluorine group. Each R of $A^{410}$ and $A^{414}$ preferably represents a hydrogen atom or a fluorine group, and more preferably a hydrogen atom. When any of $A^{407}$ to $A^{409}$ and $A^{411}$ to $A^{413}$ represents C—R, R's may be linked to each other to form a ring.

Of the platinum complexes represented by formula (C-2), one of more preferred embodiments is a platinum complex represented by the following formula (C-5).

(C-5)

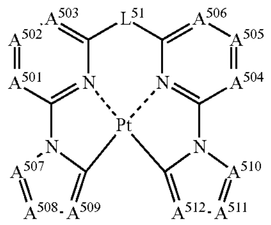

In formula (C-5), each of $A^{501}$ to $A^{512}$ independently represents C—R or a nitrogen atom. R represents a hydrogen atom or a substituent. $L^{51}$ represents a single bond or a divalent linking group.

Formula (C-5) is described below. $A^{501}$ to $A^{506}$ and $L^{51}$ respectively have the same meanings with those of $A^{301}$ to $A^{306}$ and $L^{31}$ in formula (C-3), and the preferred ranges are also the same.

Each of $A^{501}$ to $A^{506}$ independently represents C—R or a nitrogen atom. R represents a hydrogen atom or a substituent, and the preferred range is the same with R in formula (C-3), but it is preferred that one or more R's represent a fluorine atom.

Each of $A^{507}$, $A^{508}$ and $A^{509}$, and $A^{510}$, $A^{511}$ and $A^{512}$ has the same meanings with those of $A^{311}$, $A^{312}$ and $A^{313}$ in formula (C-3), and the preferred range is also the same.

Of the platinum complexes represented by formula (C-1), more preferred another embodiment is a platinum complex represented by the following formula (C-6).

formula (C-6)

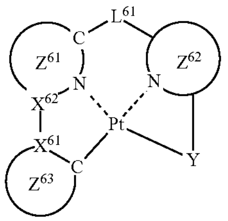

In formula (C-6), $L^{61}$ represents a single bond or a divalent linking group. Each of $Z^{61}$ and $Z^{62}$ independently represents a 5- or 6-membered nitrogen-containing aromatic heterocyclic ring. $Z^{63}$ represents a benzene ring or a 5- or 6-membered aromatic heterocyclic ring. Y represents an anionic acyclic ligand to be bonded to Pt. Each of $Z^{61}$ and $Z^{63}$ may independently have 1 to 4 substituents, and the substituents may be bonded to each other to form a ring, provided that at least either $Z^{61}$ or $Z^{63}$ has one or more substituents. $Z^{62}$ may have a substituent. Each of $X^{61}$ and $X^{62}$ independently represents a carbon atom or a nitrogen atom.

Formula (C-6) is described below. $L^{61}$ has the same meaning with the meaning of $L^1$ in formula (C-1) and the preferred range is also the same.

$X^{61}$ and $X^{62}$ have the same meaning with that of $X^1$ and $X^2$ in formula (C-1) and the preferred range is also the same.

$Z^{61}$ and $Z^{62}$ have the same meaning with that of $Z^{21}$ and $Z^{22}$ in formula (C-2) and the preferred range is also the same. $Z^{63}$ has the same meaning with that of $Z^{23}$ in formula (C-2) and the preferred range is also the same.

Y represents an anionic acyclic ligand to be bonded to Pt. The acyclic ligand is a ligand in which the atoms to be bonded to Pt do not form a ring in a state of a ligand. As the atoms in Y to be bonded to Pt, a carbon atom, a nitrogen atom, an oxygen atom, and a sulfur atom are preferred, more preferably a nitrogen atom and an oxygen atom, and most preferably an oxygen atom. As Y to be bonded to Pt via a carbon atom, a vinyl ligand is exemplified. As Y to be bonded to Pt via a nitrogen atom, an amino ligand and an imino ligand are exemplified. As Y to be bonded to Pt via an oxygen atom, an alkoxy ligand, an aryloxy ligand, a heteroaryloxy ligand, an acyloxy ligand, a silyloxy ligand, a carboxyl ligand, a phosphoric acid ligand, and a sulfonic acid ligand are exemplified. As Y to be bonded to Pt via a sulfur atom, an alkylmercapto ligand, an arylmercapto ligand, a heteroarylmercapto ligand, and a thiocarboxylic acid ligand are exemplified.

The ligand represented by Y may have a substituent, and the substituents described above as substituent group A are arbitrarily applied. The substituents may be linked to each other.

The ligand represented by Y is preferably a ligand to be bonded to Pt via an oxygen atom, more preferably an acyloxy ligand, an alkyloxy ligand, an aryloxy ligand, a heteroaryloxy ligand, or a silyloxy ligand, and still more preferably an acyloxy ligand.

In formula (C-6), as the substituents that $Z^{61}$ and $Z^{63}$ may have, the substituents selected from substituent group A are exemplified, and the preferred range is the same with the range of $R^1$ and $R^2$ in formula (1). The preferred number of substituents is also the same as in formula (1).

It is preferred that at least one of $Z^{61}$ and $Z^{63}$ has a fluorine substituent. The number of the fluorine substituent is not particularly restricted, but from the viewpoint of controlling layer separation, three or less per one ring is preferred.

The substituents that $Z^{62}$ may have and the preferred range are the same with those of $Z^{61}$ and $Z^{63}$.

Of the platinum complexes represented by formula (C-6), one of more preferred embodiments is a platinum complex represented by the following formula (C-7).

formula (C-7)

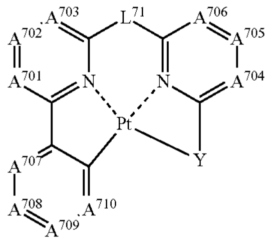

In formula (C-7), each of $A^{701}$ to $A^{710}$ independently represents C—R or a nitrogen atom. R represents a hydrogen atom or a substituent. $L^{71}$ represents a single bond or a divalent linking group. Y represents an anionic acyclic ligand to be bonded to Pt.

Formula (C-7) is described below. $L^{71}$ has the same meaning with that of $L^{61}$ in formula (C-6) and the preferred range is also the same. $A^{701}$ to $A^{710}$ respectively have the same meanings with those of $A^{301}$ to $A^{310}$ in formula (C-3) and the preferred ranges are also the same. Y has the same meaning as in formula (C-6) and the preferred range is also the same.

Each of $A^{701}$ to $A^{706}$ independently represents C—R or a nitrogen atom. R represents a hydrogen atom or a substituent; and the preferred range is the same with the meaning of R in formula (C-3), but it is preferred that one or more R's represent a fluorine atom.

As the platinum complexes represented by formula (C-1), specifically the following compounds are exemplified: the compounds described in JP-A-2005-310733, paragraphs [0143] to [0152], [0157] to [0158], [0162] to [0168], the compounds described in JP-A-2006-256999, paragraphs [0065] to [0083], the compounds described in JP-A-2006-93542, paragraphs [0065] to [0090], the compounds described in JP-A-2007-73891, paragraphs [0063] to [0071], the compounds described in JP-A-2007-324309, paragraphs [0079] to [0083], the compounds described in JP-A-2007-96255, paragraphs [0055] to [0071], and the compounds described in JP-A-2006-313796, paragraphs [0043] to [0046]. In addition to the above, the following shown platinum complexes are exemplified.

The specific examples of the structures of metal complexes A and B in the case where M in formula (1) represents Pt, and the content of metal complex B are shown below, but the invention is not restricted thereto. The kinds of metal complexes A and B and the contents of metal complexes B to the contents of metal complexes A are shown in the following Tables 1 to 10, Table 21 and Table 22.

compound 1

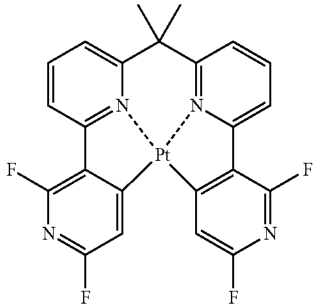

a1

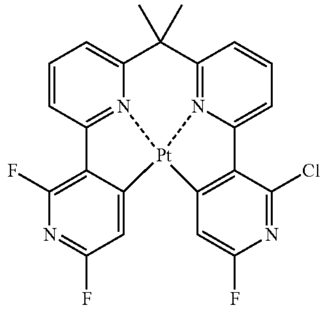

-continued b1

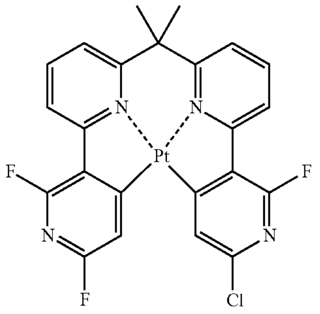

c1

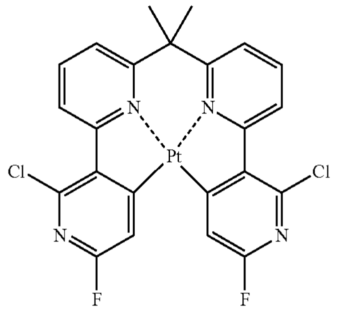

d1

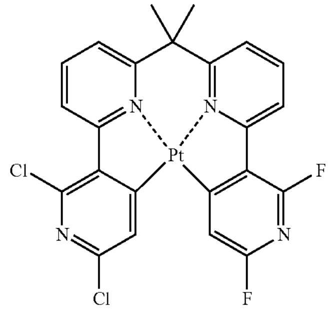

e1

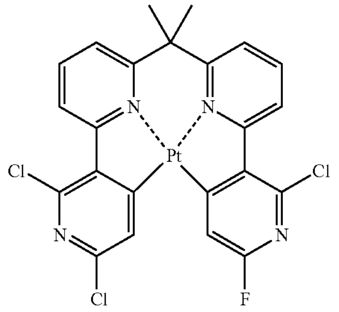

f1

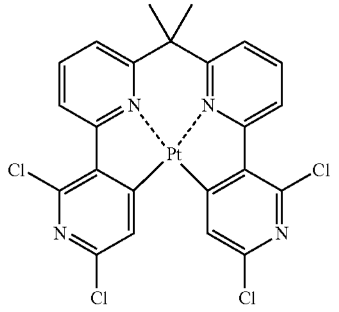

-continued
g1
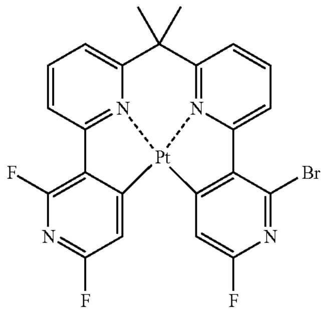
h1
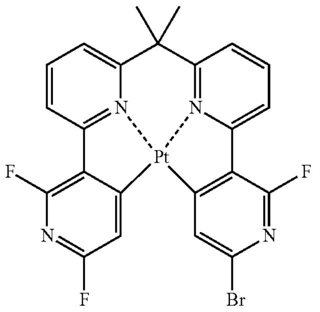
i1
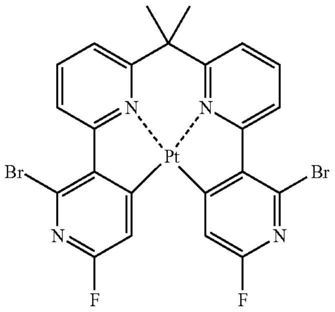
j1
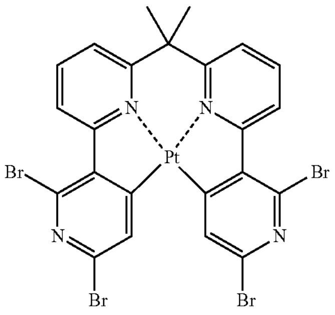
k1
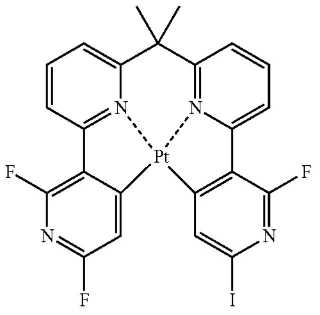
-continued
l1
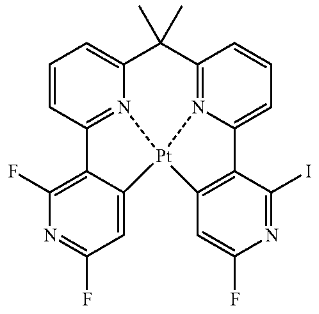
m1
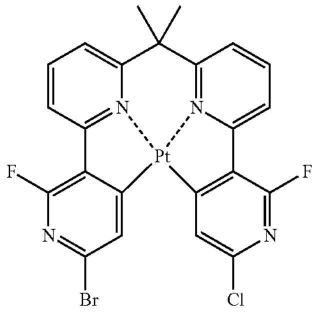
n1
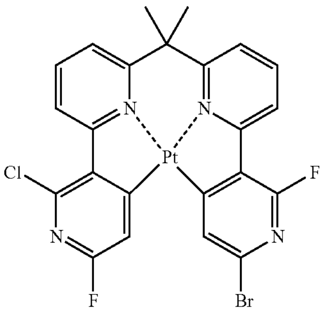
o1
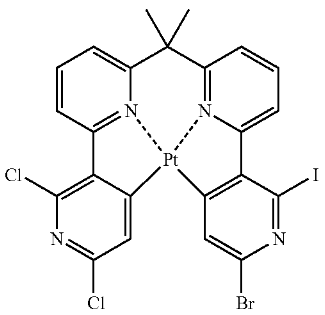
p1
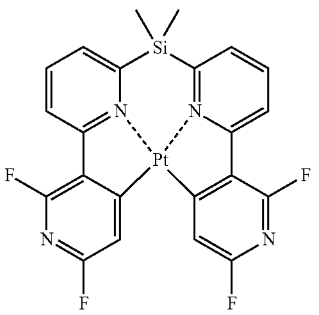

-continued
q1
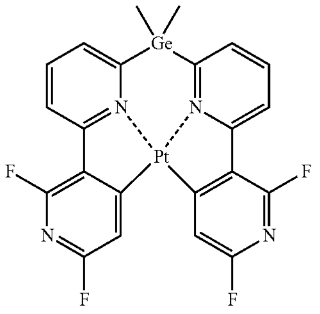
r1
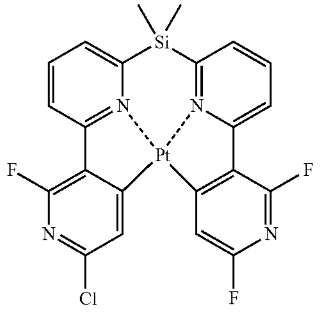
compound 2
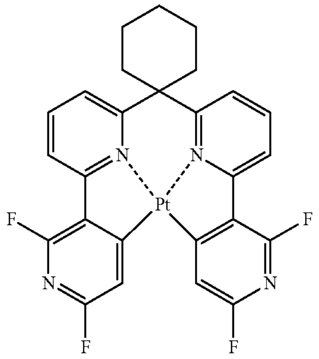
a2
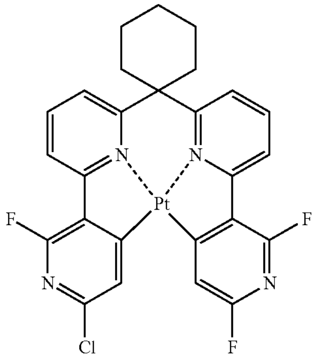
-continued
b2
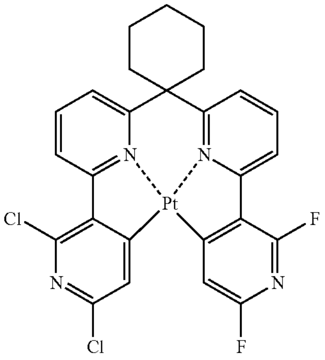
c2
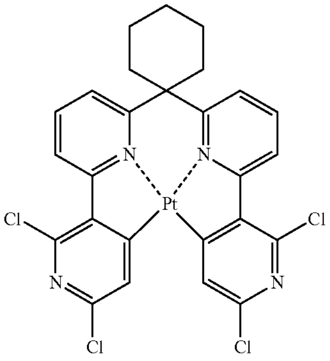
d2
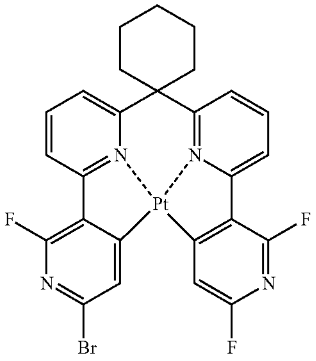
e2
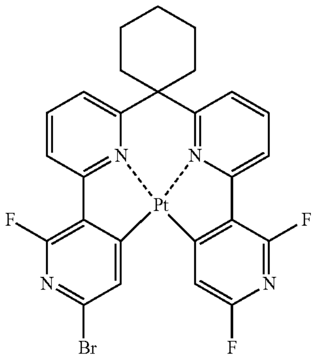

-continued
f2
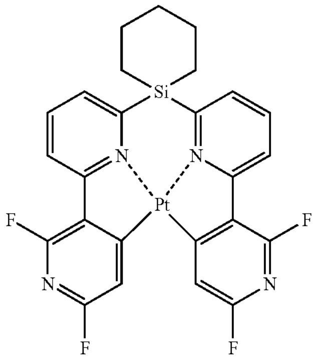
compound 3
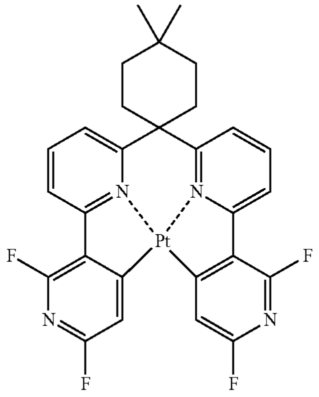
a3
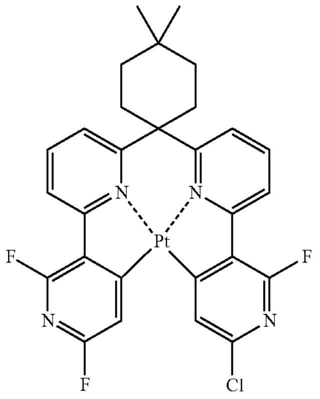
b3
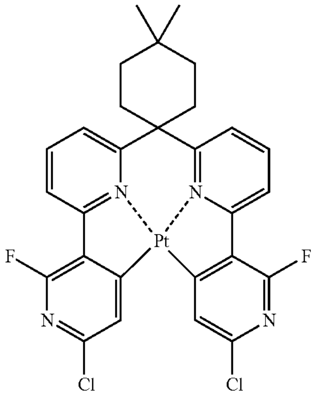
-continued
c3
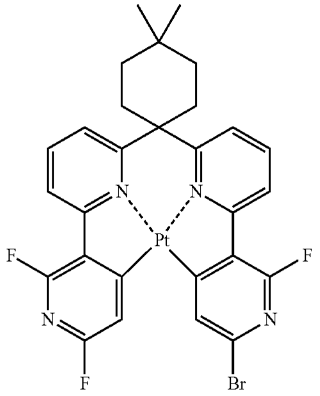
compound 4
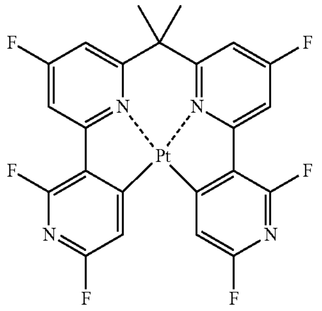
a4
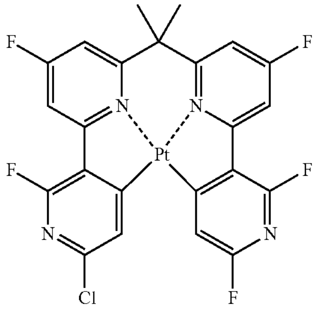
b4
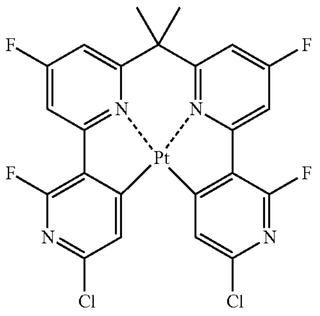

-continued
c4
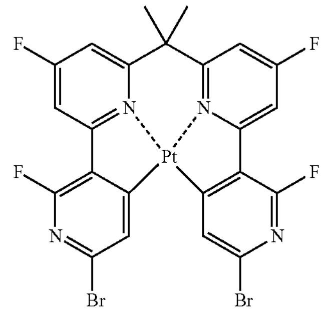
d4
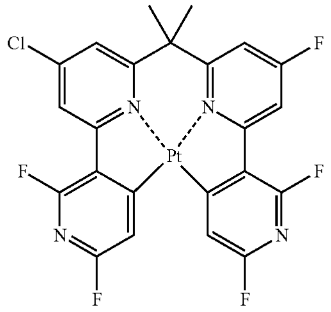
e4
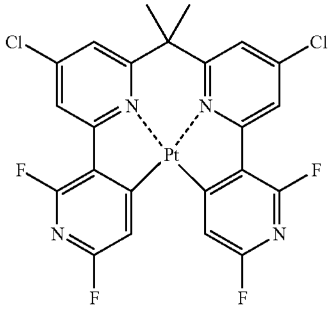
f4
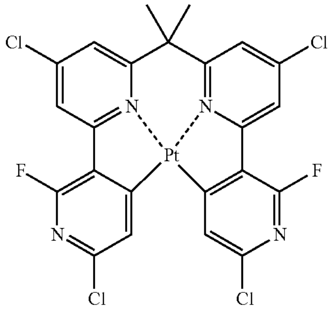
g4
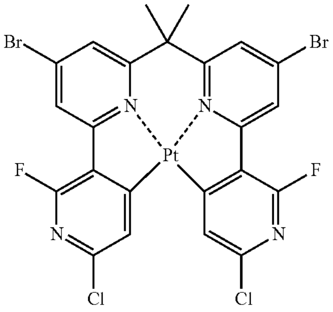
-continued
h4
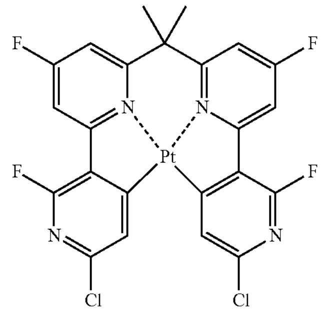
i4
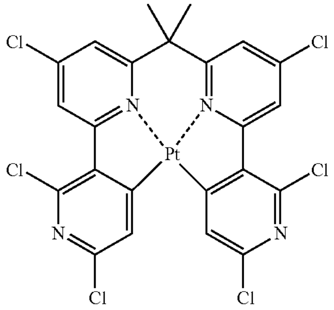
compound 5
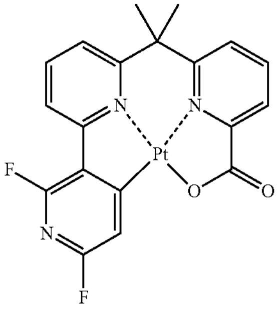
a5
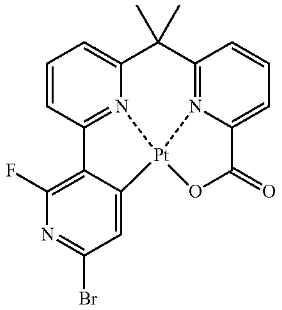
b5
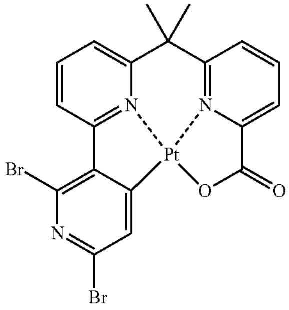

-continued
c5
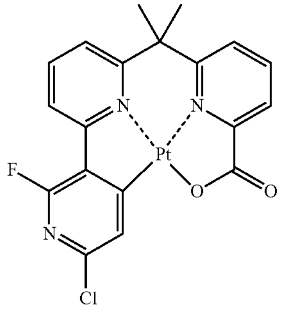
d5
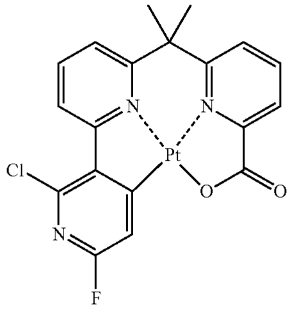
e5
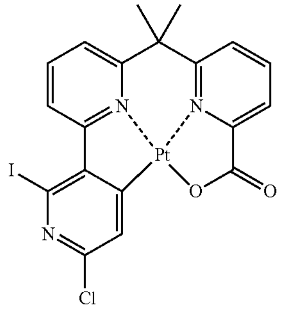
f5
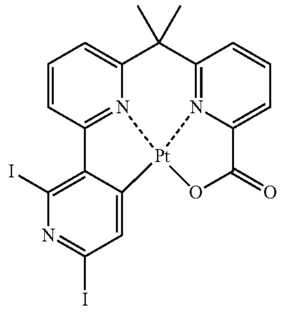
compound 6
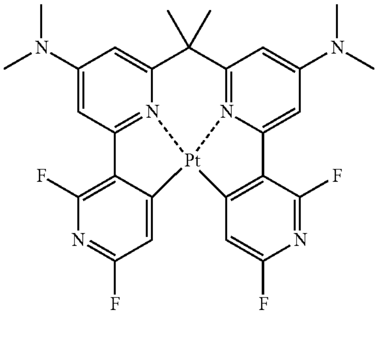
-continued
a6
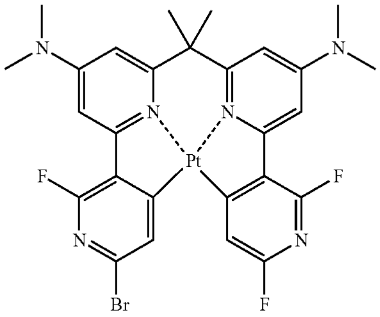
b6
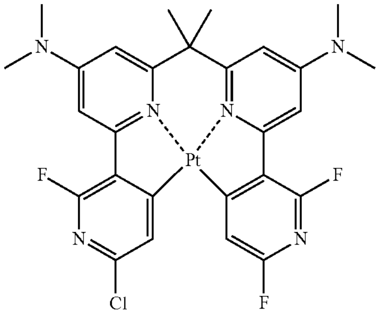
compound 7
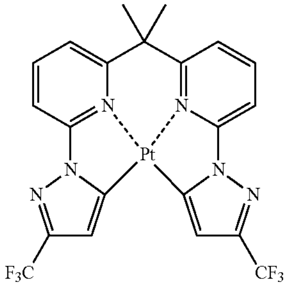
a7
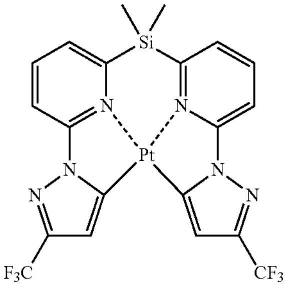
compound 8
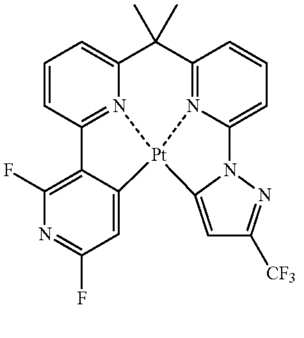

-continued
a8
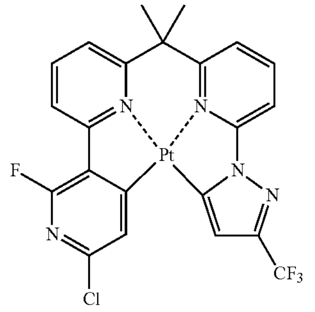
b8
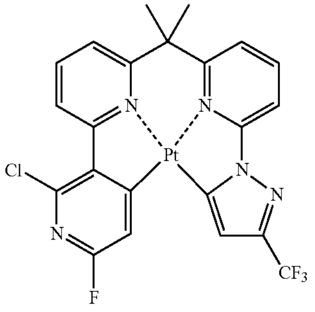
c8
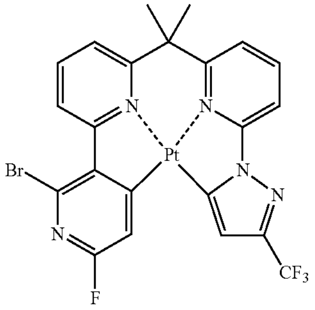
d8
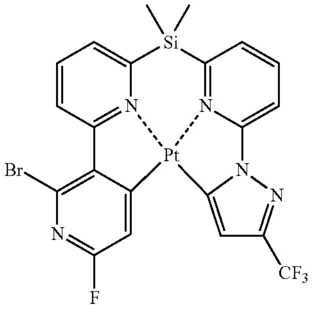
compound 9
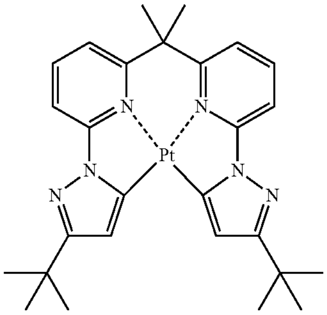
-continued
a9
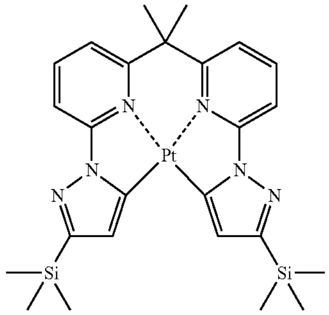
b9
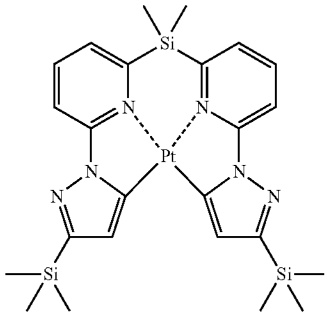
compound 10
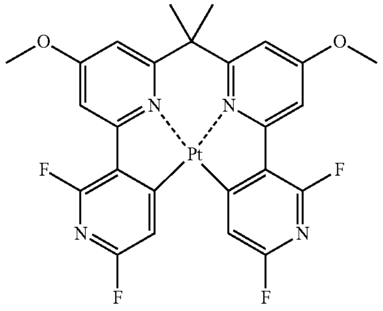
a10
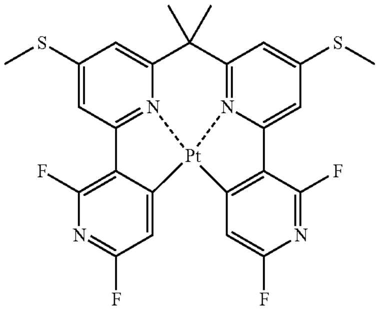
b10
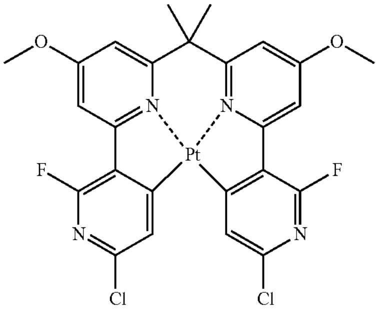

-continued
c10
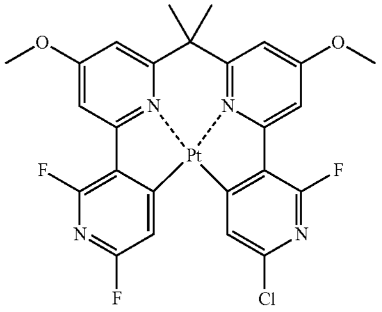
d10
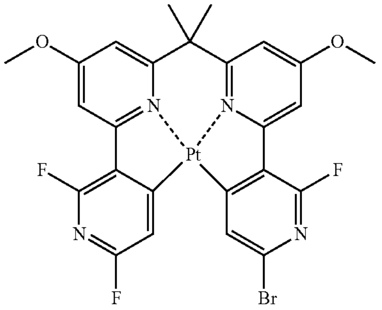
e10
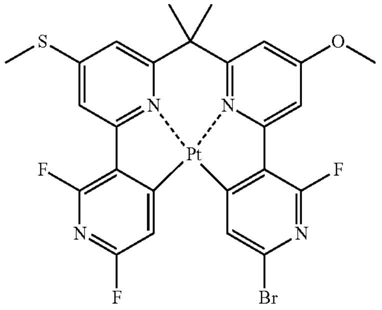
f10
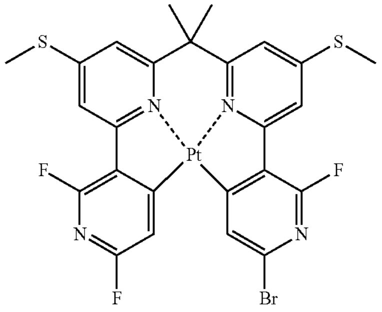
compound 11
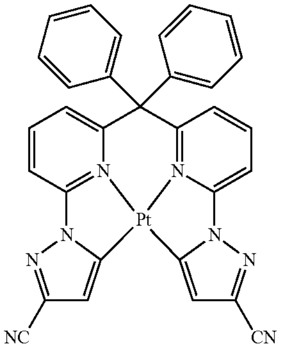
-continued
a11
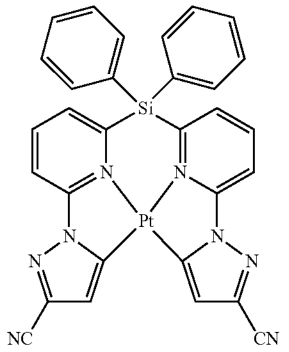
compound 12
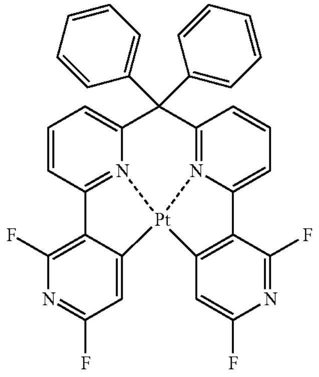
a12
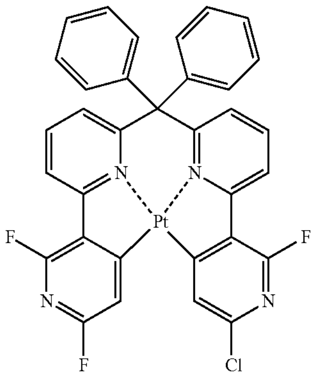
b12
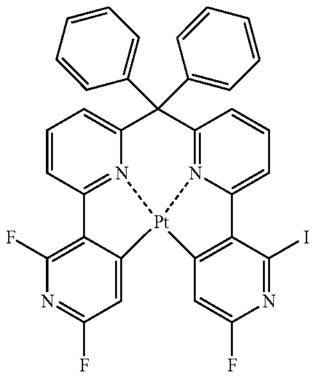

-continued
c12
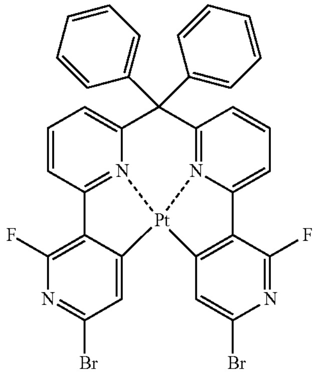
compound 13
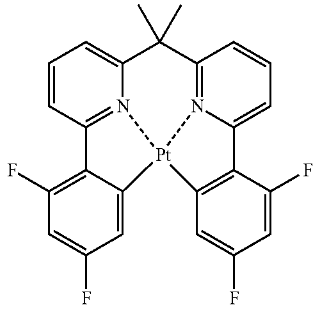
a13
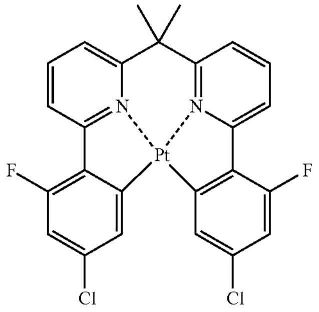
b13
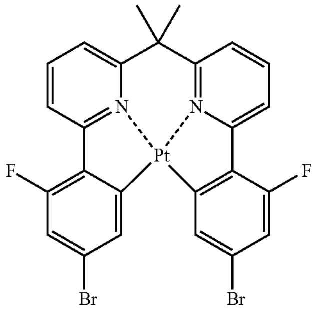
c13
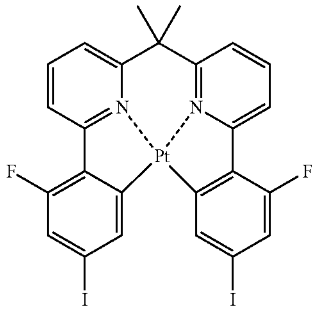
-continued
compound 14
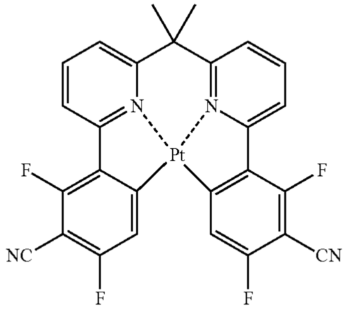
a14
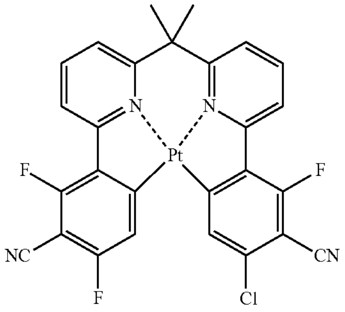
b14
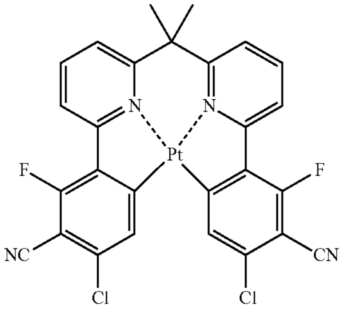
compound 15
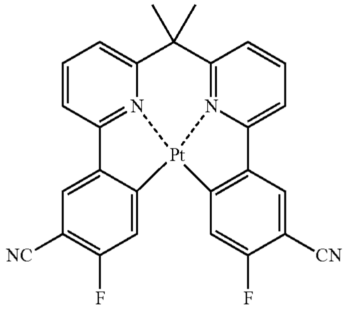
a15
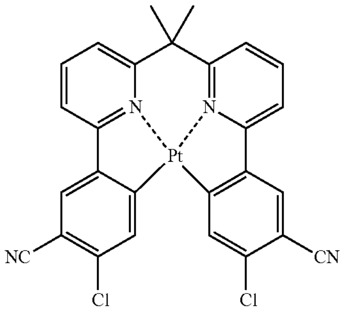

-continued
b15
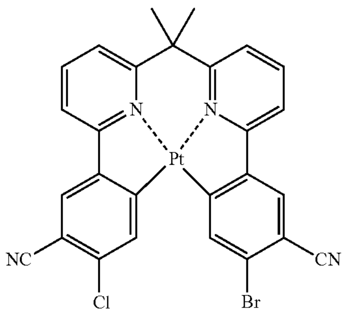
compound 16
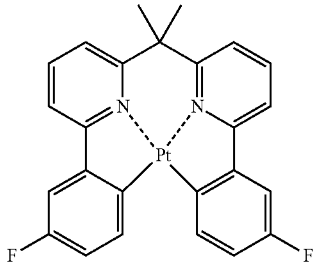
a16
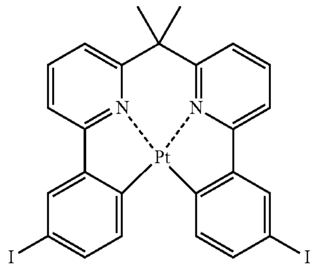
b16
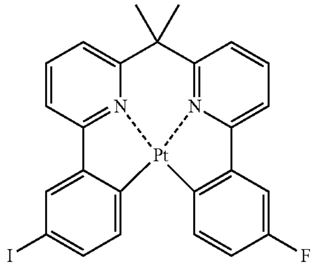
compound 17
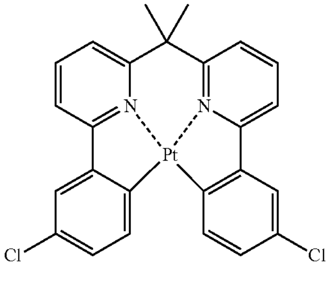
-continued
a17
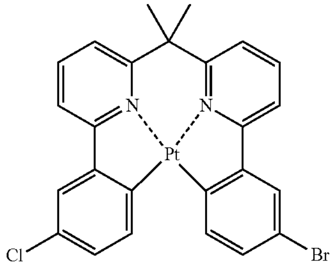
b17
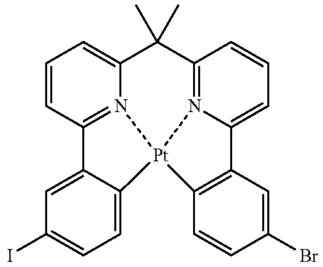
c17
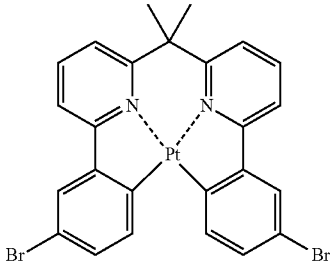
compound 18
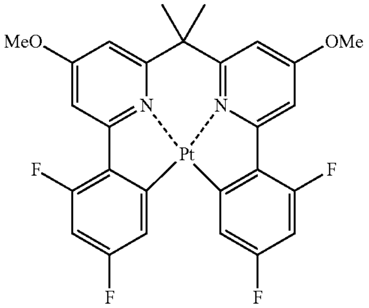
a18
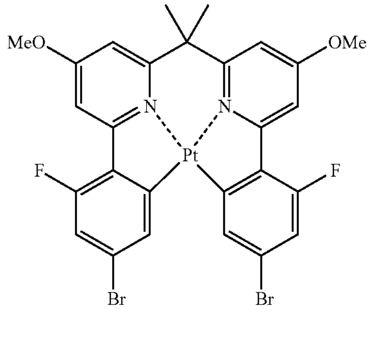

-continued
b18
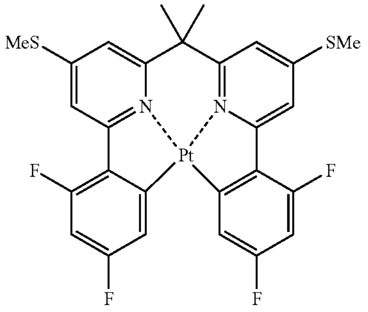
compound 19
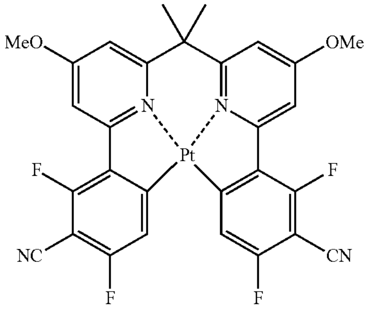
a19
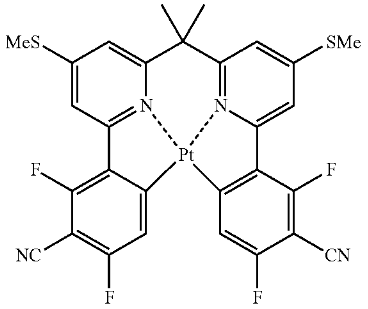
b19
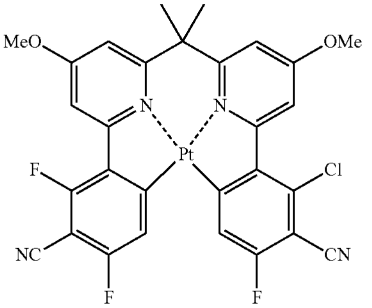
compound 20
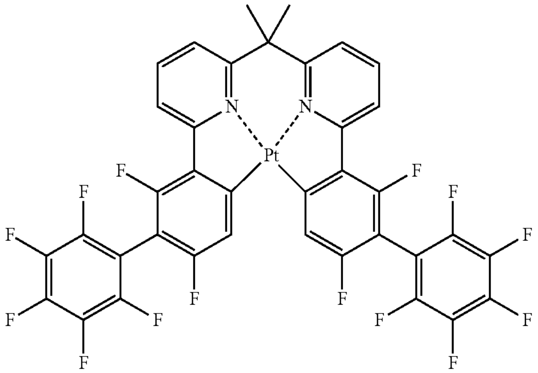
-continued
a20
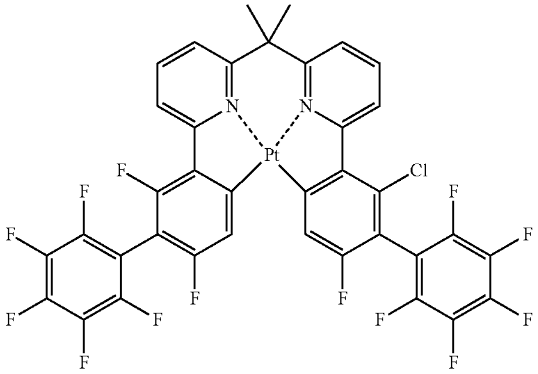
b20
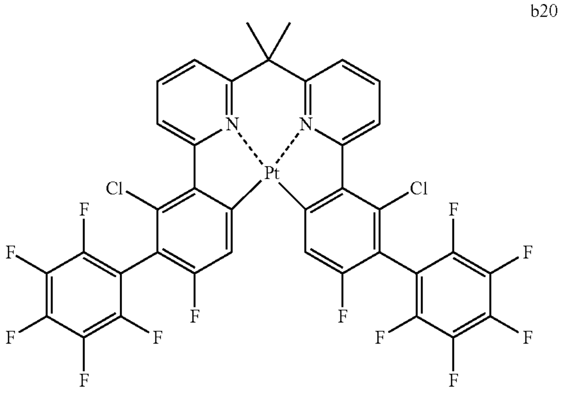
c20
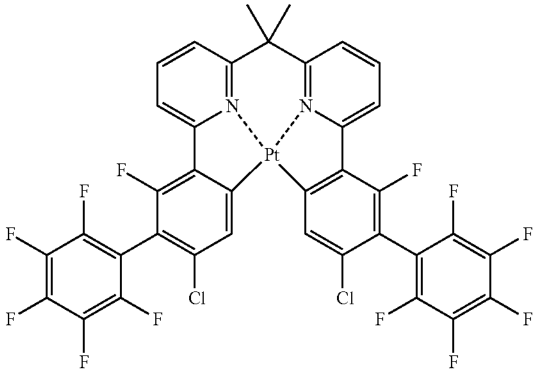
compound 21
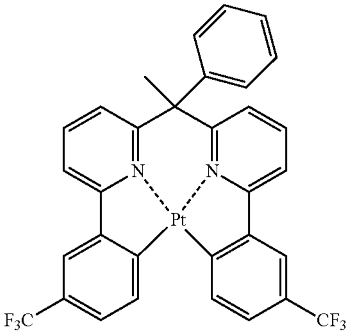

-continued
a21
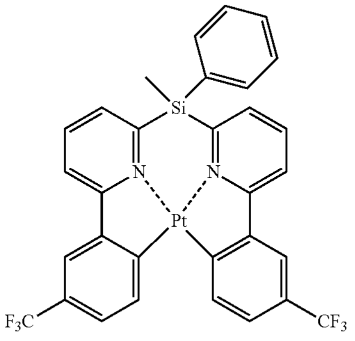
b21
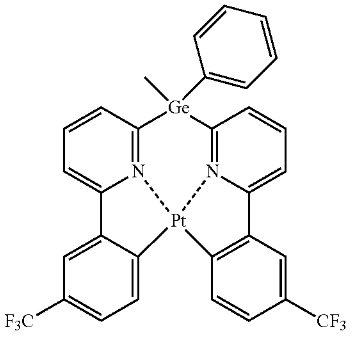
compound 22
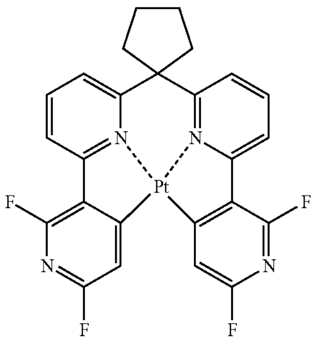
a22
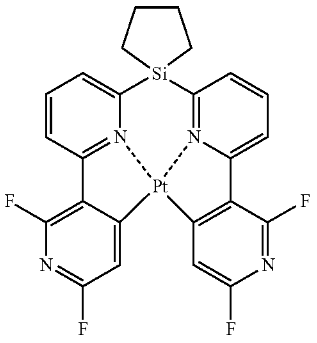
-continued
b22
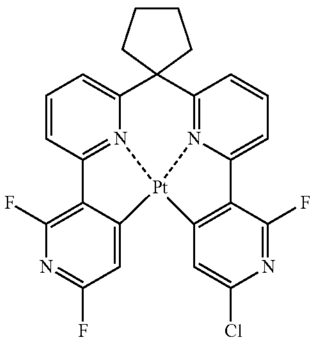
c22
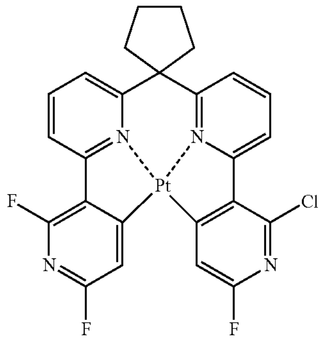
d22
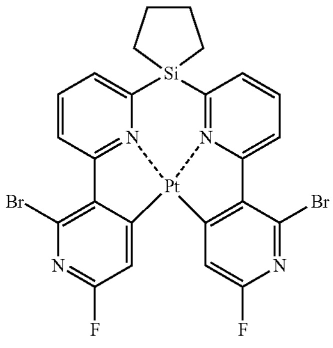
e22
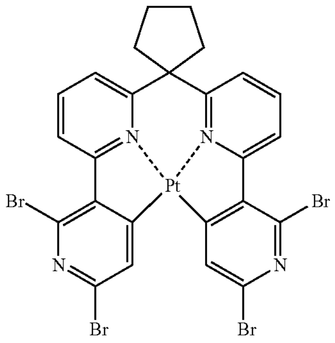

compound 23
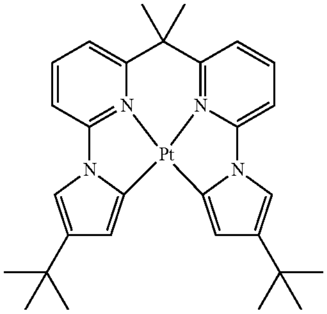
a23
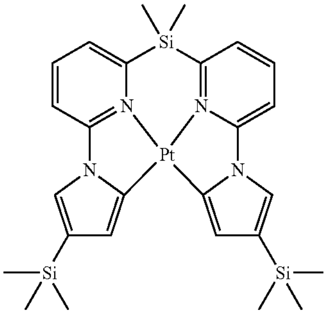
b23
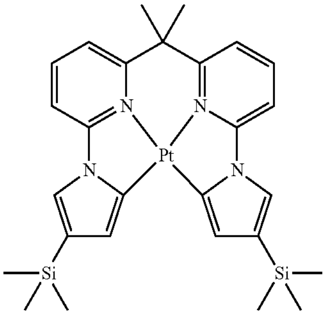
compound 24
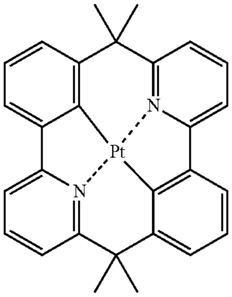
a24
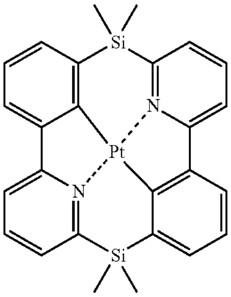
compound 25
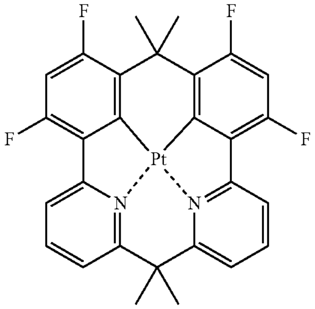
a25
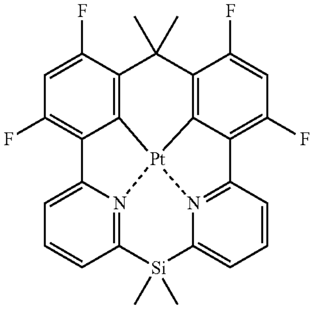
b25
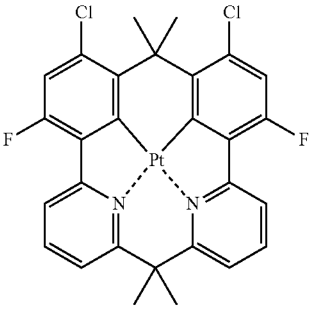
c25
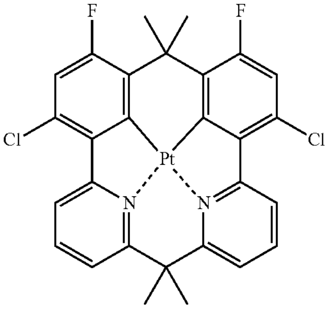
compound 26
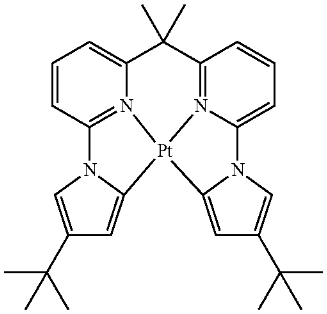

-continued
a26
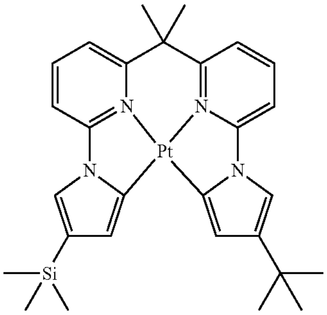
b26
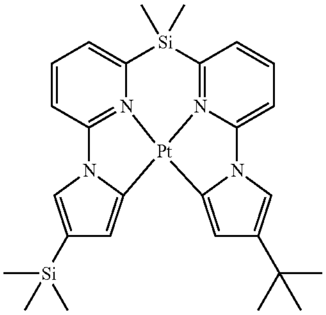
compound 27
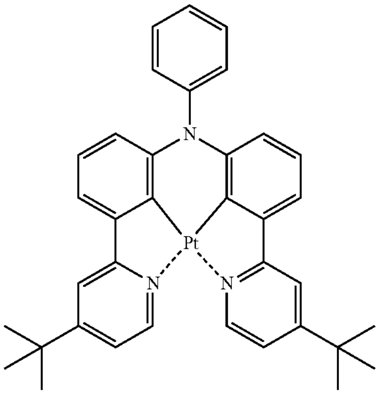
a27
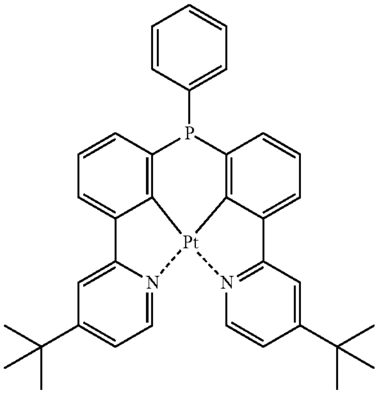
-continued
b27
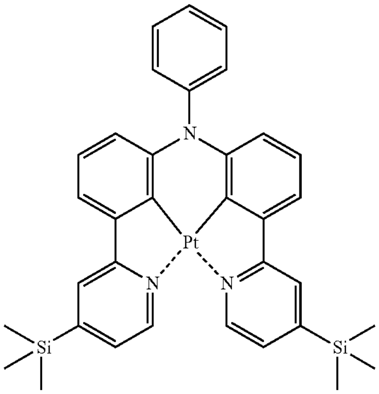
compound 28
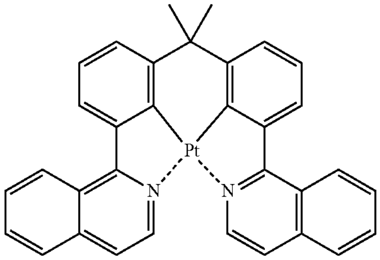
a28
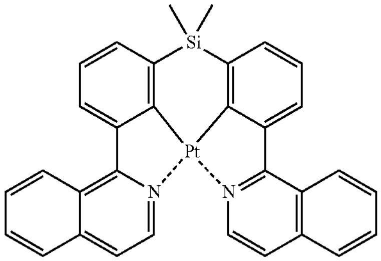
compound 29
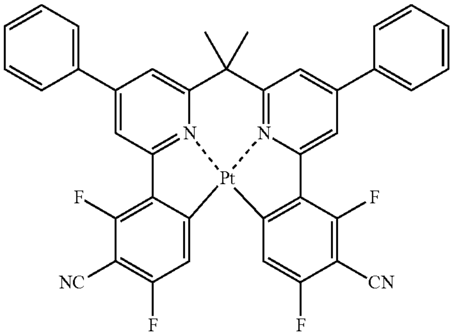
a29
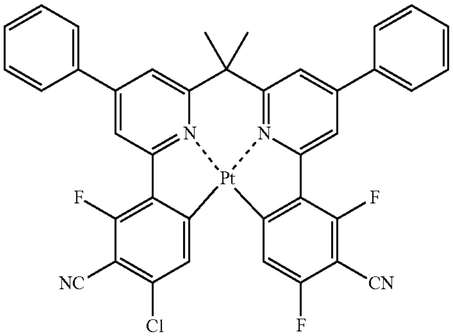

-continued
b29
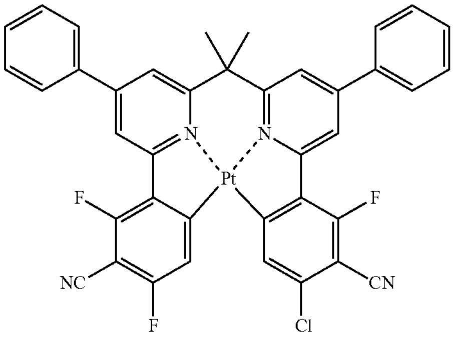
compound 30
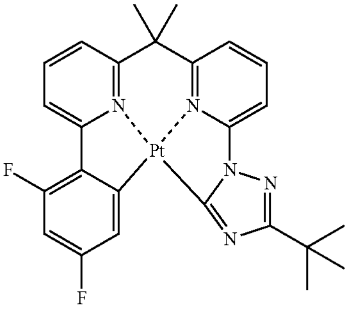
a30
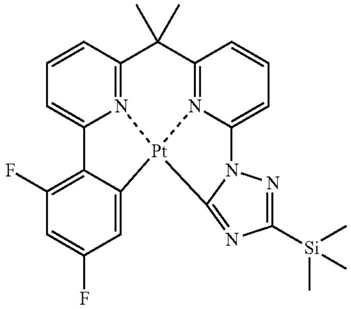
b30
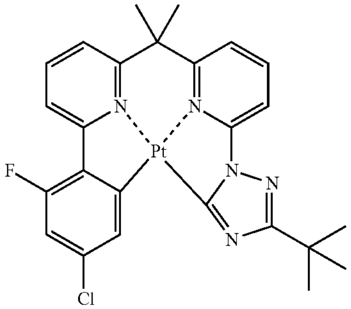
c30
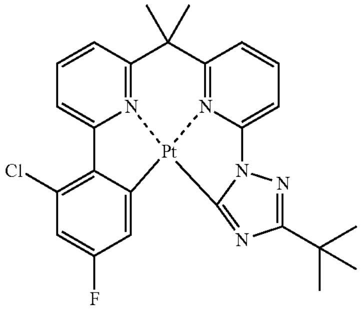
-continued
compound 31
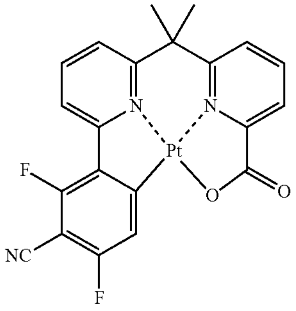
a31
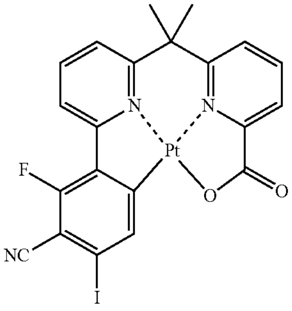
b31
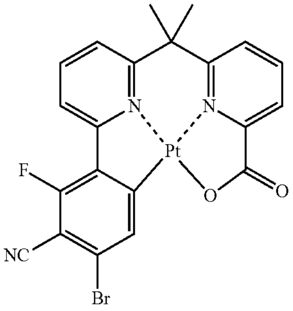
c31
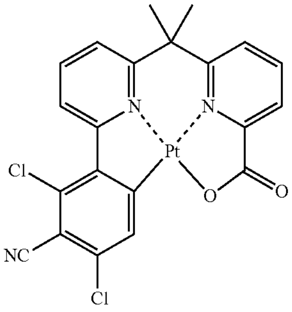
compound 32
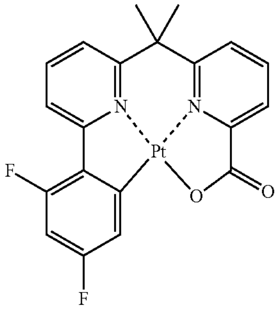

-continued
a32
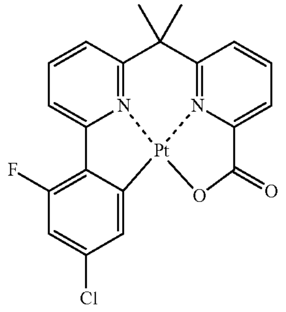
b32
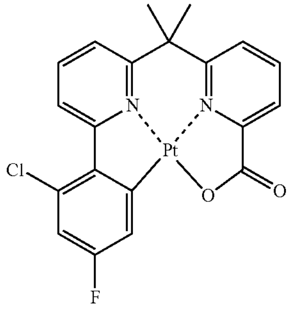
c32
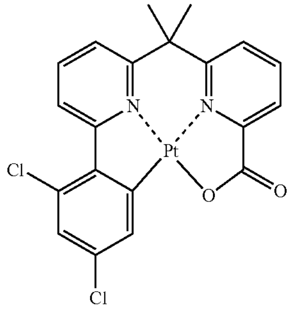
compound 33
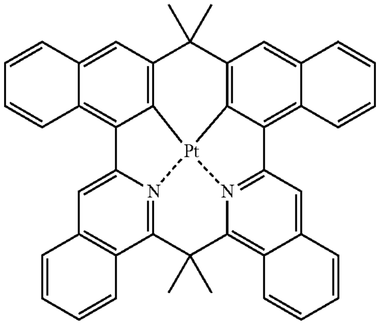
a33
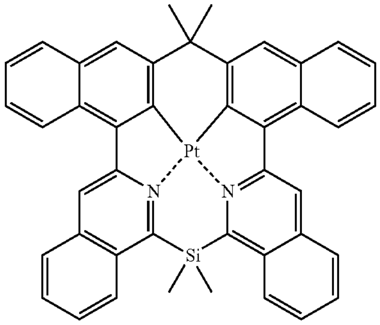
-continued
b33
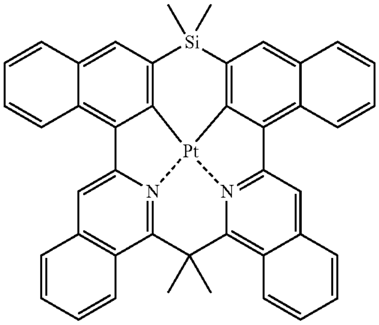
compound 34
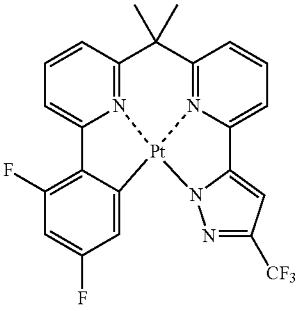
a34
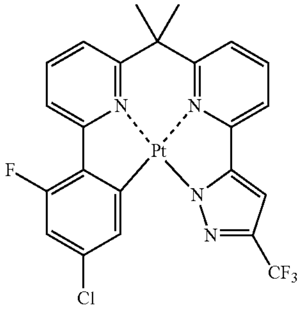
b34
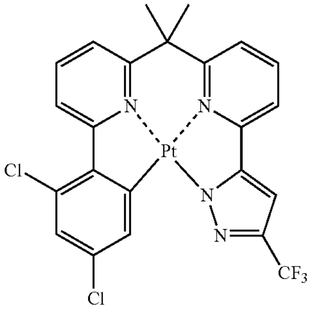
c34
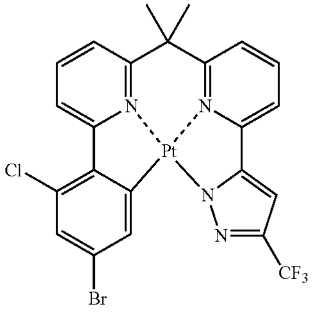

compound 35
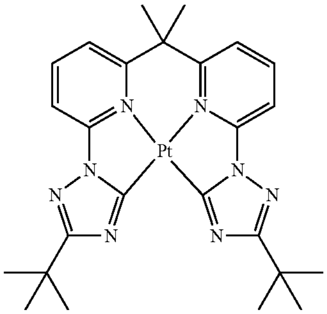
a35
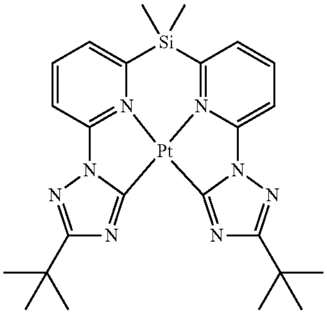
b35
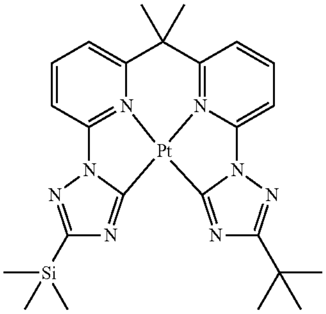
c35
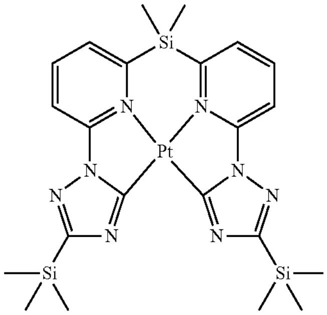
compound 36
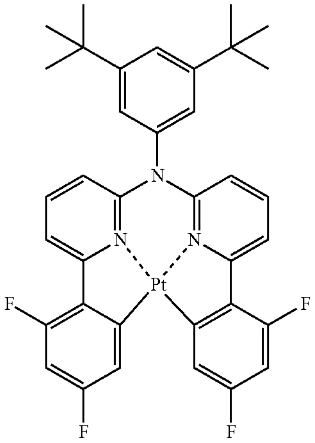
a36
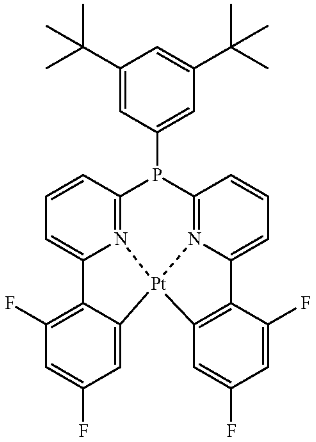
b36
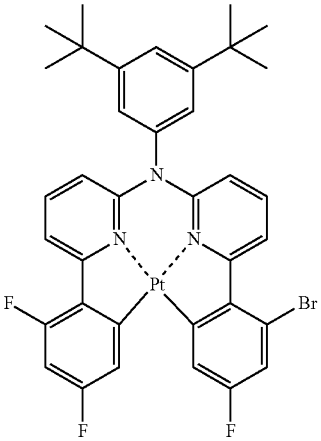

-continued
c36
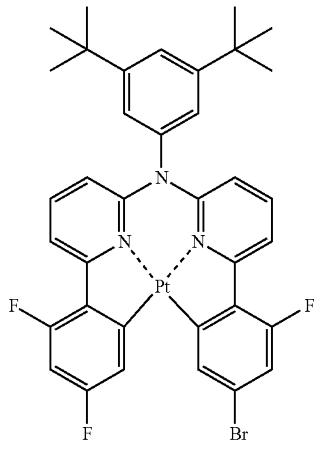
compound 37
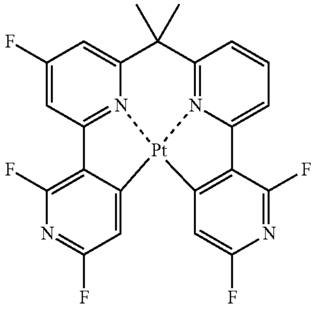
a37
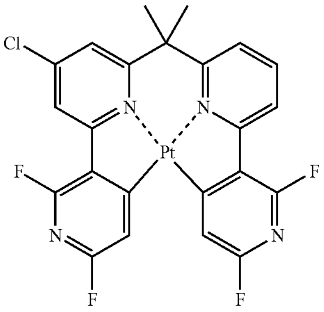
b37
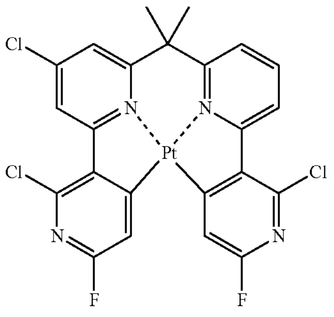
-continued
c37
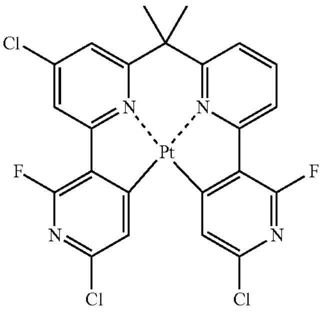
compound 38
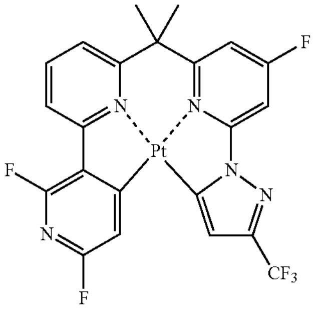
a38
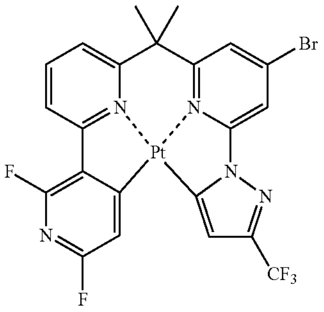
b38
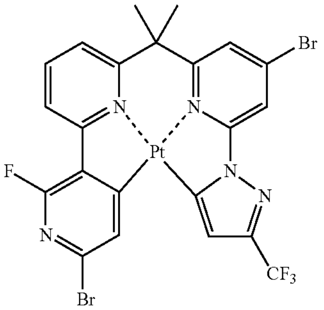
c38
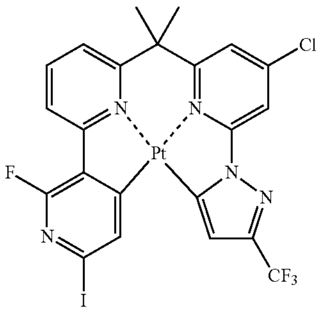

-continued
compound 39
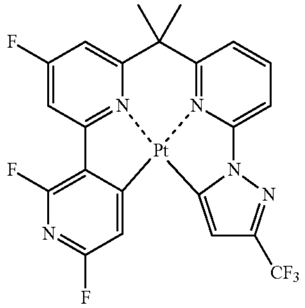
a39
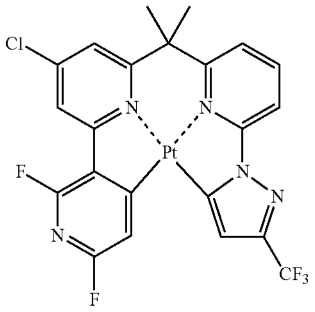
b39
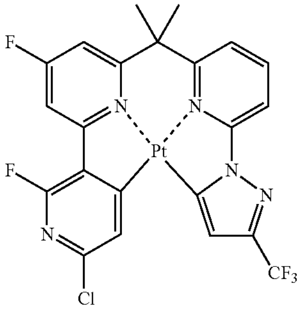
c39
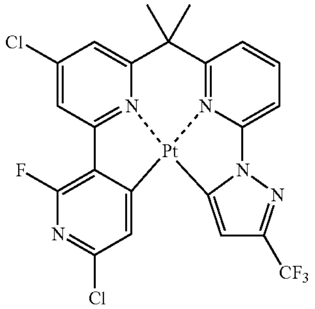
compound 40
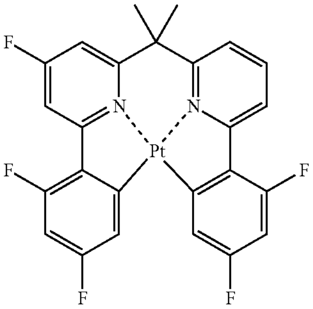
-continued
a40
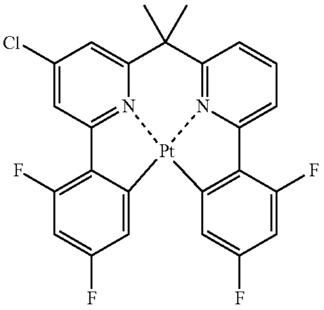
b40
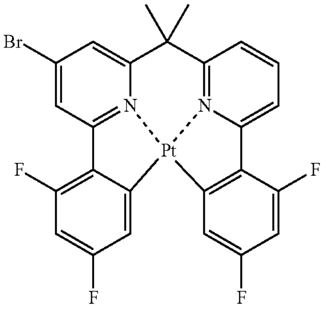
c40
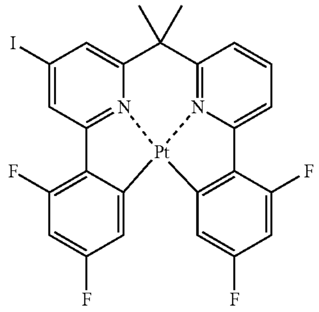
compound 41
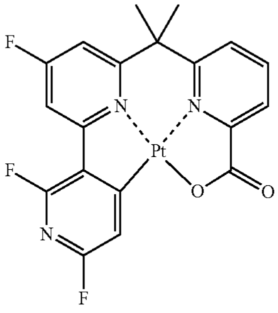
a41
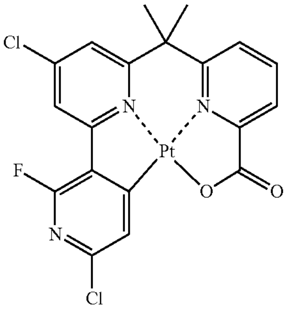

-continued
b41
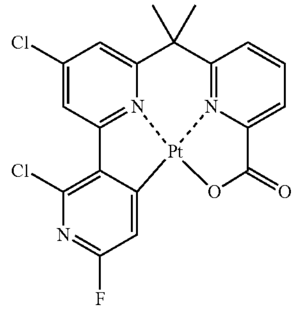
c41
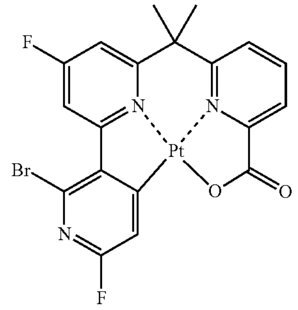
compound 42
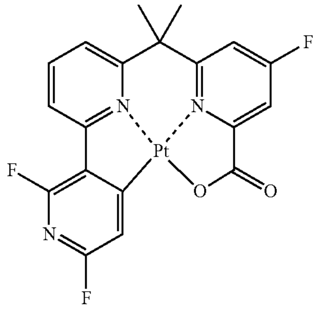
a42
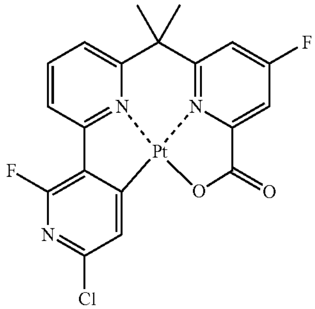
b42
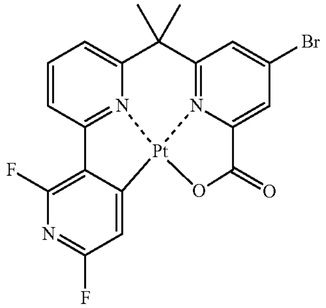
-continued
c42
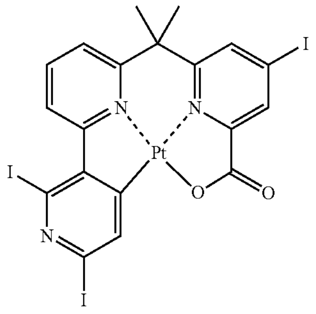
compound 43
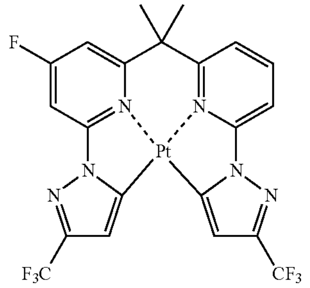
a43
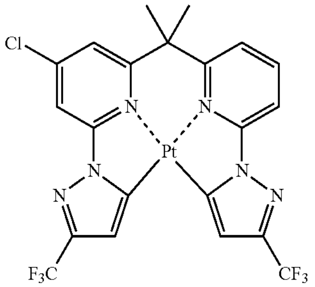
b43
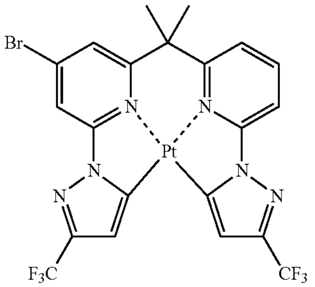
c43
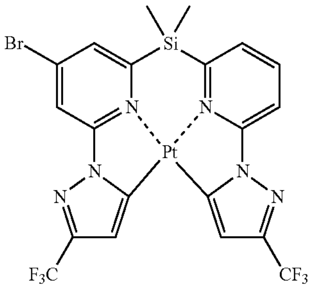

-continued
compound 44
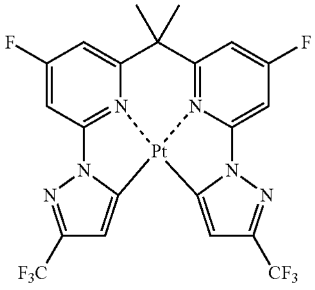
a44
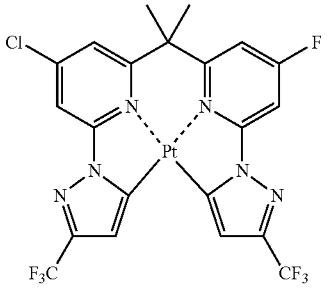
b44
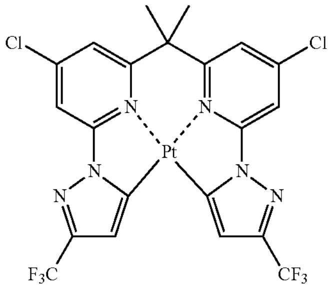
c44
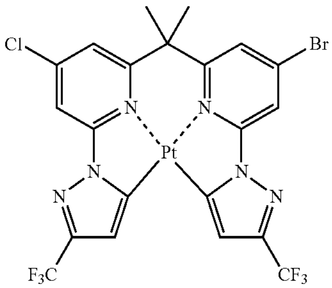
compound 45
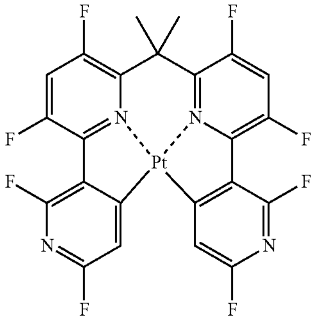
-continued
a45
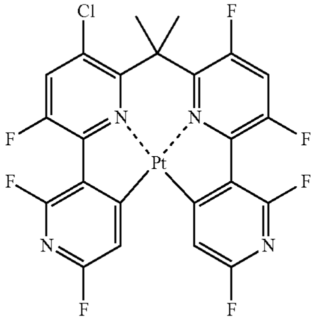
b45
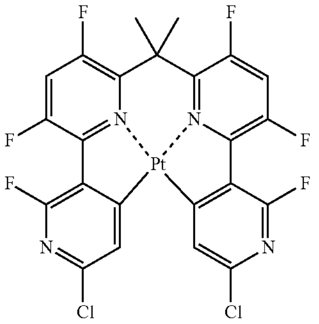
c45
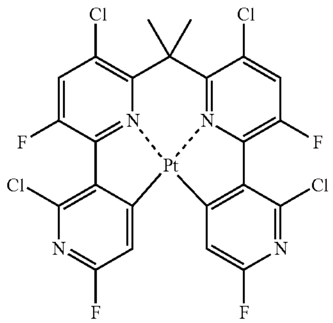
compound 70
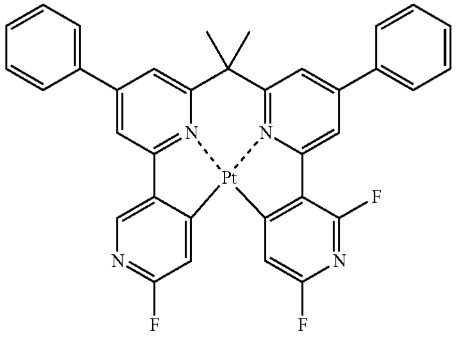

-continued
a70
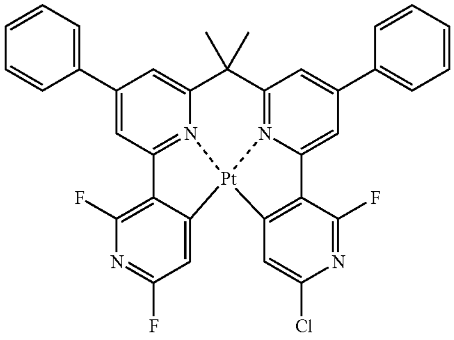
b70
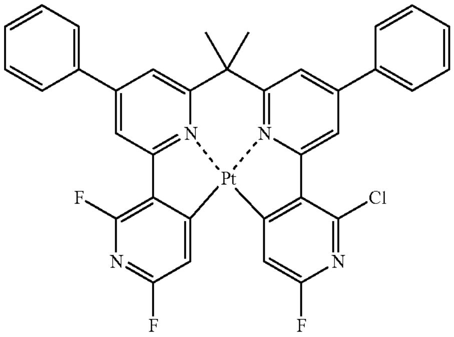
c70
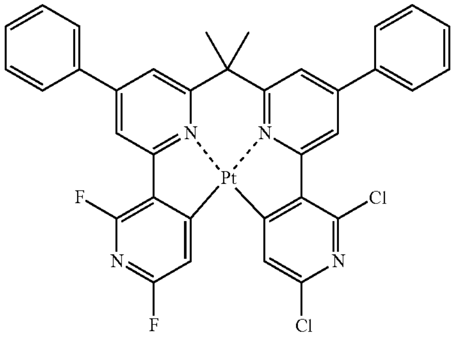
d70
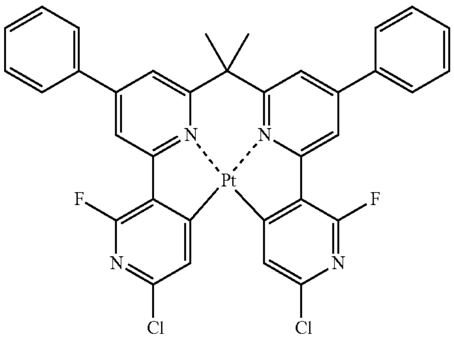
-continued
compound 71
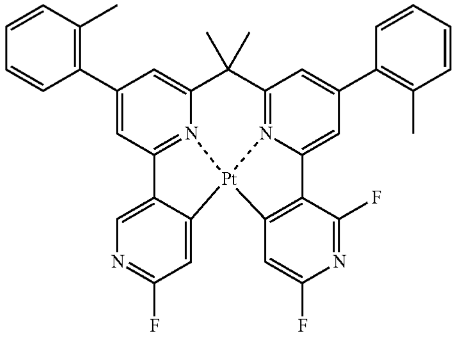
a71
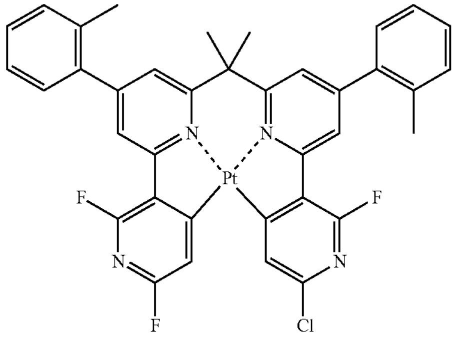
b71
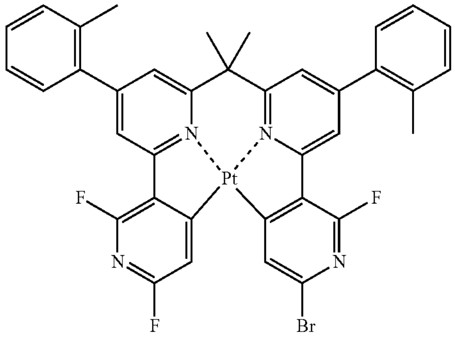
compound 72
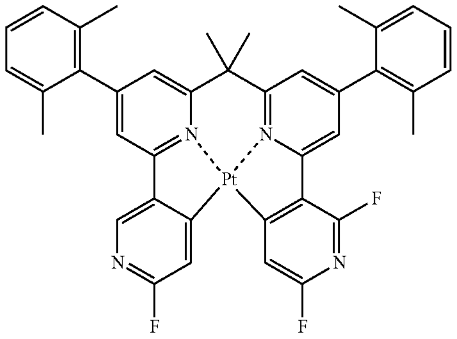

-continued
a72
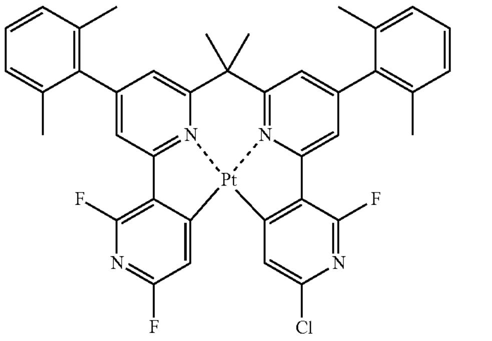
b72
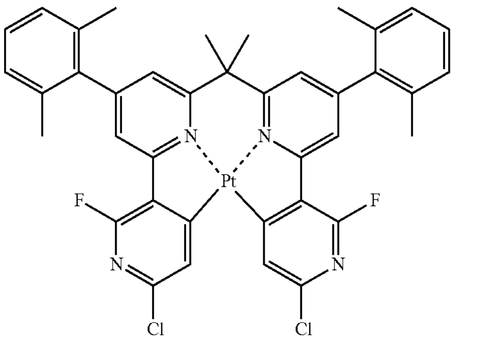
compound 73
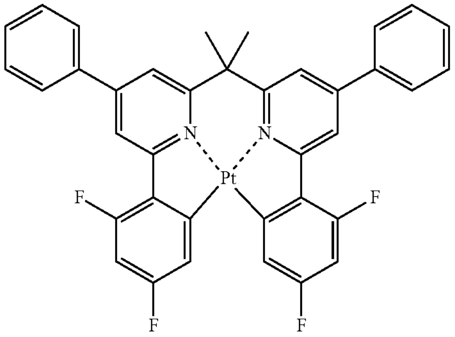
a73
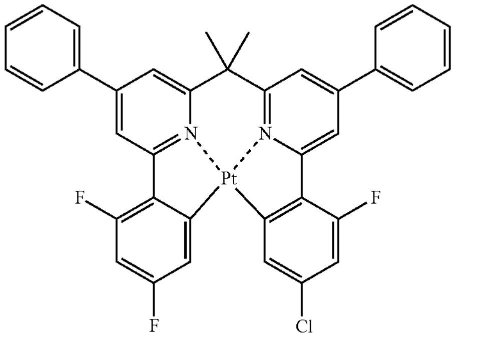
-continued
b73
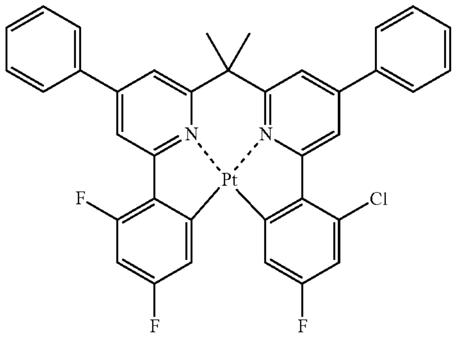
c73
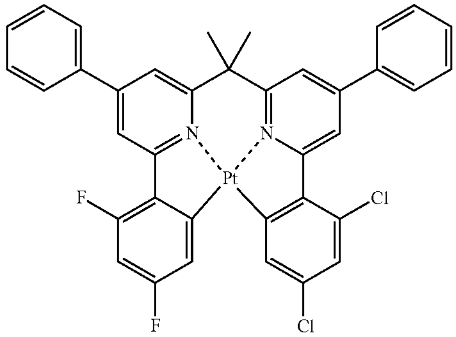
compound 74
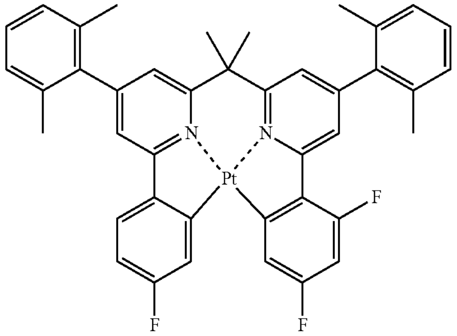
a74
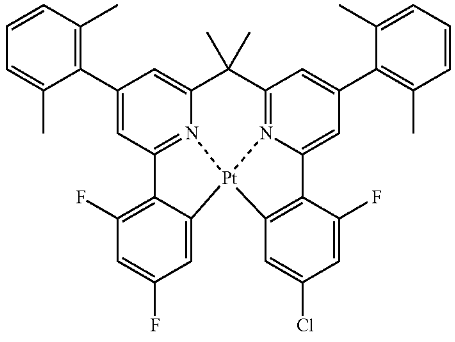

-continued
b74
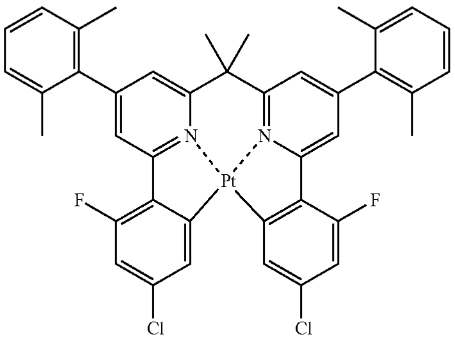
compound 75
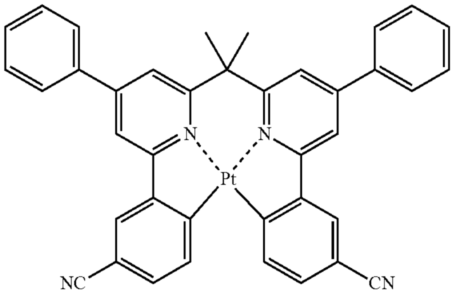
a75
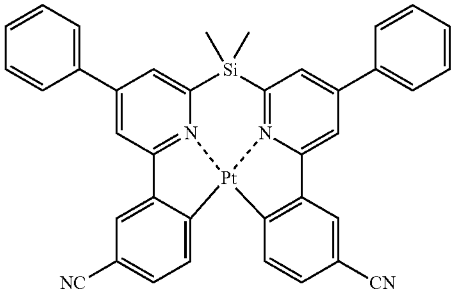
b75
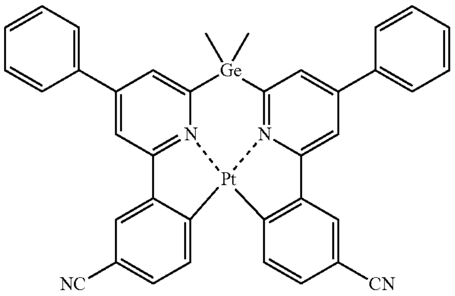
compound 76
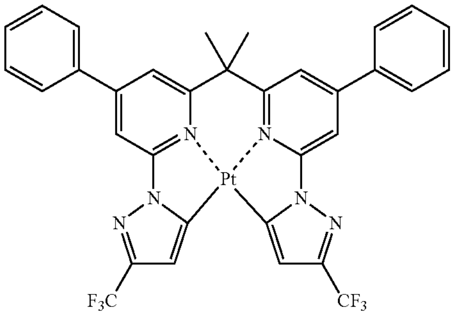
-continued
a76
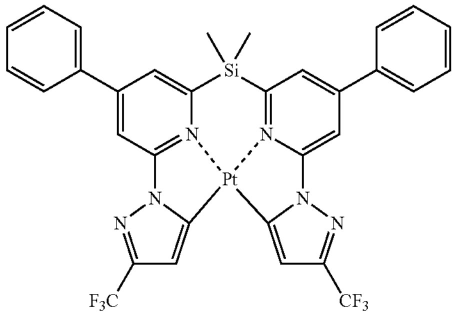
compound 77
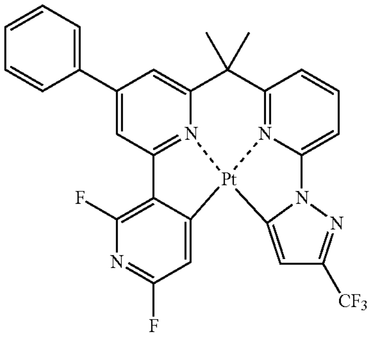
a77
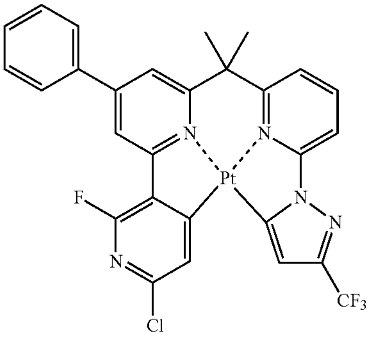
b77
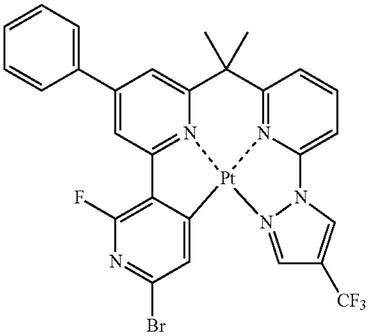

-continued
c77
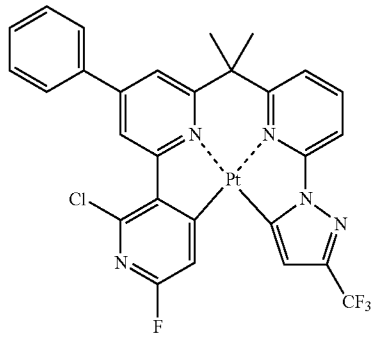
compound 78
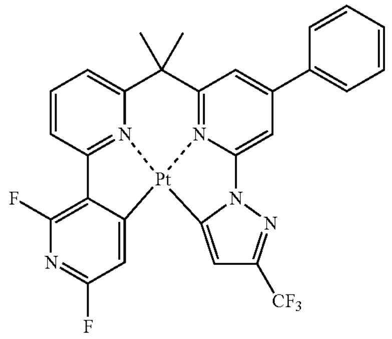
a78
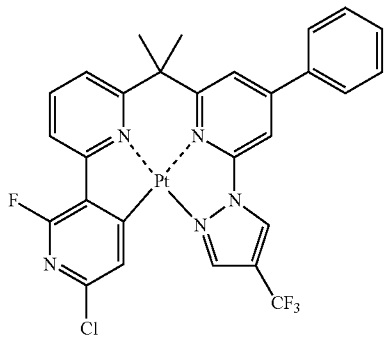
b78
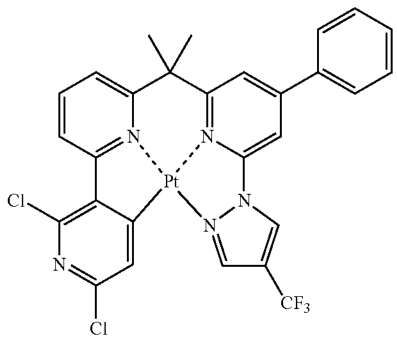
-continued
c78
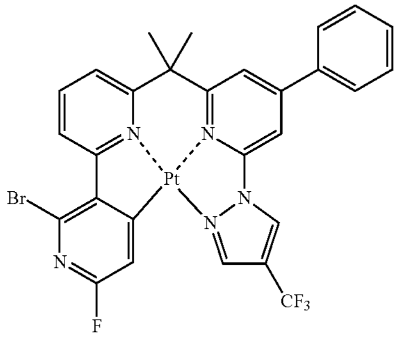
compound 79
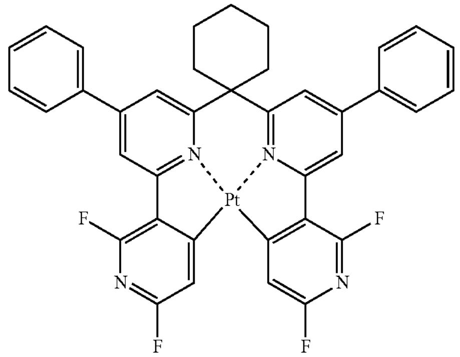
a79
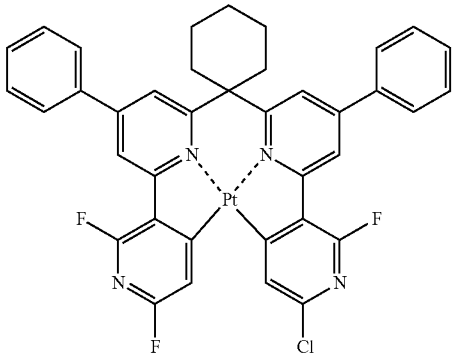
b79
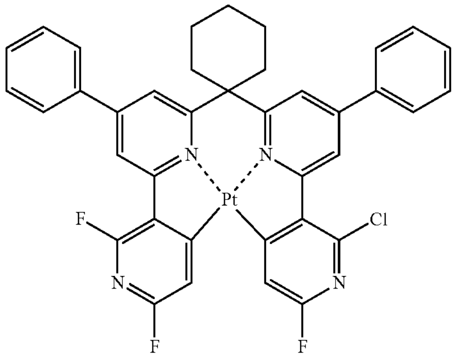

TABLE 1

| Specific Example No. | Metal Complex A Compound No. | Metal Complex B Compound No. | Metal Complex B Content (% by mass) |
|---|---|---|---|
| 1-1-1 | 1 | a1 | 0.05 |
| 1-1-2 | 1 | a1 | 0.06 |
| 1-1-3 | 1 | a1 | 0.07 |
| 1-1-4 | 1 | a1 | 0.08 |
| 1-1-5 | 1 | a1 | 0.09 |
| 1-1-6 | 1 | a1 | 0.1 |
| 1-1-7 | 1 | a1 | 0.2 |
| 1-1-8 | 1 | a1 | 0.3 |
| 1-1-9 | 1 | a1 | 0.4 |
| 1-1-10 | 1 | a1 | 0.5 |
| 1-1-11 | 1 | a1 | 0.6 |
| 1-1-12 | 1 | a1 | 0.7 |
| 1-1-13 | 1 | a1 | 0.8 |
| 1-1-14 | 1 | a1 | 0.9 |
| 1-1-15 | 1 | a1 | 1 |
| 1-1-16 | 1 | a1 | 1.1 |
| 1-1-17 | 1 | a1 | 1.2 |
| 1-1-18 | 1 | a1 | 1.3 |
| 1-1-19 | 1 | a1 | 1.4 |
| 1-1-20 | 1 | a1 | 1.5 |
| 1-1-21 | 1 | a1 | 1.6 |
| 1-1-22 | 1 | a1 | 1.7 |
| 1-1-23 | 1 | a1 | 1.8 |
| 1-1-24 | 1 | a1 | 1.9 |
| 1-1-25 | 1 | a1 | 2 |
| 1-2-1 | 1 | b1 | 0.05 |
| 1-2-2 | 1 | b1 | 0.06 |
| 1-2-3 | 1 | b1 | 0.07 |
| 1-2-4 | 1 | b1 | 0.08 |
| 1-2-5 | 1 | b1 | 0.09 |
| 1-2-6 | 1 | b1 | 0.1 |
| 1-2-7 | 1 | b1 | 0.2 |
| 1-2-8 | 1 | b1 | 0.3 |
| 1-2-9 | 1 | b1 | 0.4 |
| 1-2-10 | 1 | b1 | 0.5 |
| 1-2-11 | 1 | b1 | 0.6 |
| 1-2-12 | 1 | b1 | 0.7 |
| 1-2-13 | 1 | b1 | 0.8 |
| 1-2-14 | 1 | b1 | 0.9 |
| 1-2-15 | 1 | b1 | 1 |
| 1-2-16 | 1 | b1 | 1.1 |
| 1-2-17 | 1 | b1 | 1.2 |
| 1-2-18 | 1 | b1 | 1.3 |
| 1-2-19 | 1 | b1 | 1.4 |
| 1-2-20 | 1 | b1 | 1.5 |
| 1-2-21 | 1 | b1 | 1.6 |
| 1-2-22 | 1 | b1 | 1.7 |
| 1-2-23 | 1 | b1 | 1.8 |
| 1-2-24 | 1 | b1 | 1.9 |
| 1-2-25 | 1 | b1 | 2 |

TABLE 2

| Specific Example No. | Metal Complex A Compound No. | Metal Complex B Compound No. | Metal Complex B Content (% by mass) |
|---|---|---|---|
| 1-3-1 | 1 | c1 | 0.05 |
| 1-3-2 | 1 | c1 | 0.08 |
| 1-3-3 | 1 | c1 | 0.1 |
| 1-3-4 | 1 | c1 | 0.2 |
| 1-3-5 | 1 | c1 | 0.5 |
| 1-3-6 | 1 | c1 | 0.6 |
| 1-3-7 | 1 | c1 | 0.8 |
| 1-3-8 | 1 | c1 | 1 |
| 1-3-9 | 1 | c1 | 1.5 |
| 1-3-10 | 1 | c1 | 1.8 |
| 1-3-11 | 1 | c1 | 2 |
| 1-4-1 | 1 | d1 | 0.05 |
| 1-4-2 | 1 | d1 | 0.055 |
| 1-4-3 | 1 | d1 | 0.1 |

TABLE 2-continued

| Specific Example No. | Metal Complex A Compound No. | Metal Complex B Compound No. | Metal Complex B Content (% by mass) |
|---|---|---|---|
| 1-4-4 | 1 | d1 | 0.15 |
| 1-4-5 | 1 | d1 | 0.35 |
| 1-4-6 | 1 | d1 | 0.6 |
| 1-4-7 | 1 | d1 | 0.8 |
| 1-4-8 | 1 | d1 | 1 |
| 1-4-9 | 1 | d1 | 1.5 |
| 1-4-10 | 1 | d1 | 1.8 |
| 1-4-11 | 1 | d1 | 2 |
| 1-5-1 | 1 | e1 | 0.05 |
| 1-5-2 | 1 | e1 | 0.075 |
| 1-5-3 | 1 | e1 | 0.1 |
| 1-5-4 | 1 | e1 | 0.125 |
| 1-5-5 | 1 | e1 | 0.25 |
| 1-5-6 | 1 | e1 | 0.345 |
| 1-5-7 | 1 | e1 | 0.5 |
| 1-5-8 | 1 | e1 | 0.75 |
| 1-5-9 | 1 | e1 | 0.95 |
| 1-5-10 | 1 | e1 | 1.125 |
| 1-5-11 | 1 | e1 | 1.5 |
| 1-5-12 | 1 | e1 | 1.55 |
| 1-5-13 | 1 | e1 | 1.75 |
| 1-5-14 | 1 | e1 | 2 |
| 1-6-1 | 1 | f1 | 0.05 |
| 1-6-2 | 1 | f1 | 0.1 |
| 1-6-3 | 1 | f1 | 0.2 |
| 1-6-4 | 1 | f1 | 0.3 |
| 1-6-5 | 1 | f1 | 0.4 |
| 1-6-6 | 1 | f1 | 0.5 |
| 1-6-7 | 1 | f1 | 1 |
| 1-6-8 | 1 | f1 | 1.1 |
| 1-6-9 | 1 | f1 | 1.5 |
| 1-6-10 | 1 | f1 | 1.6 |
| 1-6-11 | 1 | f1 | 1.7 |
| 1-6-12 | 1 | f1 | 1.8 |
| 1-6-13 | 1 | f1 | 1.9 |
| 1-6-14 | 1 | f1 | 2 |

TABLE 3

| Specific Example No. | Metal Complex A Compound No. | Metal Complex B Compound No. | Metal Complex B Content (% by mass) |
|---|---|---|---|
| 1-7-1 | 1 | g1 | 0.1 |
| 1-7-2 | 1 | g1 | 0.3 |
| 1-7-3 | 1 | g1 | 0.9 |
| 1-7-4 | 1 | g1 | 1.4 |
| 1-7-5 | 1 | g1 | 1.95 |
| 1-8-1 | 1 | h1 | 0.055 |
| 1-8-2 | 1 | h1 | 0.06 |
| 1-8-3 | 1 | h1 | 0.065 |
| 1-8-4 | 1 | h1 | 0.15 |
| 1-8-5 | 1 | h1 | 0.205 |
| 1-9-1 | 1 | i1 | 0.06 |
| 1-9-2 | 1 | i1 | 0.2 |
| 1-9-3 | 1 | i1 | 0.5 |
| 1-9-4 | 1 | i1 | 0.8 |
| 1-9-5 | 1 | i1 | 1.75 |
| 1-10-1 | 1 | j1 | 0.07 |
| 1-10-2 | 1 | j1 | 0.09 |
| 1-10-3 | 1 | j1 | 0.1 |
| 1-10-4 | 1 | j1 | 0.5 |
| 1-10-5 | 1 | j1 | 0.9 |
| 1-11-1 | 1 | k1 | 0.09 |
| 1-11-2 | 1 | k1 | 1.1 |
| 1-11-3 | 1 | k1 | 1.4 |
| 1-11-4 | 1 | k1 | 1.6 |
| 1-11-5 | 1 | k1 | 1.99 |
| 1-12-1 | 1 | l1 | 0.05 |
| 1-12-2 | 1 | l1 | 0.06 |
| 1-12-3 | 1 | l1 | 0.5 |

TABLE 3-continued

| Specific Example No. | Metal Complex A Compound No. | Metal Complex B Compound No. | Metal Complex B Content (% by mass) |
|---|---|---|---|
| 1-12-4 | 1 | l1 | 0.55 |
| 1-12-5 | 1 | l1 | 1.55 |
| 1-13-1 | 1 | m1 | 0.1 |
| 1-13-2 | 1 | m1 | 0.35 |
| 1-13-3 | 1 | m1 | 0.4 |
| 1-13-4 | 1 | m1 | 0.6 |
| 1-13-5 | 1 | m1 | 0.8 |
| 1-14-1 | 1 | n1 | 1 |
| 1-14-2 | 1 | n1 | 1.2 |
| 1-14-3 | 1 | n1 | 1.4 |
| 1-14-4 | 1 | n1 | 1.6 |
| 1-14-5 | 1 | n1 | 1.8 |
| 1-15-1 | 1 | o1 | 0.05 |
| 1-15-2 | 1 | o1 | 1 |
| 1-15-3 | 1 | o1 | 1.1 |
| 1-15-4 | 1 | o1 | 1.2 |
| 1-15-5 | 1 | o1 | 1.6 |
| 1-16-1 | 1 | p1 | 0.2 |
| 1-16-2 | 1 | p1 | 0.6 |
| 1-16-3 | 1 | p1 | 0.7 |
| 1-16-4 | 1 | p1 | 0.95 |
| 1-16-5 | 1 | p1 | 1.3 |

TABLE 4

| Specific Example No. | Metal Complex A Compound No. | Metal Complex B Compound No. | Metal Complex B Content (% by mass) |
|---|---|---|---|
| 1-17-1 | 1 | q1 | 0.08 |
| 1-17-2 | 1 | q1 | 0.2 |
| 1-17-3 | 1 | q1 | 0.25 |
| 1-17-4 | 1 | q1 | 0.7 |
| 1-17-5 | 1 | q1 | 1.25 |
| 1-18-1 | 1 | r1 | 0.1 |
| 1-18-2 | 1 | r1 | 0.3 |
| 1-18-3 | 1 | r1 | 0.9 |
| 1-18-4 | 1 | r1 | 1.4 |
| 1-18-5 | 1 | r1 | 1.95 |
| 2-1-1 | 2 | a2 | 0.05 |
| 2-1-2 | 2 | a2 | 0.06 |
| 2-1-3 | 2 | a2 | 0.07 |
| 2-1-4 | 2 | a2 | 0.08 |
| 2-1-5 | 2 | a2 | 0.09 |
| 2-1-6 | 2 | a2 | 0.1 |
| 2-1-7 | 2 | a2 | 0.2 |
| 2-1-8 | 2 | a2 | 0.3 |
| 2-1-9 | 2 | a2 | 0.4 |
| 2-1-10 | 2 | a2 | 0.5 |
| 2-1-11 | 2 | a2 | 0.6 |
| 2-1-12 | 2 | a2 | 0.7 |
| 2-1-13 | 2 | a2 | 0.8 |
| 2-1-14 | 2 | a2 | 0.9 |
| 2-1-15 | 2 | a2 | 1 |
| 2-1-16 | 2 | a2 | 1.1 |
| 2-1-17 | 2 | a2 | 1.2 |
| 2-1-18 | 2 | a2 | 1.3 |
| 2-1-19 | 2 | a2 | 1.4 |
| 2-1-20 | 2 | a2 | 1.5 |
| 2-1-21 | 2 | a2 | 1.6 |
| 2-1-22 | 2 | a2 | 1.7 |
| 2-1-23 | 2 | a2 | 1.8 |
| 2-1-24 | 2 | a2 | 1.9 |
| 2-1-25 | 2 | a2 | 2 |
| 2-2-1 | 2 | b2 | 0.05 |
| 2-2-2 | 2 | b2 | 0.06 |
| 2-2-3 | 2 | b2 | 0.08 |
| 2-2-4 | 2 | b2 | 0.1 |
| 2-2-5 | 2 | b2 | 0.2 |
| 2-2-6 | 2 | b2 | 0.5 |
| 2-2-7 | 2 | b2 | 0.6 |

TABLE 4-continued

| Specific Example No. | Metal Complex A Compound No. | Metal Complex B Compound No. | Metal Complex B Content (% by mass) |
|---|---|---|---|
| 2-2-8 | 2 | b2 | 0.7 |
| 2-2-9 | 2 | b2 | 0.8 |
| 2-2-10 | 2 | b2 | 1.1 |
| 2-2-11 | 2 | b2 | 1.3 |
| 2-2-12 | 2 | b2 | 1.4 |
| 2-2-13 | 2 | b2 | 1.5 |
| 2-2-14 | 2 | b2 | 1.9 |
| 2-2-15 | 2 | b2 | 2 |

TABLE 5

| Specific Example No. | Metal Complex A Compound No. | Metal Complex B Compound No. | Metal Complex B Content (% by mass) |
|---|---|---|---|
| 2-3-1 | 2 | c2 | 0.1 |
| 2-3-2 | 2 | c2 | 0.5 |
| 2-3-3 | 2 | c2 | 1 |
| 2-3-4 | 2 | c2 | 1.5 |
| 2-3-5 | 2 | c2 | 2 |
| 2-4-1 | 2 | d2 | 0.1 |
| 2-4-2 | 2 | d2 | 0.3 |
| 2-4-3 | 2 | d2 | 0.9 |
| 2-4-4 | 2 | d2 | 1.4 |
| 2-4-5 | 2 | d2 | 1.95 |
| 2-5-1 | 2 | e2 | 0.08 |
| 2-5-2 | 2 | e2 | 0.2 |
| 2-5-3 | 2 | e2 | 0.25 |
| 2-5-4 | 2 | e2 | 0.7 |
| 2-5-5 | 2 | e2 | 1.25 |
| 2-6-1 | 2 | f2 | 0.07 |
| 2-6-2 | 2 | f2 | 0.08 |
| 2-6-3 | 2 | f2 | 0.13 |
| 2-6-4 | 2 | f2 | 0.15 |
| 2-6-5 | 2 | f2 | 0.67 |
| 3-1-1 | 3 | a3 | 1 |
| 3-1-2 | 3 | a3 | 1.5 |
| 3-1-3 | 3 | a3 | 2 |
| 3-2-1 | 3 | b3 | 1 |
| 3-2-2 | 3 | b3 | 1.5 |
| 3-2-3 | 3 | b3 | 2 |
| 3-3-1 | 3 | c3 | 0.05 |
| 3-3-2 | 3 | c3 | 0.5 |
| 3-3-3 | 3 | c3 | 2 |
| 4-1-1 | 4 | a4 | 0.05 |
| 4-1-2 | 4 | a4 | 0.07 |
| 4-1-3 | 4 | a4 | 0.08 |
| 4-1-4 | 4 | a4 | 0.09 |
| 4-1-5 | 4 | a4 | 0.1 |
| 4-1-6 | 4 | a4 | 0.2 |
| 4-1-7 | 4 | a4 | 0.5 |
| 4-1-8 | 4 | a4 | 0.6 |
| 4-1-9 | 4 | a4 | 0.7 |
| 4-1-10 | 4 | a4 | 0.8 |
| 4-1-11 | 4 | a4 | 0.9 |
| 4-1-12 | 4 | a4 | 1 |
| 4-1-13 | 4 | a4 | 1.2 |
| 4-1-14 | 4 | a4 | 1.3 |
| 4-1-15 | 4 | a4 | 1.4 |
| 4-1-16 | 4 | a4 | 1.5 |
| 4-1-17 | 4 | a4 | 1.6 |
| 4-1-18 | 4 | a4 | 1.7 |
| 4-1-19 | 4 | a4 | 1.8 |
| 4-1-20 | 4 | a4 | 1.9 |
| 4-1-21 | 4 | a4 | 2 |

TABLE 6

| Specific Example No. | Metal Complex A Compound No. | Metal Complex B Compound No. | Metal Complex B Content (% by mass) |
|---|---|---|---|
| 4-2-1 | 4 | b4 | 0.07 |
| 4-2-2 | 4 | b4 | 0.08 |
| 4-2-3 | 4 | b4 | 0.13 |
| 4-2-4 | 4 | b4 | 0.15 |
| 4-2-5 | 4 | b4 | 0.67 |
| 4-3-1 | 4 | c4 | 0.05 |
| 4-3-2 | 4 | c4 | 0.06 |
| 4-3-3 | 4 | c4 | 0.5 |
| 4-3-4 | 4 | c4 | 0.55 |
| 4-3-5 | 4 | c4 | 1.55 |
| 4-4-1 | 4 | d4 | 0.2 |
| 4-4-2 | 4 | d4 | 0.6 |
| 4-4-3 | 4 | d4 | 0.7 |
| 4-4-4 | 4 | d4 | 0.95 |
| 4-4-5 | 4 | d4 | 1.3 |
| 4-5-1 | 4 | e4 | 0.05 |
| 4-5-2 | 4 | e4 | 0.1 |
| 4-5-3 | 4 | e4 | 0.5 |
| 4-5-4 | 4 | c4 | 1 |
| 4-5-5 | 4 | e4 | 2 |
| 4-6-1 | 4 | f4 | 0.08 |
| 4-6-2 | 4 | f4 | 0.2 |
| 4-6-3 | 4 | f4 | 0.25 |
| 4-6-4 | 4 | f4 | 0.7 |
| 4-6-5 | 4 | f4 | 1.25 |
| 4-7-1 | 4 | g4 | 0.6 |
| 4-7-2 | 4 | g4 | 0.8 |
| 4-7-3 | 4 | g4 | 1.2 |
| 4-8-1 | 4 | h4 | 0.8 |
| 4-8-2 | 4 | h4 | 1.4 |
| 4-8-3 | 4 | h4 | 1.6 |
| 4-9-1 | 4 | i4 | 1.7 |
| 4-9-2 | 4 | i4 | 1.9 |
| 4-9-3 | 4 | i4 | 2 |
| 5-1-1 | 5 | a5 | 0.05 |
| 5-1-2 | 5 | a5 | 0.07 |
| 5-1-3 | 5 | a5 | 0.08 |
| 5-1-4 | 5 | a5 | 0.2 |
| 5-1-5 | 5 | a5 | 0.5 |
| 5-1-6 | 5 | a5 | 0.8 |
| 5-1-7 | 5 | a5 | 0.9 |
| 5-1-8 | 5 | a5 | 1 |
| 5-1-9 | 5 | a5 | 1.2 |
| 5-1-10 | 5 | a5 | 1.3 |
| 5-1-11 | 5 | a5 | 1.5 |
| 5-1-12 | 5 | a5 | 1.6 |
| 5-1-13 | 5 | a5 | 1.7 |
| 5-1-14 | 5 | a5 | 1.8 |
| 5-1-15 | 5 | a5 | 1.9 |
| 5-1-16 | 5 | a5 | 2 |

TABLE 7

| Specific Example No. | Metal Complex A Compound No. | Metal Complex B Compound No. | Metal Complex B Content (% by mass) |
|---|---|---|---|
| 5-2-1 | 5 | b5 | 0.1 |
| 5-2-2 | 5 | b5 | 0.5 |
| 5-3-1 | 5 | c5 | 0.1 |
| 5-3-2 | 5 | c5 | 0.5 |
| 5-4-1 | 5 | d5 | 0.1 |
| 5-4-2 | 5 | d5 | 0.5 |
| 5-5-1 | 5 | e5 | 0.1 |
| 5-5-2 | 5 | e5 | 0.5 |
| 5-6-1 | 5 | f5 | 2 |
| 6-1-1 | 6 | a6 | 0.6 |
| 6-1-2 | 6 | a6 | 0.8 |
| 6-1-3 | 6 | a6 | 1.2 |
| 6-2-1 | 6 | b6 | 0.1 |
| 6-2-2 | 6 | b6 | 0.3 |

TABLE 7-continued

| Specific Example No. | Metal Complex A Compound No. | Metal Complex B Compound No. | Metal Complex B Content (% by mass) |
|---|---|---|---|
| 6-2-3 | 6 | b6 | 0.9 |
| 6-2-4 | 6 | b6 | 1.4 |
| 6-2-5 | 6 | b6 | 1.95 |
| 7-1-1 | 7 | a7 | 1 |
| 8-1-1 | 8 | a8 | 1.2 |
| 8-1-2 | 8 | a8 | 1.3 |
| 8-1-3 | 8 | a8 | 1.4 |
| 8-1-4 | 8 | a8 | 1.5 |
| 8-1-5 | 8 | a8 | 1.6 |
| 8-1-6 | 8 | a8 | 1.7 |
| 8-1-7 | 8 | a8 | 1.8 |
| 8-1-8 | 8 | a8 | 1.9 |
| 8-1-9 | 8 | a8 | 1.95 |
| 8-1-10 | 8 | a8 | 2 |
| 8-2-1 | 8 | b8 | 0.08 |
| 8-2-2 | 8 | b8 | 0.2 |
| 8-2-3 | 8 | b8 | 0.5 |
| 8-2-4 | 8 | b8 | 0.8 |
| 8-2-5 | 8 | b8 | 0.9 |
| 8-2-6 | 8 | b8 | 1 |
| 8-2-7 | 8 | b8 | 1.2 |
| 8-2-8 | 8 | b8 | 1.3 |
| 8-2-9 | 8 | b8 | 1.5 |
| 8-2-10 | 8 | b8 | 1.6 |
| 8-3-1 | 8 | c8 | 1 |
| 8-3-2 | 8 | c8 | 1.3 |
| 8-4-1 | 8 | d8 | 0.7 |
| 8-4-2 | 8 | d8 | 0.75 |
| 9-1-1 | 9 | a9 | 1.1 |
| 9-2-1 | 9 | b9 | 1.3 |
| 10-1-1 | 10 | a10 | 1.1 |
| 10-1-2 | 10 | a10 | 1.9 |
| 10-2-1 | 10 | b10 | 0.05 |
| 10-2-2 | 10 | b10 | 0.07 |
| 10-3-1 | 10 | c10 | 0.05 |
| 10-3-2 | 10 | c10 | 0.99 |

TABLE 8

| Specific Example No. | Metal Complex A Compound No. | Metal Complex B Compound No. | Metal Complex B Content (% by mass) |
|---|---|---|---|
| 10-4-1 | 10 | d10 | 0.5 |
| 10-5-1 | 10 | e10 | 1 |
| 10-6-1 | 10 | f10 | 0.05 |
| 11-1-1 | 11 | a11 | 0.05 |
| 11-1-2 | 11 | a11 | 0.07 |
| 11-1-3 | 11 | a11 | 0.08 |
| 12-1-1 | 12 | a12 | 0.2 |
| 12-1-2 | 12 | a12 | 0.77 |
| 12-1-3 | 12 | a12 | 0.8 |
| 12-1-4 | 12 | a12 | 1.1 |
| 12-1-5 | 12 | a12 | 1.85 |
| 12-2-1 | 12 | b12 | 0.05 |
| 12-2-2 | 12 | b12 | 2 |
| 12-3-1 | 12 | c12 | 0.05 |
| 12-3-2 | 12 | c12 | 2 |
| 13-1-1 | 13 | a13 | 0.055 |
| 13-1-2 | 13 | a13 | 0.09 |
| 13-1-3 | 13 | a13 | 0.15 |
| 13-2-1 | 13 | b13 | 0.08 |
| 13-2-2 | 13 | b13 | 0.16 |
| 13-2-3 | 13 | b13 | 1.1 |
| 13-3-1 | 13 | c13 | 0.4 |
| 13-3-2 | 13 | c13 | 0.9 |
| 14-1-1 | 14 | a14 | 0.5 |
| 14-1-2 | 14 | b14 | 0.5 |
| 15-1-1 | 15 | a15 | 1.4 |
| 15-1-2 | 15 | a15 | 1.8 |
| 15-2-1 | 15 | b15 | 2 |

TABLE 8-continued

| Specific Example No. | Metal Complex A Compound No. | Metal Complex B Compound No. | Metal Complex B Content (% by mass) |
|---|---|---|---|
| 16-1-1 | 16 | a16 | 0.5 |
| 16-2-1 | 16 | b16 | 1 |
| 17-1-1 | 17 | a17 | 0.05 |
| 17-1-2 | 17 | a17 | 1 |
| 17-1-3 | 17 | a17 | 1.8 |
| 17-2-1 | 17 | b17 | 2 |
| 17-3-1 | 17 | c17 | 0.5 |
| 17-3-2 | 17 | c17 | 0.9 |
| 18-1-1 | 18 | a18 | 0.09 |
| 18-1-2 | 18 | a18 | 0.5 |
| 18-2-1 | 18 | b18 | 0.5 |
| 19-1-1 | 19 | a19 | 0.5 |
| 19-2-1 | 19 | b19 | 0.5 |
| 20-1-1 | 20 | a20 | 1 |
| 20-2-1 | 20 | b20 | 1 |
| 20-3-1 | 20 | c20 | 1 |
| 21-1-1 | 21 | a21 | 2 |
| 21-2-1 | 21 | b21 | 2 |
| 22-1-1 | 22 | a22 | 0.05 |
| 22-1-2 | 22 | a22 | 0.5 |
| 22-1-3 | 22 | a22 | 1 |
| 22-1-4 | 22 | a22 | 2 |

TABLE 9

| Specific Example No. | Metal Complex A Compound No. | Metal Complex B Compound No. | Metal Complex B Content (% by mass) |
|---|---|---|---|
| 22-2-1 | 22 | b22 | 0.07 |
| 22-2-2 | 22 | b22 | 0.1 |
| 22-2-3 | 22 | b22 | 0.16 |
| 22-2-4 | 22 | b22 | 0.26 |
| 22-2-5 | 22 | b22 | 0.33 |
| 22-2-6 | 22 | b22 | 0.75 |
| 22-2-7 | 22 | b22 | 0.95 |
| 22-3-1 | 22 | c22 | 0.06 |
| 22-3-2 | 22 | c22 | 0.1 |
| 22-3-3 | 22 | c22 | 0.5 |
| 22-3-4 | 22 | c22 | 0.75 |
| 22-3-5 | 22 | c22 | 1 |
| 22-3-6 | 22 | c22 | 1.2 |
| 22-3-7 | 22 | c22 | 1.5 |
| 22-4-1 | 22 | d22 | 0.5 |
| 22-4-2 | 22 | d22 | 1.7 |
| 22-5-1 | 22 | e22 | 1.09 |
| 23-1-1 | 23 | a23 | 0.7 |
| 23-2-1 | 23 | b23 | 0.7 |
| 24-1-1 | 24 | a24 | 0.05 |
| 25-1-1 | 25 | a25 | 0.06 |
| 25-2-1 | 25 | b25 | 0.05 |
| 25-3-1 | 25 | c25 | 0.055 |
| 26-1-1 | 26 | a26 | 0.5 |
| 26-2-1 | 26 | b26 | 0.8 |
| 27-1-1 | 27 | a27 | 0.08 |
| 27-1-2 | 27 | a27 | 0.2 |
| 27-1-3 | 27 | a27 | 0.25 |
| 27-1-4 | 27 | a27 | 0.7 |
| 27-1-5 | 27 | a27 | 1.25 |
| 27-2-1 | 27 | b27 | 0.1 |
| 28-1-1 | 28 | a28 | 0.5 |
| 28-1-1 | 28 | a28 | 1 |
| 29-1-1 | 29 | a29 | 1.5 |
| 29-2-1 | 29 | b29 | 1 |
| 30-1-1 | 30 | a30 | 1.5 |
| 30-2-1 | 30 | b30 | 1.1 |
| 30-3-1 | 30 | c30 | 1.1 |
| 31-1-1 | 31 | a31 | 0.4 |
| 31-1-2 | 31 | a31 | 0.6 |
| 31-2-1 | 31 | b31 | 1 |
| 31-3-1 | 31 | c31 | 1.5 |

TABLE 9-continued

| Specific Example No. | Metal Complex A Compound No. | Metal Complex B Compound No. | Metal Complex B Content (% by mass) |
|---|---|---|---|
| 32-1-1 | 32 | a32 | 0.8 |
| 32-1-2 | 32 | a32 | 1 |
| 32-1-3 | 32 | a32 | 1.7 |
| 32-2-1 | 32 | b32 | 0.5 |
| 32-3-1 | 32 | c32 | 1.5 |
| 33-1-1 | 33 | a33 | 1 |
| 33-1-2 | 33 | a33 | 1.7 |
| 33-2-1 | 33 | b33 | 0.05 |
| 33-2-2 | 33 | b33 | 0.08 |

TABLE 10

| Specific Example No. | Metal Complex A Compound No. | Metal Complex B Compound No. | Metal Complex B Content (% by mass) |
|---|---|---|---|
| 34-1-1 | 34 | a34 | 0.05 |
| 34-1-2 | 34 | a34 | 0.35 |
| 34-1-3 | 34 | a34 | 0.5 |
| 34-2-1 | 34 | b34 | 0.5 |
| 34-3-1 | 34 | c34 | 0.5 |
| 35-1-1 | 35 | a35 | 0.5 |
| 35-2-1 | 35 | b35 | 0.5 |
| 35-3-1 | 35 | c35 | 0.5 |
| 36-1-1 | 36 | a36 | 0.05 |
| 36-1-2 | 36 | a36 | 0.06 |
| 36-1-3 | 36 | a36 | 0.5 |
| 36-1-4 | 36 | a36 | 0.55 |
| 36-1-5 | 36 | a36 | 1.55 |
| 36-2-1 | 36 | b36 | 0.5 |
| 36-2-2 | 36 | b36 | 0.8 |
| 36-3-1 | 36 | c36 | 1 |
| 37-1-1 | 37 | a37 | 0.9 |
| 37-1-2 | 37 | a37 | 1 |
| 37-1-3 | 37 | a37 | 2 |
| 37-2-1 | 37 | b37 | 0.5 |
| 37-3-1 | 37 | c37 | 0.5 |
| 38-1-1 | 38 | a38 | 0.08 |
| 38-1-2 | 38 | a38 | 0.09 |
| 38-1-3 | 38 | a38 | 0.1 |
| 38-2-1 | 38 | b38 | 0.05 |
| 38-2-2 | 38 | b38 | 1 |
| 38-3-1 | 38 | c38 | 0.05 |
| 39-1-1 | 39 | a39 | 0.25 |
| 39-2-1 | 39 | b39 | 0.25 |
| 39-3-1 | 39 | c39 | 0.2 |
| 40-1-1 | 40 | a40 | 0.5 |
| 40-2-1 | 40 | b40 | 0.5 |
| 40-3-1 | 40 | c40 | 0.5 |
| 41-1-1 | 41 | a41 | 0.05 |
| 41-1-2 | 41 | a41 | 0.4 |
| 41-1-3 | 41 | a41 | 0.95 |
| 41-2-1 | 41 | b41 | 1 |
| 41-3-1 | 41 | c41 | 1.31 |
| 42-1-1 | 42 | a42 | 0.1 |
| 42-1-2 | 42 | a42 | 1 |
| 42-1-3 | 42 | a42 | 2 |
| 42-2-1 | 42 | b42 | 0.05 |
| 42-2-2 | 42 | b42 | 1 |
| 42-3-1 | 42 | c42 | 1 |
| 43-1-1 | 43 | a43 | 0.05 |
| 43-2-1 | 43 | b43 | 0.05 |
| 43-3-1 | 43 | c43 | 0.05 |
| 44-1-1 | 44 | a44 | 0.05 |
| 44-2-1 | 44 | b44 | 0.05 |
| 44-3-1 | 44 | c44 | 0.05 |
| 45-1-1 | 45 | a45 | 0.05 |
| 45-2-1 | 45 | b45 | 0.05 |
| 45-3-1 | 45 | c45 | 0.05 |

TABLE 21

| Specific Example No. | Metal Complex A Compound No. | Metal Complex B Compound No. | Metal Complex B Content (% by mass) |
|---|---|---|---|
| 70-1-1 | 70 | a70 | 0.05 |
| 70-1-2 | 70 | a70 | 0.01 |
| 70-1-3 | 70 | a70 | 0.2 |
| 70-1-4 | 70 | a70 | 0.5 |
| 70-1-5 | 70 | a70 | 1 |
| 70-1-6 | 70 | a70 | 1.2 |
| 70-1-7 | 70 | a70 | 1.5 |
| 70-1-8 | 70 | a70 | 2 |
| 70-2-1 | 70 | b70 | 0.01 |
| 70-2-2 | 70 | b70 | 0.1 |
| 70-2-3 | 70 | b70 | 0.2 |
| 70-2-4 | 70 | b70 | 0.5 |
| 70-2-5 | 70 | b70 | 1 |
| 70-2-6 | 70 | b70 | 1.2 |
| 70-2-7 | 70 | b70 | 1.5 |
| 70-2-8 | 70 | b70 | 2 |
| 70-3-1 | 70 | c70 | 0.05 |
| 70-3-2 | 70 | c70 | 0.5 |
| 70-3-3 | 70 | c70 | 1 |
| 70-3-4 | 70 | c70 | 1.5 |
| 70-3-5 | 70 | c70 | 2 |
| 70-4-1 | 70 | d70 | 0.05 |
| 70-4-2 | 70 | d70 | 0.5 |
| 70-4-3 | 70 | d70 | 1 |
| 70-4-4 | 70 | d70 | 1.5 |
| 70-4-5 | 70 | d70 | 2 |
| 71-1-1 | 71 | a71 | 0.05 |
| 71-1-2 | 71 | a71 | 0.2 |
| 71-1-3 | 71 | a71 | 1 |
| 71-1-4 | 71 | a71 | 1.3 |
| 71-1-5 | 71 | a71 | 2 |
| 71-2-1 | 71 | b71 | 0.005 |
| 71-2-2 | 71 | b71 | 1 |
| 71-2-3 | 71 | b71 | 2 |
| 72-1-1 | 72 | a72 | 0.005 |
| 72-1-2 | 72 | a72 | 0.1 |
| 72-1-3 | 72 | a72 | 0.5 |
| 72-1-4 | 72 | a72 | 1.2 |

TABLE 22

| Specific Example No. | Metal Complex A Compound No. | Metal Complex B Compound No. | Metal Complex B Content (% by mass) |
|---|---|---|---|
| 72-2-1 | 72 | b72 | 0.0075 |
| 72-2-2 | 72 | b72 | 0.05 |
| 72-2-3 | 72 | b72 | 2 |
| 73-1-1 | 73 | a73 | 0.01 |
| 73-1-2 | 73 | a73 | 0.15 |
| 73-1-3 | 73 | a73 | 1.25 |
| 73-2-1 | 73 | b73 | 0.05 |
| 73-2-2 | 73 | b73 | 0.8 |
| 73-3-1 | 73 | c73 | 0.15 |
| 73-3-2 | 73 | c73 | 1.5 |
| 74-1-1 | 74 | a74 | 0.005 |
| 74-1-2 | 74 | a74 | 0.1 |
| 74-2-1 | 74 | b74 | 0.01 |
| 74-2-2 | 74 | b74 | 0.7 |
| 74-2-3 | 74 | b74 | 1 |
| 75-1-1 | 75 | a75 | 0.5 |
| 75-2-1 | 75 | b75 | 0.5 |
| 76-1-1 | 76 | a76 | 0.005 |
| 76-1-2 | 76 | a76 | 0.1 |
| 77-1-1 | 77 | a77 | 0.5 |
| 77-2-1 | 77 | b77 | 0.05 |
| 77-2-2 | 77 | b77 | 0.75 |
| 77-3-1 | 77 | c77 | 0.5 |
| 77-3-2 | 77 | c77 | 1.9 |
| 78-1-1 | 78 | a78 | 0.5 |
| 78-1-2 | 78 | a78 | 0.7 |
| 78-2-1 | 78 | b78 | 0.25 |
| 78-2-2 | 78 | b78 | 0.8 |
| 78-2-3 | 78 | b78 | 1.5 |
| 78-3-1 | 78 | c78 | 0.005 |
| 78-3-2 | 78 | c78 | 0.007 |
| 79-1-1 | 79 | a79 | 0.01 |
| 79-1-2 | 79 | a79 | 0.15 |
| 79-1-3 | 79 | a79 | 0.3 |
| 79-2-1 | 79 | b79 | 0.005 |
| 79-2-2 | 79 | b79 | 0.6 |
| 79-2-3 | 79 | b79 | 1.15 |

The platinum complex compounds represented by formula (C-1) can be synthesized by various methods, for example, the method described in GR. Newkome et al., Journal of Organic Chemistry, 53, 786, (1988), page 789, left column, line 53 to right column, line 7, the method described in page 790, left column, line 18 to line 38, the method described in page 790, right column, line 19 to line 30, and combinations of these methods, and the method described in H. Lexy et al., Chemische Berichte, 113, 2749 (1980), page 2752, line 26 to line 35 can be used.

For example, the platinum complex represented by formula (C-1) can be obtained at room temperature or lower or by heating a ligand or the dissociation product thereof and a metal compound (other than ordinary heating, a method of heating with a microwave is also effective) in the presence of a solvent (e.g., a halogen solvent, an alcohol solvent, an ether solvent, an ester solvent, a ketone solvent, a nitrile solvent, an amide solvent, a sulfone solvent, a sulfoxide solvent, and water can be exemplified) or in the absence of a solvent, in the presence of a base (various organic and inorganic bases, e.g., sodium methoxide, potassium t-butoxide, triethylamine, potassium carbonate can be exemplified) or in the absence of a base.

Metal complexes in the case where M in formula (1) represents Ir (also referred to as specific iridium complexes) are described.

It is preferred for specific iridium complexes to have a bidentate ligand represented by the following formula (A1), (A2), (A3) or (A4). Incidentally, in formulae of ligands in the invention, * is a coordination site to iridium and bonding of $E_{1a}$ to iridium and bonding of $E_{1p}$, to iridium may be independently via a covalent bond or a coordinate bond.

(A1)

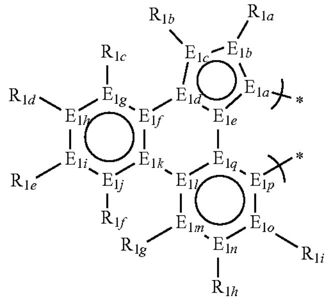

-continued (A2)

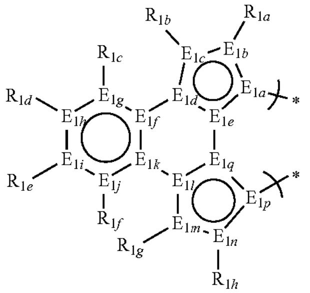

(A3)

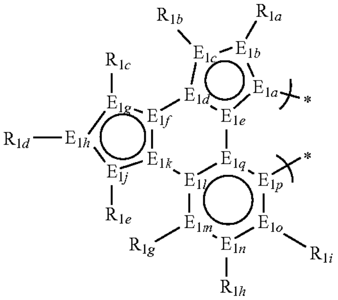

(A4)

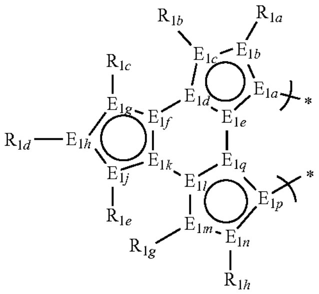

In formulae (A1) to (A4), each of $E_{1a}$ to $E_{1q}$ independently represents a carbon atom or a hetero atom. Each of $R_{1a}$ to $R_{1i}$ independently represents a hydrogen atom or a substituent. Each of the structures represented by any of formulae (A1) to (A4) has in total of 18 π-electronic structures. However, in formulae (A1) and (A3), at least one of $R_{1a}$ to $R_{1i}$; represents a substituent. In formulae (A2) and (A4), at least one of $R_{1a}$ to $R_{1i}$ represents a substituent.

Each of $E_{1a}$ to $E_{1q}$ is selected from a carbon atom or a hetero atom, and preferably selected from a carbon atom or a nitrogen atom. It is preferred that $E_{1a}$ and $E_{1p}$ are different atoms. The structure has 18 π-electronic structures.

In the formulae of ligands in the invention, * is a coordination site to a metal and bonding of $E_{1a}$ to a metal and bonding of $E_{1p}$, to a metal may be independently via a covalent bond or a coordinate bond.

The bidentate ligand may be bonded to other ligands to form a tridentate ligand, a tetradentate ligand, a pentadentate ligand, or a hexadentate ligand.

The hetero atom means atoms other than a carbon atom or a hydrogen atom. As the examples of hetero atoms, e.g., oxygen, nitrogen, phosphorus, sulfur, selenium, arsenic, chlorine, bromine, silicon and fluorine are exemplified.

A 5-membered ring formed by $E_{1a}$ to $E_{1c}$ is a 5-membered heterocyclic ring. As the 5-membered heterocyclic rings, specifically oxazole, thiazole, isoxazole, isothiazole, pyrrole, imidazole, pyrazole, triazole, and tetrazole are exemplified, preferably imidazole and pyrazole, and more preferably imidazole. These 5-membered rings may be condensed with other rings.

At least one of $E_{1a}$ to $E_{1e}$, preferably represents a nitrogen atom, more preferably two or three of $E_{1a}$ to $E_{1e}$ represent a nitrogen atom, and especially preferably two of $E_{1a}$ to $E_{1e}$ represent a nitrogen atom. When two of $E_{1a}$ to $E_{1e}$ represent a nitrogen atom, preferably two of $E_{1a}$, $E_{1d}$ and $E_{1e}$ represent a nitrogen atom, more preferably $E_{1a}$ and $E_{1d}$ or $E_{1a}$ and $E_{1e}$ represent a nitrogen atom, and still more preferably $E_{1a}$ and $E_{1d}$ represent a nitrogen atom.

A ring formed by $E_{1f}$ to $E_{1k}$ is a 5- or 6-membered aromatic hydrocarbon ring or heterocyclic ring, preferably a 6-membered ring, and more preferably a 6-membered aromatic hydrocarbon ring. As the specific examples of the rings formed by $E_{1f}$ to $E_{1k}$, benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine, and triazine are exemplified, preferably pyridine and benzene, and more preferably benzene.

A ring formed by $E_{1l}$ to $E_{1q}$ is a 5- or 6-membered aromatic hydrocarbon ring or heterocyclic ring, preferably a 6-membered ring, and more preferably a 6-membered aromatic hydrocarbon ring. As the specific examples of the rings formed by $E_{1l}$ to $E_{1q}$, benzene, oxazole, thiazole, isoxazole, isothiazole, oxadiazole, thiadiazole, furan, thiophene, pyrrole, imidazole, pyrazole, triazole, pyridine, pyrazine, pyrimidine, pyridazine, and triazine are exemplified, preferably pyridine and benzene, and more preferably benzene.

Each of $R_{1a}$ to $R_{1i}$ independently represents a hydrogen atom or a substituent. The substituent is preferably a group selected from substituent group A. However, in formulae (A1) and (A3), at least one of $R_{1a}$ to $R_{1i}$ represents a substituent. In formulae (A2) and (A4), at least one of $R_{1a}$ to $R_{ib}$ represents a substituent.

It is preferred that at least one of $R_{1a}$, $R_{1b}$, $R_{1g}$, $R_{1h}$ and $R_{1i}$ represents a substituent.

In formulae (A1) and (A3), the substituents represented by $R_{1a}$ to $R_{1i}$ have the same meaning with the meaning of $R^1$ and $R^2$ in formula (1), and the preferred range is also the same.

In formulae (A2) and (A4), the substituents represented by $R_{1a}$ to $R_{1b}$ have the same meaning with the meaning of $R^1$ and $R^2$ in formula (1), and the preferred range is also the same.

Each of $R_{1a}$ to $R_{1i}$ preferably represents a hydrogen atom, a halogen atom, a hydrocarbon substituent (preferably an alkyl group, a cycloalkyl group or an aryl group), a cyano group, $OR_{2a}$, $SR_{2a}$, $NR_{2a}R_{2b}$, $BR_{2a}R_{2b}$, or $SiR_{2a}R_{2b}R_{2c}$. Each of $R_{2a}$ to $R_{2c}$ independently represents a hydrocarbon substituent, or a hydrocarbon substituent substituted with a hetero atom, and two of $R_{1a}$ to $R_{1i}$, and $R_{2a}$ to $R_{2c}$ may be bonded to each other to form a saturated or unsaturated, aromatic or non-aromatic ring. When bonding to a nitrogen atom, $R_{1a}$ to $R_{1i}$ are not present.

It is preferred that at least one of $R_{1a}$ to $R_{1i}$ is an aryl group having a dihedral angle of 70° or more to the mother structure, more preferably a substituent represented by the following formula (ss-1), still more preferably a 2,6-di-substituted aryl group, and most preferably $R_{1b}$ is a 2,6-di-substituted aryl group.

Formula (ss-1)

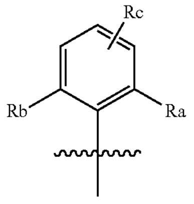

ss-1

In formula (ss-1), each of Ra, Rb and Rc independently represents a hydrogen atom, an alkyl group or an aryl group. The number of Rc is 0 to 3.

The alkyl group represented by each of Ra, Rb and Rc is preferably an alkyl group having 1 to 30 carbon atoms, more preferably 1 to 20 carbon atoms, and especially preferably 1 to 10 carbon atoms, e.g., methyl, ethyl, n-propyl, isopropyl, n-butyl, tert-butyl, n-octyl, n-nonyl, n-decyl, n-dodecyl, n-octadecyl, n-hexadecyl, cyclopropyl, cyclobutyl, cyclopentyl, cyclohexyl, cyclooctyl, 1-adamantyl, and trifluoromethyl are exemplified, and a methyl group and an isopropyl group are preferred.

The aryl group represented by each of Ra, Rb and Rc is preferably an aryl group having preferably 6 to 30 carbon atoms, more preferably 6 to 20 carbon atoms and especially preferably 6 to 12 carbon atoms, e.g., phenyl, o-methylphenyl, m-methylphenyl, p-methylphenyl, 2,6-xylyl, p-cumenyl, mesityl, naphthyl, and anthranyl are exemplified, and a phenyl group, a 2,6-xylyl group and a mesityl group are preferred, and a phenyl group is more preferred.

At least one of Ra and Rb is preferably selected from an alkyl group or an aryl group, at least one of Ra and Rb is more preferably selected from an alkyl group, still more preferably both Ra and Rb are alkyl groups, and most preferably both Ra and Rb are methyl groups or isopropyl groups.

Preferred as the 2,6-di-substituted aryl groups are a 2,6-dimethylphenyl group, a 2,4,6-trimethylphenyl group, a 2,6-diisopropylphenyl group, a 2,4,6-triisopropyl-phenyl group, a 2,6-dimethyl-4-phenylphenyl group, a 2,6-dimethyl-4-(2,6-dimethyl-pyridin-4-yl)phenyl group, a 2,6-diphenylphenyl group, a 2,6-diphenyl-4-isopropyl-phenyl group, a 2,4,6-triphenylphenyl group, a 2,6-diisopropyl-4-(4-isopropylphenyl)-phenyl group, a 2,6-diisopropyl-4-(3,5-dimethylphenyl) phenyl group, a 2,6-diisopropyl-4-(pyridin-4-yl)phenyl group, and a 2,6-di(3,5-dimethylphenyl)phenyl group.

The number of Rc is preferably 0 or 1. Plural Rc may be the same with or different from each other.

On the other hand, with regard to $R_{1a}$ to $R_{1i}$, it is preferred that at least one represents an alkyl group, and more preferably $R_{1e}$ represents an alkyl group. The alkyl group is preferably an alkyl group which is branched at a site apart from benzylic position including 4 or more carbon atoms, preferably a methyl group or a neopentyl group, and more preferably a neopentyl group.

At least one of $R_{1a}$ and $R_{1b}$ is preferably an electron donating group, more preferably $R_{1a}$ is an electron donating group, still more preferably $R_{1a}$ is a methyl group.

The hydrocarbon substituent is a monovalent or divalent, straight chain, branched or cyclic substituent including a carbon atom and a hydrogen atom alone.

As the examples of monovalent hydrocarbon substituents, an alkyl group having 1 to 20 carbon atoms; an alkyl group having 1 to 20 carbon atoms substituted with one or more groups selected from an alkyl group having 1 to 20 carbon atoms, a cycloalkyl group having 3 to 8 carbon atoms, and an aryl group; a cycloalkyl group having 3 to 8 carbon atoms; a cycloalkyl group having 3 to 8 carbon atoms substituted with one or more groups selected from an alkyl group having 1 to 20 carbon atoms, a cycloalkyl group having 3 to 8 carbon atoms, and an aryl group; an aryl group having 6 to 18 carbon atoms; and an aryl group substituted with one or more groups selected from an alkyl group having 1 to 20 carbon atoms, a cycloalkyl group having 3 to 8 carbon atoms, and an aryl group are exemplified.

As the examples of divalent hydrocarbon groups, $-CH_2-$, $-CH_2CH_2-$, $-CH_2CH_2CH_2-$, and a 1,2-phenylene group are exemplified.

The bidentate ligand represented by any of formulae (A1) to (A4) is preferably a bidentate ligand represented by formula (A1) or (A3).

The bidentate ligand represented by formula (A1) or (A3) is preferably a mono-anionic bidentate ligand represented by the following formula (A1-1) or (A3-1).

(A1-1)

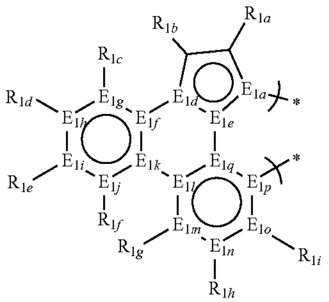

(A3-1)

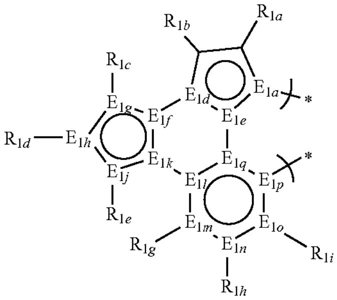

In formulae (A1-1) and (A3-1), each of $E_{1a}$, $E_{1d}$, $E_{1e}$ to $E_{1q}$ independently represents a carbon atom or a hetero atom. Each of $R_{1a}$ to $R_{1i}$ independently represents a hydrogen atom or a substituent. Each of the structures represented by formulae (A1-1) and (A3-1) has in total of 18 π-electronic structures. However, at least one of $R_{1a}$ to $R_{1i}$ represents a substituent.

In formulae (A1-1) and (A3-1), preferred $E_{ia}$, $E_{ld}$, $E_{ie}$ to $E_{iq}$ and $R_{1a}$ to $R_{1i}$ are respectively the same with $E_{1a}$, $E_{1d}$, $E_{1e}$ to $E_{1q}$ and $R_{1a}$ to $R_{1i}$; in formulae (A1) and (A3).

In the invention, the mono-anionic bidentate ligand represented by formula (A1-1) is more preferred.

The bidentate ligand represented by formula (A1-1) or (A3-1) is preferably a mono-anionic bidentate ligand represented by the following formula (A1-2) or (A3-2).

(A1-2)

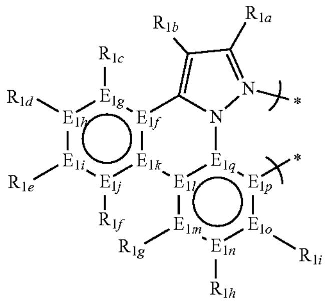

(A3-2)

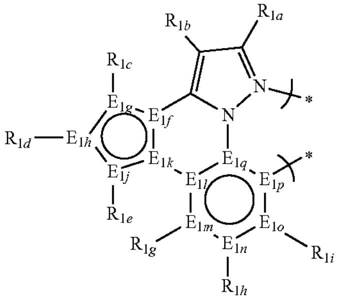

In formulae (A1-2) and (A3-2), each of $E_{1f}$ to $E_{N}$ independently represents a carbon atom or a hetero atom. Each of $R_{1a}$ to $R_{1i}$ independently represents a hydrogen atom or a substituent. Each of the structures represented by formulae (A1-2) and (A3-2) has in total of 18 π-electronic structures. However, at least one of $R_{1a}$, to $R_{1i}$ represents a substituent.

In formulae (A1-2) and (A3-2), preferred $E_{1l}$ to $E_{1q}$ and $R_{1a}$ to $R_{1i}$ are respectively the same with $E_{11}$ to $E_{1q}$ and $R_{1a}$ to $R_{1i}$; in formulae (A1-1) and (A3-1).

The mono-anionic bidentate ligand represented by formula (A1-1) or (A3-1) is more preferably a mono-anionic bidentate ligand represented by the following formula (A1-3) or (A3-3).

(A1-3)

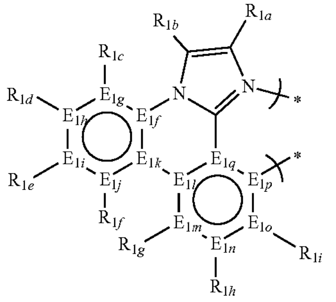

(A3-3)

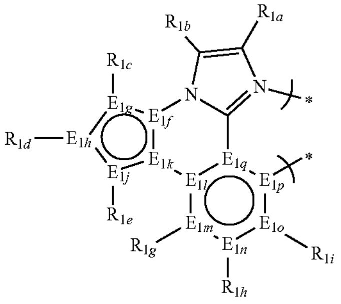

In formulae (A1-3) and (A3-3), each of $E_{1f}$ to $E_{1q}$ independently represents a carbon atom or a hetero atom. Each of $R_{1a}$ to $R_{1i}$ independently represents a hydrogen atom or a substituent. Each of the structures represented by formulae (A1-3) and (A3-3) has in total of 18 π-electronic structures. However, at least one of $R_{1a}$ to $R_{1i}$ represents a substituent.

In formulae (A1-3) and (A3-3), preferred $E_{1l}$ to $E_{1q}$ and $R_{1a}$ to $R_{1i}$ are respectively the same with $E_{1l}$ to $E_{1q}$ and $R_{1a}$ to $R_{1i}$ in formulae (A1-1) and (A3-1).

The mono-anionic bidentate ligand represented by formula (A1-3) or (A3-3) is more preferably a mono-anionic bidentate ligand represented by the following formula (A 1-4) or (A3-4).

(A1-4)

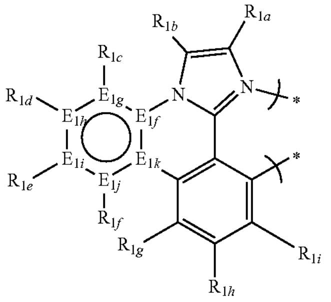

(A3-4)

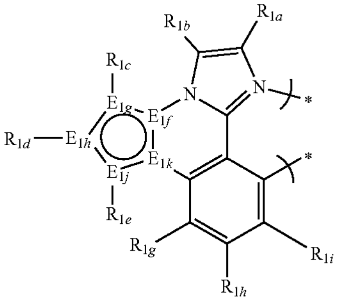

In formulae (A1-4) and (A3-4), each of $E_{1f}$ to $E_{1k}$ independently represents a carbon atom or a hetero atom. Each of $R_{1a}$ to $R_{1i}$; independently represents a hydrogen atom or a substituent. Each of the structures represented by formulae (A1-4) and (A3-4) has in total of 18 π-electronic structures. However, at least one of $R_{1a}$ to $R_{1i}$ represents a substituent.

In formulae (A1-4) and (A3-4), preferred $E_{1f}$ to $E_{1k}$ and $R_{1a}$ to $R_{1i}$ are respectively the same with $E_{1l}$ to $E_{1q}$ and $R_{1a}$ to $R_{1i}$ in formulae (A1-1) and (A3-1).

The mono-anionic bidentate ligand represented by formula (A1-4) or (A3-4) is more preferably a mono-anionic bidentate ligand represented by the following formula (A1-5).

(A1-5)

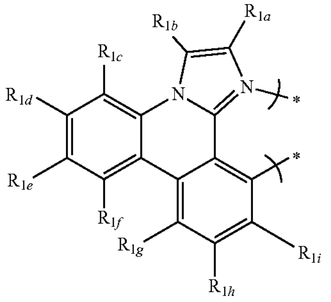

In formula (A1-5), each of $R_{1a}$ to $R_{1i}$ independently represents a hydrogen atom or a substituent. However, at least one of $R_{1a}$ to $R_{1i}$ represents a substituent.

In formula (A1-5), preferred $R_{1a}$ to $R_{1i}$; are the same with $R_{1a}$ to $R_{1i}$; in formula (A1-3).

The bidentate ligand represented by formula (A1-5) is preferably a bidentate ligand represented by the following formula (A1-6).

(A1-6)

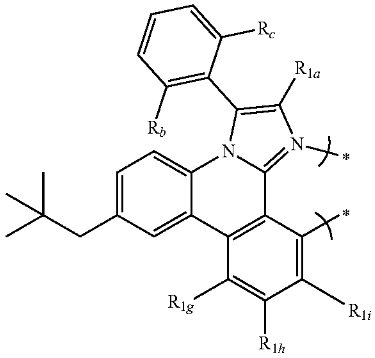

In formula (A1-6), each of $R_{1a}$, $R_{1g}$, $R_{1h}$ and $R_{1i}$ independently represents a hydrogen atom or a substituent. Each of Rb and Rc independently represents a hydrogen atom, an alkyl group or an aryl group, provided that at least one of $R_{1a}$, $R_{1g}$, $R_{1h}$ and $R_{1i}$ represents a substituent.

In formula (A1-6), preferred $R_{1a}$, $R_{1g}$, $R_{1h}$ and $R_{1i}$ are the same with $R_{1a}$, $R_{1g}$, $R_{1h}$ and $R_{1i}$ in formula (A1-1). Further, preferred Rb and Rc are the same with Rb and Rc in formula (ss-1).

In the invention, the specific iridium complex is preferably a phosphorescent metal complex represented by the following formula (A10).

(A10)

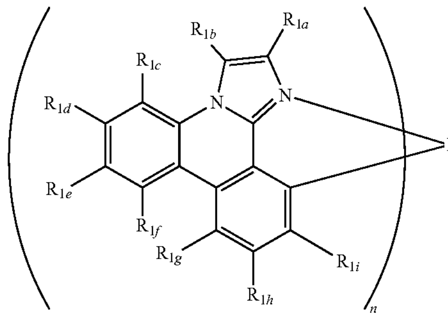

In formula (A10), each of $R_{1a}$ to $R_{1i}$ independently represents a hydrogen atom or a substituent. X—Y represents a bidentate mono-anionic ligand. n represents an integer of 1 to 3. However, at least one of $R_{1a}$ to $R_{1i}$; represents a substituent.

In formula (A10), preferred $R_{1a}$ to $R_{1i}$ are the same with preferred $R_{1a}$ to $R_{1i}$ in formulae (A1).

X—Y represents a bidentate mono-anionic sub-ligand. These sub-ligands are considered not to directly contribute to light emission characteristics but to be capable of controlling light emission characteristics of molecules. It is possible that "3−n" is 0, 1 or 2. Bidentate mono-anionic ligands for use in light-emitting materials can be selected from among those well-known in the industry. As bidentate mono-anionic ligands, the ligands described, for example, in Lamansky et al., PCT Application WO 02/15645, pages 89 to 90 can be exemplified, but the invention is not restricted thereto. Preferred bidentate mono-anionic sub-ligands include acetylacetonate (acac), picolinate (pic), and derivatives thereof.

In the invention, the metal complex including the main ligand represented by any of formulae (A1) to (A1-6) may consist of a combination of the main ligand or a tautomer thereof and the sub-ligand or a tautomer thereof, or all of the ligands of the metal complex may include the main ligand or the partial structure represented by the tautomer thereof alone.

In view of preferably obtaining the advantage of the invention, the kind of ligand in a complex is preferably consisting of one or two kinds, and more preferably consisting of one kind. In introducing a reactive group into complex molecules, it is also preferred that the ligand is consisting of two kinds for easiness of synthesis.

As sub-ligands for use in conventionally known metal complexes, various kinds of ligands are known. For example, the ligands as described in H. Yersin, Photochemistry and Photophysics of Coordination Compounds, published by Springer Verlag (1987), Akio Yamamoto, Yuki Kinzoku Kagaku—Kiso to Ouyou—(Organometallic Chemistry—Fundamentals and Applications—), Shokabo Publishing Co., Ltd. (1982) (e.g., halogen ligands (preferably chlorine ligands), nitrogen-containing heteroaryl ligands (e.g., bipyridyl, phenanthroline and the like), diketone ligands (e.g., acetylacetone and the like)) are exemplified. Sub-ligands preferred in the invention are diketones or picolinic acid derivatives.

The examples of sub-ligands are specifically shown below, but the invention is not restricted thereto.

(I-1)

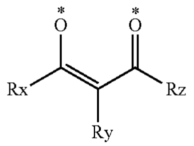

(I-2)

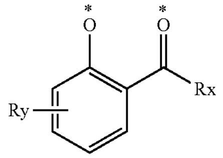

(1-3)

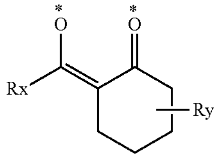

(I-4)

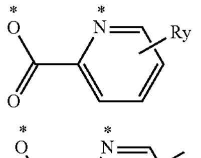

(I-5)

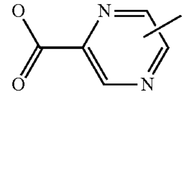

-continued (I-6)

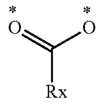

(I-7)

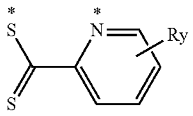

(I-8)

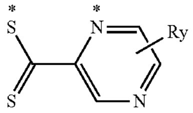

(I-9)

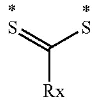

(I-10)

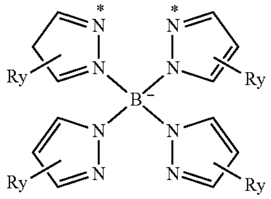

(I-11)

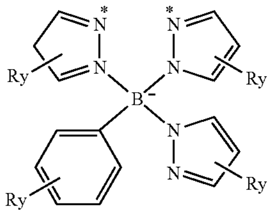

(I-12)

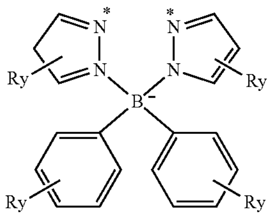

(1-13)

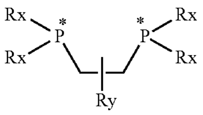

(I-14)

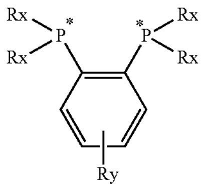

* Means a coorination position to a metal.

Each of the above Rx, Ry and Rz independently represents a hydrogen atom or a substituent. As the substituents, substituents selected from substituent group A are exemplified.

Preferably each of Rx and Rz independently represents any of an alkyl group, a perfluoroalkyl group, a halogen atom and an aryl group, more preferably an alkyl group having 1 to 4 carbon atoms, a perfluoroalkyl group having 1 to 4 carbon atoms, a fluorine atom, or a phenyl group which may be substituted, and most preferably a methyl group, an ethyl group, a trifluoromethyl group, a fluorine atom, or a phenyl group. Ry preferably represents any of a hydrogen atom, an alkyl group, a perfluoroalkyl group, a halogen atom and an aryl group, more preferably a hydrogen atom, an alkyl group having 1 to 4 carbon atoms, or a phenyl group which may be substituted, and most preferably either a hydrogen atom or a methyl group. Since these sub-ligands are considered not to be the site to transport electric charge in a device or the site where electrons are converged by excitation, it is enough for Rx, Ry and Rz to be chemically stable substituents, and so the invention is not affected.

In the above specific examples of sub-ligands, formulae (1-1), (1-4) and (1-5) are more preferred, (1-1) and (1-4) are still more preferred, and (1-1) is especially preferred.

In the light of stability of complex and light-emitting quantum yield, it is preferred that the bidentate mono-anionic ligand in the invention is acetylacetonate (acac).

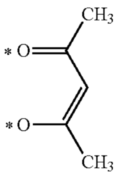

acac

In formula (A10), from the point of easiness of synthesis, n is preferably 3, but it is also preferred in view of the reduction of manufacturing cost to replace the ligand with an inexpensive sub-ligand by making n1 or 2.

When n is 3, formula (A10) is represented by the following formula (A10-1).

(A10-1)

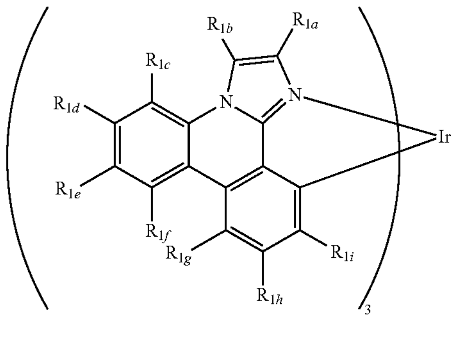

In formula (A10-1), each of $R_{1a}$ to $R_{1i}$ independently represents a hydrogen atom or a substituent, provided that at least one of $R_{1a}$ to represents a substituent.

In formula (A10-1), preferred $R_{1a}$ to $R_{1i}$ are the same with preferred $R_{1a}$ to $R_{1i}$ in formulae (A1).

The specific examples of specific iridium complexes having a bidentate ligand represented by any of formulae (A1) to (A4) are shown below. The kinds of metal complexes A and B and the contents of metal complexes B to the contents of metal complexes A are shown in the following Tables 11 and 12.

-continued
compound 46
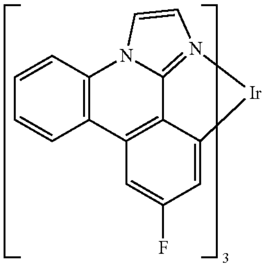
a46
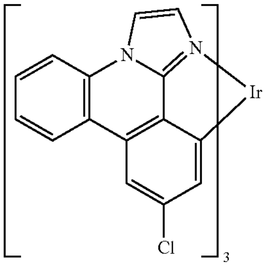
b46
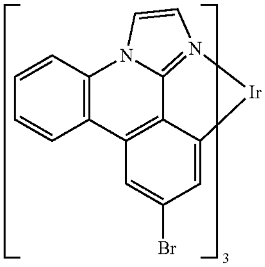
compound 47
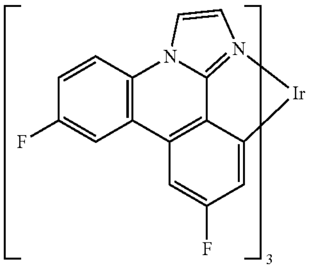
a47
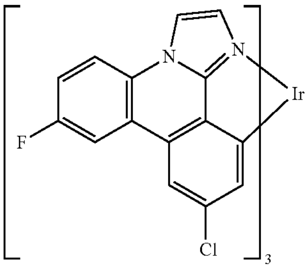
b47
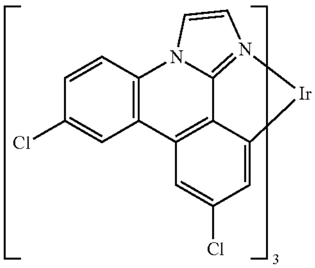
compound 48
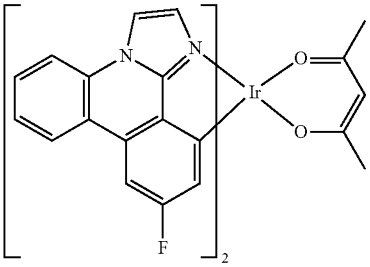
a48
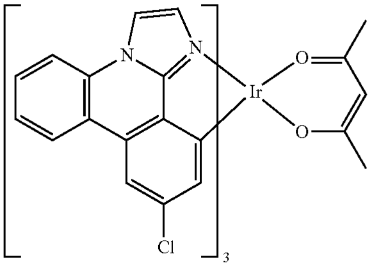
b48
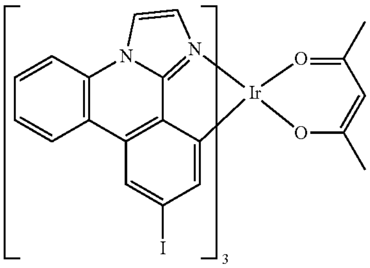
compound 49
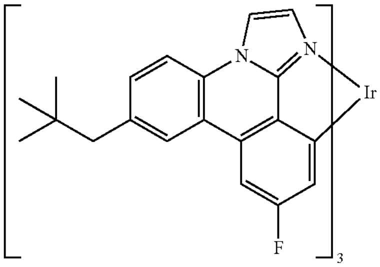
a49
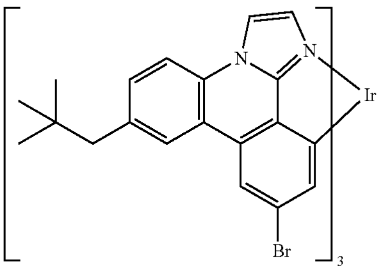
b49
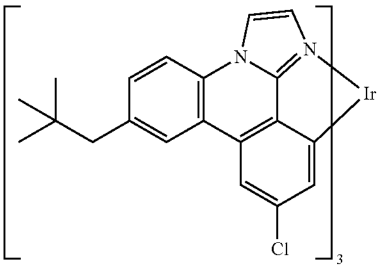

-continued
compound 50
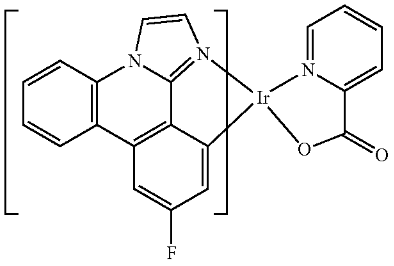
a50
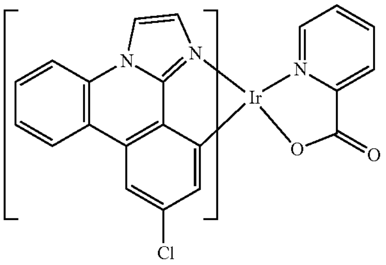
b50
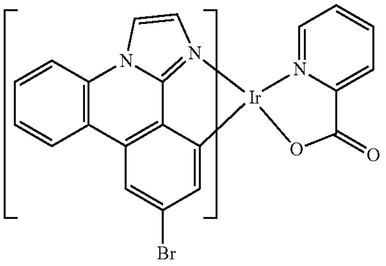
compound 51
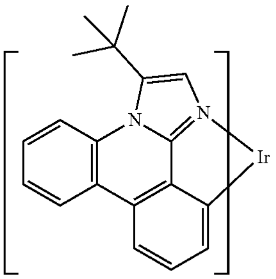
a51
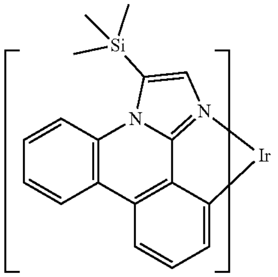
compound 52
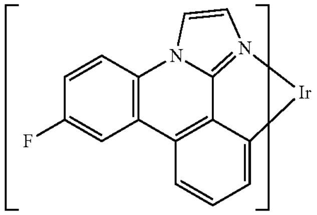
-continued
a52
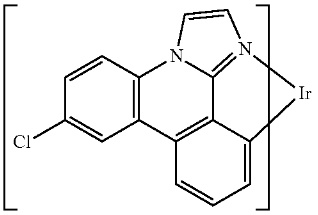
b52
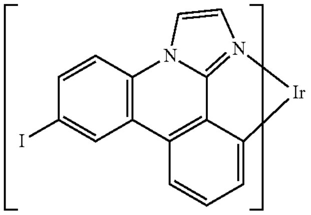
compound 53
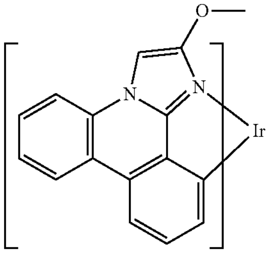
a53
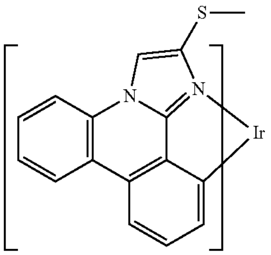
TABLE 11
| | | Metal Complex B | |
|---|---|---|---|
| Specific Example No. | Metal Complex A Compound No. | Compound No. | Content (% by mass) |
| 46-1-1 | 46 | a46 | 0.05 |
| 46-1-2 | 46 | a46 | 0.06 |
| 46-1-3 | 46 | a46 | 0.07 |
| 46-1-4 | 46 | a46 | 0.08 |
| 46-1-5 | 46 | a46 | 0.09 |
| 46-1-6 | 46 | a46 | 0.1 |
| 46-1-7 | 46 | a46 | 0.2 |
| 46-1-8 | 46 | a46 | 0.3 |
| 46-1-9 | 46 | a46 | 0.4 |
| 46-1-10 | 46 | a46 | 0.5 |
| 46-1-11 | 46 | a46 | 0.6 |
| 46-1-12 | 46 | a46 | 0.7 |
| 46-1-13 | 46 | a46 | 0.8 |
| 46-1-14 | 46 | a46 | 0.9 |
| 46-1-15 | 46 | a46 | 1 |
| 46-1-16 | 46 | a46 | 1.1 |
| 46-1-17 | 46 | a46 | 1.2 |
| 46-1-18 | 46 | a46 | 1.3 |
| 46-1-19 | 46 | a46 | 1.4 |
| 46-1-20 | 46 | a46 | 1.5 |
| 46-1-21 | 46 | a46 | 1.6 |
| 46-1-22 | 46 | a46 | 1.7 |
| 46-1-23 | 46 | a46 | 1.8 |

TABLE 11-continued

| Specific Example No. | Metal Complex A Compound No. | Metal Complex B Compound No. | Metal Complex B Content (% by mass) |
|---|---|---|---|
| 46-1-24 | 46 | a46 | 1.9 |
| 46-1-25 | 46 | a46 | 2 |
| 46-2-1 | 46 | b46 | 0.05 |
| 46-2-2 | 46 | b46 | 0.1 |
| 46-2-3 | 46 | b46 | 0.5 |
| 46-2-4 | 46 | b46 | 0.75 |
| 46-2-5 | 46 | b46 | 1 |
| 46-2-6 | 46 | b46 | 1.2 |
| 46-2-7 | 46 | b46 | 1.5 |
| 47-1-1 | 47 | a47 | 0.05 |
| 47-1-2 | 47 | a47 | 0.06 |
| 47-1-3 | 47 | a47 | 0.07 |
| 47-1-4 | 47 | a47 | 0.08 |
| 47-1-5 | 47 | a47 | 0.09 |
| 47-1-6 | 47 | a47 | 0.1 |
| 47-1-7 | 47 | a47 | 0.4 |
| 47-1-8 | 47 | a47 | 0.8 |
| 47-1-9 | 47 | a47 | 1.5 |
| 47-1-10 | 47 | a47 | 1.9 |
| 47-2-1 | 47 | b47 | 0.05 |
| 47-2-2 | 47 | b47 | 0.1 |
| 47-2-3 | 47 | b47 | 0.5 |
| 47-2-4 | 47 | b47 | 0.75 |
| 47-2-5 | 47 | b47 | 1 |
| 47-2-6 | 47 | b47 | 1.2 |
| 47-2-7 | 47 | b47 | 1.5 |
| 47-2-8 | 47 | b47 | 2 |

TABLE 12

| Specific Example No. | Metal Complex A Compound No. | Metal Complex B Compound No. | Metal Complex B Content (% by mass) |
|---|---|---|---|
| 48-1-1 | 48 | a48 | 0.05 |
| 48-1-2 | 48 | a48 | 0.1 |
| 48-1-3 | 48 | a48 | 0.5 |
| 48-1-4 | 48 | a48 | 0.75 |
| 48-1-5 | 48 | a48 | 1 |
| 48-1-6 | 48 | a48 | 1.2 |
| 48-1-7 | 48 | a48 | 1.5 |
| 48-1-8 | 48 | a48 | 1.6 |
| 48-1-9 | 48 | a48 | 1.7 |
| 48-1-10 | 48 | a48 | 1.99 |
| 48-2-1 | 48 | b48 | 0.6 |
| 48-2-2 | 48 | b48 | 0.8 |
| 48-2-3 | 48 | b48 | 1.4 |
| 49-1-1 | 49 | a49 | 0.05 |
| 49-2-1 | 49 | b49 | 0.1 |
| 49-2-2 | 49 | b49 | 0.3 |
| 49-2-3 | 49 | b49 | 0.6 |
| 49-2-4 | 49 | b49 | 1.4 |
| 49-2-5 | 49 | b49 | 1.8 |
| 50-1-1 | 50 | a50 | 0.08 |
| 50-1-2 | 50 | a50 | 0.09 |
| 50-1-3 | 50 | a50 | 0.1 |
| 50-1-4 | 50 | a50 | 0.5 |
| 50-2-1 | 50 | b50 | 0.05 |
| 50-2-2 | 50 | b50 | 0.5 |
| 50-2-3 | 50 | b50 | 2 |
| 51-1-1 | 51 | a51 | 0.05 |
| 51-1-2 | 51 | a51 | 1 |
| 51-1-3 | 51 | a51 | 1.1 |
| 51-1-4 | 51 | a51 | 1.2 |
| 52-1-1 | 52 | a52 | 1.3 |
| 52-1-2 | 52 | a52 | 1.4 |
| 52-1-3 | 52 | a52 | 1.5 |
| 52-1-4 | 52 | a52 | 1.7 |
| 52-1-5 | 52 | a52 | 1.9 |
| 52-2-1 | 52 | b52 | 0.05 |
| 52-2-2 | 52 | b52 | 0.06 |

TABLE 12-continued

| Specific Example No. | Metal Complex A Compound No. | Metal Complex B Compound No. | Metal Complex B Content (% by mass) |
|---|---|---|---|
| 52-2-3 | 52 | b52 | 0.08 |
| 52-2-4 | 52 | b52 | 0.1 |
| 52-2-5 | 52 | b52 | 0.2 |
| 53-1-1 | 53 | a53 | 0.05 |
| 53-1-2 | 53 | a53 | 0.06 |
| 53-1-3 | 53 | a53 | 0.07 |
| 53-1-4 | 53 | a53 | 0.08 |
| 53-1-5 | 53 | a53 | 0.09 |
| 53-1-6 | 53 | a53 | 0.1 |
| 53-1-7 | 53 | a53 | 0.4 |
| 53-1-8 | 53 | a53 | 0.5 |
| 53-1-9 | 53 | a53 | 0.6 |
| 53-1-10 | 53 | a53 | 0.9 |

$R_{1a}$, to $R_{1i}$ have the same meaning with the meaning of $R_{1a}$ to $R_{1i}$ in formula (A1), and the preferred range is also the same.

A phosphorescent metal complex containing a mono-anionic bidentate ligand represented by any of formulae (A1) to (A4) and a metal having an atomic weight of 40 or more can be synthesized by various methods, for example, the methods described in U.S. Patents 2007/0,190,359 and 2008/0,297,033.

It is also preferred that specific iridium complex is a compound represented by the following formula (P-1).

(P-1)

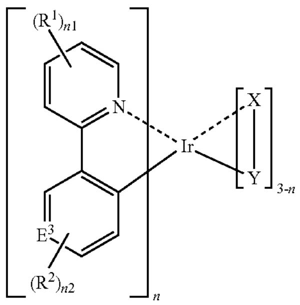

In formula (P-1), each of $R^1$ and $R^2$ independently represents a substituent. When two or more $R^1$'s and $R^2$'s are present, respective $R^1$'s and $R^2$'s may be the same with or different from each other. When two or more $R^1$'s and $R^2$'s are present, they may be bonded to each other to form a ring. Each of n1 and n2 independently represents an integer of 0 to 4, but there is no case where the sum of n1 and n2 is 0. $E^3$ represents a carbon atom or a nitrogen atom. X—Y represents a mono-anionic bidentate ligand. n represents an integer of 1 to 3.

n is preferably 2 or 3 and more preferably 2. $E^3$ preferably represents a carbon atom for the reason of the improvement of chemical stability of the complex. It is also preferred that $E^3$ represents a nitrogen atom from the viewpoint of short wave light emission.

$R^1$, $R^2$, n1 and n2 respectively have the same meaning with $R^1$, $R^2$, n1 and n2 in formula (1), and the preferred range of each is also the same.

As $R^1$ and $R^2$, the substituents selected from the above substituent group A are preferred, such as a halogen atom, a hydrocarbon substituent (preferably an alkyl group, a cycloalkyl group, an alkenyl group, an alkynyl group, a heteroalkyl group, an aryl group, a heteroaryl group), $OR_{2a}$, $SR_{2a}$, $NR_{2a}R_{2b}$, $BR_{2a}R_{2b}$, or $SiR_2$, $R_{2b}R_{2c}$. Each of $R_{2a}$, $R_{2b}$ and $R_{2c}$ independently represents a hydrocarbon substituent, or a hydrocarbon substituent substituted with a hetero atom. Two of $R_{1a}$ to $R_{1i}$ and $R_{2a}$ to $R_{2c}$ may be bonded to each other to form a saturated or unsaturated aromatic or non-aromatic ring.

When each of $R^1$ and $R^2$ represents an alkyl group, the alkyl group may further have a substituent, may be saturated or unsaturated, and as groups which may substitute, the following shown substituent Z can be exemplified. The alkyl group is preferably an alkyl group having total carbon atoms of 1 to 8, and more preferably an alkyl group having total carbon atoms of 1 to 6, e.g., a methyl group, an ethyl group, an i-propyl group, a cyclohexyl group, and a t-butyl group are exemplified.

As substituent Z, a halogen atom, —R', —OR', —N(R')$_2$, —SR', —C(O)R', —C(O)OR', —C(O)N(R')$_2$, —CN, —$NO_2$, —$SO_2$, —SOR', —$SO_2$R', and —$SO_3$R' are exemplified. Each of R' independently represents a hydrogen atom, an alkyl group, a perhaloalkyl group, an alkenyl group, an alkynyl group, a heteroalkyl group, an aryl group or a heteroaryl group.

When each of $R^1$ and $R^2$ represents a cycloalkyl group, the cycloalkyl group may further have a substituent, may be saturated or unsaturated, and as groups which may substitute, the above substituent Z can be exemplified. The cycloalkyl group is preferably a 4- to 7-membered cycloalkyl group, more preferably a cycloalkyl group having total carbon atoms of 5 or 6, e.g., a cyclopentyl group and a cyclohexyl group are exemplified.

When each of $R^1$ and $R^2$ represents an alkenyl group, the alkenyl group is preferably an alkenyl group having 2 to 30 carbon atoms, more preferably 2 to 20 carbon atoms, and especially preferably 2 to 10 carbon atoms, e.g., vinyl, allyl, 1-propenyl, 1-isopropenyl, 1-butenyl, 2-butenyl and 3-pentenyl are exemplified.

When each of $R^1$ and $R^2$ represents an alkynyl group, the alkynyl group is preferably an alkynyl group having 2 to 30 carbon atoms, more preferably 2 to 20 carbon atoms, and especially preferably 2 to 10 carbon atoms, e.g., ethynyl, propargyl, 1-propynyl, and 3-pentynyl are exemplified.

When each of $R^1$ and $R^2$ represents a heteroalkyl group, a group obtained by substituting at least one carbon atom of the alkyl group with O, NR or S can be exemplified.

When each of $R^1$ and $R^2$ represents a heteroaryl group, the heteroaryl group is preferably a heteroaryl group having 5 to 8 carbon atoms, and more preferably a 5- or 6-mbmered substituted or unsubstituted heteroalkyl group, e.g., a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulforanyl group, a carbazolyl group, a dibenzofuryl group, a dibenzothienyl group, and a 7 pyridoindolyl group are exemplified. Preferred examples of these groups are a pyridyl group, a pyrimidinyl group, an imidazolyl group, and a thienyl group, and more preferred are a pyridyl group and a pyrimidinyl group.

Each of $R^1$ and $R^2$ preferably represents an alkyl group, a cycloalkyl group, a cyano group, a perfluoroalkyl group, a dialkylamino group, an aryl group, a heteroaryl group or a halogen atom, more preferably an alkyl group, a cyano group, a perfluoromethyl group, an aryl group, or a halogen atom, still more preferably an alkyl group, an aryl group, a trifluoromethyl group or a halogen atom, and especially preferably a methyl group, an isobutyl group, a phenyl group or a fluorine atom.

As substituent Z, an alkyl group, an alkoxy group, a fluoro group, a cyano group, and a dialkylamino group are preferred, and an alkyl group is more preferred.

In formula (P-1), when plural $R^1$ and $R^2$ are present, they may be bonded to each other to form a ring. As a ring to be formed, a condensed 4- to 7-membered ring is preferred, and the condensed 4- to 7-membered ring is more preferably a cycloalkyl group, a cycloheteroalkyl group, an aryl group, or a heteroaryl group, and still more preferably an aryl group.

X—Y represents a mono-anionic bidentate ligand. It is possible that "3−n" is 0, 1 or 2. Bidentate mono-anionic ligands for use in light-emitting materials can be selected from among those well-known in the industry. As bidentate mono-anionic ligands, the ligands described, for example, in Lamansky et al., PCT Application WO 02/15645, pages 89 to 90 can be exemplified, but the invention is not restricted thereto. Preferred bidentate mono-anionic ligands include acetylacetonate (acac), picolinate (pic), and derivatives thereof.

In view of preferably obtaining the advantage of the invention, the kind of ligand in a complex is preferably consisting of one or two kinds, and more preferably consisting of one kind. In introducing a reactive group into complex molecules, it is also preferred that the ligand is consisting of two kinds for easiness of synthesis.

As ligands for use in conventionally known metal complexes, various kinds of ligands are known. For example, the ligands as described in H. Yersin, Photochemistry and Photophysics of Coordination Compounds, published, by Springer Verlag (1987), Akio Yamamoto, Yuki Kinzoku Kagaku —Kiso to Ouyou—(Organometallic Chemistry—Fundamentals and Applications—), Shokabo Publishing Co., Ltd. (1982) (e.g., halogen ligands (preferably chlorine ligands), nitrogen-containing heteroaryl ligands (e.g., bipyridyl, phenanthroline and the like), diketone ligands (e.g., acetylacetone and the like)) are exemplified. Preferred as X—Y are diketones or picolinic acid derivatives.

The preferred range of ligands is the same with X—Y in formula (A10). One of more preferred embodiments of the compound represented by formula (P-1) is a compound represented by the following formula (P-2).

(P-2)

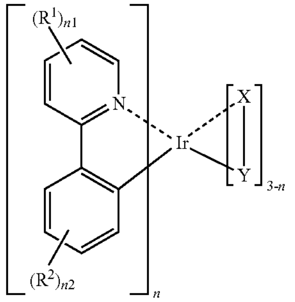

In formula (P-2), each of $R^1$ and $R^2$ independently represents an alkyl group, an alkenyl group, an alkynyl group, —CN, a perfluoroalkyl group, —$NR_2$, a halogen atom, an aryl group or a heteroaryl group, and each of these groups may further have a substituent Z. Each R independently represents a hydrogen atom, an alkyl group, an alkenyl group, an alkynyl group, a heteroalkyl group, an aryl group, or a heteroaryl group, and these groups may further have a substituent Z.

Contiguous arbitrary $R^1$ and $R^2$ are not bonded to each other to form a condensed ring.

Substituent Z independently represents a halogen atom, —R', —OR', —$N(R')_2$, —SR' or —CN. Each R' independently represents a hydrogen atom, an alkyl group, a perhaloalkyl group, an alkenyl group, an alkynyl group, a heteroalkyl group, an aryl group or a heteroaryl group.

Each of n1 and n2 independently represents an integer of 0 to 4, but there is no case where the sum of n1 and n2 is 0.

X—Y represents a bidentate mono-anionic ligand.

n represents an integer of 1 to 3.

In formula (P-2), the preferred ranges of $R^1$, $R^2$, n1, n2, X—Y and n are the same as in formula (P-1).

The compound represented by formula (P-2) is preferably a compound represented by the following formula (P-3).

(P-3)

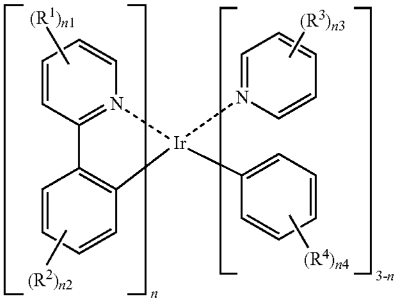

In formula (P-3), each of $R^1$, $R^2$, $R^3$ and $R^4$ independently represents an alkyl group, an alkenyl group, an alkynyl group, —CN, a perfluoroalkyl group, —$NR_2$, a halogen atom, an aryl group, or a heteroaryl group, and these groups may further have substituent Z. Each R independently represents a hydrogen atom, an alkyl group, an alkenyl group, an alkynyl group, a heteroalkyl group, an aryl group, or a heteroaryl group, and these groups may further have substituent Z.

Contiguous arbitrary $R^1$ and $R^2$ are not bonded to each other to form a condensed ring.

Substituent Z independently represents a halogen atom, —R', —OR', —$N(R')_2$, —SR' or —CN. Each R' independently represents a hydrogen atom, an alkyl group, a perhaloalkyl group, an alkenyl group, an alkynyl group, a heteroalkyl group, an aryl group or a heteroaryl group.

Each of n1, n2, n3 and n4 independently represents an integer of 0 to 4, but there is no case where the sum of n1, n2, n3 and n4 is 0.

n represents an integer of 1 or 2.

In formula (P-3), the preferred ranges of $R^1$, $R^2$, n1, n2 and n are the same as in formula (P-1). The preferred range of $R^3$ and $R^4$ is the same with the preferred range of $R^1$ and $R^2$, and the preferred range of n3 and n4 is the same with the preferred range of n1 and n2.

Another preferred embodiment of the compound represented by formula (P-1) is a compound represented by the following formula (P-4).

(P-4)

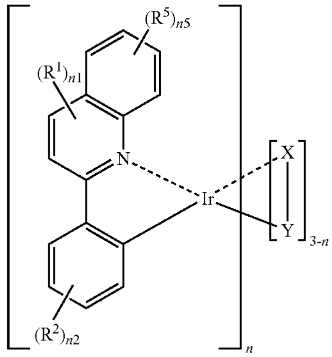

In formula (P-4), each of $R^1$, $R^2$ and $R^5$ independently represents a substituent. When two or more $R^1$'s, $R^2$'s and $R^5$'s are present, respective $R^1$'s, $R^2$'s and $R^5$'s may be the same with or different from each other. When the $R^1$'s, the $R^2$'s and the $R^5$'s are present, they may be bonded to each other to form a ring. n1 represents an integer of 0 to 2, n2 represents 0 to 4, and n5 represents 0 to 4, but there is no case where the sum of n1, n2 and n5 is 0. X—Y represents a bidentate mono-anionic ligand. n represents an integer of 1 to 3.

In formula (P-4), the preferred ranges of $R^1$, $R^2$, n1, n2, X—Y and n are the same as in formula (P-1). The preferred range of $R^5$ is the same with the preferred range of $R^1$ and $R^2$, and the preferred range of n5 is the same with the preferred range of n2.

Another preferred embodiment of the compound represented by formula (P-1) is a compound represented by the following formula (P-5).

(P-5)

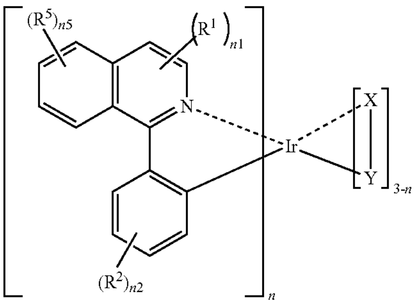

In formula (P-5), each of $R^1$, $R^2$ and $R^5$ independently represents a substituent.

When two or more $R^1$'s, $R^2$'s and $R^5$'s are present, respective $R^1$'s, $R^2$'s and $R^5$'s may be the same with or different from each other. When the $R^1$'s, the $R^2$'s and the $R^5$'s are present, they may be bonded to each other to form a ring. n1 represents an integer of 0 to 2, n2 represents 0 to 4, and n5 represents 0 to 4, but there is no case where the sum of n1, n2 and n5 is 0. X—Y represents a bidentate mono-anionic ligand. n represents an integer of 1 to 3.

In formula (P-5), the preferred ranges of $R^1$, $R^2$, n1, n2, X—Y and n are the same as in formula (P-1). The preferred range of $R^5$ is the same with the preferred range of $R^1$ and $R^2$, and the preferred range of n5 is the same with the preferred range of n2.

The specific examples of the compounds represented by formula (P-1) are shown below, but the invention is by no means limited thereto. The kinds of metal complexes A and B and the contents of metal complexes B to the contents of metal complexes A are shown in the following Tables 13 to 15 and 23.
compound 54
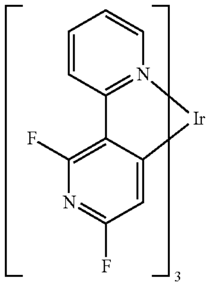
a54
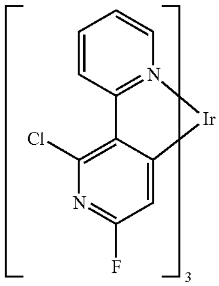
b54
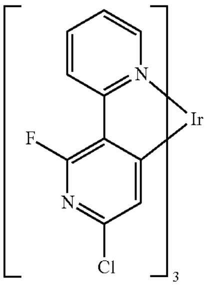
c54
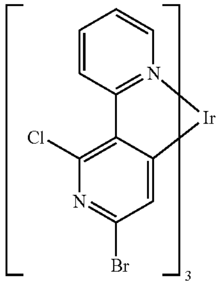
d54
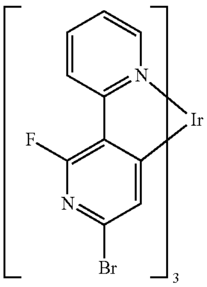
-continued
compound 55
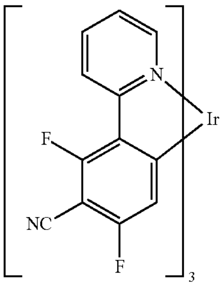
a55
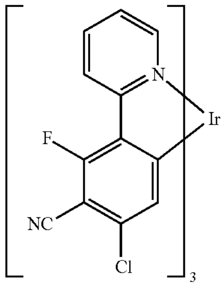
b55
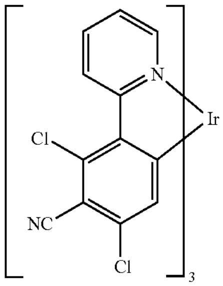
c55
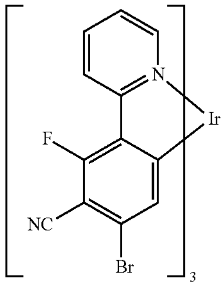
d55
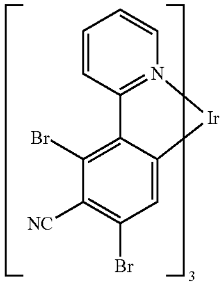

-continued
compound 56
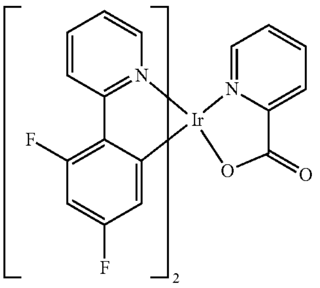
a56
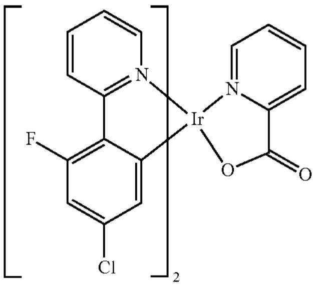
b56
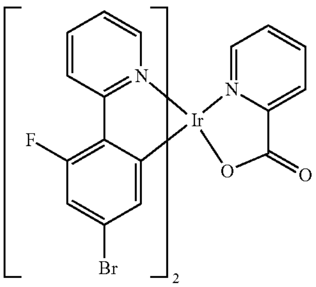
compound 57
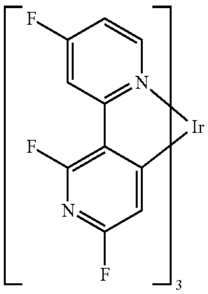
a57
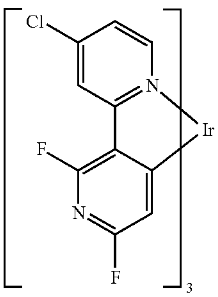
-continued
b57
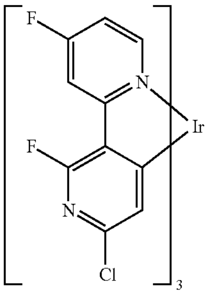
c57
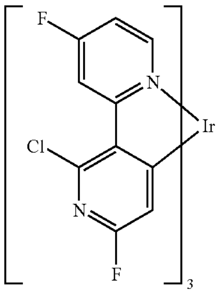
d57
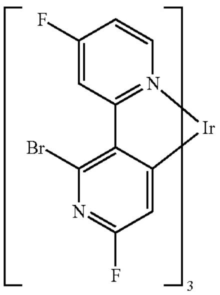
compound 58
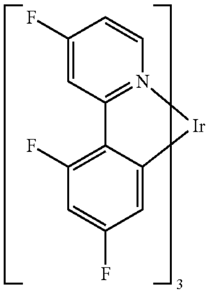
a58
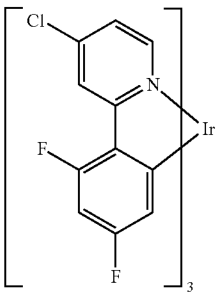

-continued
b58
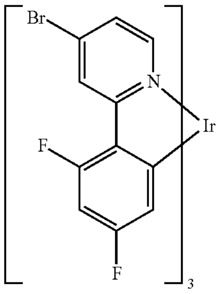
c58
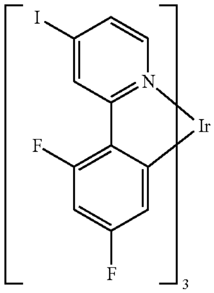
d58
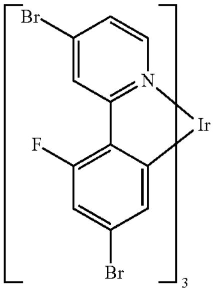
compound 59
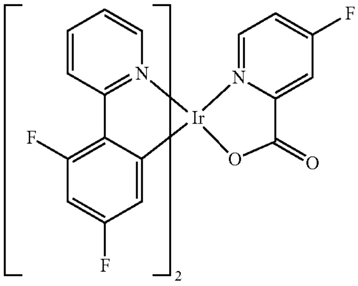
a59
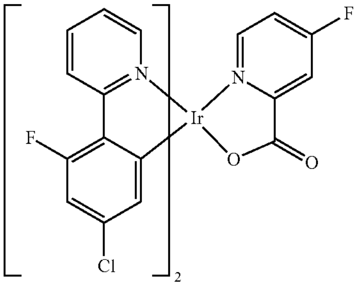
-continued
b59
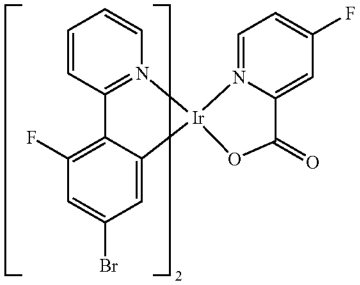
compound 60
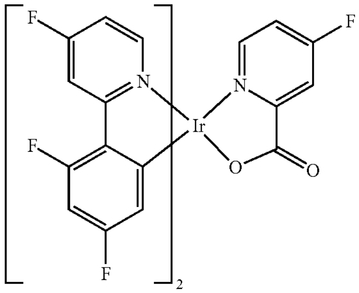
a60
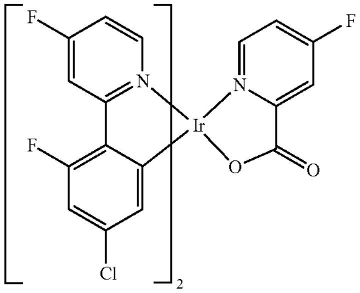
b60
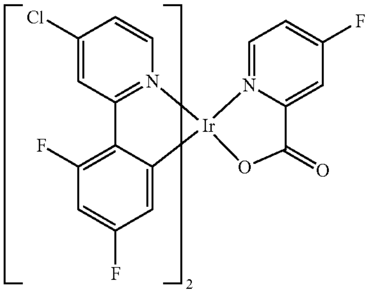
compound 61
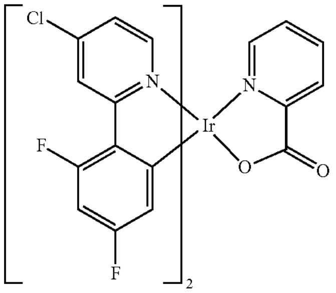

-continued
a61
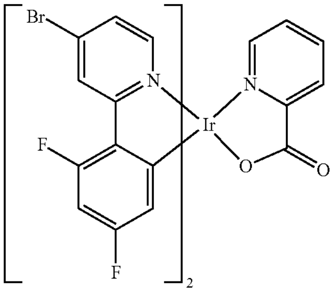
b61
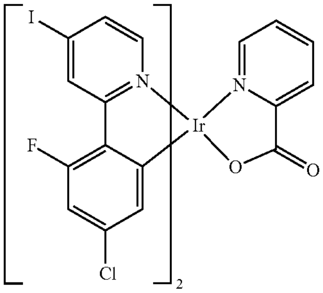
compound 62
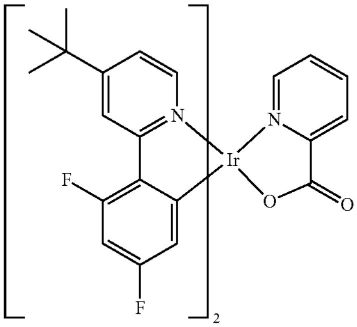
a62
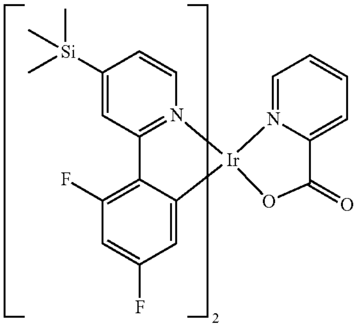
b62
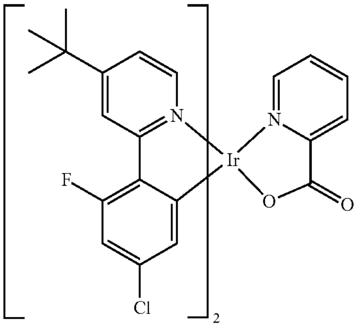
-continued
compound 63
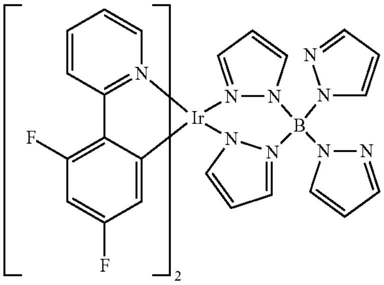
a63
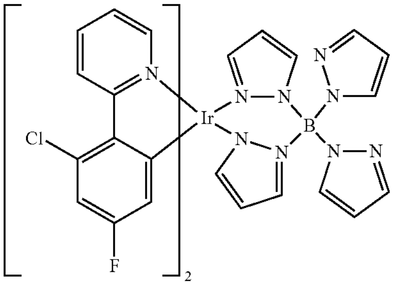
compound 64
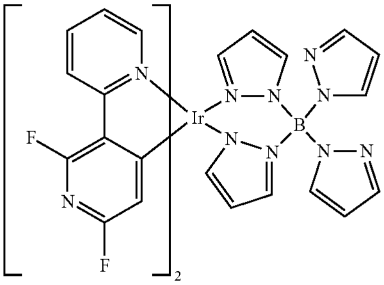
a64
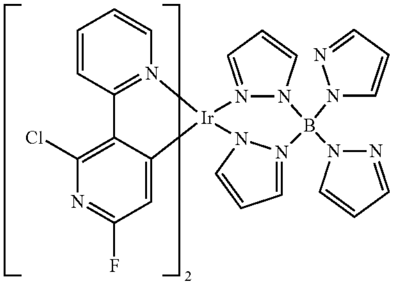
compound 65
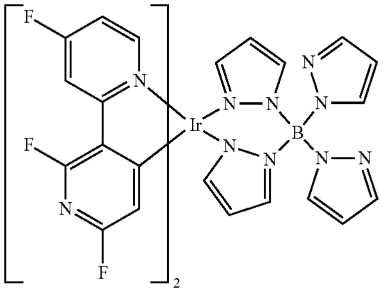

-continued
a65
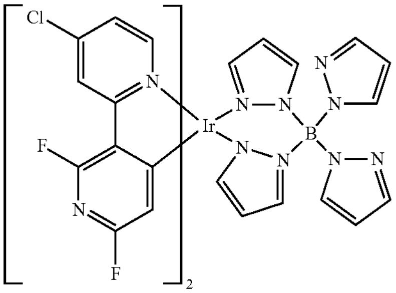
compound 66
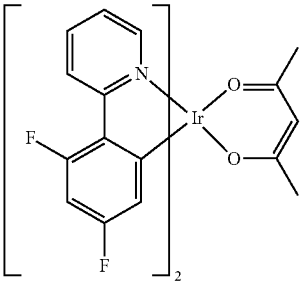
a66
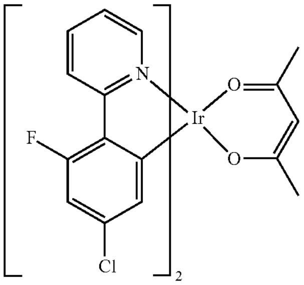
b66
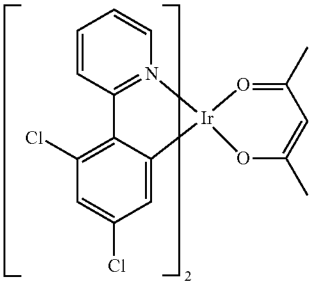
compound 90
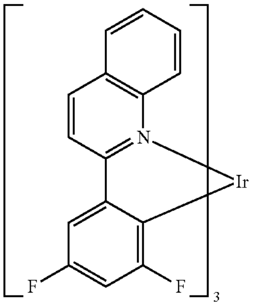
-continued
a90
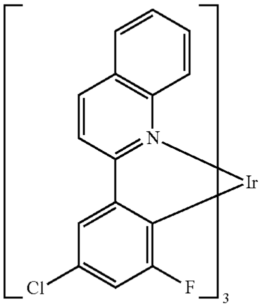
b90
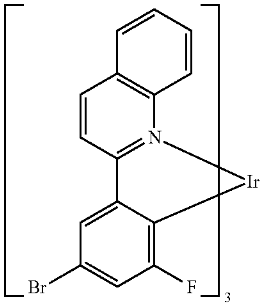
compound 91
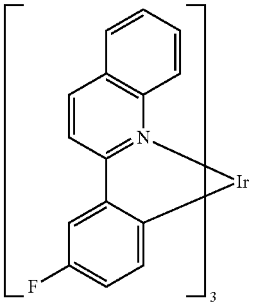
a91
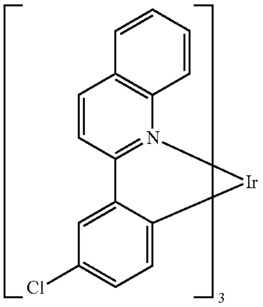
b91
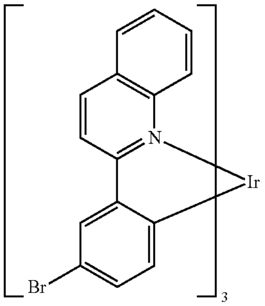

-continued
compound 92
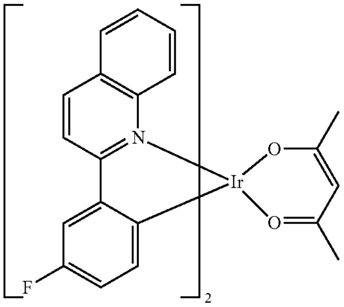
a92
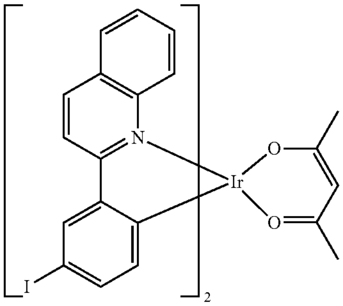
b92
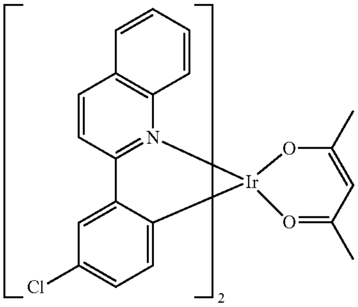
compound 93
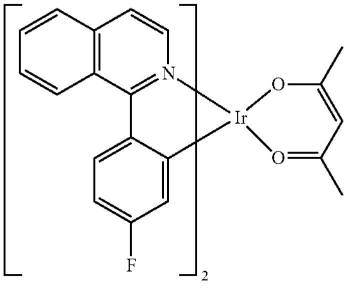
a93
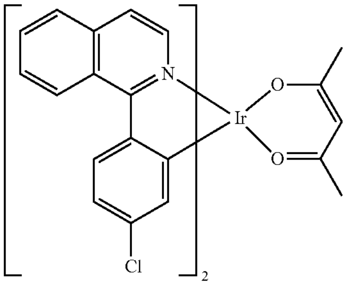
-continued
compound 94
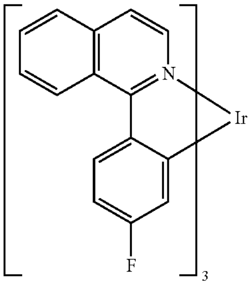
a94
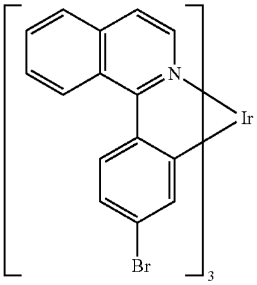
TABLE 13
| Specific Example No. | Metal Complex A Compound No. | Metal Complex B Compound No. | Metal Complex B Content (% by mass) |
|---|---|---|---|
| 54-1-1 | 54 | a54 | 0.05 |
| 54-1-2 | 54 | a54 | 0.06 |
| 54-1-3 | 54 | a54 | 0.07 |
| 54-1-4 | 54 | a54 | 0.08 |
| 54-1-5 | 54 | a54 | 0.09 |
| 54-1-6 | 54 | a54 | 0.1 |
| 54-1-7 | 54 | a54 | 0.2 |
| 54-1-8 | 54 | a54 | 0.3 |
| 54-1-9 | 54 | a54 | 0.4 |
| 54-1-10 | 54 | a54 | 0.5 |
| 54-1-11 | 54 | a54 | 1 |
| 54-1-12 | 54 | a54 | 1.2 |
| 54-1-13 | 54 | a54 | 1.5 |
| 54-1-14 | 54 | a54 | 1.8 |
| 54-1-15 | 54 | a54 | 2 |
| 54-2-1 | 54 | b54 | 0.05 |
| 54-2-2 | 54 | b54 | 0.06 |
| 54-2-3 | 54 | b54 | 0.07 |
| 54-2-4 | 54 | b54 | 0.08 |
| 54-2-5 | 54 | b54 | 0.09 |
| 54-2-6 | 54 | b54 | 0.1 |
| 54-2-7 | 54 | b54 | 0.2 |
| 54-2-8 | 54 | b54 | 0.3 |
| 54-2-9 | 54 | b54 | 0.4 |
| 54-2-10 | 54 | b54 | 0.5 |
| 54-3-1 | 54 | c54 | 0.05 |
| 54-3-2 | 54 | c54 | 0.2 |
| 54-3-3 | 54 | c54 | 0.6 |
| 54-3-4 | 54 | c54 | 0.7 |
| 54-3-5 | 54 | c54 | 0.95 |
| 54-4-1 | 54 | d54 | 0.2 |
| 54-4-2 | 54 | d54 | 0.6 |
| 54-4-3 | 54 | d54 | 0.7 |
| 54-4-4 | 54 | d54 | 0.95 |
| 54-4-5 | 54 | d54 | 1.3 |
| 55-1-1 | 55 | a55 | 0.05 |
| 55-1-2 | 55 | a55 | 0.1 |
| 55-1-3 | 55 | a55 | 0.2 |
| 55-1-4 | 55 | a55 | 0.6 |
| 55-1-5 | 55 | a55 | 0.7 |
| 55-1-6 | 55 | a55 | 0.95 |
| 55-1-7 | 55 | a55 | 1.9 |

TABLE 13-continued

| Specific Example No. | Metal Complex A Compound No. | Metal Complex B Compound No. | Metal Complex B Content (% by mass) |
|---|---|---|---|
| 55-2-1 | 55 | b55 | 0.8 |
| 55-2-2 | 55 | b55 | 0.9 |
| 55-2-3 | 55 | b55 | 1.6 |
| 55-3-1 | 55 | c55 | 1.1 |
| 55-3-2 | 55 | c55 | 1.9 |
| 55-4-1 | 55 | d55 | 1.5 |
| 55-4-2 | 55 | d55 | 2 |

TABLE 14

| Specific Example No. | Metal Complex A Compound No. | Metal Complex B Compound No. | Metal Complex B Content (% by mass) |
|---|---|---|---|
| 56-1-1 | 56 | a56 | 0.1 |
| 56-1-2 | 56 | a56 | 0.3 |
| 56-1-3 | 56 | a56 | 0.6 |
| 56-1-4 | 56 | a56 | 1.4 |
| 56-1-5 | 56 | a56 | 1.8 |
| 56-2-1 | 56 | b56 | 0.05 |
| 56-2-2 | 56 | b56 | 2 |
| 57-1-1 | 57 | a57 | 0.05 |
| 57-1-2 | 57 | a57 | 0.07 |
| 57-1-3 | 57 | a57 | 0.08 |
| 57-1-4 | 57 | a57 | 0.1 |
| 57-1-5 | 57 | a57 | 0.2 |
| 57-1-6 | 57 | a57 | 0.5 |
| 57-1-7 | 57 | a57 | 0.7 |
| 57-1-8 | 57 | a57 | 1 |
| 57-1-9 | 57 | a57 | 1.44 |
| 57-1-10 | 57 | a57 | 2 |
| 57-2-1 | 57 | b57 | 0.05 |
| 57-2-2 | 57 | b57 | 0.1 |
| 57-2-3 | 57 | b57 | 0.5 |
| 57-2-4 | 57 | b57 | 1 |
| 57-2-5 | 57 | b57 | 1.8 |
| 57-2-6 | 57 | b57 | 1.9 |
| 57-2-7 | 57 | b57 | 2 |
| 57-3-1 | 57 | c57 | 0.05 |
| 57-3-2 | 57 | c57 | 0.06 |
| 57-3-3 | 57 | c57 | 0.07 |
| 57-3-4 | 57 | c57 | 0.08 |
| 57-3-5 | 57 | c57 | 0.09 |
| 57-3-6 | 57 | c57 | 0.1 |
| 57-3-7 | 57 | c57 | 1 |
| 57-4-1 | 57 | d57 | 1 |
| 58-1-1 | 58 | a58 | 0.1 |
| 58-1-2 | 58 | a58 | 1 |
| 58-1-3 | 58 | a58 | 1.5 |
| 58-2-1 | 58 | b58 | 0.1 |
| 58-2-2 | 58 | b58 | 1. |
| 58-2-3 | 58 | b58 | 1.5 |
| 58-3-1 | 58 | c58 | 2 |
| 58-4-1 | 58 | d58 | 0.06 |
| 58-4-2 | 58 | d58 | 0.07 |
| 59-1-1 | 59 | a59 | 0.1 |
| 59-1-2 | 59 | a59 | 0.5 |
| 59-1-3 | 59 | a59 | 0.9 |
| 59-2-1 | 59 | b59 | 0.05 |
| 59-2-2 | 59 | b59 | 0.1 |
| 59-2-3 | 59 | b59 | 0.5 |
| 59-2-4 | 59 | b59 | 1 |
| 59-2-5 | 59 | b59 | 1.8 |

TABLE 15

| Specific Example No. | Metal Complex A Compound No. | Metal Complex B Compound No. | Metal Complex B Content (% by mass) |
|---|---|---|---|
| 60-1-1 | 60 | a60 | 0.08 |
| 60-1-2 | 60 | a60 | 0.2 |
| 60-1-3 | 60 | a60 | 0.25 |
| 60-1-4 | 60 | a60 | 0.7 |
| 60-1-5 | 60 | a60 | 1.25 |
| 60-2-1 | 60 | b60 | 0.2 |
| 60-2-2 | 60 | b60 | 2 |
| 61-1-1 | 61 | a61 | 0.05 |
| 61-2-1 | 61 | a61 | 0.1 |
| 61-3-1 | 61 | a61 | 0.11 |
| 62-1-1 | 62 | a62 | 0.5 |
| 62-2-1 | 62 | b62 | 0.1 |
| 62-2-2 | 62 | b62 | 0.5 |
| 62-2-3 | 62 | b62 | 0.9 |
| 62-2-4 | 62 | b62 | 1.5 |
| 62-2-5 | 62 | b62 | 1.7 |
| 63-1-1 | 63 | a63 | 0.05 |
| 63-1-2 | 63 | a63 | 0.05 |
| 63-1-3 | 63 | a63 | 0.06 |
| 63-1-4 | 63 | a63 | 0.07 |
| 63-1-5 | 63 | a63 | 0.08 |
| 64-1-1 | 64 | a64 | 0.09 |
| 64-1-2 | 64 | a64 | 0.1 |
| 64-1-3 | 64 | a64 | 0.2 |
| 64-1-4 | 64 | a64 | 0.3 |
| 64-1-5 | 64 | a64 | 0.4 |
| 64-1-6 | 64 | a64 | 0.5 |
| 64-1-7 | 64 | a64 | 1 |
| 65-1-1 | 65 | a65 | 0.08 |
| 65-1-2 | 65 | a65 | 0.2 |
| 65-1-3 | 65 | a65 | 0.25 |
| 65-1-4 | 65 | a65 | 0.7 |
| 65-1-5 | 65 | a65 | 1.25 |
| 66-1-1 | 66 | a66 | 0.1 |
| 66-1-2 | 66 | a66 | 0.55 |
| 66-1-3 | 66 | a66 | 1 |
| 66-2-1 | 66 | b66 | 0.05 |
| 66-2-2 | 66 | b66 | 2 |

TABLE 23

| Specific Example No. | Metal Complex A Compound No. | Metal Complex B Compound No. | Metal Complex B Content (% by mass) |
|---|---|---|---|
| 90-1-1 | 90 | a90 | 0.005 |
| 90-1-2 | 90 | a90 | 0.05 |
| 90-1-3 | 90 | a90 | 0.01 |
| 90-1-4 | 90 | a90 | 0.2 |
| 90-1-5 | 90 | a90 | 0.5 |
| 90-1-6 | 90 | a90 | 1 |
| 90-1-7 | 90 | a90 | 1.2 |
| 90-1-8 | 90 | a90 | 1.5 |
| 90-1-9 | 90 | a90 | 2 |
| 90-2-1 | 90 | b90 | 0.005 |
| 90-2-2 | 90 | b90 | 0.6 |
| 90-2-3 | 90 | b90 | 1.15 |
| 91-1-1 | 91 | a91 | 0.05 |
| 91-1-2 | 91 | a91 | 0.5 |
| 91-1-3 | 91 | a91 | 1 |
| 91-1-4 | 91 | a91 | 1.5 |
| 91-1-5 | 91 | a91 | 2 |
| 91-2-1 | 91 | b91 | 0.05 |
| 91-2-2 | 91 | b91 | 0.5 |
| 91-2-3 | 91 | b91 | 1 |
| 91-2-4 | 91 | b91 | 1.5 |
| 91-2-5 | 91 | b91 | 2 |
| 92-1-1 | 92 | a92 | 0.5 |
| 92-2-1 | 92 | b92 | 0.5 |
| 92-2-2 | 92 | b92 | 2 |
| 93-1-1 | 93 | a93 | 0.005 |

TABLE 23-continued

| Specific Example No. | Metal Complex A Compound No. | Metal Complex B Compound No. | Metal Complex B Content (% by mass) |
|---|---|---|---|
| 93-1-2 | 93 | a93 | 0.05 |
| 93-1-3 | 93 | a93 | 0.01 |
| 93-1-4 | 93 | a93 | 0.2 |
| 93-1-5 | 93 | a93 | 0.5 |
| 93-1-6 | 93 | a93 | 1 |
| 93-1-7 | 93 | a93 | 1.2 |
| 93-1-8 | 93 | a93 | 1.5 |
| 93-1-9 | 93 | a93 | 2 |
| 94-1-1 | 94 | a94 | 0.005 |
| 94-1-2 | 94 | a94 | 0.6 |
| 94-1-3 | 94 | a94 | 1.15 |
| 94-1-4 | 94 | a94 | 1.5 |

The compounds represented by formula (P-1) can be synthesized by combining various known synthesis methods, for example, these compounds can be synthesized according to the methods disclosed in WO 2009/073245 and WO 2009/073246.

(Phosphorescent Metal Complex B)

The material for an organic electroluminescence device of the invention contains at least metal complex A and metal complex B, which are specific phosphorescent metal complexes, and the ratio of the content of metal complex B to the content of metal complex A is 0.005% by mass or more and 2% by mass or less. From the point of not changing the light emission characteristics of the device, the content of metal complex B is the smaller the better, so long as the advantage of the invention can be obtained, preferably 0.005% by mass or more and 1% by mass or less. However, since it is difficult to maintain mixing ratio when the content is too small, the content is more preferably 0.01% by mass or more and 1% by mass or less, and most preferably 0.01% by mass or more and 0.5% by mass or less.

Metal complex B in the invention has the same structure with metal complex A except that, in at least one substituent of $R^1$ and $R^2$ in formula (1), one or more atoms directly bonding to $Q^1$ or $Q^2$ are substituted with atoms belonging to the same group of the atoms and having a greater atomic weight. For example, when metal complex A has a fluorine atom, metal complex B is a metal complex in which the fluorine atom of metal complex A is substituted with an atom other than the fluorine atom and having a greater atomic weight, e.g., a halogen atom (e.g., a chlorine atom). It is preferred that atoms directly bonding to $Q^1$ or $Q^2$ are preferably selected from Group XIV to Group XVII of the Periodic Table. As the atoms belonging to Group XIV, a carbon atom and a silicon atom are preferred, and a carbon atom is more preferred. As the atoms belonging to Group XV, a nitrogen atom and a phosphorus atom are preferred, and a nitrogen atom is more preferred. As the atoms belonging to Group XVI, an oxygen atom and a sulfur atom are preferred, and an oxygen atom is more preferred. From the aspect of maintaining light emission wavelength when made to a device, the atoms belonging to Group XVII, i.e., a halogen atom, is more preferred. It is preferred that metal complex A contains a fluorine atom as at least one of $R^1$ and $R^2$ in formula (1), and in metal complex B, at least one of the fluorine atoms of metal complex A is substituted with a halogen atom other than a fluorine atom, and it is especially preferred that metal complex B is substituted with a chlorine atom.

When plural substituents are present in metal complex A, atoms bonding to $Q^1$ and $Q^2$ in all of these substituents may be substituted with "atoms belonging to the same group and having a greater atomic weight" in metal complex B, or may be partially substituted.

The reason why the material for an organic electroluminescence device in the invention is excellent in stability under visible light is not proved in detail, but it is considered that the complexes accepted light excitation by visible light do not decompose themselves but transport energy to complexes scattered in aggregation in a solid state, and decomposition occurs at that part by convergence of light excitation energy. When metal complex B having a different structure is contained in metal complex A in a content ratio of a specific range as in the invention, metal complex B functions as an additive to disturb configuration in a solid state, thus it is considered that energy load under visible light is dispersed and stability is improved. When mixing rate of metal complex B is too great, this effect is considered to weaken. This effect conspicuously functions in a case where metal complex B has a substituent having an excluded volume in a crystal state greater than that of metal complex A, and so preferred. On the other hand, even when excluded volume of a substituent is great, in a case where metal complex B has atoms in a substituent which are the atoms not belonging to the same group with the atoms of metal complex A, T1 value and chemical stability greatly differ between two kinds of metal complexes due to difference in the effect of substituent, light emission efficiency lowers by trapping of energy and charge in the device, which causes durability deterioration at driving time and the above effect cannot be obtained. Further, when the device is driven at high luminance, a deactivation phenomenon generally called T-T annihilation occurs and triplet energy formed in the complex is lost. This is considered for the reason that when complexes in an excitation state are present in close vicinity, energy transfer is caused by bimolecular impingement and the other party is deactivated to a ground state (Kinzoku Sakutai no Kohkagaku (Photochemistry of Metal Complexes), page 162, Sankyo Publishing Co., Ltd.). It is presumed that relative configuration and distance from the complex in close vicinity vary by the presence of the second complex at this time, and T-T annihilation is difficult to occur. The best effect of this function is seen when fluorine atoms which conspicuously lessen intermolecular interaction are substituted with other halogen atoms.

The invention also relates to a composition containing at least metal complex A and metal complex B, i.e., specific phosphorescent metal complexes.

By using the composition according to the invention, a material for an organic electroluminescence device which can be stably preserved under visible light and excellent in efficiency when the device is driven at high luminance can be obtained.

Other components can be further added to the composition of the invention.

The content in total of metal complexes A and B in the composition of the invention is preferably 1% by mass or more and 30% by mass or less to all the solids content in the composition, and more preferably 5% by mass or more and 20% by mass or less.

[Organic Electroluminescence Device]

The organic electroluminescence device according to the invention will be described below.

The organic electroluminescence device according to the invention includes a substrate having thereon a pair of electrodes and at least one organic layer including a light-emitting layer between the pair of electrodes, wherein at least one layer of the organic layer contains a phosphorescent metal complex containing a mono-anionic bidentate ligand and a metal having an atomic weight of 40 or more.

The organic electroluminescence device according to the invention preferably contains metal complexes A and B which are the specific phosphorescent metal complexes.

In the organic electroluminescence device according to the invention, the light-emitting layer is an organic layer and the device may further include plural organic layers.

From the nature of the electroluminescence device, it is preferred that at least one electrode of the anode and cathode is transparent or translucent.

FIG. 1 is a drawing showing an example of the constitution of the organic electroluminescence device according to the invention. Organic electroluminescence device 10 according to the invention shown in FIG. 1 includes substrate 2 having thereon light-emitting layer 6 between anode 3 and cathode 9. Specifically, hole-injecting layer 4, hole-transporting layer 5, light-emitting layer 6, hole-blocking layer 7, and electron-transporting layer 8 are laminated in this order between anode 3 and cathode 9.

<Constitution of Organic Layer>

The layer constitution of the organic layer is not especially restricted and the organic layer can be arbitrarily selected according to the use and purpose of the organic electroluminescence device, but the organic layer is preferably formed on the transparent electrode or back electrode. In this case, the organic layer is formed on the front or on one side on the transparent electrode or back electrode.

The shape, size and thickness of the organic layer are not especially restricted and these can be arbitrarily selected according to purposes.

As the specific layer constitutions, the following are exemplified but the invention is not restricted to these constitutions.

Anode/hole-transporting layer/light-emitting layer/electron-transporting layer/cathode Anode/hole-transporting layer/light-emitting layer/blocking layer/electron transporting layer/cathode Anode/hole-transporting layer/light-emitting layer/blocking layer/electron transporting layer/electron-injecting layer/cathode Anode/hole-injecting layer/hole-transporting layer/light-emitting layer/blocking layer/electron-transporting layer/cathode Anode/hole-injecting layer/hole-transporting layer/light-emitting layer/blocking layer/electron-transporting layer/electron-injecting layer/cathode The constitutions of devices, substrates, cathodes and anodes of organic electroluminescence devices are described in detail in, e.g., JP-A-2008-270736, and the items described therein can be applied to the invention.

<Substrate>

The substrate for use in the invention is preferably a substrate that does not scatter or attenuate the light emitted from the organic layer. Organic materials are preferably excellent in heat resistance, dimensional stability, solvent resistance, an electric insulating property and a processing property.

<Anode>

The anode is generally sufficient to have the function as the electrode to supply holes to the organic layer. The shape, structure and size of the anode are not especially restricted, and these can be arbitrarily selected from known materials of electrode in accordance with the intended use and purpose of the luminescence device. As described above, the anode is generally provided as a transparent anode.

<Cathode>

The cathode is generally sufficient to have the function as the electrode to inject electrons to the organic layer. The shape, structure and size of the cathode are not especially restricted, and these can be arbitrarily selected from known materials of electrode in accordance with the intended use and purpose of the luminescence device.

Regarding the substrate, anode and cathode, descriptions in JP-A-2008-270736, paragraphs [0070] to [0089] can be applied to the invention.

<Organic Layer>

The organic layer in the invention is described below.

—Formation of Organic Layers—

In the organic electroluminescence device of the invention, each organic layer can be preferably formed by any of dry film-forming processes such as a vacuum deposition method, a sputtering method, and solution-coating processes such as a transfer method, a printing method, a spin coating method, a bar coating method, an inkjet method, a spraying method, and the like. It is considered that the use of solution-coating processes leads to improvement of productivity and realization of organic EL devices of a large area.

As dry processes, a vacuum deposition method and a sputtering method can be used, and as wet processes, a dipping method, a spin coating method, a dip coating method, a casting method, a die coating method, a roll coating method, a bar coating method, a gravure coating method, a spray coating method and an inkjet method can be used. These film-forming methods can be arbitrarily selected according to the materials of organic layers. A layer formed by any of wet processes may be dried after forming the film. Conditions such as temperature and pressure are selected so as not to damage the coated layer.

The coating solution for use in the above wet processes (coating processes) generally includes the material of an organic layer and a solvent for dissolving or dispersing the material. Solvents are not especially restricted and selected according to the material for use in the organic layer.

When a material for an organic electroluminescence device is used as a coating solution, the content of the material in the coating solution is preferably 0.1% by mass to 50% by mass on the basis of all the solids content, more preferably 0.3% by mass to 40% by mass, and still more preferably 0.3% by mass to 30% by mass. Viscosity is usually preferably 1 mPa·s to 30 mPa·s, more preferably 1.5 mPa·s to 20 mPa·s, and still more preferably 1.5 mPa·s to 15 mPa·s.

A material for an organic electroluminescence device is preferably dissolved in a prescribed organic solvent, and after filtering, coated on a prescribed support or layer. The pore size of the filter for use in filtration is preferably 2.0 μm or less, more preferably 0.5 μm or less, and still more preferably 0.3 μm or less, and filters made of polytetrafluoroethylene (PTFE), polyethylene, or nylon are preferably used.

As solvents, well-known organic solvents, for example, aromatic hydrocarbon solvents, alcohol solvents, ketone solvents, aliphatic hydrocarbon solvents, and amide solvents can be exemplified.

As aromatic hydrocarbon solvents, e.g., benzene, toluene, xylene, trimethylbenzene, tetramethylbenzene, cumene, ethylbenzene, methylpropylbenzene, and methylisopropylbenzene are exemplified, and toluene, xylene, cumene, and trimethylbenzene are more preferred. Dielectric constant of aromatic hydrocarbon solvents is generally 3 or less.

As alcohol solvents, methanol, ethanol, butanol, benzyl alcohol, and cyclohexanol are exemplified, and butanol, benzyl alcohol, and cyclohexanol are more preferred. Dielectric constant of alcohol solvents is generally 10 to 40.

As ketone solvents, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetylcarbinol, acetophenone, methyl naphthyl ketone, isophorone, and propylene carbonate are exemplified, and methyl ethyl ketone, methyl isobutyl ketone, and propylene carbonate are preferred. Dielectric constant of ketone solvents is generally 10 to 90.

As aliphatic hydrocarbon solvents, pentane, hexane, octane and decane are exemplified, and octane and decane are preferred. Dielectric constant of aliphatic hydrocarbon solvents is generally 1.5 to 2.0.

As amide solvents, N-methyl-2-pyrrolidone, N-ethyl-2-pyrrolidone, N,N-dimethylacetamide, N,N-dimethylformamide, 1,3-dimethyl-2-imidazolidinone are exemplified, and N-methyl-2-pyrrolidone and 1,3-dimethyl-2-imidazolidinone are preferred. Dielectric constant of amide solvents is generally 30 to 40.

The above solvents may be used singly, or two or more kinds may be used in combination.

Further, an aromatic hydrocarbon solvent (hereinafter also referred to as "first solvent") and a second solvent having dielectric constant higher than that of the first solvent may be used as mixture.

As the second solvent, it is preferred to use alcohol solvents, amide solvents and ketone solvents, and use of alcohol solvents is more preferred.

The mixing ratio (by mass) of the first solvent and the second solvent is 1/99 to 99/1, preferably 10/90 to 90/10, and more preferably 20/80 to 70/30. A mixed solvent containing 60% by mass or more of the first solvent is preferred.

In a case where a compound having a polymerizable group is added to a coating solution for forming an organic layer, and a polymer for forming an organic layer is formed by polymerization reaction of the compound having a polymerizable group, the polymer can be formed by heating or irradiation after coating an organic film to accelerate the polymerization reaction.

Heating temperature and time after coating are not especially restricted so long as polymerization reaction proceeds, but heating temperature is generally 100° C. to 200° C., and preferably 120° C. to 160° C. Heating time is generally 1 minute to 120 minutes, preferably 1 minute to 60 minutes; and more preferably 1 minute to 30 minutes.

Polymerization reaction by UV irradiation, polymerization reaction with a platinum catalyst and polymerization reaction with an iron catalyst such as iron chloride are exemplified. These polymerization methods may be used in combination with a polymerization method by heating.

(Light-Emitting Layer)

<Light-Emitting Material>

It is preferred for the light-emitting layer according to the invention to contain a material for an organic electroluminescence device containing metal complex A and metal complex B which are specific phosphorescent metal complexes of the invention. It is also preferred for the light-emitting layer to contain a light-emitting material, and the light-emitting material is preferably a material for an organic electroluminescence device according to the invention.

A light-emitting material in a light-emitting layer is contained in an amount of generally 0.1% by mass to 50% by mass to the content of all the compounds forming the light-emitting layer, preferably 1% by mass to 50% by mass from the point of durability and external quantum efficiency, and more preferably 2% by mass to 40% by mass.

The thickness of a light-emitting layer is not especially restricted, but is generally preferably 2 nm to 500 nm, more preferably 3 nm to 200 nm from the viewpoint of external quantum efficiency, and still more preferably 5 nm to 100 nm.

The light-emitting layer in the device of the invention may include a light-emitting material alone, or the light-emitting layer may be a mixed layer of a host material and a light-emitting material. The light-emitting material may be a fluorescent material or may be a phosphorescent material, and dopant may be one kind alone or two or more kinds may be used. The host material is preferably a charge transporting material. The host material to be used may be one kind alone or two or more kinds may be used, for example, constitution consisting of a mixture of an electron transporting host material and a hole transporting host material is exemplified. Further, a material not having a charge-transporting property and not emitting light may be contained in the light-emitting layer.

The light-emitting layer may include monolayer or multilayer of two or more layers. Each layer may emit light in different luminescent colors.

<Host Material>

As the host materials for use in the invention, the following compounds may be contained. For example, pyrrole, indole, carbazole (e.g., CBP [4,4'-di(9-carbazoyl)biphenyl]), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, polysilane-based compounds, poly(N-vinylcarbazole), aniline-based copolymers, thiophene oligomers, conductive polymeric oligomers such as polythiophene, etc., organic silane, a carbon film, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic ring tetracarboxylic anhydride such as naphthaleneperylene, phthalocyanine, various kinds of metal complexes represented by metal complex of 8-quinolinol derivative, metal phthalocyanine, and metal complexes having benzoxazole or benzothiazole as a ligand, and derivatives thereof (which may have a substituent or a condensed ring) can be exemplified.

In the light-emitting layer of the invention, in the points of color purity, light emitting efficiency and driving durability, it is preferred that the minimum triplet excited state energy ($T_1$ energy) of the host material is higher than $T_1$ energy of the phosphorescent material.

The content of the host compound in the invention is not especially restricted but from the viewpoints of light emitting efficiency and driving voltage, the content is preferably 15% by mass or more and 95% by mass or less based on the mass of all the compounds constituting the light-emitting layer.

It is preferred for the light-emitting layer to contain metal complexes A and B, which are the specific phosphorescent metal complexes, and further a host material. The host material may be a hole-transporting host material or an electron-transporting host material, but a hole-transporting host material can be used.

In the invention, it is preferred for the light-emitting layer to contain metal complexes A and B of the specific phosphorescent metal complexes, and further at least one compound represented by the following formula (4-1) or (4-2).

The compound represented by formula (4-1) or (4-2) is preferably contained in the light-emitting layer in an amount of 30% by mass to 99% by mass, more preferably 40% by mass to 97% by mass, and especially preferably 50% by mass to 95% by mass. When the compound represented by formula (4-1) or (4-2) is contained in two or more organic layers, it is preferred to contain the compound in each layer in the above range.

The compound represented by formula (4-1) or (4-2) may be contained alone in any organic layer or a plurality of the compounds represented by formula (4-1) or (4-2) may be contained in combination in an arbitrary ratio.

The host material is preferably a compound represented by the following formula (4-1) or (4-2).

(4-1)

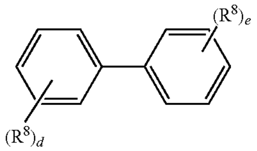

(4-2)

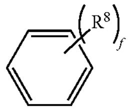

In formulae (4-1) and (4-2), each of d and e represents an integer of 0 to 3, and at least either one is 1 or more. f represents an integer of 1 to 4. $R_8$ represents a substituent, and each of d, e and f represents 2 or more, two or more $R_8$ may be different from or the same with each other. At least one $R_8$ represents a carbazole group represented by the following formula (5).

(5)

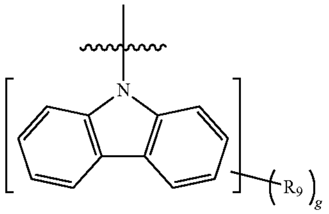

In formula (5), each $R_9$ independently represents a substituent. g represents an integer of 0 to 8.

Each $R_8$ independently represents a substituent. The specific examples of the substituents include a halogen atom, an alkoxy group, a cyano group, a nitro group, an alkyl group, an aryl group, a heterocyclic group, and the substituent represented by formula (5). When $R_8$ does not represent formula (5), the substituent is preferably an alkyl group having 10 or less carbon atoms or a substituted or unsubstituted aryl group having 10 or less carbon atoms, and more preferably an alkyl group having 6 or less carbon atoms.

Each $R_9$ independently represents a substituent. The specific examples of the substituents include a halogen atom, an alkoxy group, a cyano group, a nitro group, an alkyl group, an aryl group, and a heterocyclic group, preferably an alkyl group having 10 or less carbon atoms, and a substituted or unsubstituted aryl group having 10 or less carbon atoms, and more preferably an alkyl group having 6 or less carbon atoms.

g represents an integer of 0 to 8. From the viewpoint of not excessively, shielding the carbazole structure for performing transportation of charge, g is preferably 0 to 4. Further, from the aspect of easiness of synthesis, when the carbazole has a substituent, those having substituents symmetrically to the nitrogen atom are preferred.

In formula (4-1), the sum of d and e is preferably 2 or more in the point of retaining charge transportation performance. It is preferred that $R_8$ is substituted at meta-position to the other benzene ring. This is for the reason that steric hindrance of contiguous substituents is great in substitution at ortho-position and cleavage of bonding is liable to occur, so that durability lowers. Further, in substitution at para-position, the molecular shape approaches to a stiff rod state and crystallization is liable to occur, as a result device easily deteriorates under high temperature conditions.

Specifically, a compound represented by the following structure is preferred.

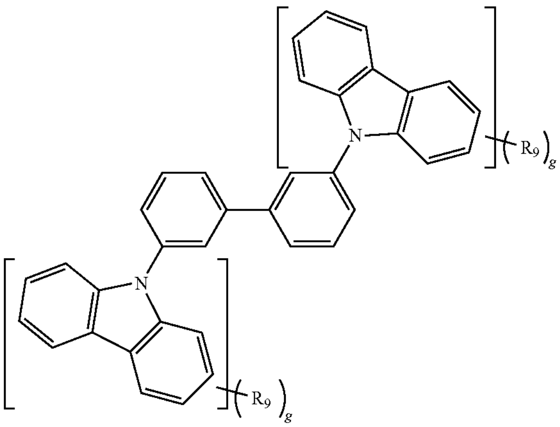

In the above formula, each of $R_9$ independently represents a substituent. g represents an integer of 0 to 8.

In formula (4-2), f is preferably 2 or more in view of retaining charge transportation performance. When f is 2 or 3, $R_8$ preferably substitute at meta-position to each other from the same viewpoint. Specifically, a compound represented by the following structure is preferred.

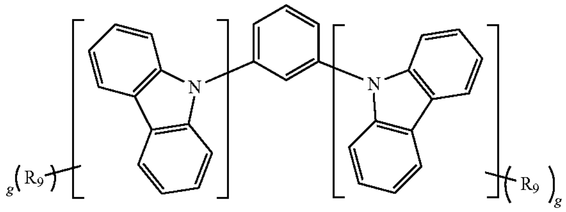

In the above formula, each of $R_9$ independently represents a substituent. g represents an integer of 0 to 8.

When formulae (4-1) and (4-2) have hydrogen atoms, isotopes of hydrogen atoms (deuterium atoms) are also included in the hydrogen atoms. In such a case, all the hydrogen atoms in the compounds may be substituted with hydrogen isotopes, or the compounds may be mixtures partially containing hydrogen isotopes. Preferred are compounds in which $R_9$ in formula (5) is substituted with a deuterium atom, and especially preferably the following structures are exemplified.

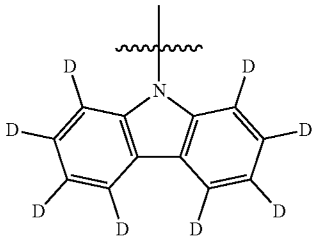

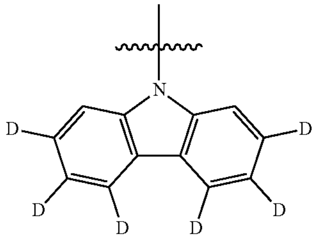

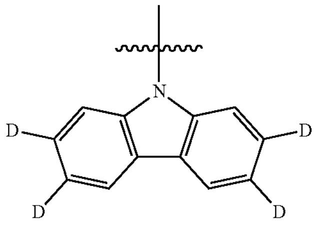

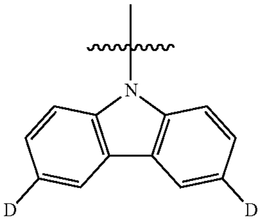

The atoms further constituting substituents also include the isotopes thereof.

The compounds represented by formulae (4-1) and (4-2) can be synthesized by combining various known synthesis methods. Most generally, concerning the carbazole compounds, synthesis by dehydrogenation aromatization after Aza-Cope arrangement of the condensation product of aryl hydrazine and cyclohexane derivative (L. F. Tieze and Th. Eicher, translated by Takano and Ogasawara, Precision Organic Syntheses, p. 339, published by Nanko-Do) is exemplified. Further, concerning the coupling reaction of the obtained carbazole compound and aryl halide compound using a palladium catalyst, the methods described in Tetrahedron Letters, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied. Concerning some compounds, such as mCP, commercially available products can be preferably used.

It is preferred that the films of the compounds represented by formulae (4-1) and (4-2) are formed according to a vacuum deposition process, but a wet process such as solution coating can also be preferably used. The molecular weight of the compound is preferably 2,000 or less in view of deposition aptitude and solubility, more preferably 1,200 or less, and especially preferably 800 or less. In view of deposition aptitude, too small a molecular weight results in too small a vapor pressure, conversion from a gaseous phase to a solid phase does not occur and it becomes difficult to form an organic layer, so that the molecular weight is preferably 250 or more, and especially preferably 300 or more.

Compounds having the structures shown below, or compounds obtained by substituting one or more hydrogen atoms of the following compounds with deuterium atoms are preferably used as the compounds of formulae (4-1) and (4-2).

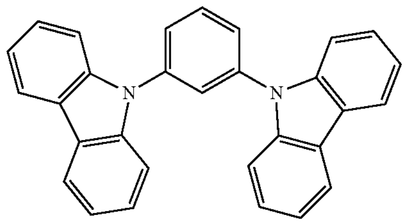

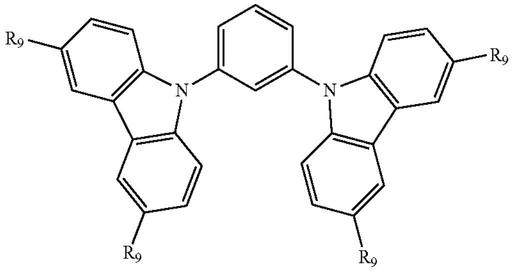

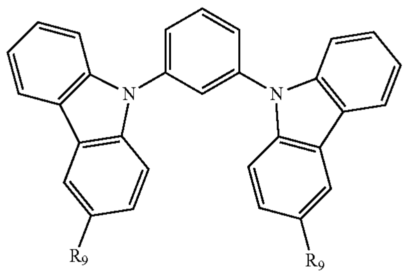

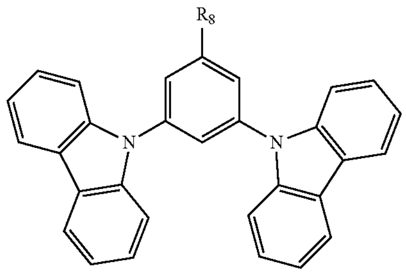

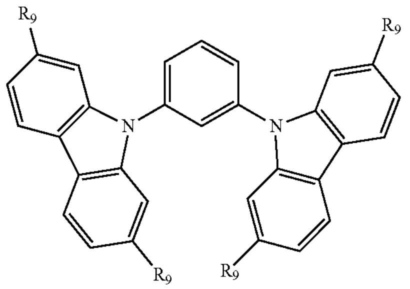

-continued
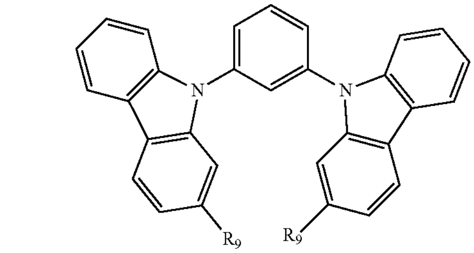
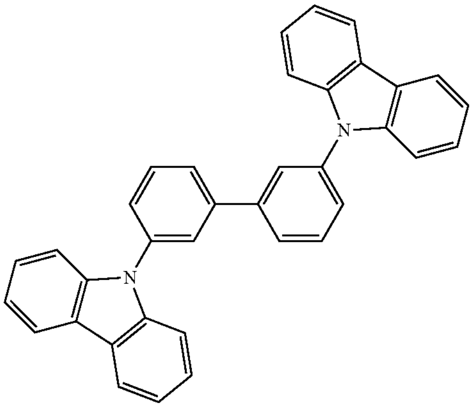
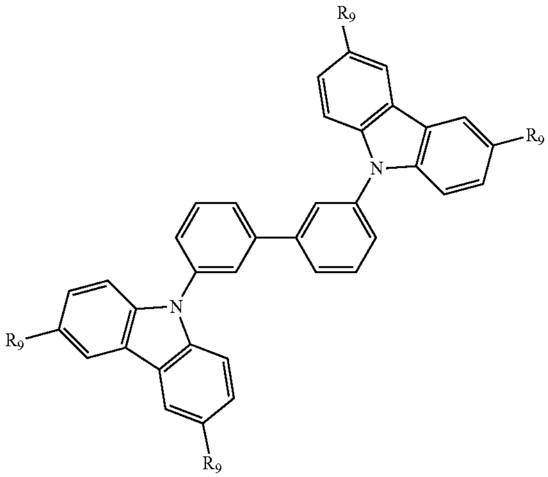
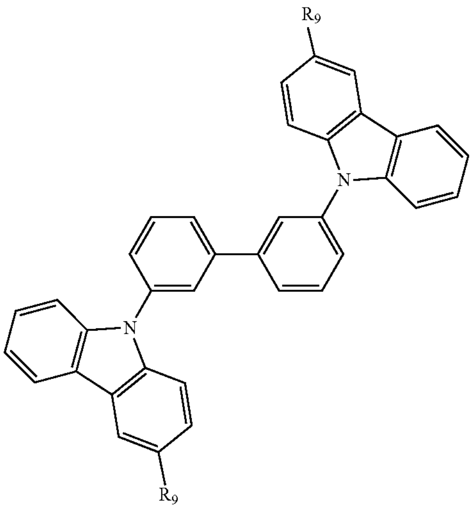
-continued
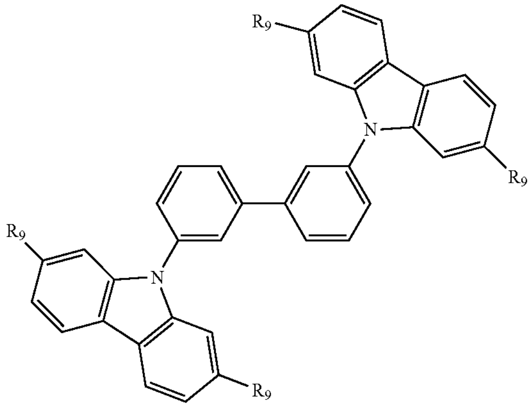
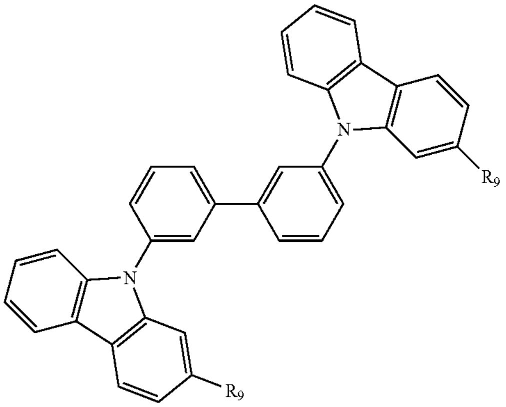
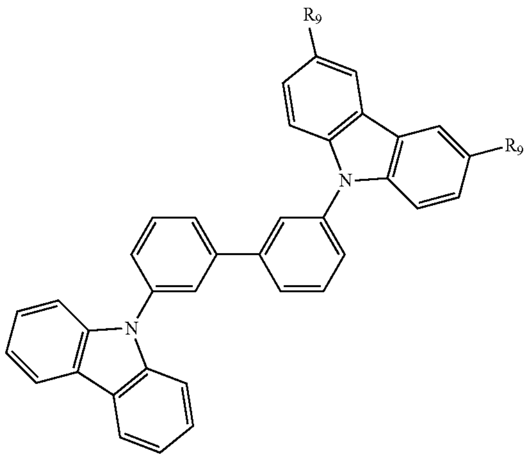
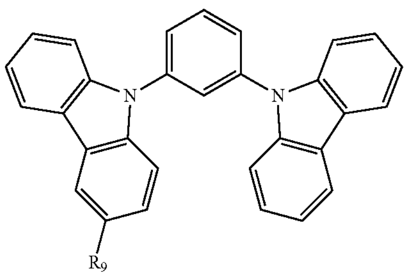

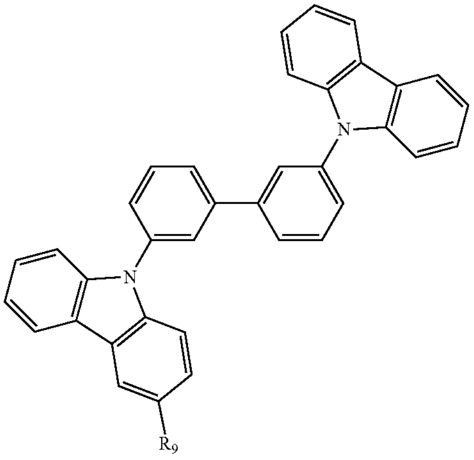
In the above formulae, each of $R_8$ and $R_9$ independently represents a substituent.
The specific examples of the compounds represented by formulae (4-1) and (4-2) of the invention are shown below, but the invention is not restricted thereto.
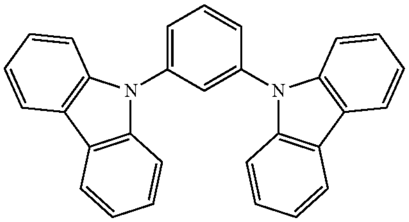
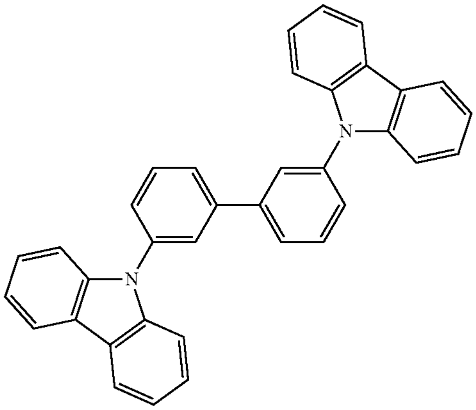
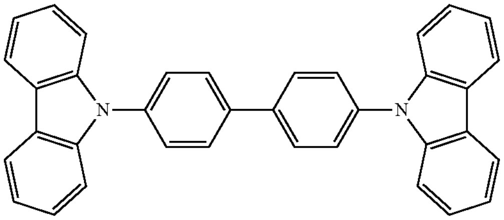
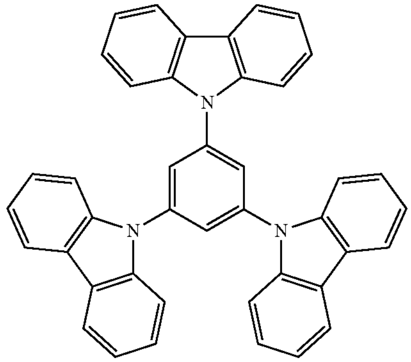
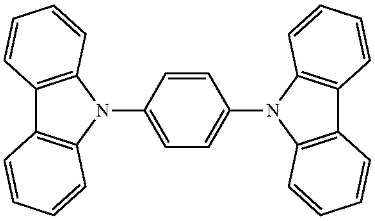
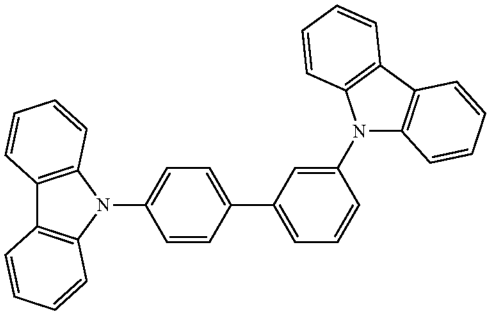
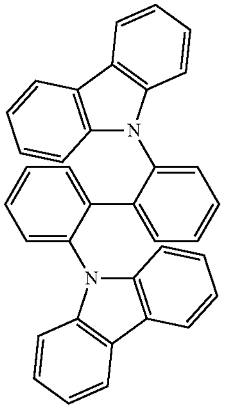
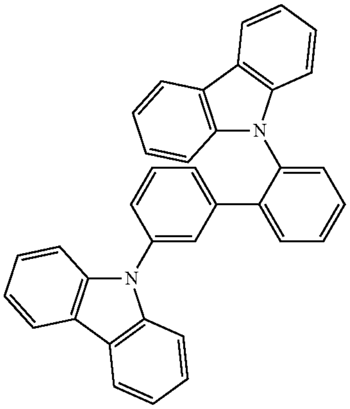

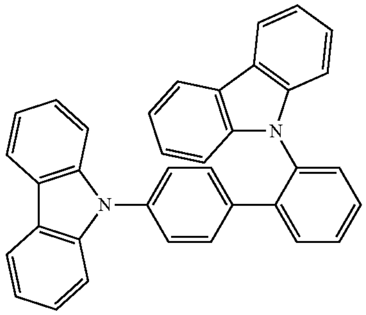
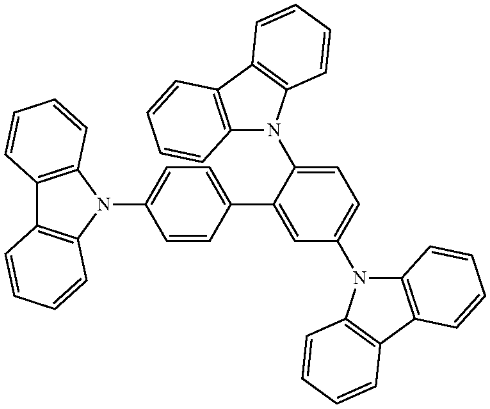
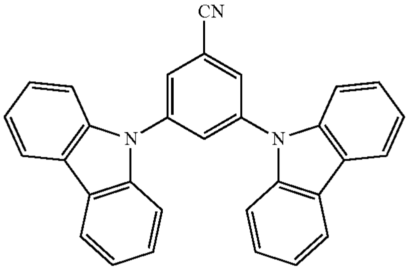
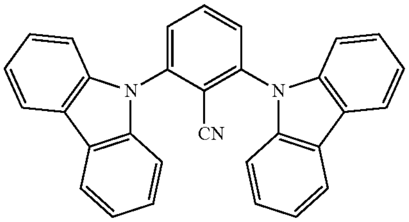
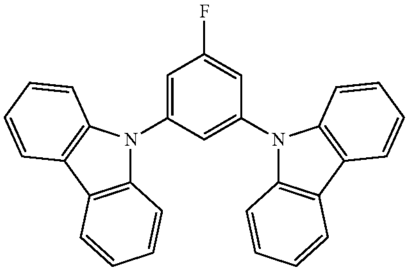
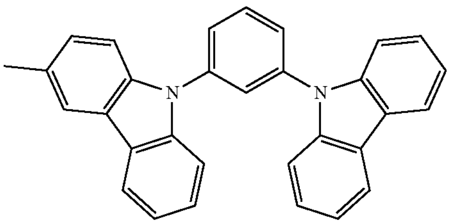
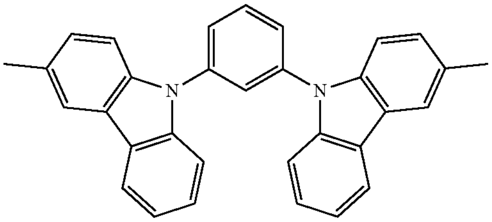
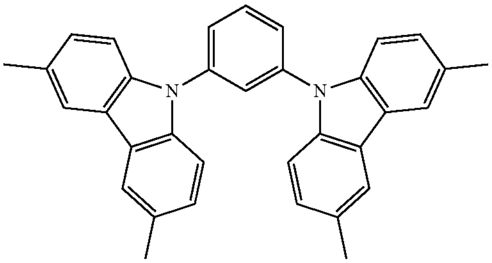
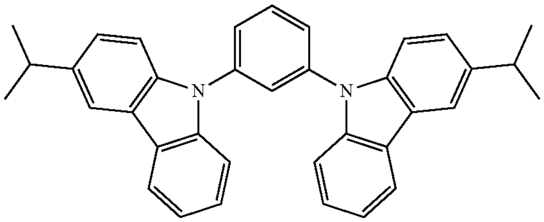
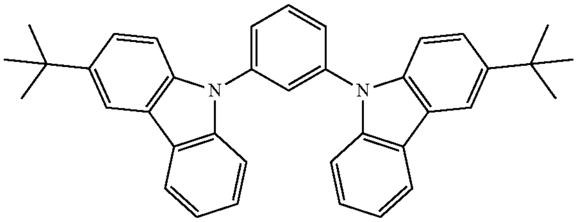
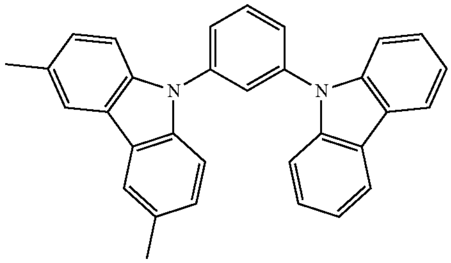
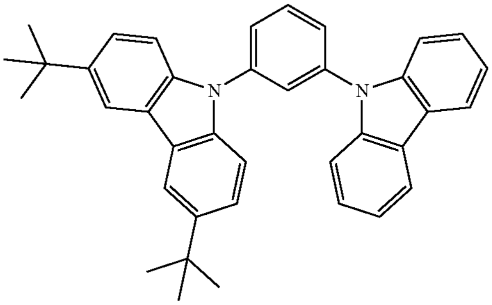

-continued
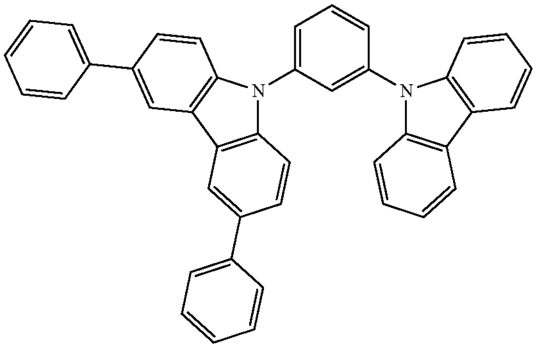
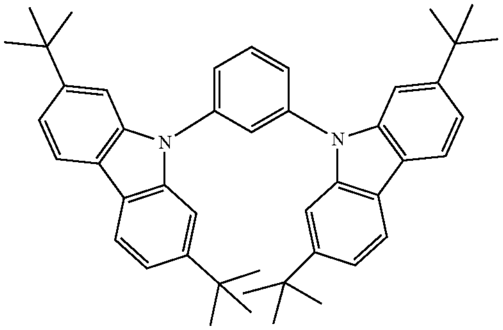
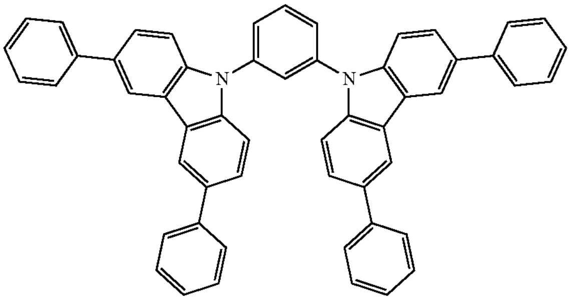
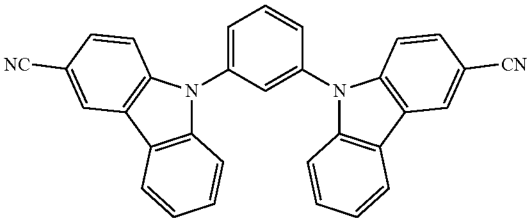
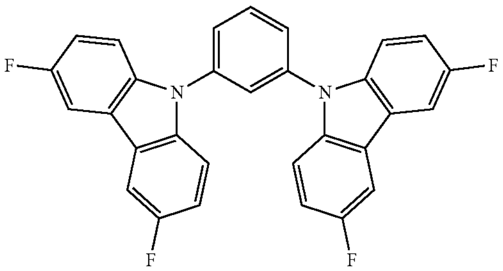
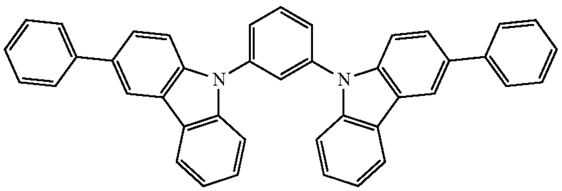
-continued
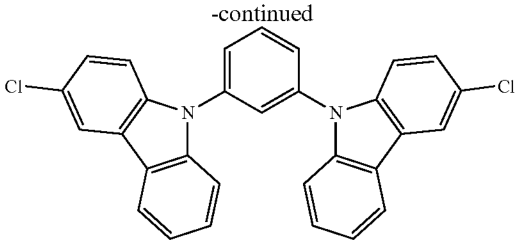
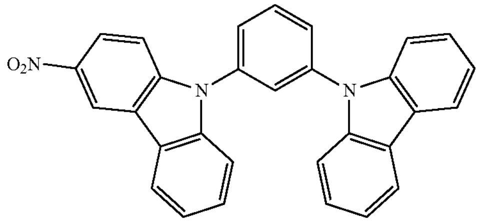
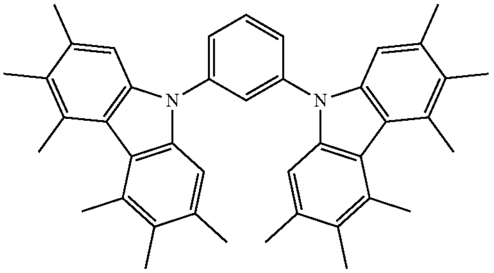
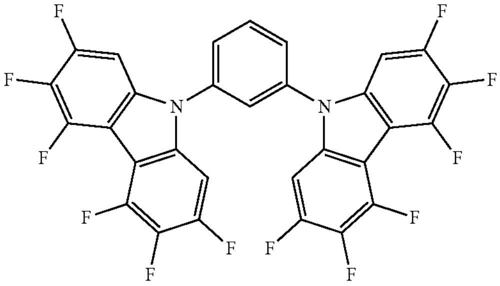
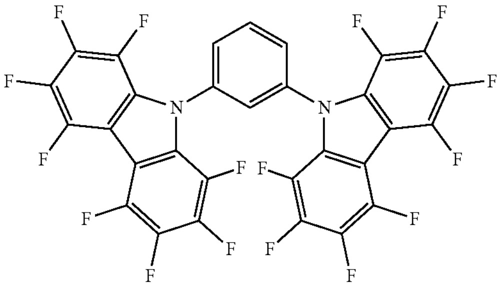
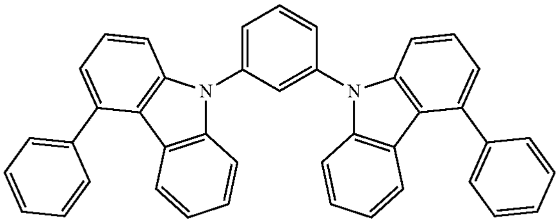
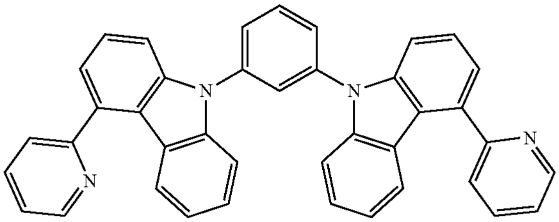

-continued
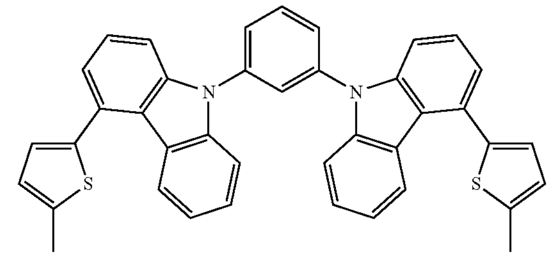
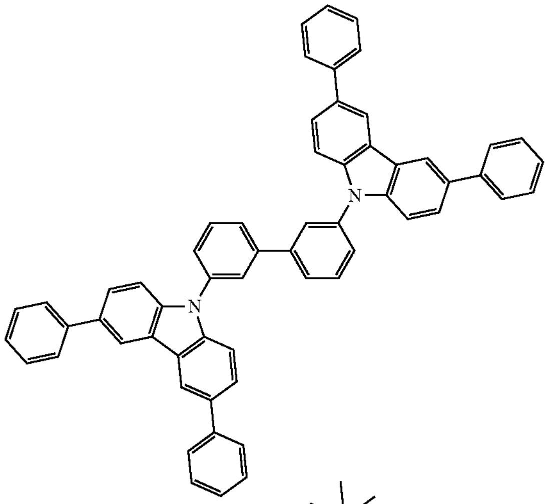
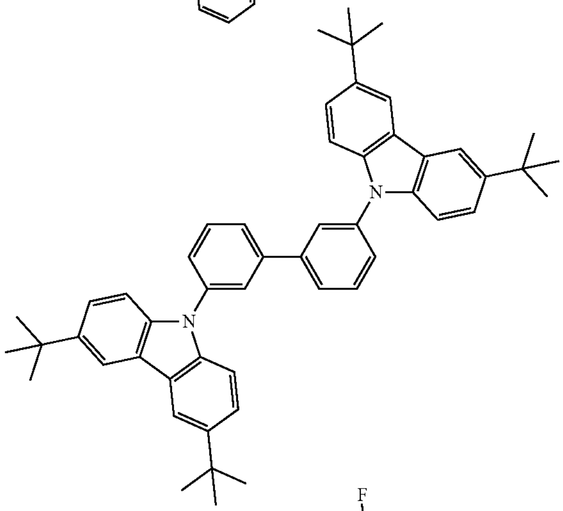
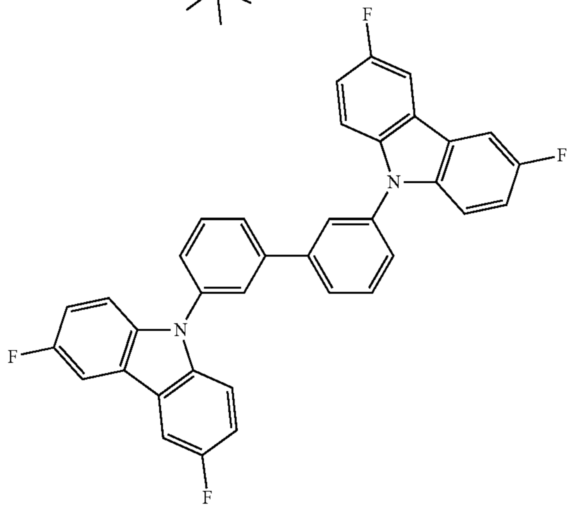
-continued
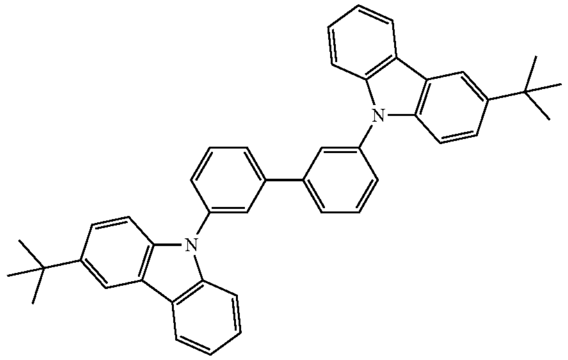
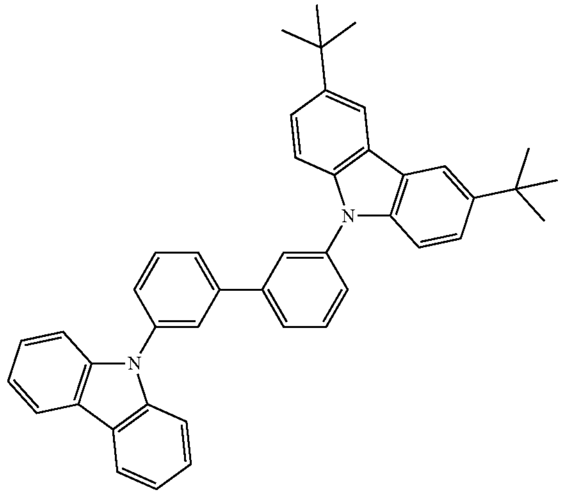
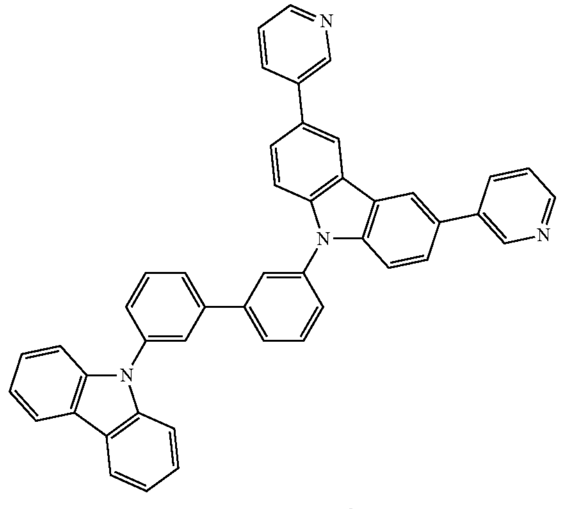
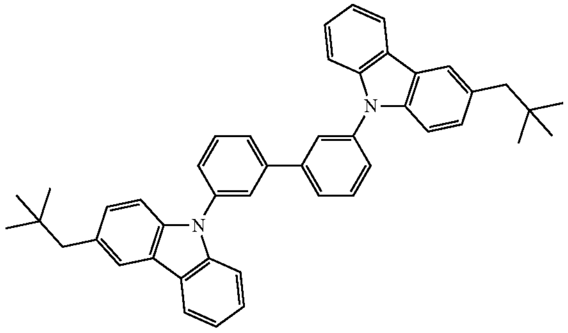

-continued
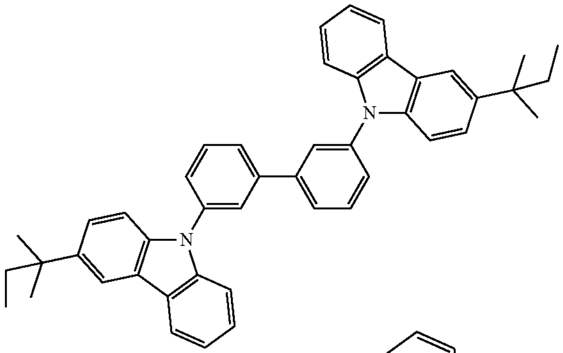
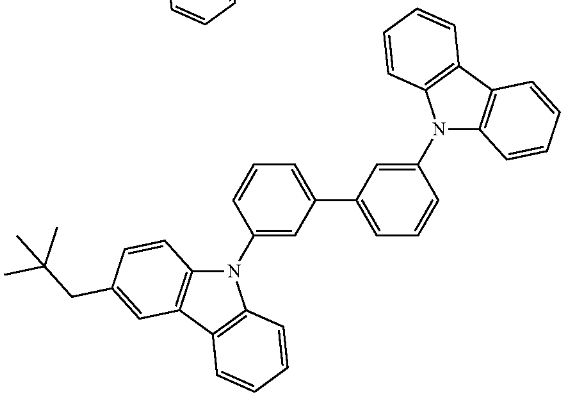
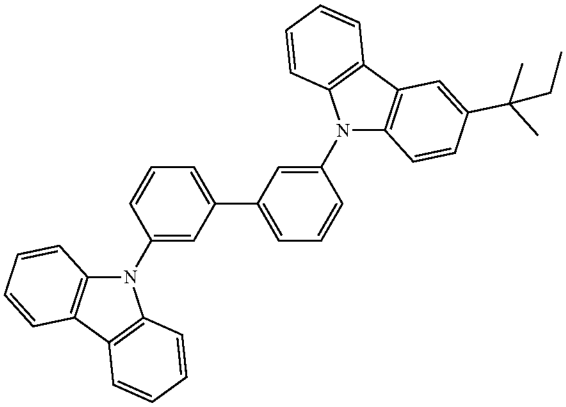
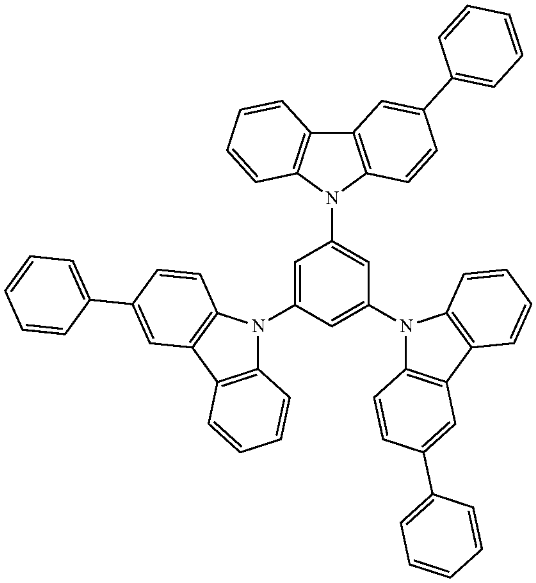
-continued
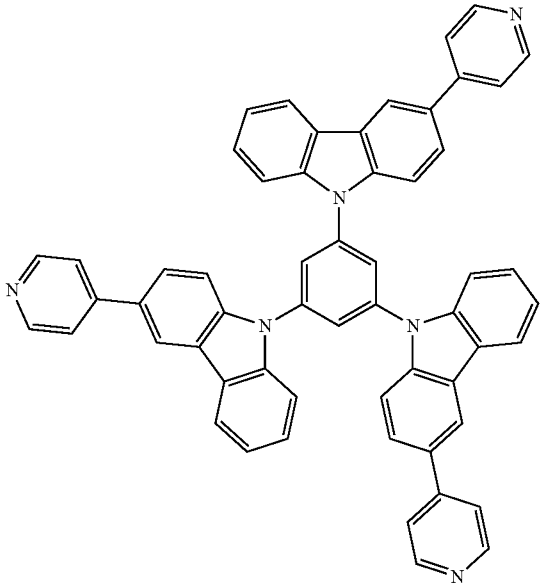
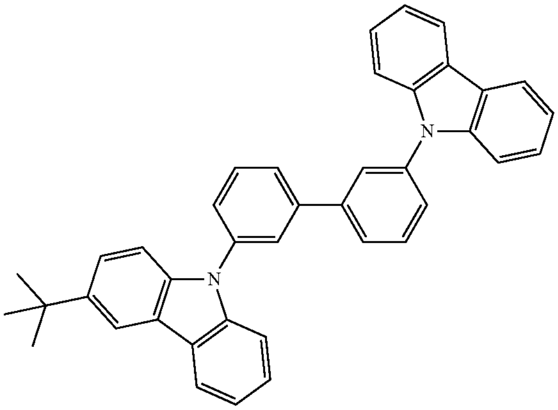
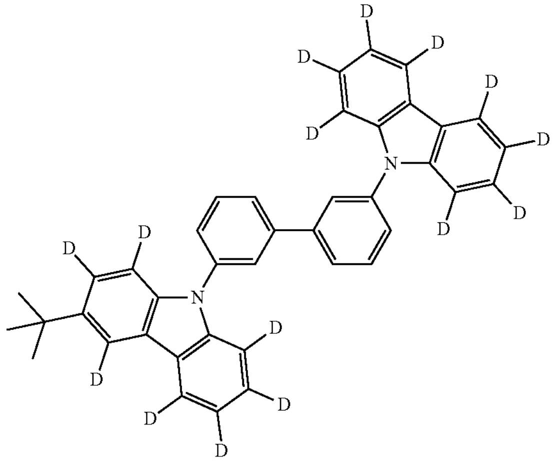

-continued
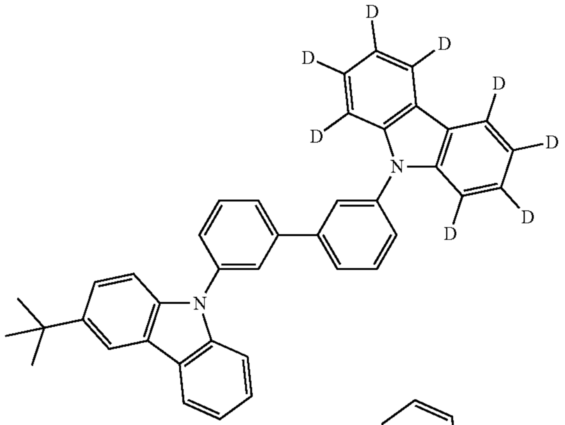
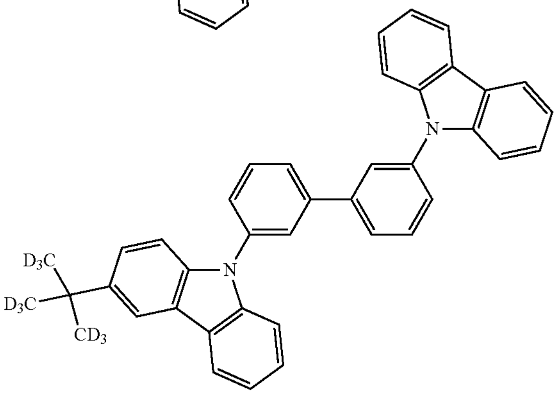
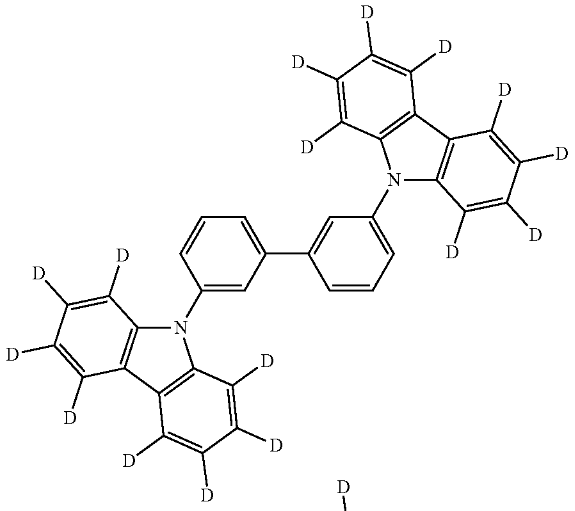
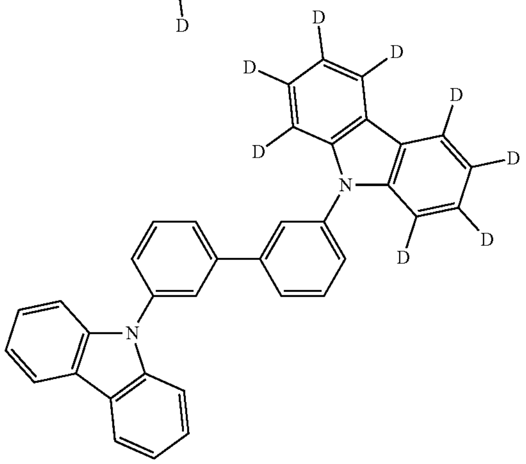
-continued
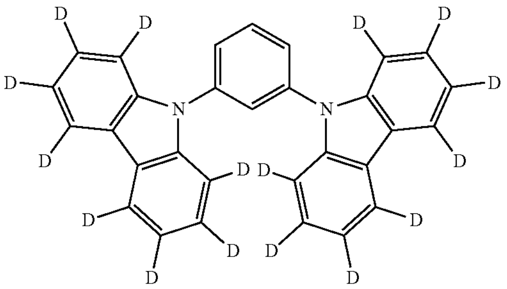
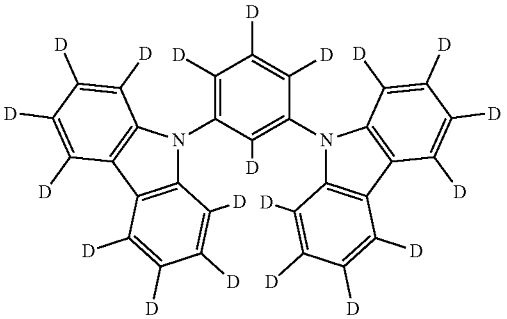
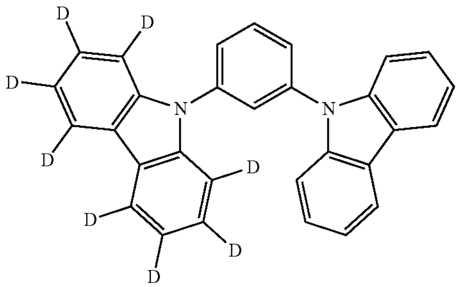
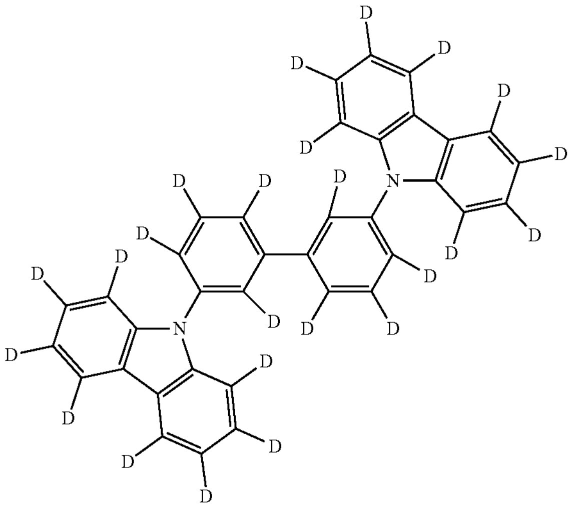
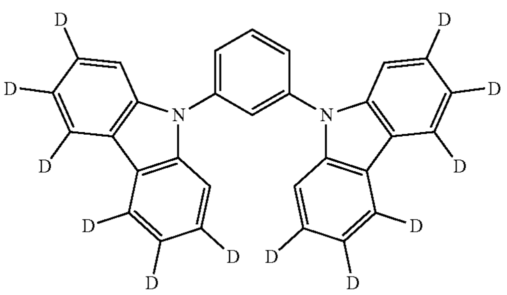

-continued

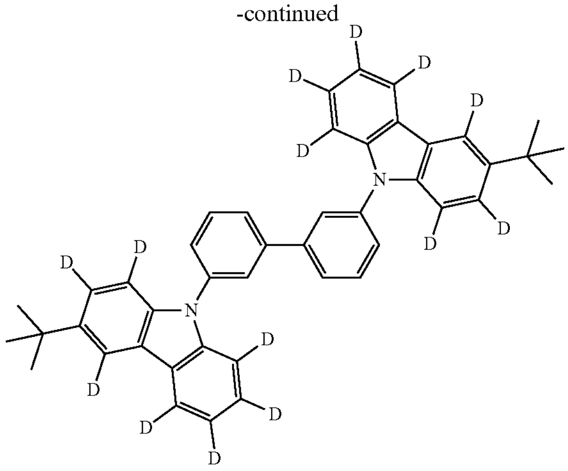

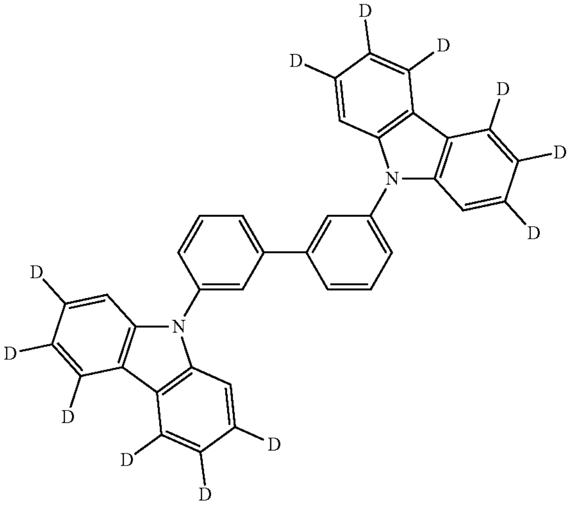 [SMILES: [2H]c1cc2c(c([2H])c1[2H])c1c([2H])c([2H])c([2H])cc1n2-c1cccc(-c2cccc(-n3c4cc([2H])c([2H])c([2H])c4c4c([2H])c([2H])c([2H])cc43)c2)c1]

(Fluorescent Material)

The examples of fluorescent materials which can be used in the invention include various complexes represented by complexes of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne compounds, 8-quinolinol derivatives, and pyrromethene derivatives, polymer compounds such as polythiophene, polyphenylene, polyphenylenevinylene, etc., and compounds such as organosilane derivatives.

(Phosphorescent Material)

As the phosphorescent materials usable in the invention, phosphorescent compounds disclosed, for example, in U.S. Pat. Nos. 6,303,238B1, 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1,211,257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259 are exemplified. As further preferred light-emitting dopants, an Ir complex, a Pt complex, a Cu complex, an Re complex, a W complex, an Rh complex, an Ru complex, a Pd complex, an Os complex, an Eu complex, a Tb complex, a Gd complex, a Dy complex, and a Ce complex are exemplified. As especially preferred dopants, an Ir complex, a Pt complex and an Re complex are exemplified. An Ir complex, a Pt complex and an Re complex including at least one coordination system of a metal-carbon bond, a metal-nitrogen bond, a metal-oxygen bond, and a metal-sulfur bond are preferred above all. Further, from the aspects of light emitting efficiency, driving durability and chromaticity, an Ir complex, a Pt complex and an Re complex each containing a tridentate or higher multidentate ligand are especially preferred.

The content of the phosphorescent material in the light-emitting layer is preferably in the range of 0.1% by mass or more and 50% by mass or less to the gross mass of the light-emitting layer, more preferably in the range of 0.2% by mass or more and 50% by mass or less, still more preferably in the range of 0.3% by mass or more and 40% by mass or less, and most preferably in the range of 5% by mass or more and 30% by mass or less.

The content of the phosphorescent material which can be used in the invention (the specific phosphorescent metal complex and/or a phosphorescent material to be used in combination) is preferably in the range of 0.1% by mass or more and 50% by mass or less based on the gross sum of the light-emitting layer, more preferably in the range of 1% by mass or more and 40% by mass or less, and most preferably in the range of 5% by mass or more and 30% by mass or less. In particular, in the range of 5% by mass or more and 30% by mass or less, the chromaticity of the light emission of the organic electroluminescence device is little in dependency on the addition concentration of the phosphorescent material.

It is most preferred for the organic electroluminescence device in the invention to contain at least one kind of the above specific phosphorescent metal complexes in an amount of 5 to 30% by mass based on the gross mass of the light-emitting layer.

(Hydrocarbon Compound)

It is preferred that the organic electroluminescence device further contains a hydrocarbon compound and the derivative thereof in any layer of the organic layers, and it is more preferred for the light-emitting layer to contain a hydrocarbon compound.

The hydrocarbon compound is preferably a compound represented by the following formula (VI).

By appropriately using the compound represented by formula (VI) with a light-emitting material, it becomes possible to properly control interaction between material molecules, and make energy gap interaction between contiguous molecules even to thereby further lower driving voltage.

The compound represented by formula (VI) which is used in the organic electroluminescence device is excellent in chemical stability, little in change of properties such as decomposition of the material during driving of the device, and reduction of efficiency of the organic electroluminescence device and reduction of duration of life of the device can be prevented.

The compound represented by formula (VI) will be described below.

(VI)

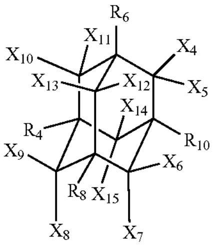

In formula (VI), each of $R_4$, $R_6$, $R_8$, $R_{10}$, $X_4$ to $X_{15}$ independently represents a hydrogen atom, an alkyl group or an aryl group.

The alkyl group represented by each of $R_4$, $R_6$, $R_8$, $R_{10}$, $X_4$ to $X_{15}$ in formula (VI) may be substituted with an adamantane structure or an aryl structure. The alkyl group is preferably an alkyl group having 1 to 70 carbon atoms, more preferably having 1 to 50 carbon atoms, still more preferably having 1 to 30 carbon atoms, still yet preferably having 1 to 10 carbon atoms, especially preferably having 1 to 6 carbon atoms, and most preferably a straight chain alkyl group having 2 to 6 carbon atoms.

As the alkyl groups represented by each of $R_4$, $R_6$, $R_8$, $R_{10}$, $X_4$ to $X_{15}$ in formula (VI), e.g., an n-$C_{50}H_{101}$ group, an n-$C_{30}H_{61}$ group, a 3-(3,5,7-triphenyl-adamantan-1-yl)propyl group (having 31 carbon atoms), a trityl group (having 19 carbon atoms), a 3-(adamantan-1-yl)propyl group (having 13 carbon atoms), a 9-decalyl group (having 10 carbon atoms), a benzyl group (having 7 carbon atoms), a cyclohexyl group (having 6 carbon atoms), an n-hexyl group (having 6 carbon atoms), an n-pentyl group (having 5 carbon atoms), an n-butyl group (having 4 carbon atoms), an n-ropyl group (having 3 carbon atoms), a cyclopropyl group (having 3 carbon atoms), an ethyl group (having 2 carbon atoms), and a methyl group (having 1 carbon atom) are exemplified.

The aryl group represented by each of $R_4$, $R_6$, $R_8$, $R_{10}$, $X_4$ to $X_{15}$ in formula (VI) may be substituted with an adamantane structure or an alkyl structure. The aryl group is preferably an aryl group having 6 to 30 carbon atoms, more preferably having 6 to 20 carbon atoms, still more preferably having 6 to 15 carbon atoms, especially preferably having 6 to 10 carbon atoms, and most preferably having 6 carbon atoms.

As the aryl groups represented by each of $R_4$, $R_6$, $R_8$, $R_{10}$, $X_4$ to $X_{15}$ in formula (VI), e.g., a 1-pyrenyl group (having 16 carbon atoms), a9-anthracenyl group (having 14 carbon atoms), a 1-naphthyl group (having 10 carbon atoms), a 2-naphthyl group (having 10 carbon atoms), a p-t-butylphenyl group (having 10 carbon atoms), a 2-m-xylyl group (having 8 carbon atoms), a 5-m-xylyl group (having 8 carbon atoms), an o-tolyl group (having 7 carbon atoms), an m-tolyl group (having 7 carbon atoms), a p-tolyl group (having 7 carbon atoms), and a phenyl group (having 6 carbon atoms) are exemplified.

Although each of $R_4$, $R_6$, $R_8$ and $R_{10}$ in formula (VI) may represent a hydrogen atom, an alkyl group or an aryl group, from the viewpoint of high glass transition temperature being preferred, preferably at least one represents an aryl group, more preferably at least two represent an aryl group, and especially preferably 3 or 4 of them represent an aryl group.

Each of $X_4$ to $X_{15}$ in formula (VI) may represent a hydrogen atom, an alkyl group or an aryl group, but preferably a hydrogen atom or an aryl group, and especially preferably a hydrogen atom.

Since the organic electroluminescence device in the invention is manufactured with a vacuum deposition process or a solution-coating process, in view of vacuum deposition aptitude and solubility, the molecular weight of the compound represented by formula (VI) in the invention is preferably 2,000 or less, more preferably 1,200 or less, and especially preferably 1,000 or less. Further, in the point of vacuum deposition aptitude, too small a molecular weight is accompanied by small vapor pressure and transition from a vapor phase to a solid phase does not occur and it becomes difficult to form an organic layer. Accordingly, the molecular weight is preferably 250 or more, more preferably 350 or more, and especially preferably 400 or more.

The compound represented by formula (VI) is preferably a solid at room temperature (25° C.), more preferably a solid in the range of room temperature (25° C.) to 40° C., and especially preferably a solid in the range of room temperature (25° C.) to 60° C.

When the compound represented by formula (VI) which does not form a solid at room temperature (25° C.) is used, a solid can be formed at room temperature by combining with other material.

The compound represented by formula (VI) is not restricted in use and may be contained in any layer in organic layers. The compound represented by formula (VI) is preferably introduced into any one or two or more layers of a light-emitting layer, a hole-injecting layer, a hole-transporting layer, an electron-transporting layer, an electron-injecting layer, an exciton-blocking layer, and a charge-blocking layer, more preferably any one or two or more layers of a light-emitting layer, a hole-injecting layer, a hole-transporting layer, an electron-transporting layer, and an electron injecting layer, especially preferably any one or two or more layers of a light-emitting layer, a hole-injecting layer, and a hole-transporting layer, and most preferably a light-emitting layer.

When the compound represented by formula (VI) is used in an organic layer, it is necessary to use the compound represented by formula (VI) in a degree of amount so as not to control charge transporting property. The content of the compound represented by formula (VI) is preferably 0.1% by mol to 70% by mol, more preferably 0.1% by mass to 30% by mass, and especially preferably 0.1% by mass to 25% by mass.

Further, when the compound represented by formula (VI) is used in two or more organic layers, it is preferred to use the compound in each layer in the above range.

One kind alone of the compound represented by formula (VI) may be contained in any organic layer or plural the compounds represented by formula (VI) may be contained in combination in an arbitrary rate.

The specific examples of the hydrocarbon compounds and derivatives thereof which can be used in the invention are shown below, but the invention is not restricted to these compounds.

(1-1)

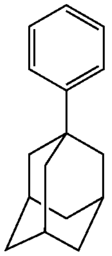

-continued
(1-2)
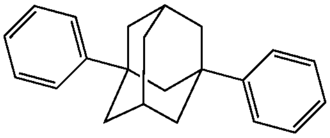
(1-3)
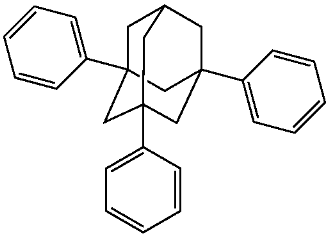
(1-4)
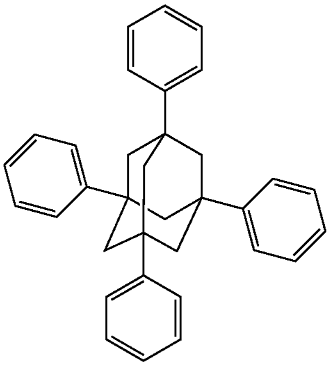
(1-5)
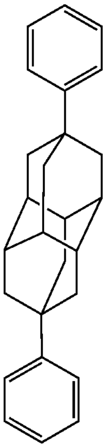
(1-6)
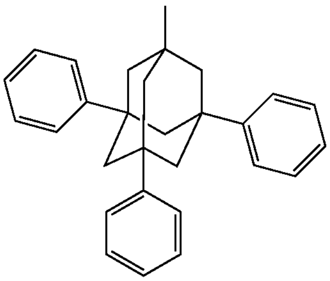
-continued
(1-7)
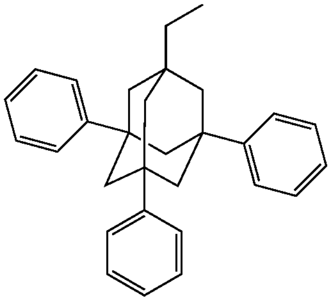
(1-8)
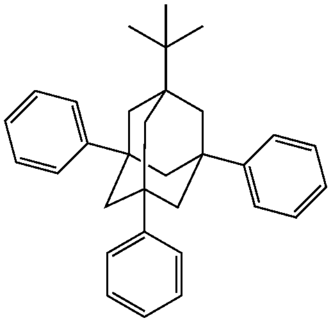
(1-9)
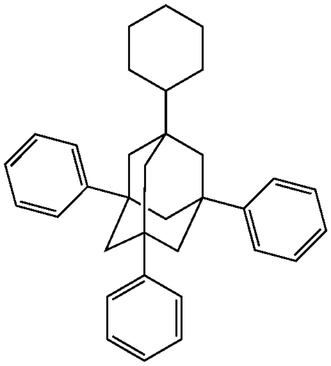
(1-10)
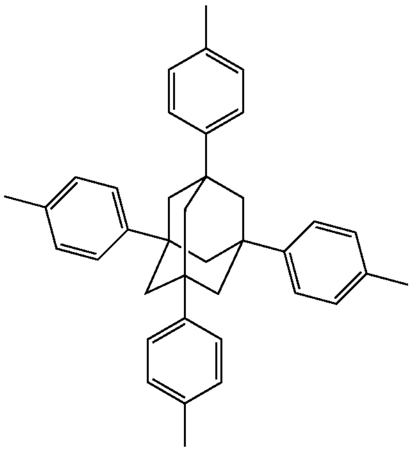

-continued
(1-11)
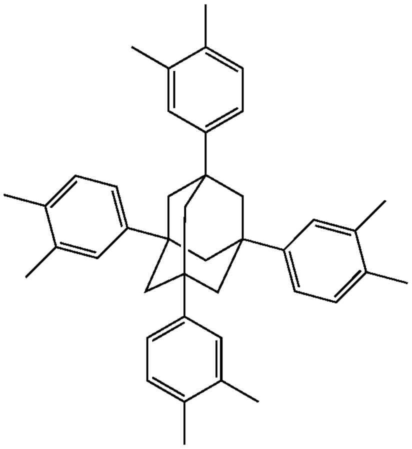
(1-12)
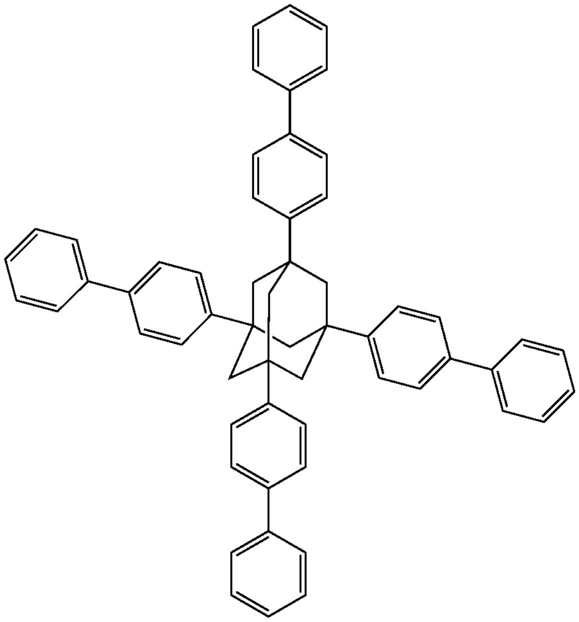
(1-13)
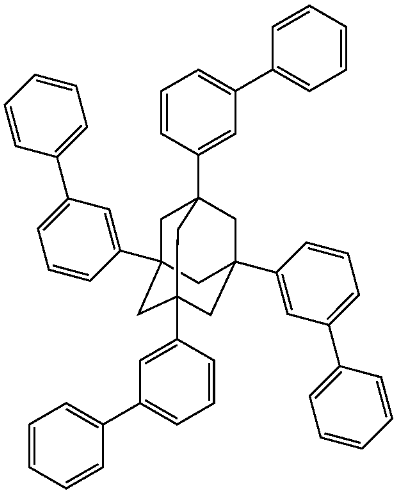
-continued
(1-14)
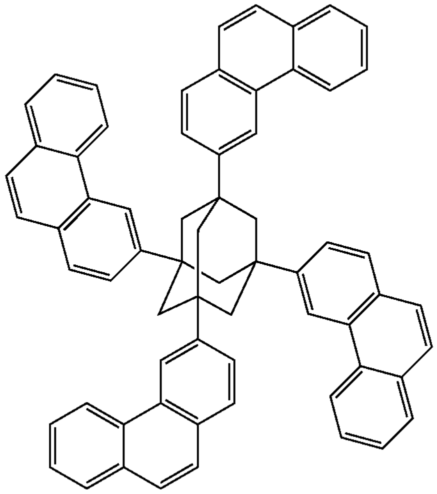
(1-15)
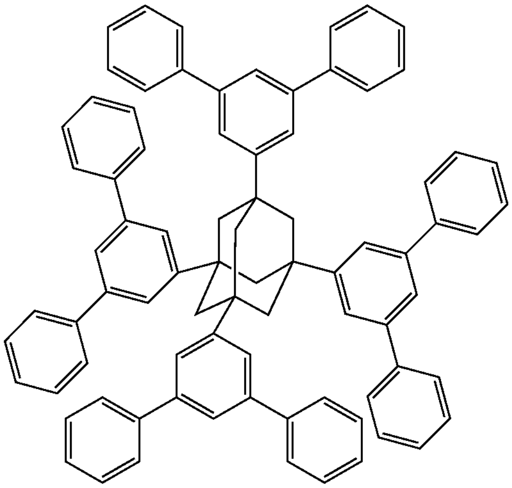
(1-16)
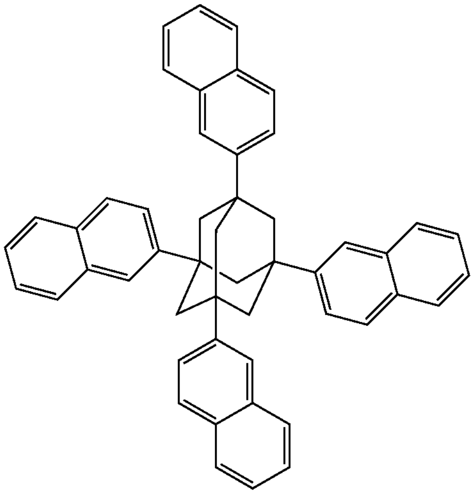

(1-17)
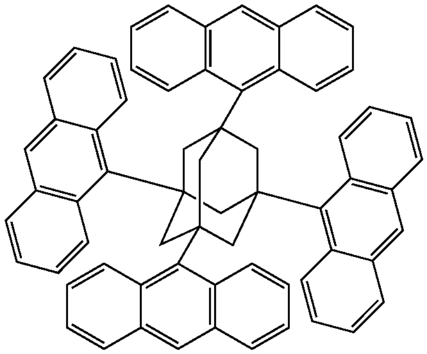
(1-18)
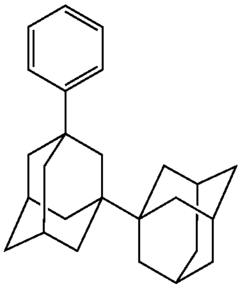
(1-19)
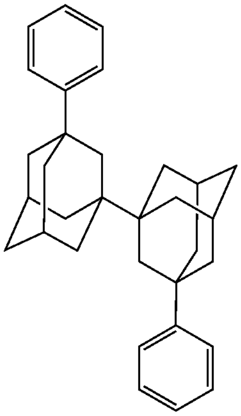
(1-20)
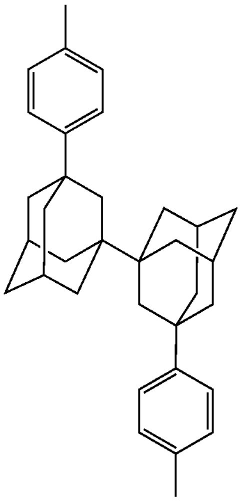
(1-21)
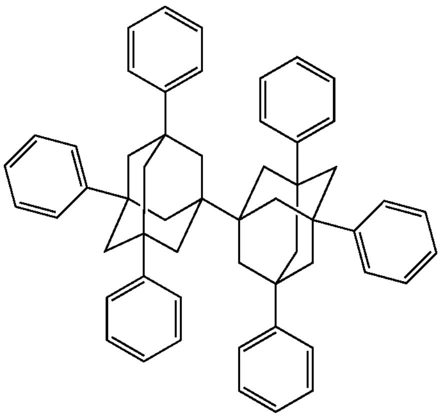
(1-22)
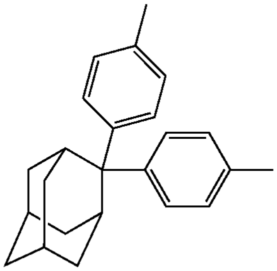
(1-23)
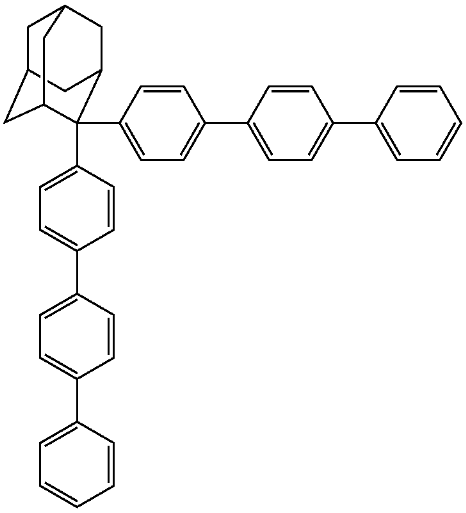
(1-24)
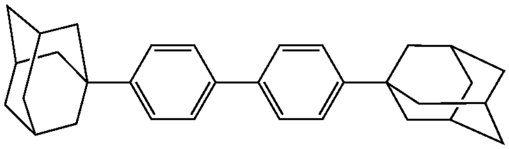
(1-25)
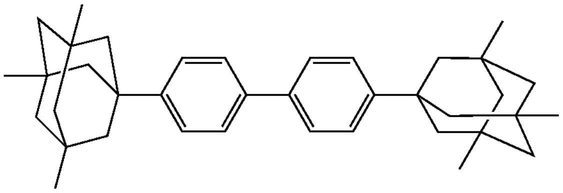

-continued
(1-26)
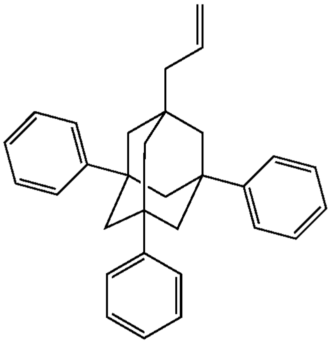
(1-27)
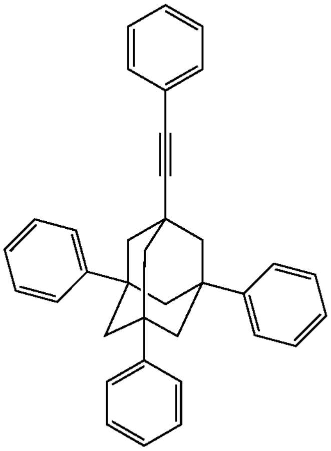
(1-28)
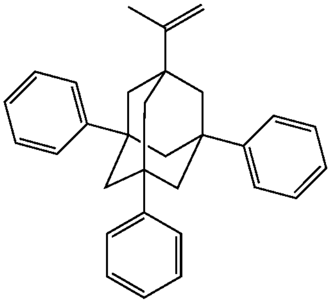
(1-29)
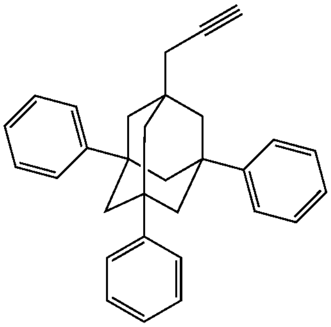
-continued
(1-30)
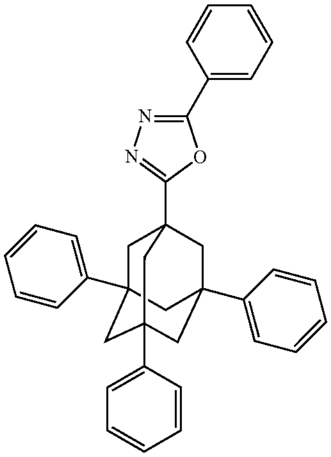
(1-31)
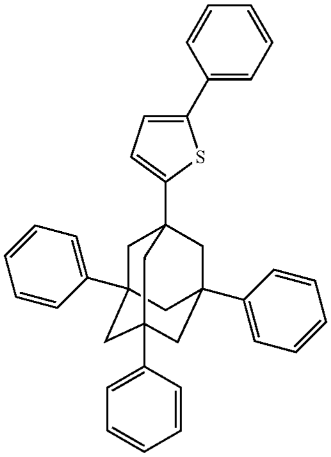
(1-32)
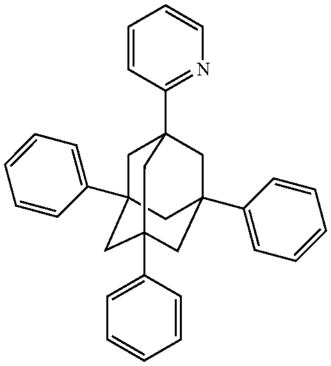
(1-33)
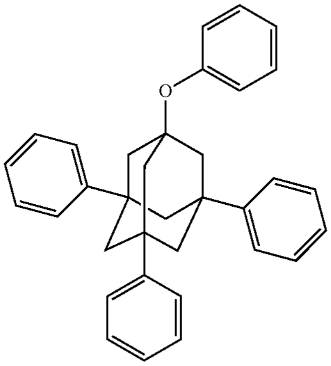

-continued
(1-34)
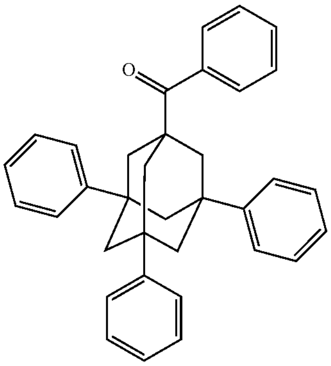
(1-35)
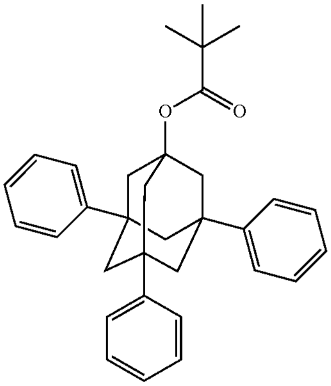
(1-36)
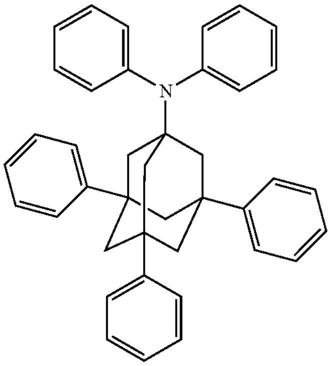
(1-37)
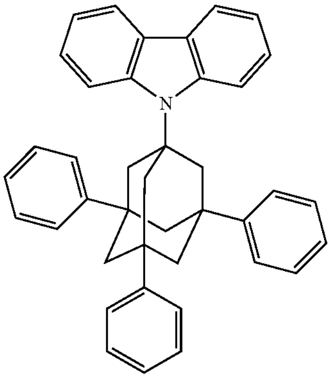
-continued
(1-38)
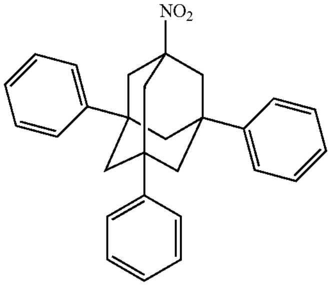
(1-39)
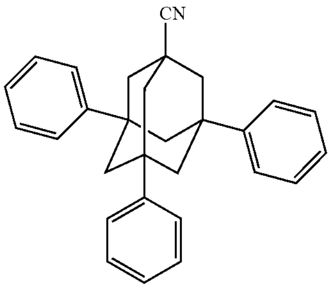
(1-40)
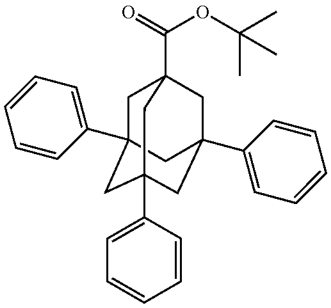
(1-41)
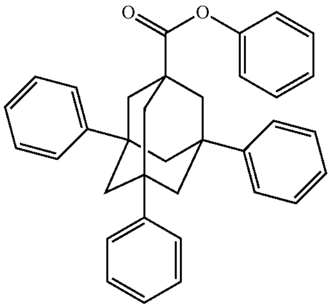
(1-42)
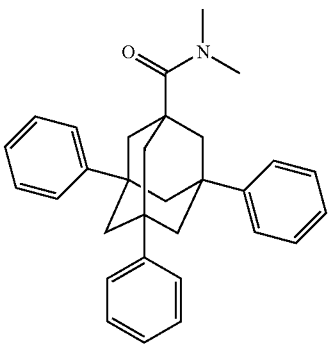

-continued (1-43)

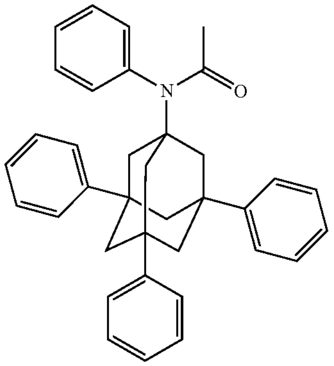

(1-44)

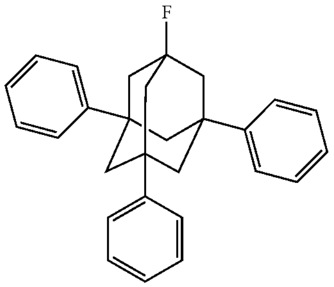

(1-45)

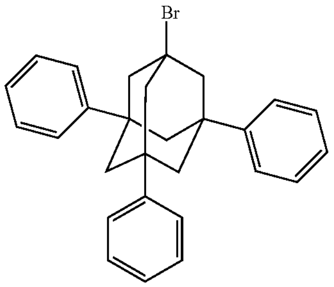

(1-46)

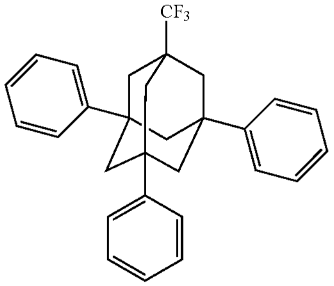

(1-47)

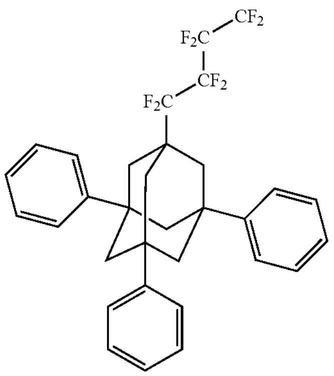

-continued (1-48)

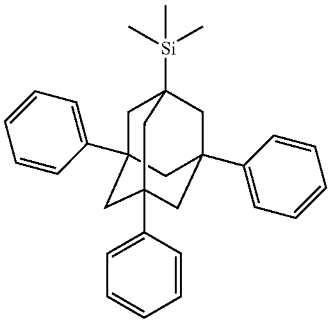

(1-49)

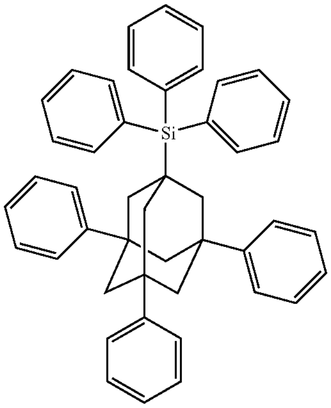

The compound represented by formula (VI) can be synthesized by properly combining adamantane or adamantane halide, and alkyl halide or alkyl magnesium halide (Grignard reagent). For example, adamantane halide and alkyl halide can be coupled by using indium (reference document 1). Alternatively, it is also possible that alkyl halide is converted to an alkylcopper reagent and coupled with a Grignard reagent of an aromatic compound (reference document 2), or alkyl halide can be coupled by using an appropriate arylboric acid and a palladium catalyst (reference document 3).

Reference document 1: Tetrahedron Lett. 39, 1998, 9557-9558

Reference document 2: Tetrahedron Lett. 39, 1998, 2095-2096

Reference document 3: J. Am. Chem. Soc. 124, 2002, 13662-13663

An adamantane structure having an aryl group can be synthesized by properly combining adamantane or adamantane halide with corresponding arylene or aryl halide.

Incidentally, in the above-shown manufacturing methods, when the defined substituent varies under the condition of a certain synthesizing method or when it is inappropriate to perform the synthesizing method, manufacture easily becomes possible by the means such as the protection or deprotection of the functional group (e.g., T. W. Greene, Protective Groups in Organic Synthesis, John Wiley & Sons Inc. (1981), etc.). It is also possible to change the order of the reaction process such as introduction of a substituent, according to necessity.

[Aromatic Hydrocarbon Compound]

It is preferred for the organic electroluminescence device in the invention to contain an aromatic hydrocarbon compound in an organic layer.

It is more preferred that the aromatic hydrocarbon compound is contained in an organic layer between a light-emitting layer and the cathode and contiguous to the light-emitting layer, but it is not limitative and may be contained in any layer of organic layers. The aromatic hydrocarbon compound according to the invention can be introduced into any one or two or more layers of a light-emitting layer, a hole-injecting layer, a hole-transporting layer, an electron-transporting layer, an electron-injecting layer, an exciton-blocking layer, and a charge-blocking layer.

The organic layer contiguous to the light-emitting layer between the light emitting layer and the cathode in which the aromatic hydrocarbon compound is contained is preferably a charge-blocking layer or an electron-transporting layer, and more preferably a charge-blocking layer.

By introducing the aromatic hydrocarbon compound into the layer contiguous to the light-emitting layer, efficiency and durability of the device are improved. When the light-emitting layer is excited, exitons are unevenly distributed to the interface of the light emitting layer and the adjacent layer and a phenomenon of destroying the contiguous layer, but the aromatic hydrocarbon compound has a highly durable structure and difficultly destroyed by excitons, therefore, it is considered that the above effect can be obtained.

From the viewpoint of easiness of synthesis, the aromatic hydrocarbon compound preferably includes a carbon atom and a hydrogen atom alone.

When the aromatic hydrocarbon compound is contained in a layer other than the light-emitting layer, the content is preferably 70% by mass to 100% by mass, and more preferably 85% by mass to 100% by mass. When the aromatic hydrocarbon compound is contained in the light-emitting layer, the content is preferably 0.1% by mass to 99% by mass to the gross mass of the light-emitting layer, more preferably 1% by mass to 95% by mass, and still more preferably 10% by mass to 95% by mass.

The aromatic hydrocarbon compound is preferably a hydrocarbon compound represented by the following formula (Tp-1) (hereinafter sometimes referred to as merely "the hydrocarbon compound").

Since the hydrocarbon compound represented by formula (Tp-1) consists of a carbon atom and a hydrogen atom alone and excellent in the point of chemical stability, the compound shows the advantages such that driving durability is high and various variations are difficult to occur at the time of high luminance driving.

The hydrocarbon compound represented by formula (Tp-1) has a molecular weight of preferably in the range of 400 to 1,200, more preferably 400 to 1,000, and still more preferably 400 to 800. When the molecular weight is 400 or more, an amorphous film of fine quality can be formed, while when the molecular weight is 1,200 or less, good solubility in a solvent is obtained, and preferred in the aspect of sublimation and vacuum deposition aptitudes.

The use of the hydrocarbon compound represented by formula (Tp-1) is not restricted, and may be contained not only in the organic layer contiguous to the light-emitting layer but also in any layer of the organic layers.

(Tp-1)

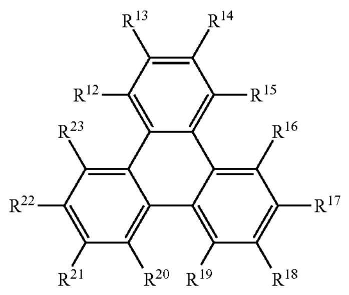

In formula (Tp-1), each of $R^{12}$ to $R^{23}$ independently represents a hydrogen atom, an alkyl group, or a phenyl, a fluorenyl group, a naphthyl group, or a triphenylenyl group (these groups may be substituted with an alkyl group, a phenyl group, a fluorenyl group, a naphthyl group or a triphenylenyl group), provided that all of $R^{12}$ to $R^{23}$ do not represent a hydrogen atom.

As the alkyl group represented by each of $R^{12}$ to $R^{23}$, for example, a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group are exemplified, each of which may be substituted or unsubstituted, preferably a methyl group, an ethyl group, an isopropyl group, a tert-butyl group, and cyclohexyl group, and more preferably a methyl group, an ethyl group, and a tert-butyl group.

Each of $R^{12}$ to $R^{23}$ preferably represents an alkyl group having 1 to 4 carbon atoms, or a phenyl group, afluorenyl group, a naphthyl group, or a triphenylenyl group (these groups may further be substituted with an alkyl group, a phenyl group, a fluorenyl group, a naphthyl group, or a triphenylenyl group), each of which may be substituted with an alkyl group having 1 to 4 carbon atoms, a phenyl group, a fluorenyl group, a naphthyl group, or a triphenylenyl group.

A benzene ring which may be substituted with a phenyl group, a fluorenyl group, a naphthyl group or a triphenylenyl group (these groups may further be substituted with an alkyl group, a phenyl group, a fluorenyl group, a naphthyl group or a triphenylenyl group) is especially preferred.

The total number of aryl rings in formula (Tp-1) is preferably 2 to 8, and more preferably 3 to 5. When the number of thearyl rings is in this range, an amorphous film of fine quality can be formed, and solubility in a solvent, sublimation and vacuum deposition aptitudes are improved.

Each of $R^{12}$ to $R^{23}$ independently preferably has total carbon atoms of 20 to 50, and more preferably total carbon atoms of 20 to 36. In this range of total carbon atoms, an amorphous film of fine quality can be formed, and solubility in a solvent, sublimation and vacuum deposition aptitudes are improved.

In one embodiment of the invention, the hydrocarbon compound represented by formula (Tp-1) is preferably a hydrocarbon compound represented by the following formula (Tp-2).

(Tp-2)

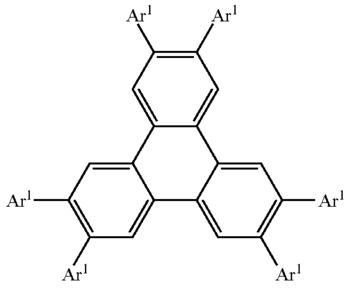

In formula (Tp-2), plural $Ar^1$ are the same with each other and represent a phenyl group, a fluorenyl group, a naphthyl group, or a triphenylenyl group which may be substituted with an alkyl group, a phenyl group, a fluorenyl group, a naphthyl, or a triphenylenyl group.

The alkyl group, and the phenyl group, fluorenyl group, naphthyl group and triphenylenyl group represented by $Ar^1$ which may be substituted with an alkyl group, a phenyl group, a fluorenyl group, a naphthyl group or a triphenylenyl group, are the same with those described in $R^{12}$ to $R^{23}$ and preferred ranges are also the same.

In another embodiment of the invention, the hydrocarbon compound represented by formula (Tp-1) is preferably a hydrocarbon compound represented by the following formula (Tp-3).

formula (Tp-3)

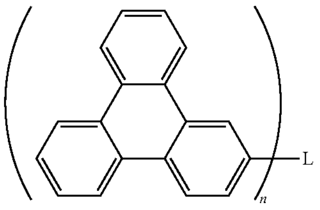

In formula (Tp-3), L represents a phenyl group, a fluorenyl group, a naphthyl group, or a triphenylenyl group which may be substituted with an alkyl group, a phenyl group, a fluorenyl group, a naphthyl group or a triphenylenyl group, or an n-valent linking group obtained by combining these groups. n represents an integer of 1 to 6.

The alkyl group, phenyl group, fluorenyl group, naphthyl group, or triphenylenyl group forming the n-valent linking group represented by L has the same meaning as described in $R^{12}$ to $R^{23}$.

L preferably represents a benzene ring or a fluorene ring which may be substituted with an alkyl group or a benzene ring, or an n-valent linking group obtained by combining these groups.

The preferred specific examples of L are shown below, but the invention is not restricted thereto. In the specific examples, L bonds to a triphenylen ring via *.

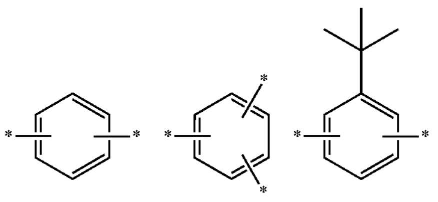

-continued

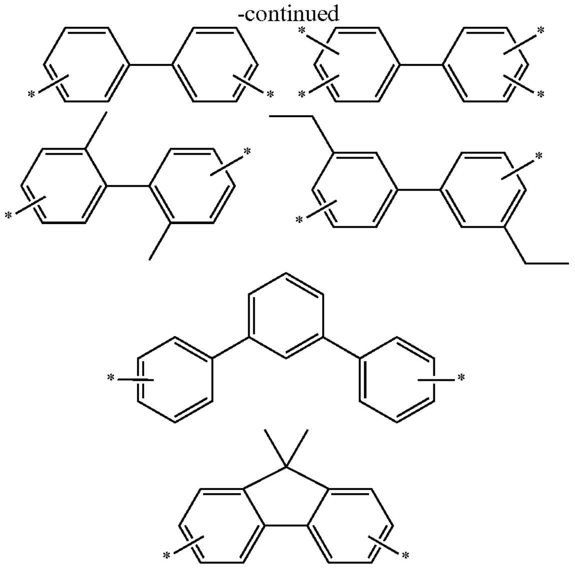

n is preferably 1 to 5, and more preferably 1 to 4.

In another embodiment of the invention, the hydrocarbon compound represented by formula (Tp-1) is preferably a hydrocarbon compound represented by the following formula (Tp-4).

(Tp-4)

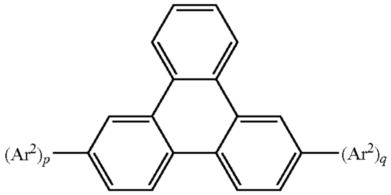

In formula (Tp-4), plural $Ar^2$ are the same with each other, and $Ar^2$ represent a group substituted with an alkyl group, a phenyl group, a naphthyl group, or a triphenylenyl group, or a group obtained by combining these groups. Each of p and q independently represents 0 or 1, provided that p and q do not represent 0 at the same time. When each of p and q represents 0, $Ar^2$ represents a hydrogen atom.

$Ar^2$ preferably represents a group obtained by combining an alkyl group having 1 to 4 carbon atoms, a phenyl group, a naphthyl group, and a triphenylenyl group, and more preferably a group obtained by combining a methyl group, a t-butyl group, a phenyl group and a triphenylenyl group.

$Ar^2$ is especially preferably a benzene ring whose meta-position is substituted with an alkyl group having 1 to 4 carbon atoms, a phenyl group, a naphthyl group, a triphenylenyl group, or a group obtained by combining these groups.

In the case where the hydrocarbon compound according to the invention is used as the host material of the light-emitting layer of the organic electroluminescence device or as the charge-transporting material of the layer contiguous to the light emitting layer, when the energy gap of the hydrocarbon compound in a film state (the lowest triplet excited state ($T_1$) energy in a film state in the case where the light-emitting material is a phosphorescent material) is greater than that of the light-emitting material, quenching of light emission can be prevented, and so advantageous in the improvement of efficiency. On the other hand, from the viewpoint of chemical stability of the hydrocarbon compound, energy gap and $T_1$ energy are preferably not too high. $T^1$ energy of the hydrocarbon compound represented by formula (Tp-1) in a film state is preferably 52 kcal/mol or more and 80 kcal/mol or less, more preferably 55 kcal/mol or more and 68 kcaUmol or less, and still more preferably 58 kcal/mol or more and 63 kcal/mol or less. In particular, when a phosphorescent material is used as the light-emitting material, it is preferred that $T_1$ energy comes into the above range.

$T_1$ energy can be found from the short wavelength end of the light emission spectrum of phosphorescence of the film of a material. For example, a film is formed in a thickness of about 50 nm by vacuum deposition of a material on a cleaned quartz glass substrate, and the light emission spectrum of phosphorescence of the film is measured with F-7000 Hitachi fluorescence spectrophotometer (manufactured by Hitachi High Technologies Corporation) under a liquid nitrogen temperature. $T_1$ energy can be found by converting the rising wavelength on the short wavelength side of the obtained light emission spectrum into an energy unit.

The specific examples of hydrocarbon compounds according to the invention are shown below, but the invention is not restricted thereto.

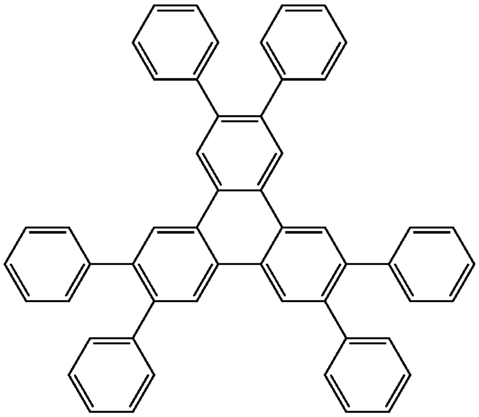

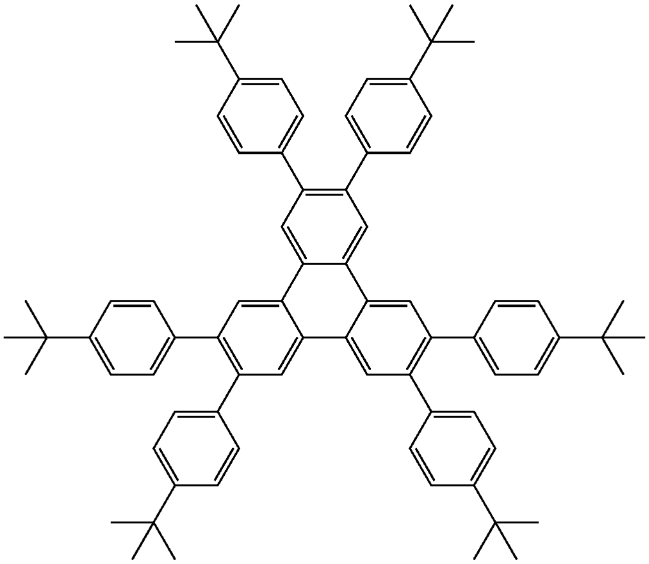

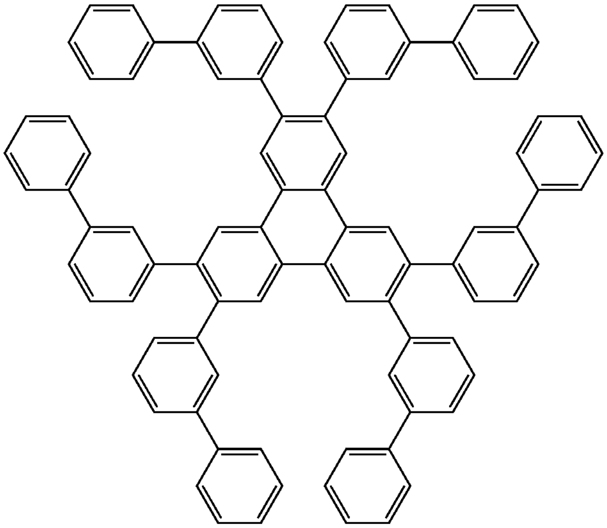

-continued
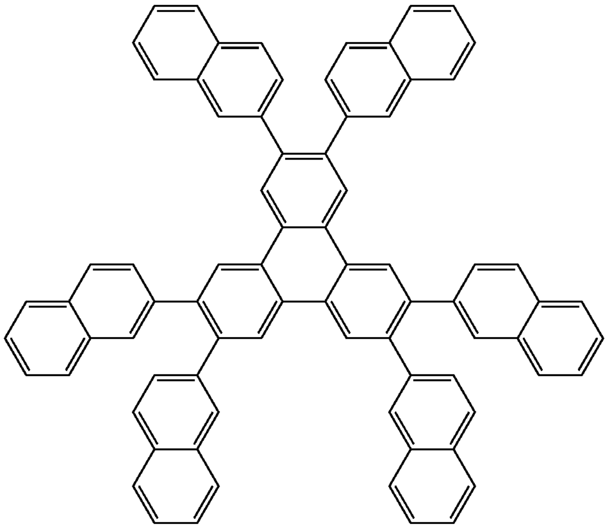
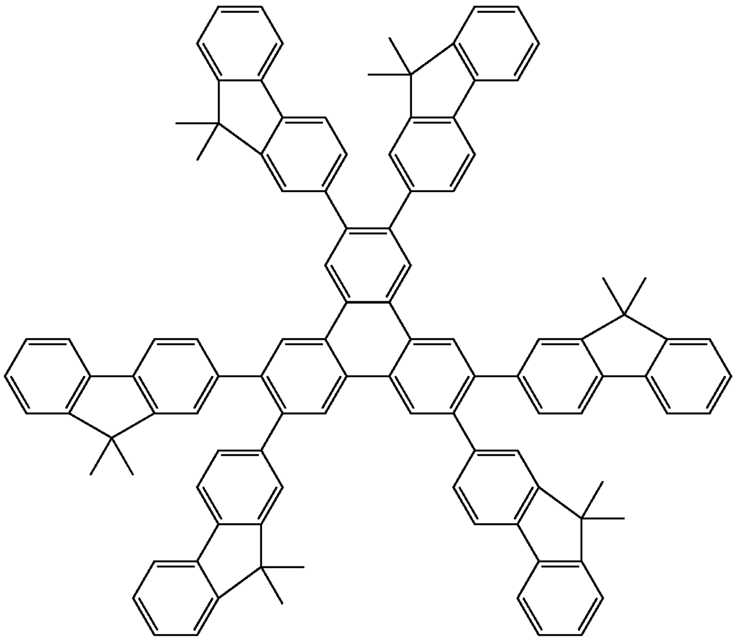
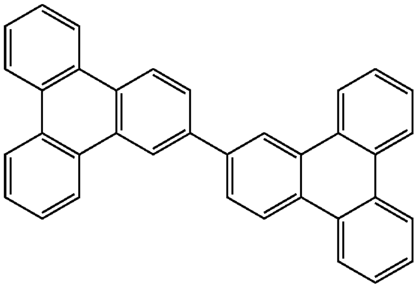
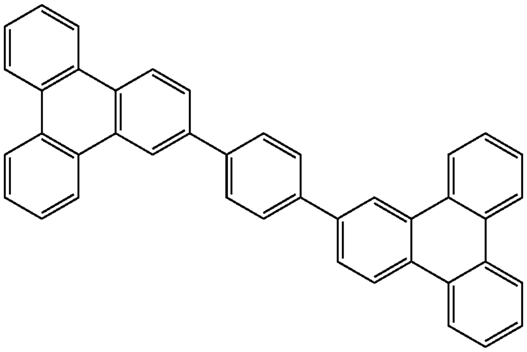
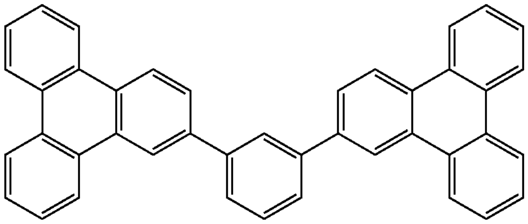

-continued
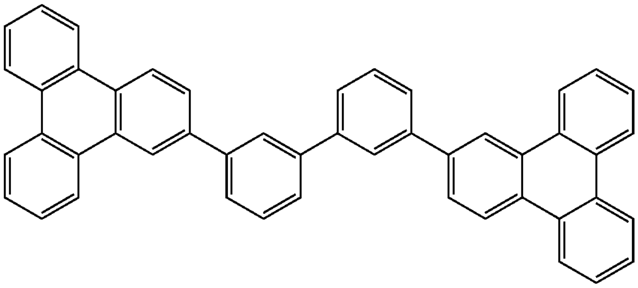
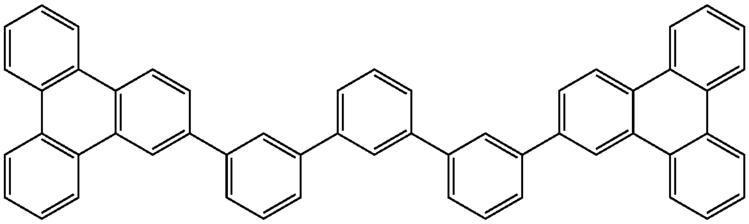
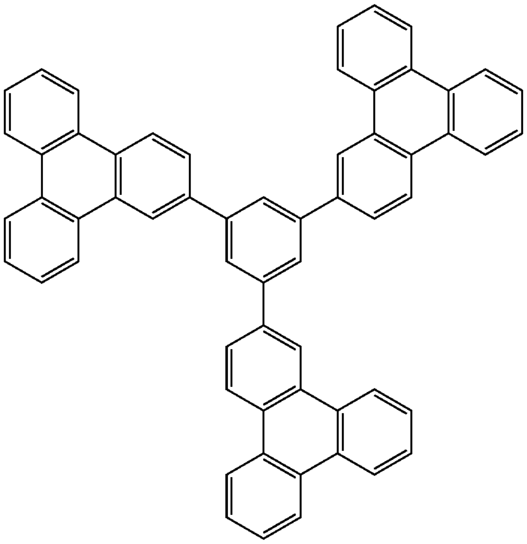
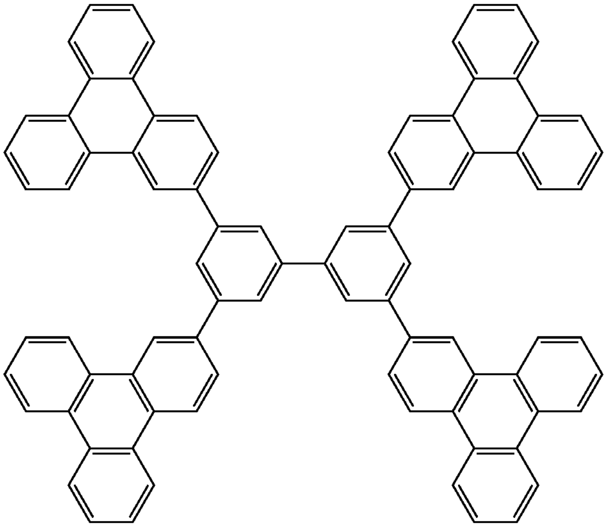
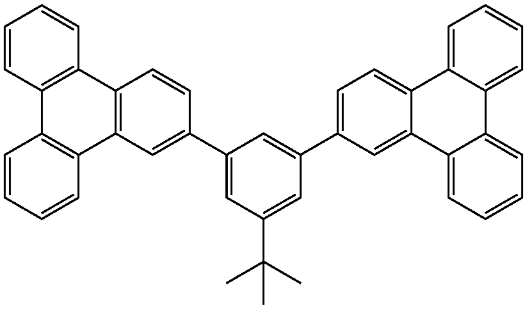
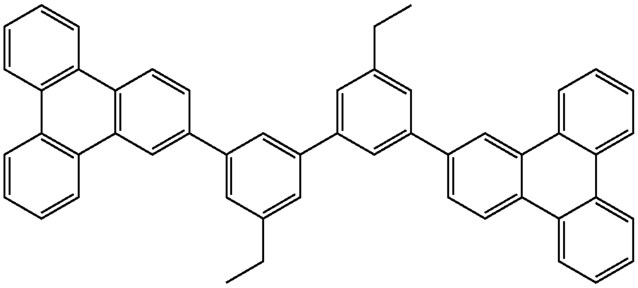
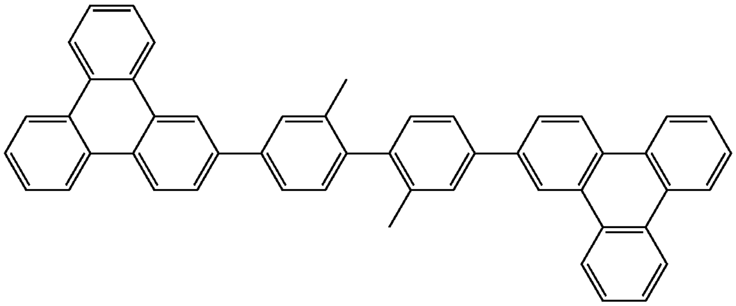

-continued
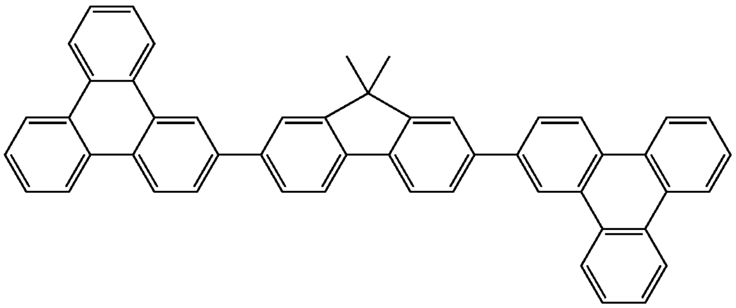
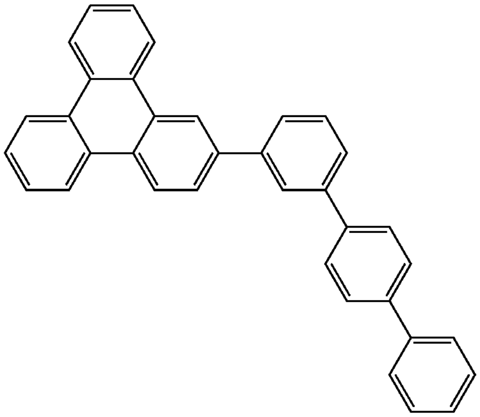
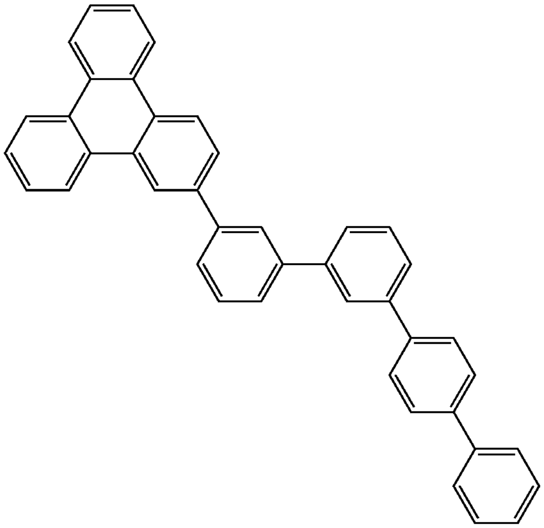
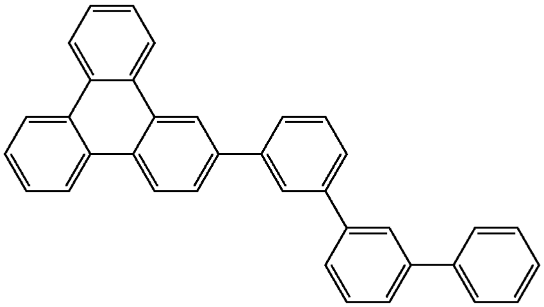
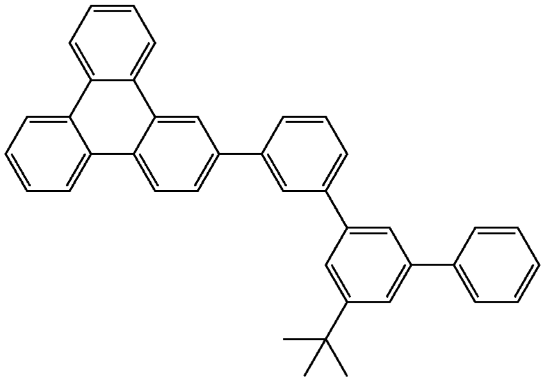
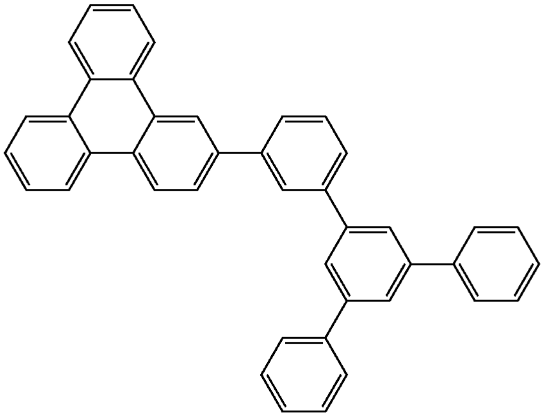
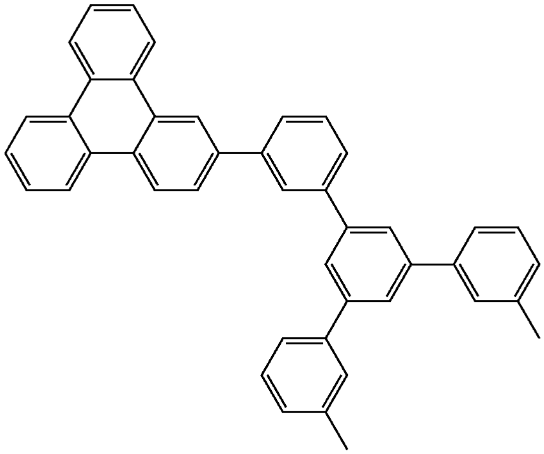

-continued
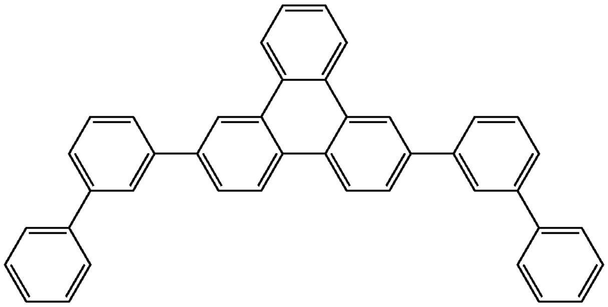
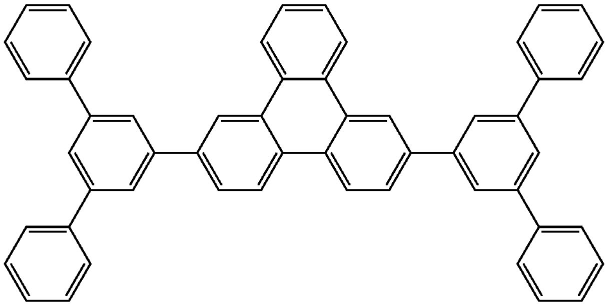
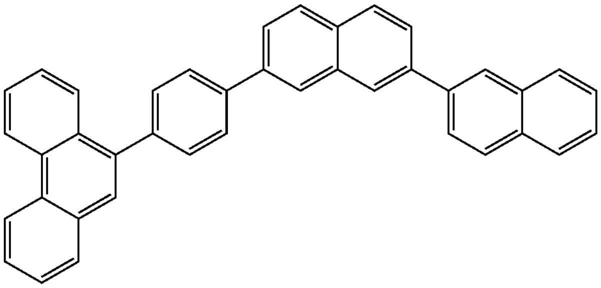
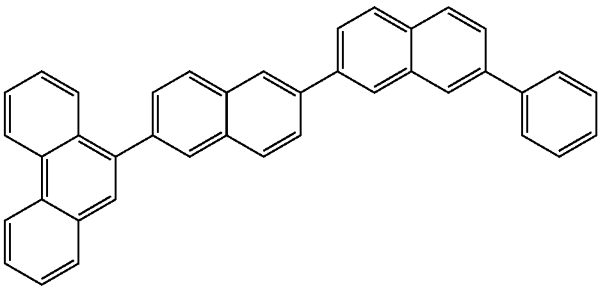
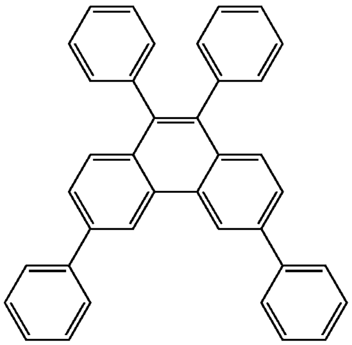
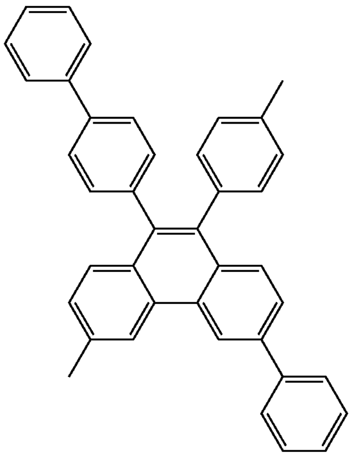
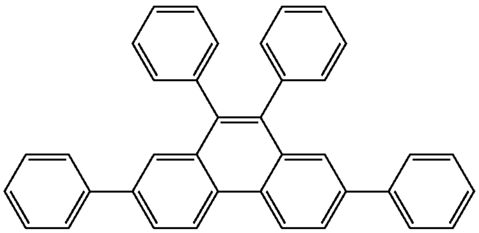

-continued
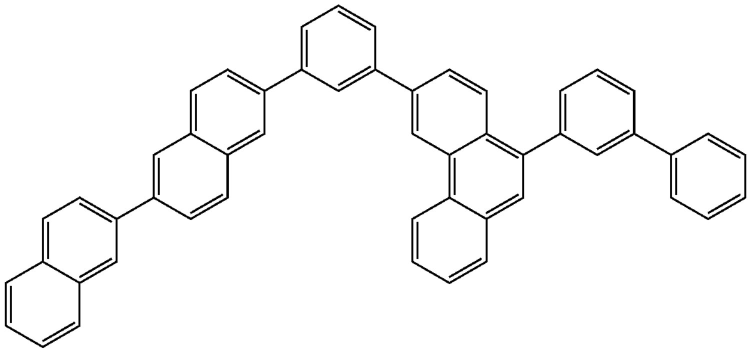
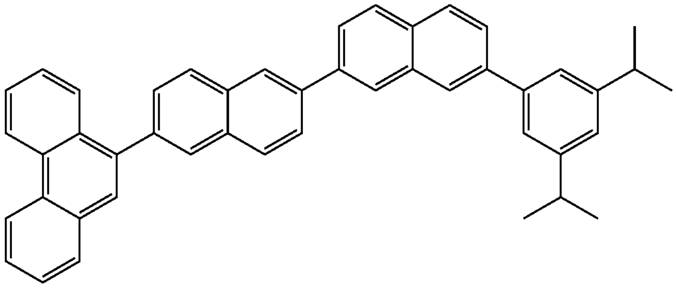
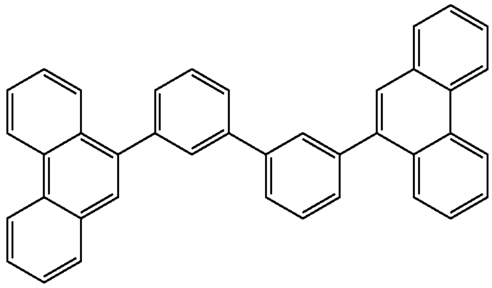
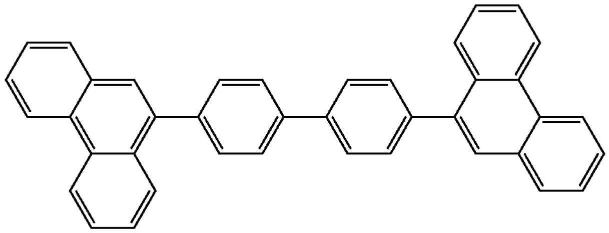
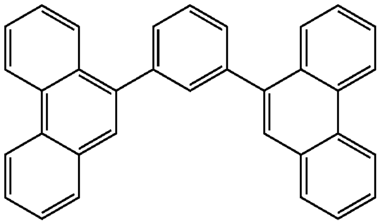
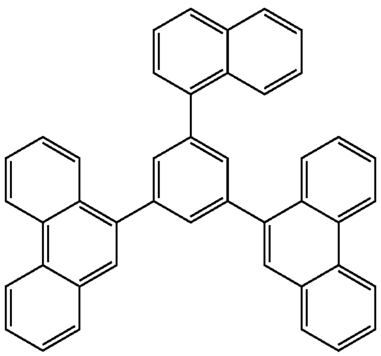
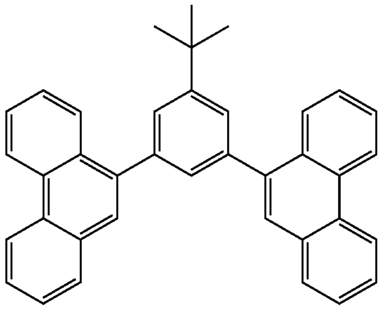
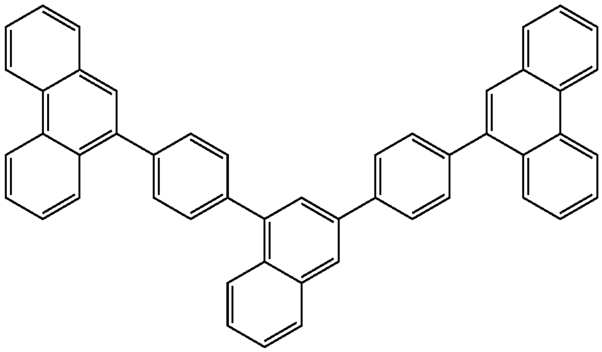

-continued
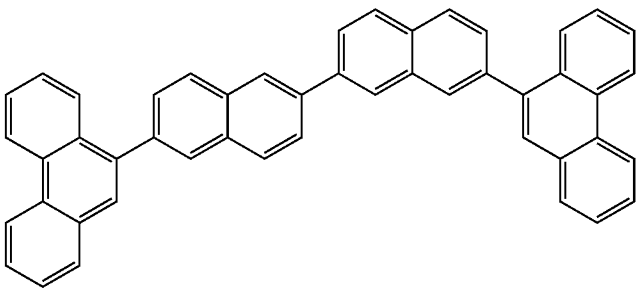
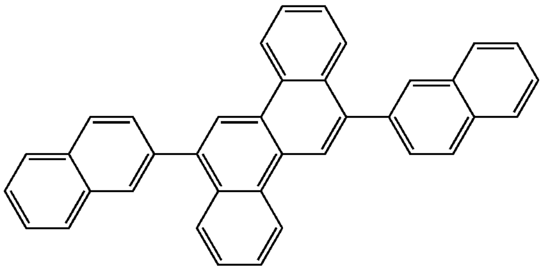
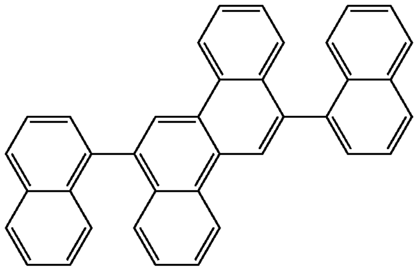
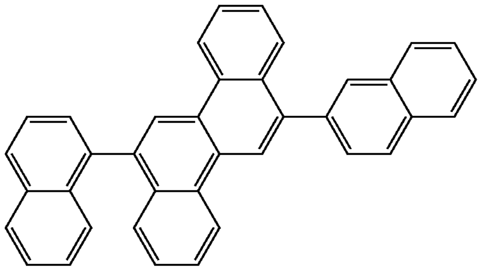
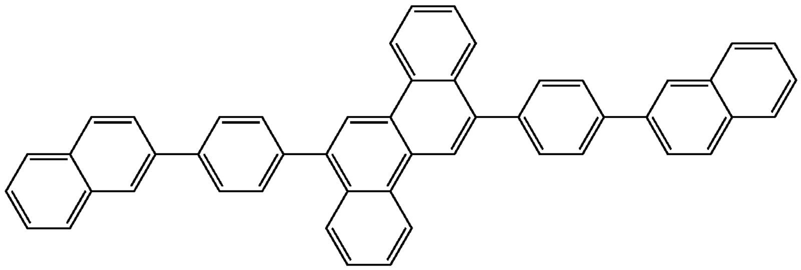
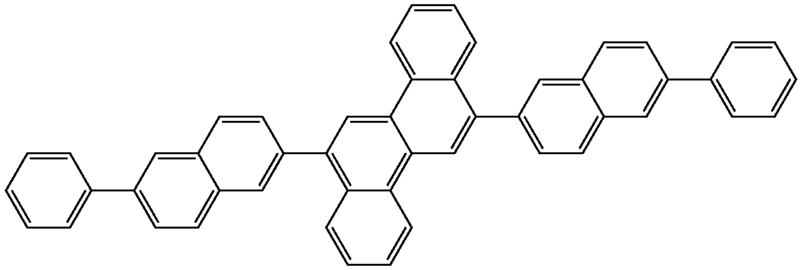
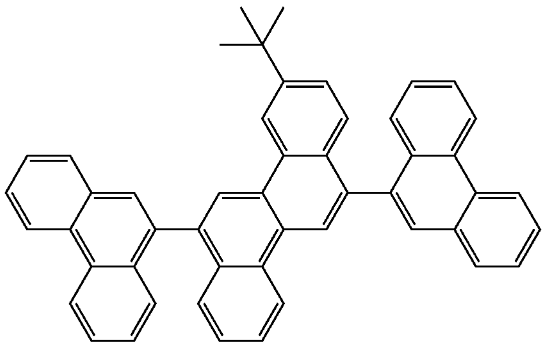
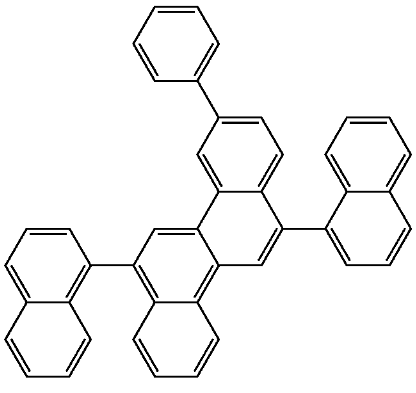

-continued
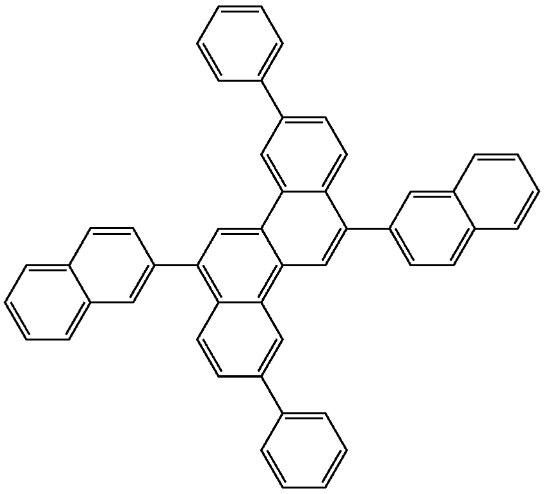
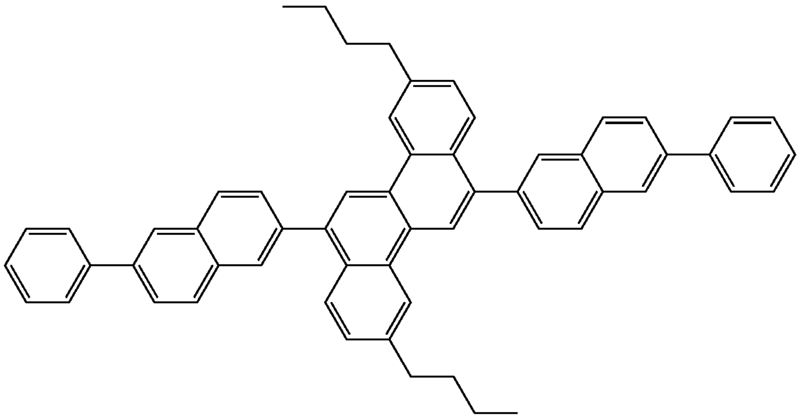
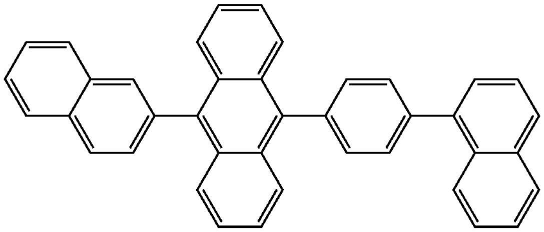
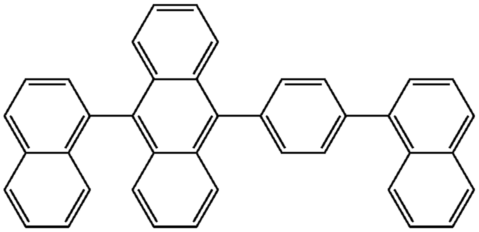
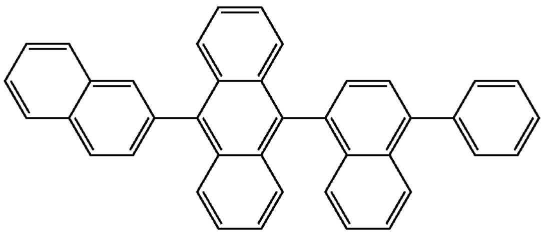
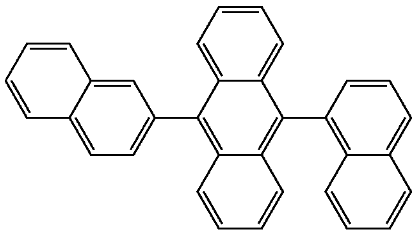
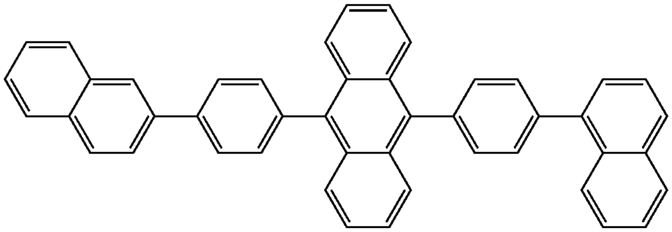

-continued
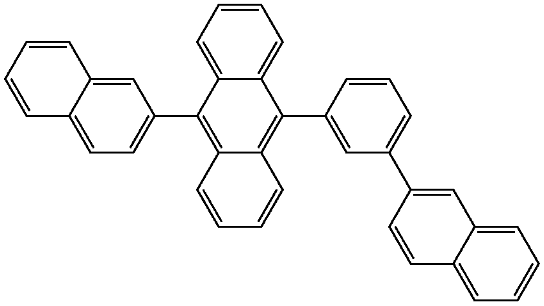
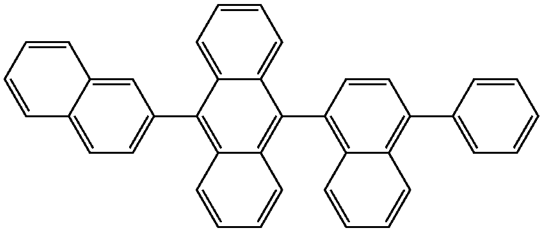
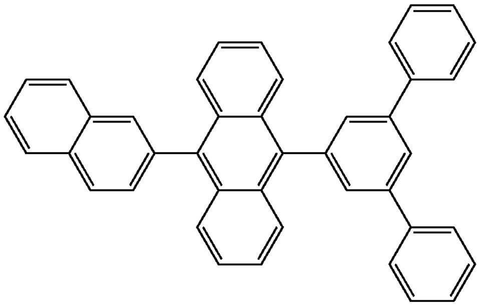
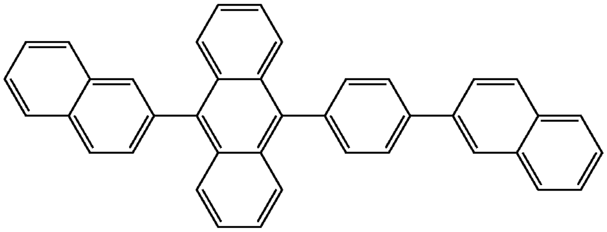
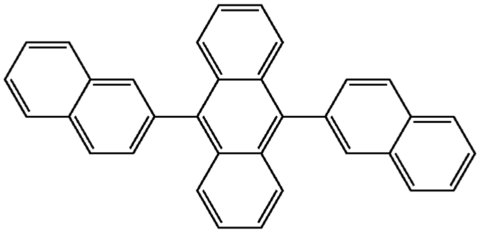
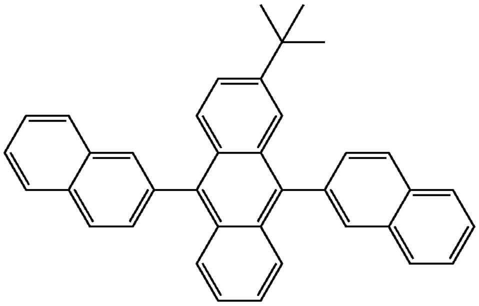
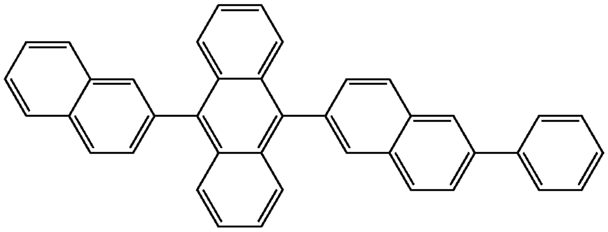
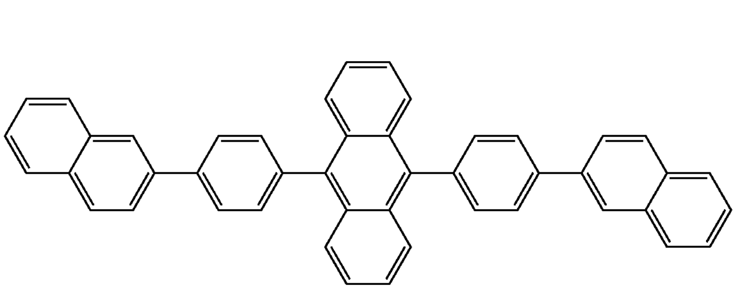

-continued
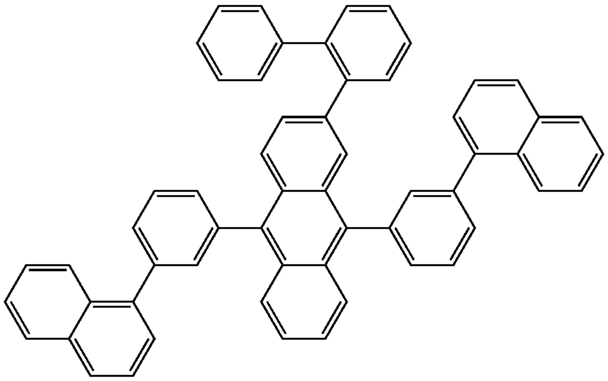
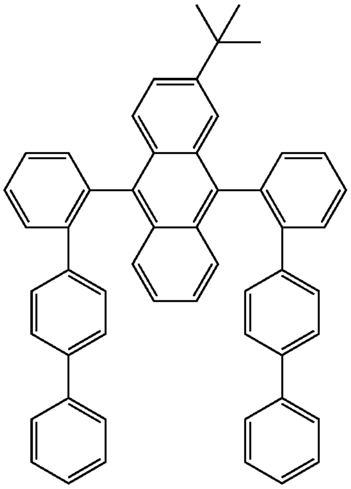
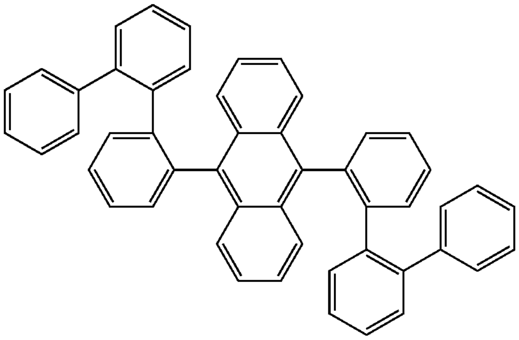
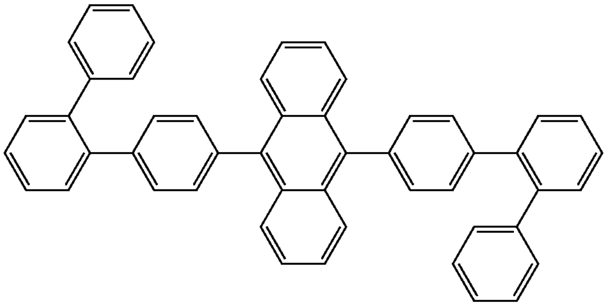
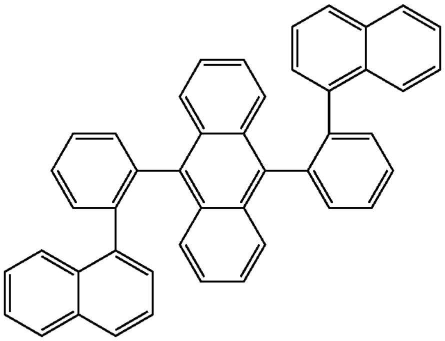
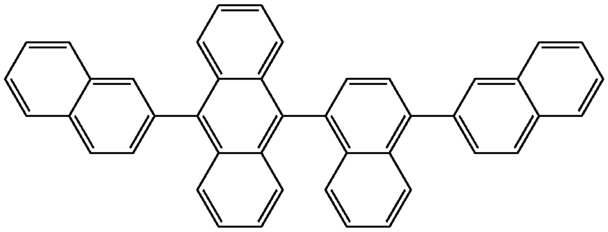
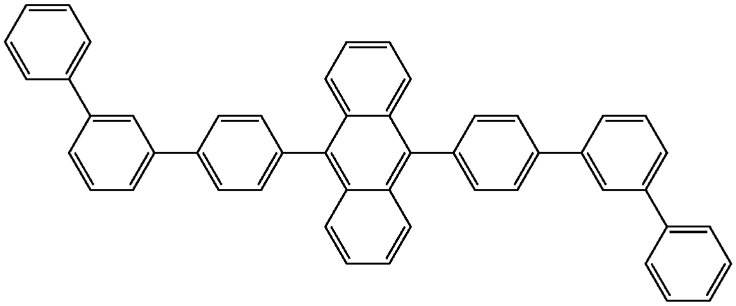

-continued
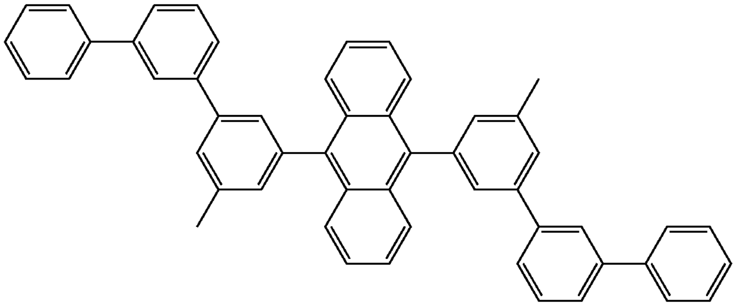
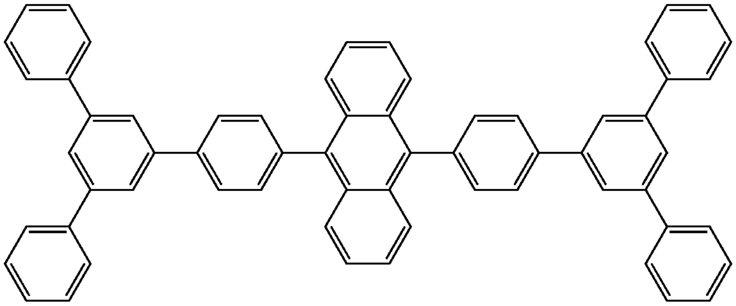
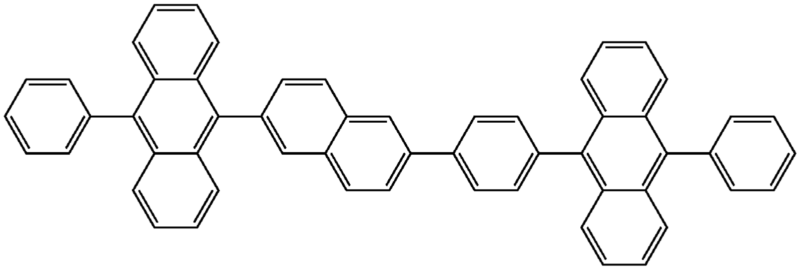
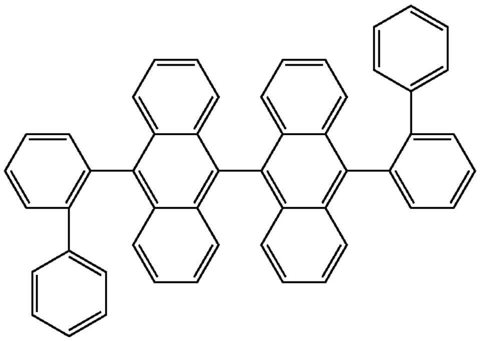
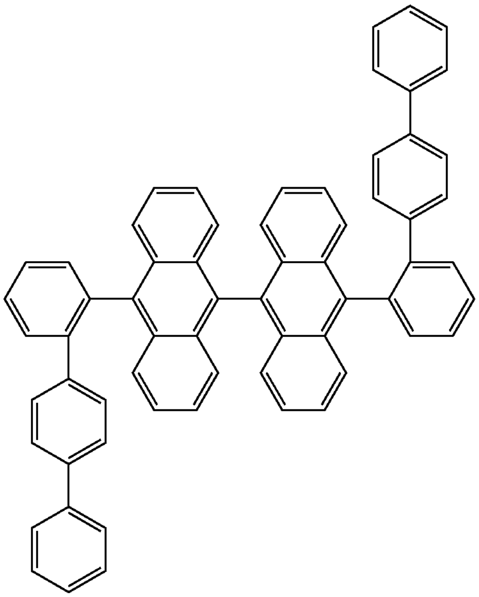
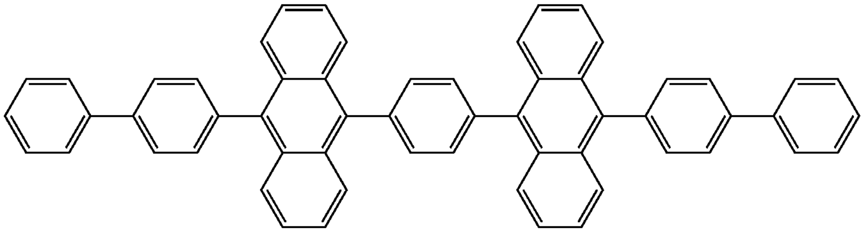

-continued
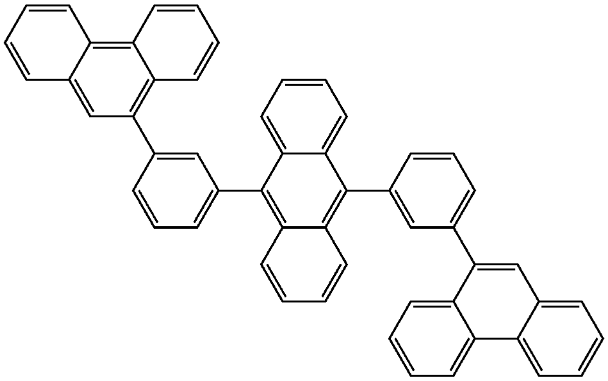
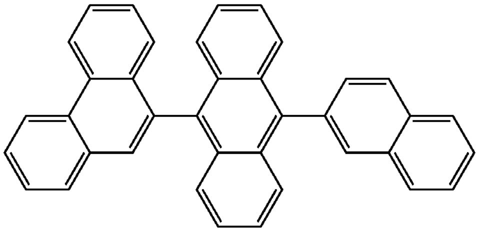
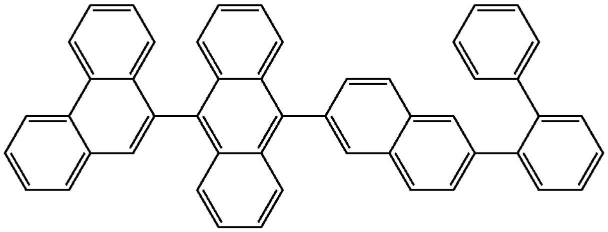
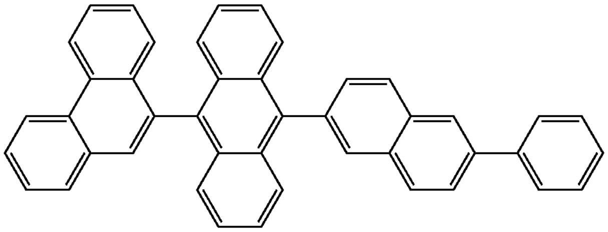
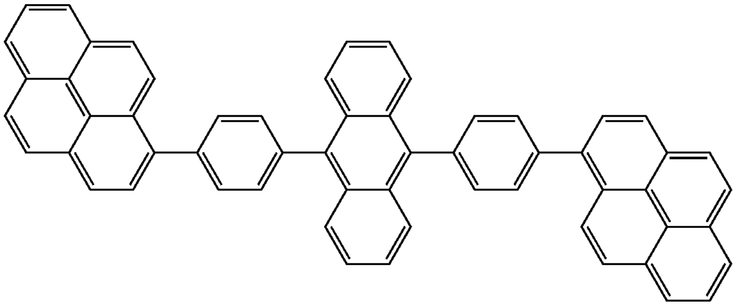
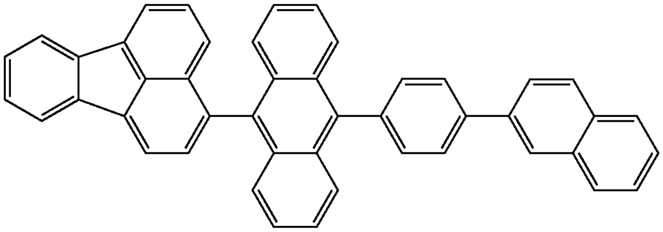
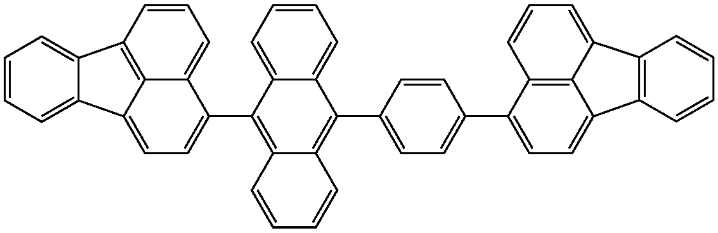

-continued
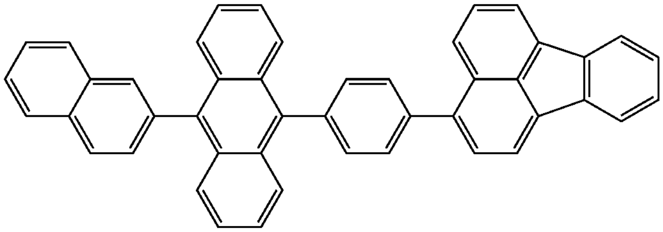
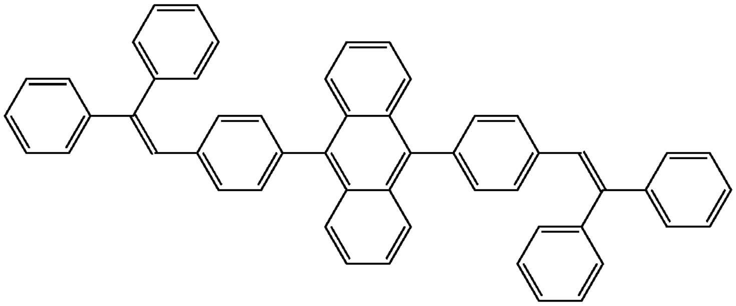
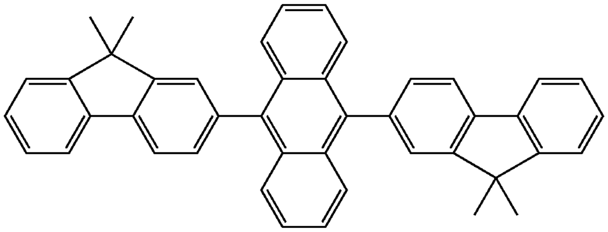
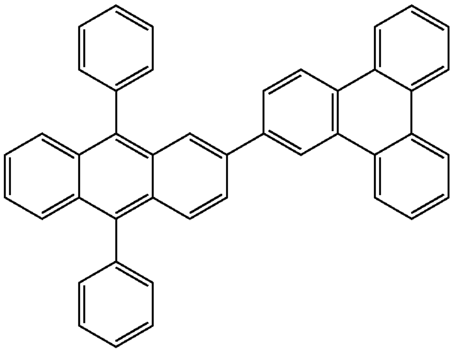
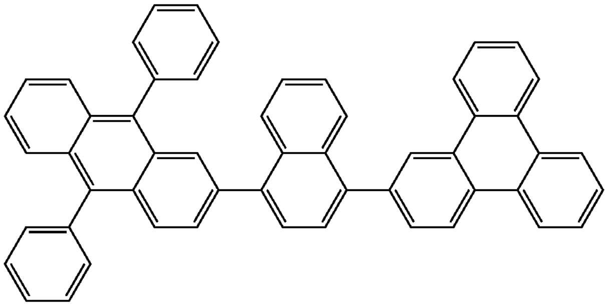
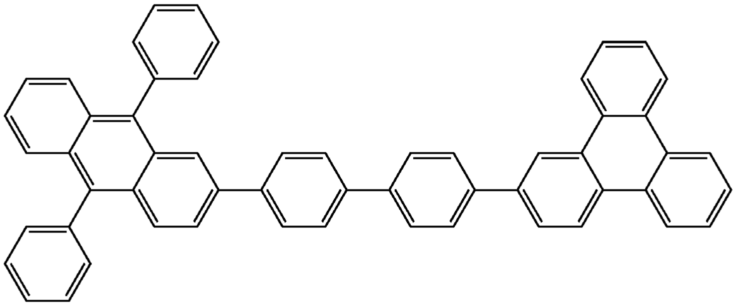

-continued
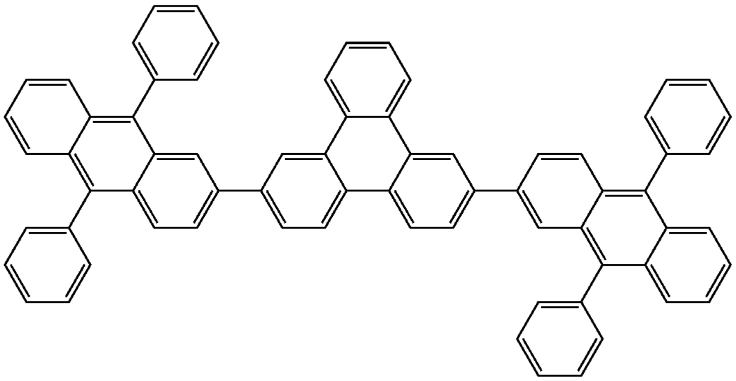
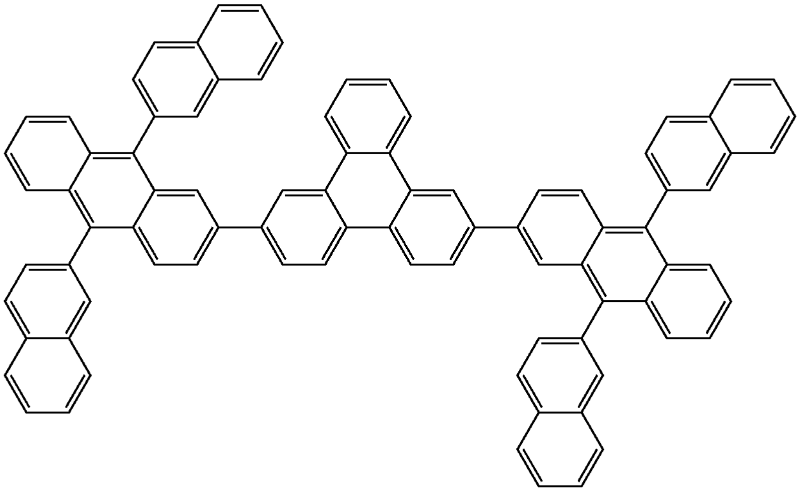
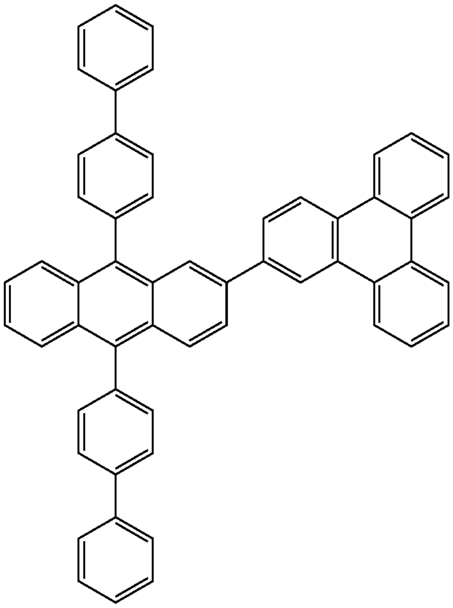
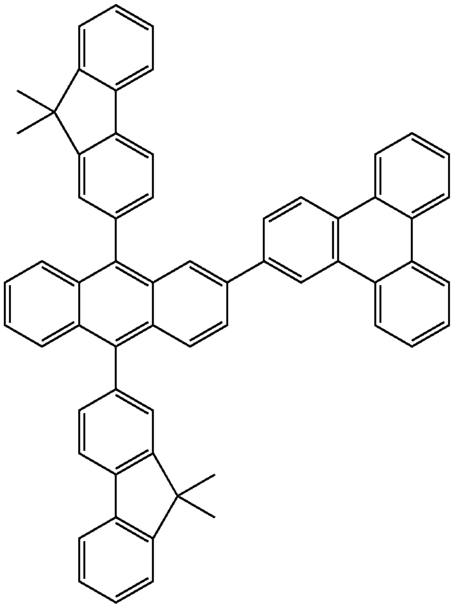

-continued
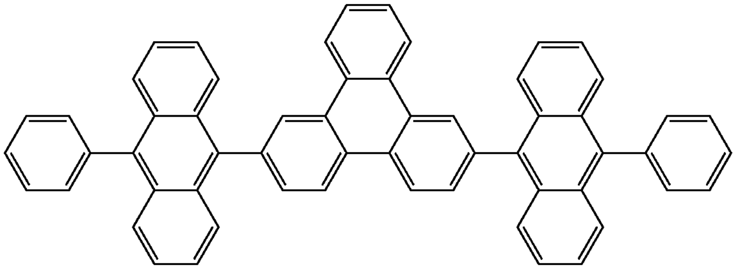
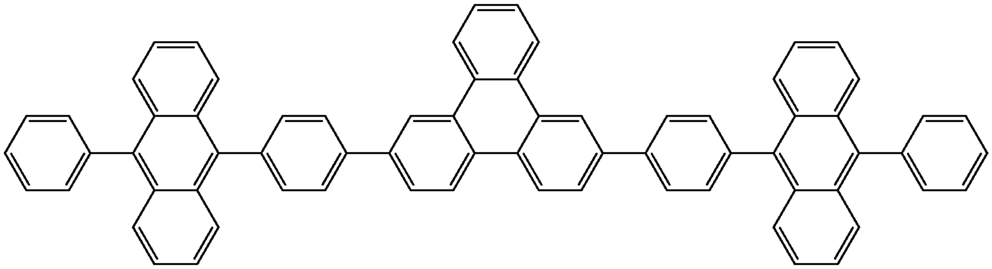
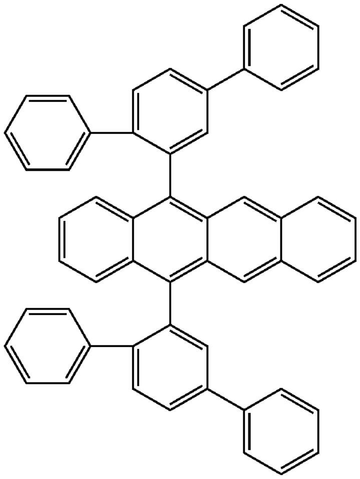
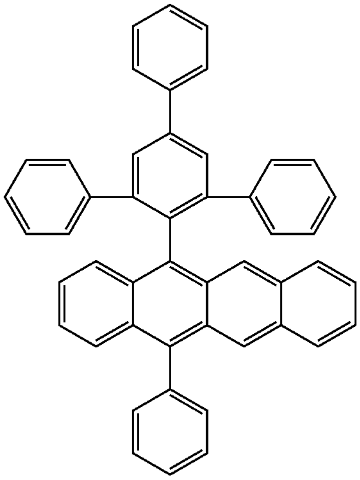
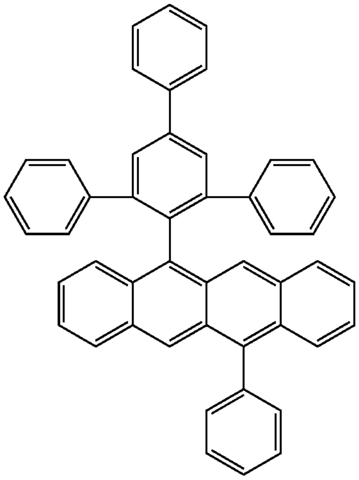
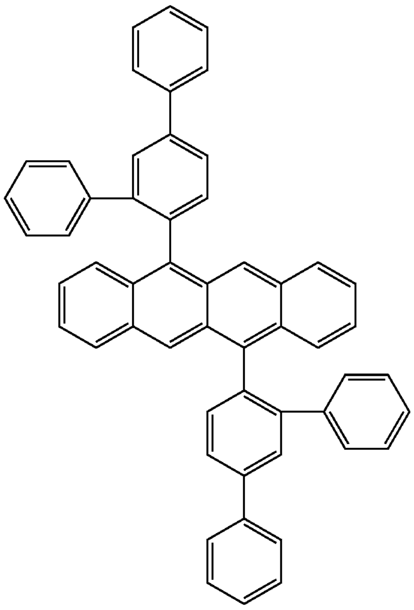
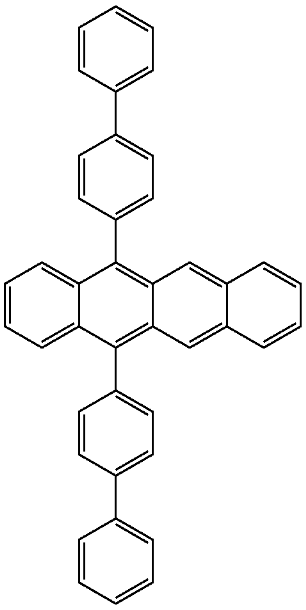
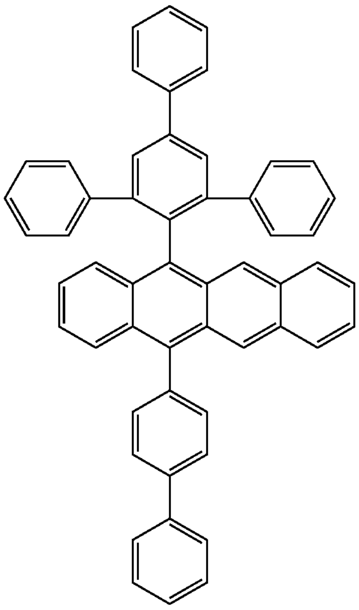

-continued
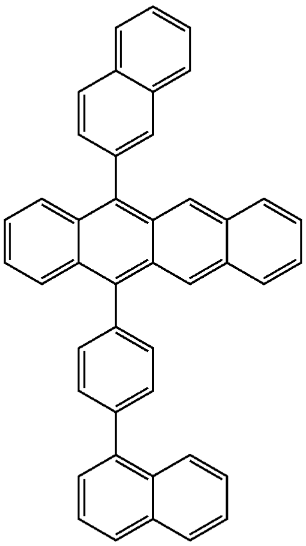
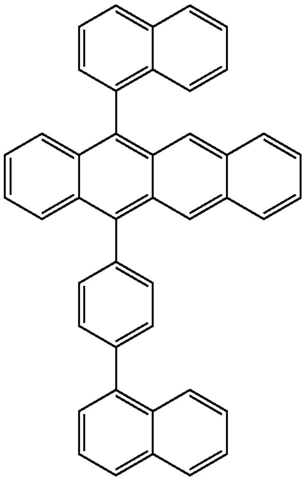
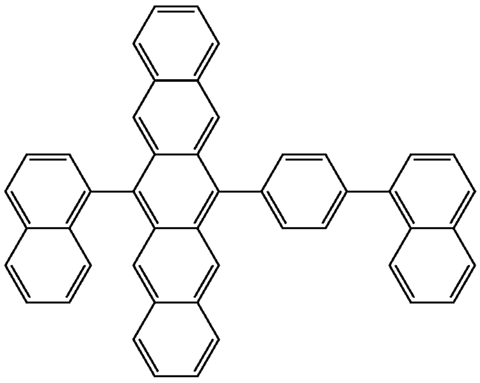
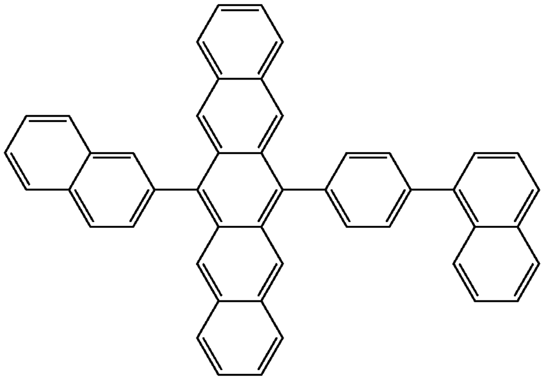
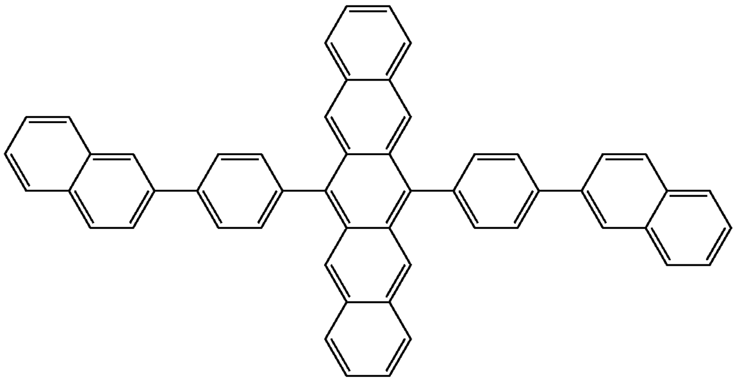
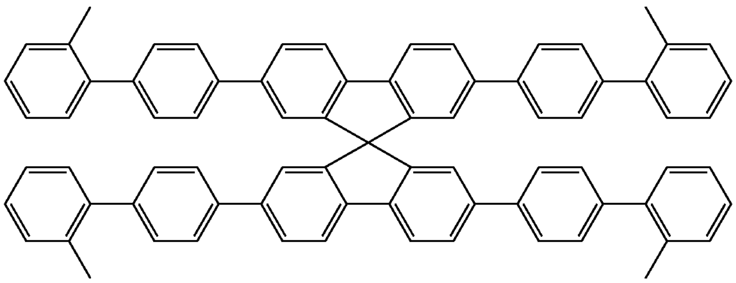

-continued
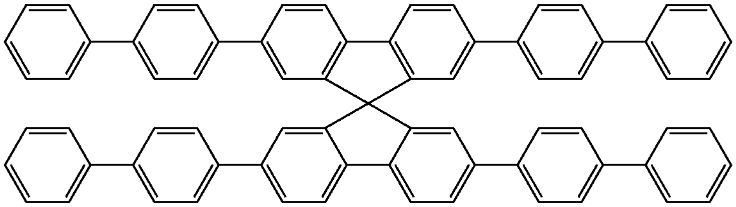
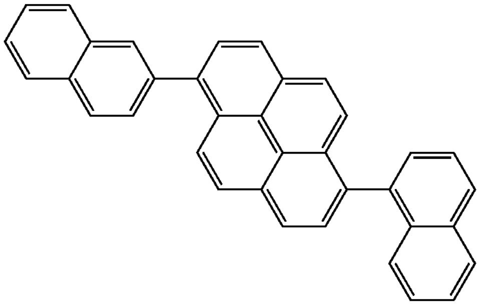
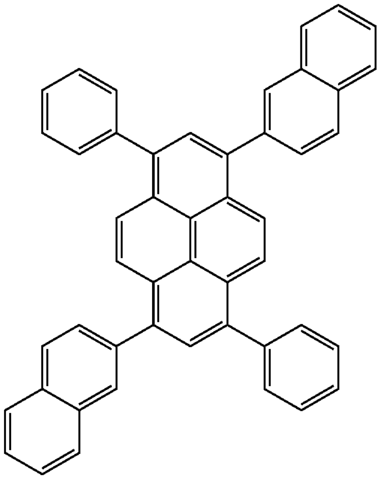
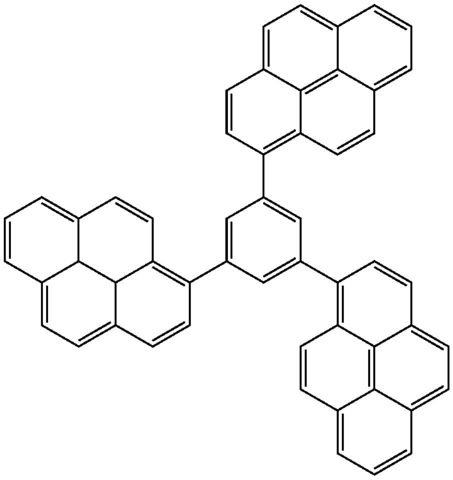
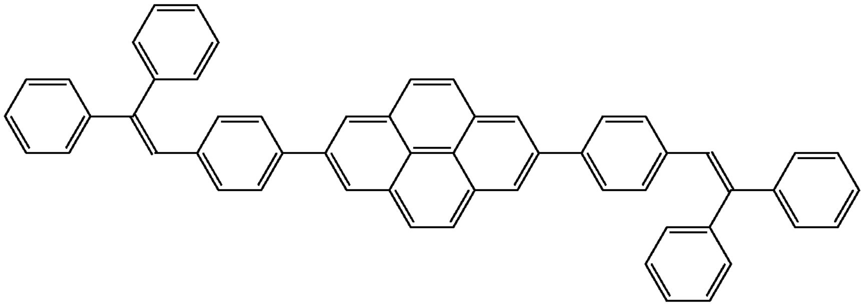
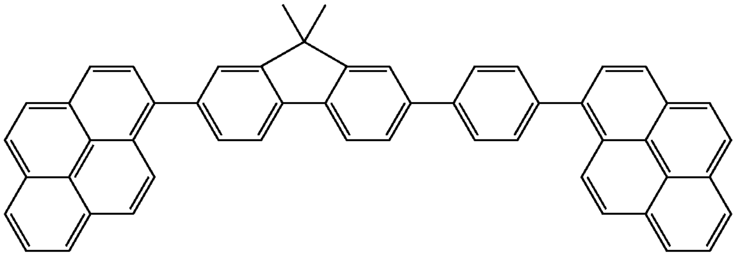

-continued

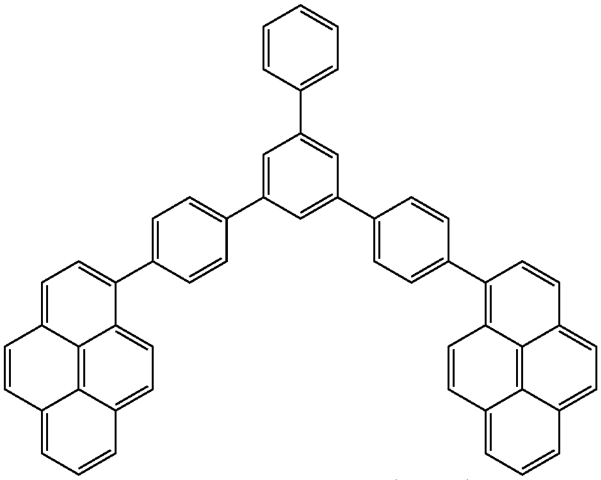

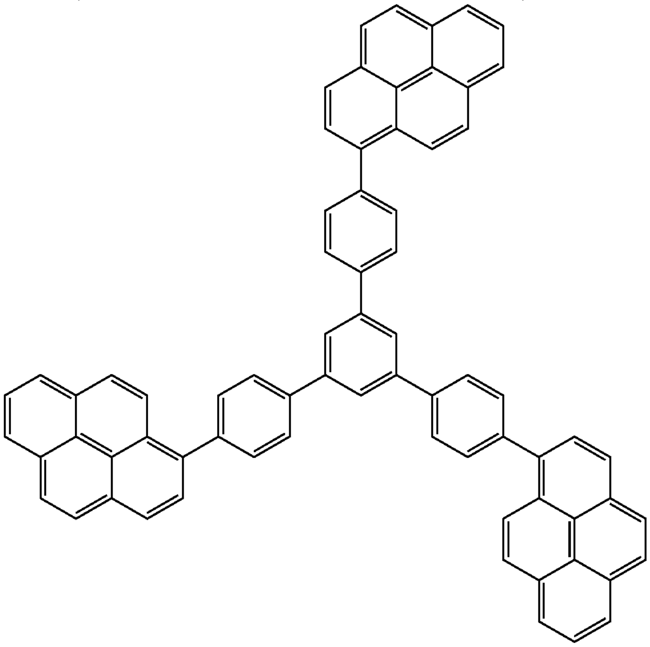

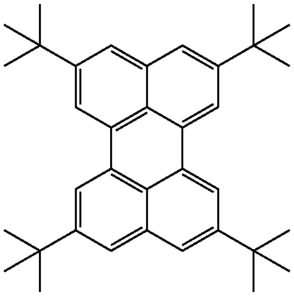

The above exemplified aromatic hydrocarbon compounds according to the invention can be synthesized by the methods described in WO 05/013388, WO 06/130598, WO 09/021, 107, U.S. Patent 2009/0,009,065, WO 09/008,311, and WO 04/018587.

The synthesized compound is preferably purified by sublimation purification after having been subjected to purification treatment by column chromatography, recrystallization and the like. Not only organic impurities can be separated but also inorganic salts and residual solvents can be effectually removed by sublimation purification.

In the electroluminescence device in the invention, the aromatic hydrocarbon compound is contained in an organic layer between a light-emitting layer and the cathode and contiguous to the light-emitting layer, but the use is not limitative and may be contained in any layer of organic layers. The aromatic hydrocarbon compound can be introduced into any one or two or more layers of a light-emitting layer, a hole-injecting layer, a hole-transporting layer, an electron-transporting layer, an electron-injecting layer, an exciton-blocking layer, and a charge-blocking layer.

The organic layer contiguous to the light-emitting layer between the light emitting layer and the cathode in which the hydrocarbon compound is contained is preferably a charge-blocking layer or an electron-transporting layer, and more preferably an electron-transporting layer.

From the aspect of driving the organic electroluminescence device stably at high temperature driving time or to the calorification during driving of the device, the glass transition temperature (Tg) of the hydrocarbon compound of the invention is preferably 60° C. or more and 400° C. or less, more preferably 65° C. or more and 300° C. or less, and still more preferably 80° C. or more and 180° C. or less.

It is preferred that in the organic electroluminescence device in the invention in the invention, the electrode includes the anode and has an organic layer between the light-emitting layer and the anode. It is preferred for the organic layer contiguous to the light-emitting layer to contain a compound having the lowest triplet excited state ($T_1$) energy in a solution of 58 kcal/mol or more, and more preferably to contain a compound of 62 kcal/mol to 75 kcal/mol. As the compound having the lowest triplet excited state ($T_1$) energy of 58 kcal/mol or more, a carbazole compound can be exemplified.

The carbazole compound is preferably a carbazole compound represented by the following formula (a).

(a)

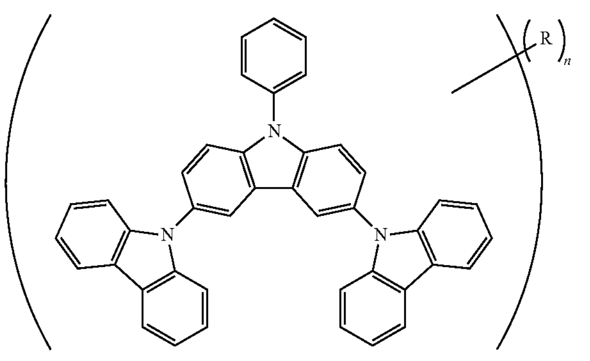

In formula (a), R represents a substituent capable of substituting on a hydrogen atom in the structure, and when two or more R are present, R may be the same with or different from each other. n represents an integer of 0 to 8.

When the compound represented by formula (a) is used in an electron transporting layer, the compound represented by formula (a) is preferably contained in the range of 50% by mass to 100% by mass, more preferably 80% by mass to 100% by mass, and especially preferably 95% by mass to 100% by mass.

Further, when the compound represented by formula (a) is used in two or more layers, it is preferred that the compound is used in each layer in the above range.

One kind alone of the compound represented by formula (a) may be contained in any organic layer or plural the compounds represented by formula (a) may be contained in combination in an arbitrary rate.

The thickness of the electron-transporting layer containing the compound represented by formula (a) is preferably 1 nm to 500 nm, more preferably 3 nm to 200 nm, and still more preferably 5 nm to 100 nm. It is also preferred that the electron transporting layer is provided in contiguous to the light-emitting layer.

The electron-transporting layer may have a monolayer structure containing one or two or more kinds of the above materials, or may have a multilayer structure including two or more layers of the same composition or different compositions.

As the substituent represented by R, a halogen atom, an alkoxy group, a cyano group, a nitro group, an alkyl group, an aryl group and an aromatic heterocyclic group Are specifically exemplified, preferably an alkyl group having 10 or less carbon atoms, and a substituted or unsubstituted aryl group having 10 or less carbon atoms, and still more preferably an alkyl group having 6 or less carbon atoms.

n represents an integer of 0 to 8, preferably 0 to 4, and more preferably 0 to 2.

The hydrogen atom constituting formula (a) also contain isotopes of hydrogen atoms (deuterium atoms). In such a case, all the hydrogen atoms in the compounds may be substituted with hydrogen isotopes, or the compounds may be mixtures partially containing hydrogen isotopes.

The compounds represented by formula (a) can be synthesized by combining various known synthesis methods. Most generally, concerning the carbazole compounds, synthesis by dehydrogenation aromatization after Aza-Cope arrangement of the condensation product of aryl hydrazine and cyclohexane derivative (L. F. Tieze and Th. Eicher, translated by Takano and Ogasawara, Precision Organic Syntheses, p. 339, published by Nanko-Do) is exemplified. Further, concerning the coupling reaction of the obtained carbazole compound and aryl halide compound using a palladium catalyst, the methods described in Tetrahedron Letters, Vol. 39, p. 617 (1998), ibid., Vol. 39, p. 2367 (1998), and ibid., Vol. 40, p. 6393 (1999) are exemplified. The reaction temperature and reaction time are not especially restricted and the conditions in the above documents are applied.

It is preferred that the film of the compound represented by formula (a) is formed according to a vacuum deposition process, but a wet process such as solution coating can also be preferably used. The molecular weight of the compound is preferably 2,000 or less in view of deposition aptitude and solubility, more preferably 1,200 or less, and especially preferably 800 or less. Further, in the point of vacuum deposition aptitude, too small a molecular weight is accompanied by small vapor pressure and transition from a vapor phase to a solid phase does not occur and it becomes difficult to form an organic layer. Accordingly, the molecular weight is preferably 250 or more, and especially preferably 300 or more.

The specific examples of the compounds represented by formula (a) in the invention are shown below, but the invention is not restricted thereto.

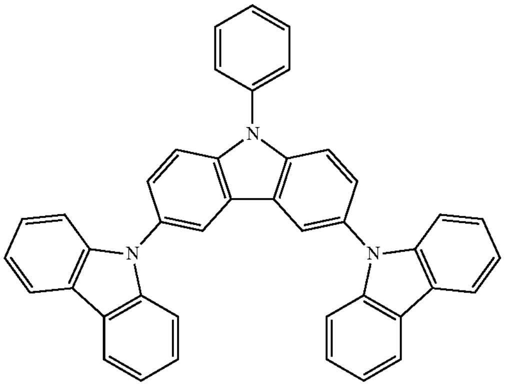

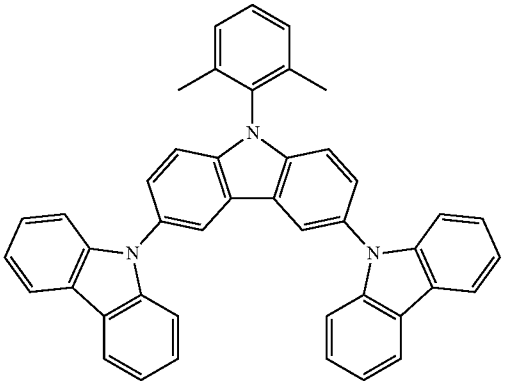

-continued
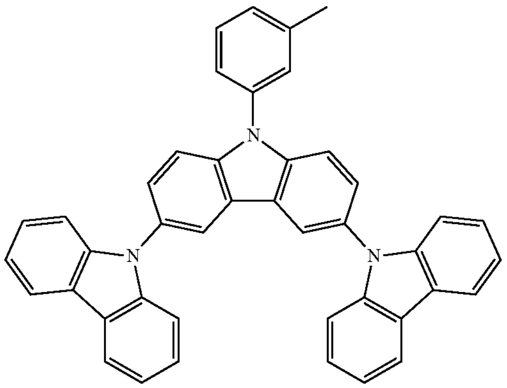
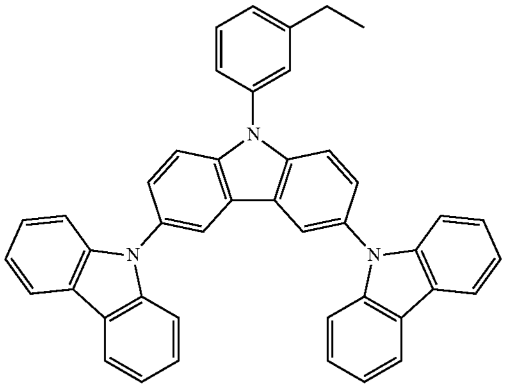
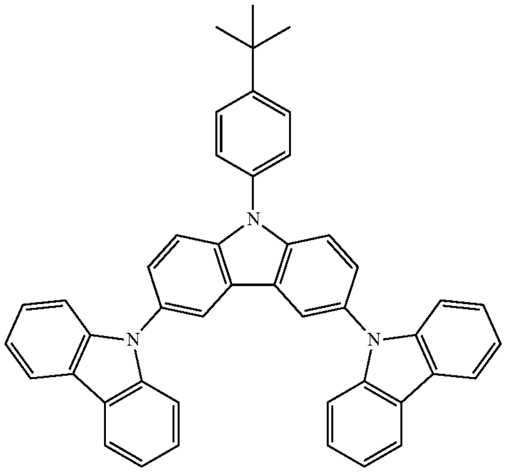
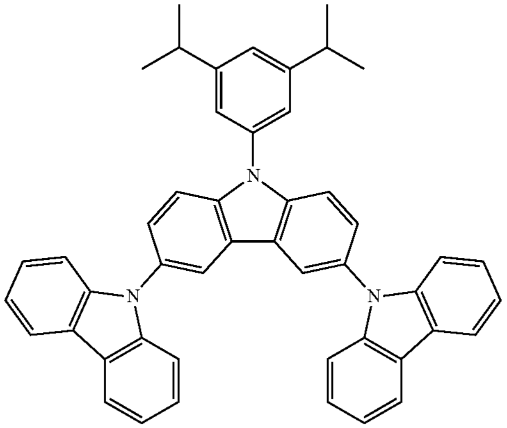
-continued
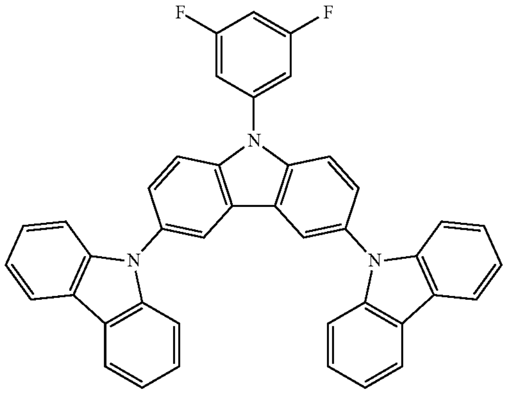
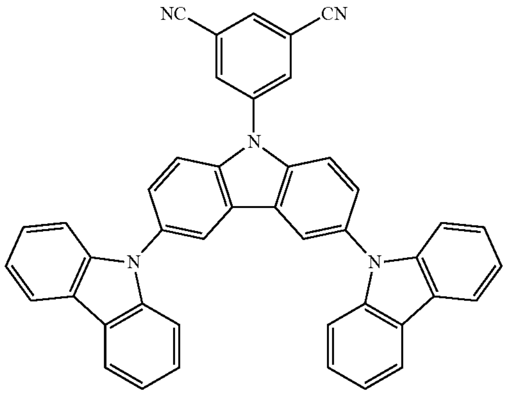
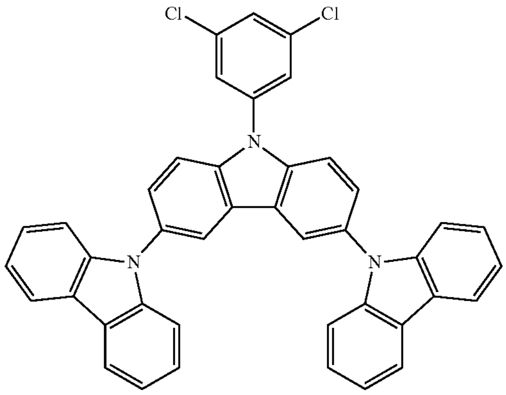
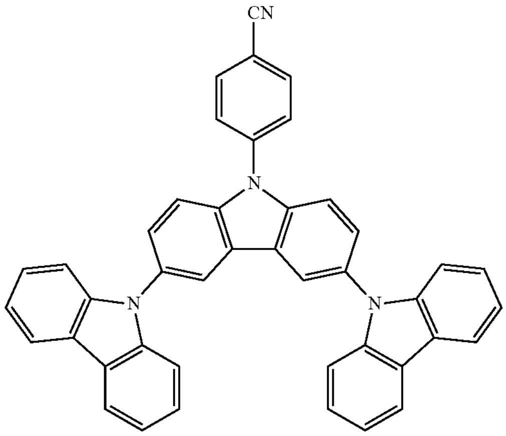

-continued
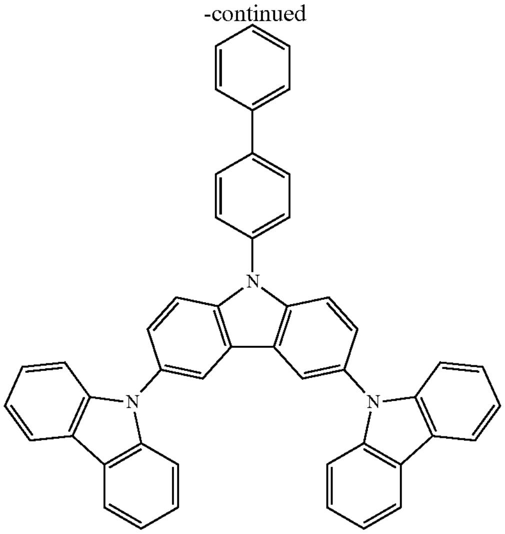
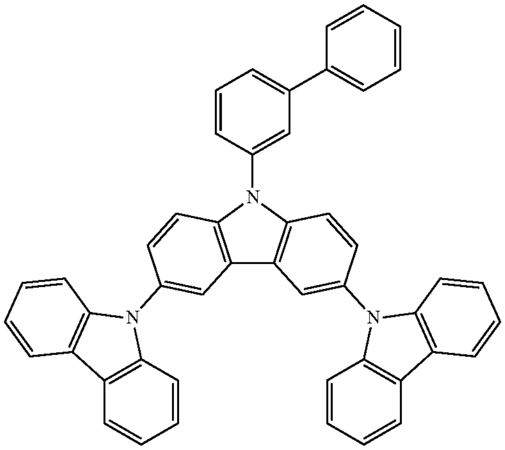
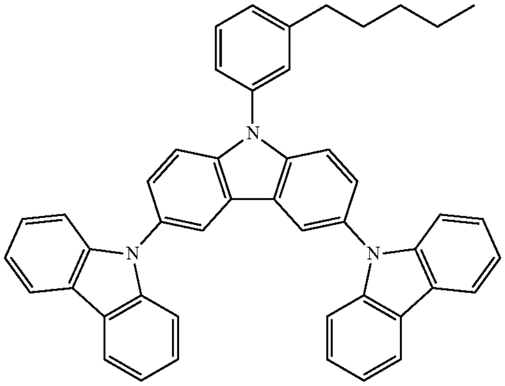
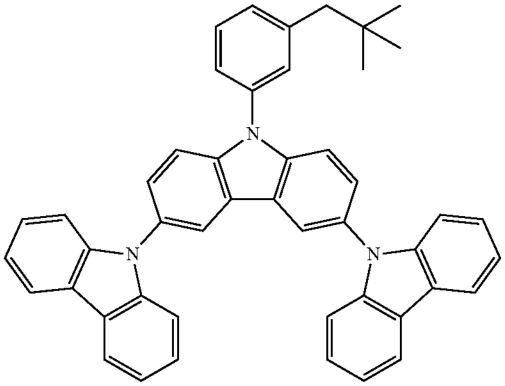
-continued
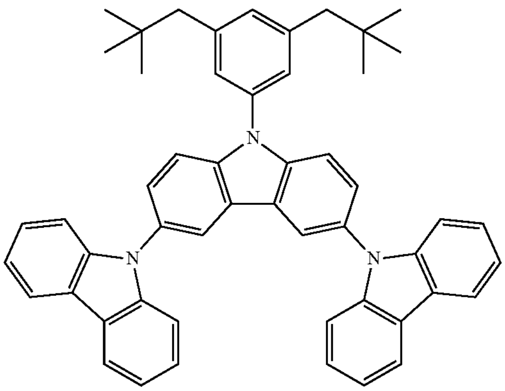
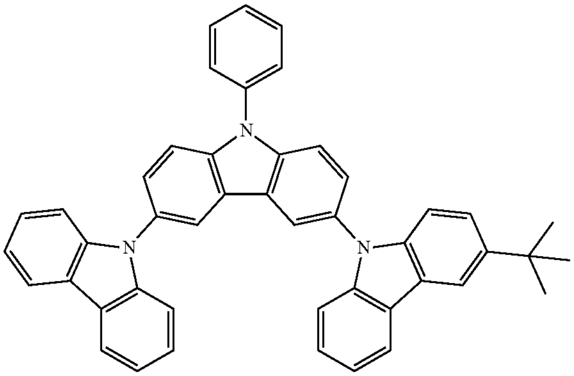
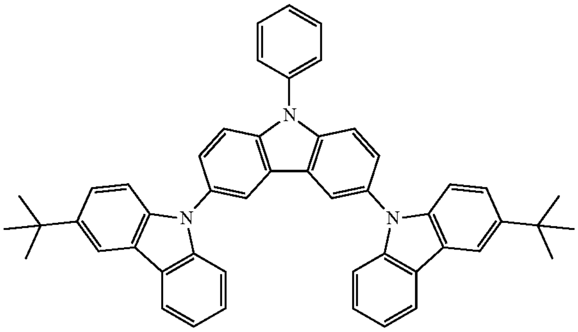
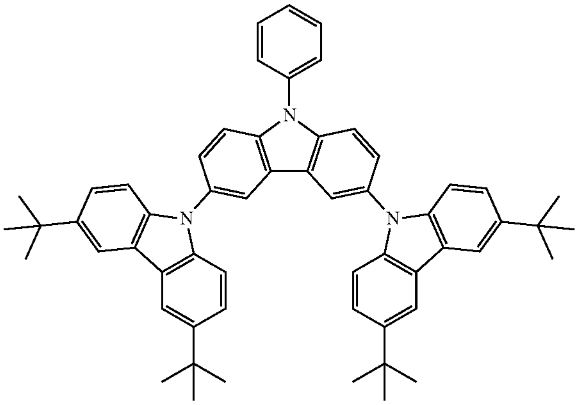

-continued
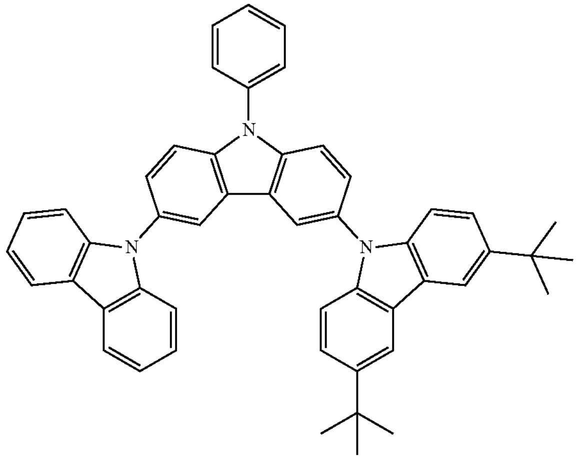
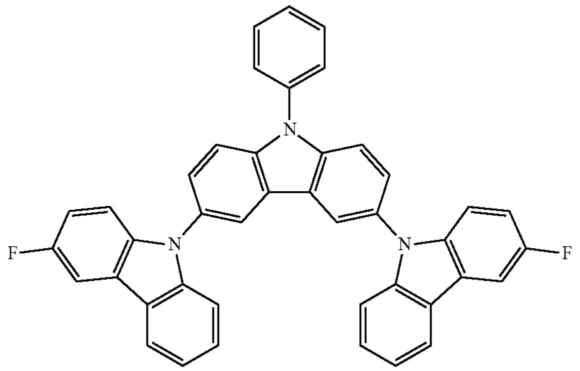
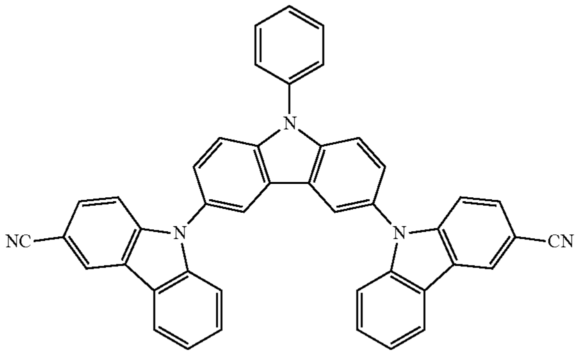
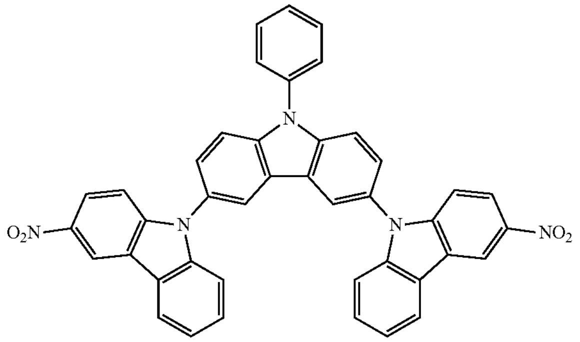
-continued
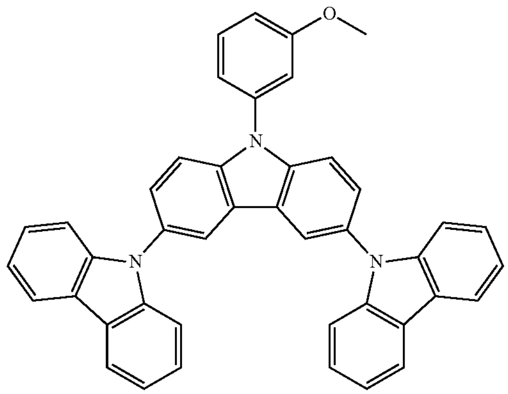
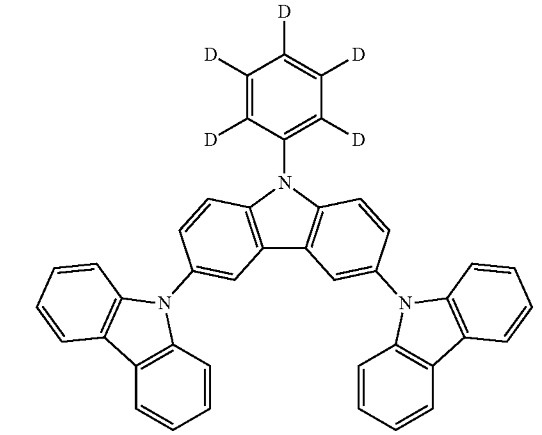
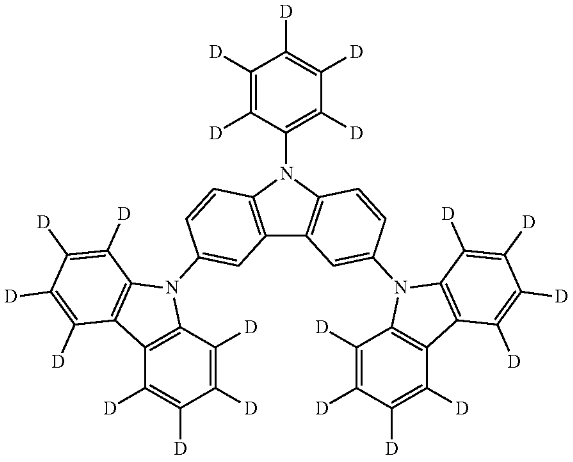
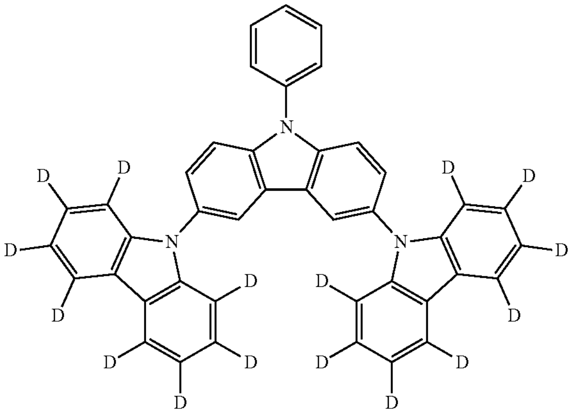

-continued

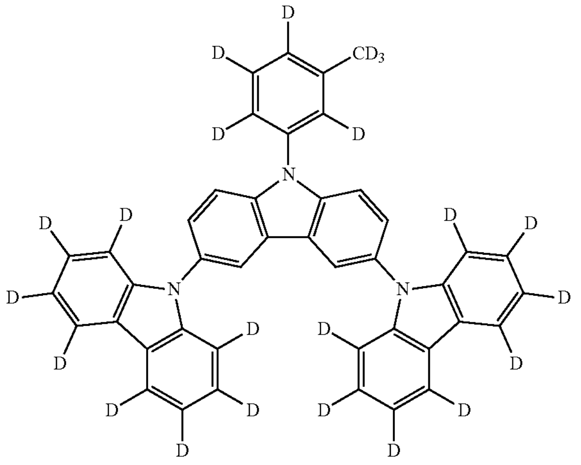

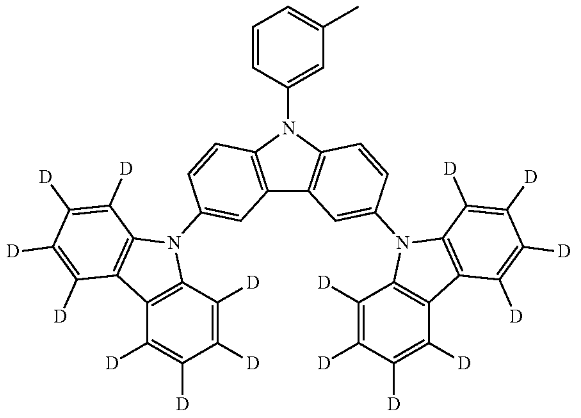

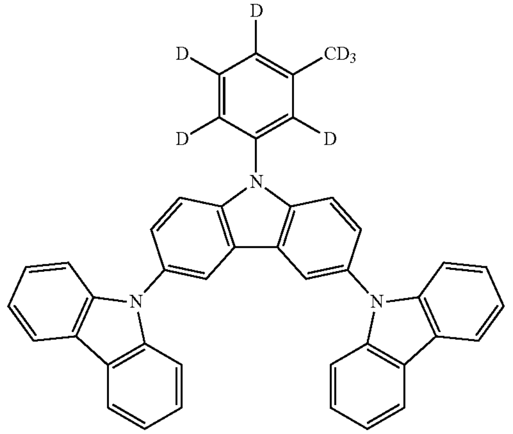

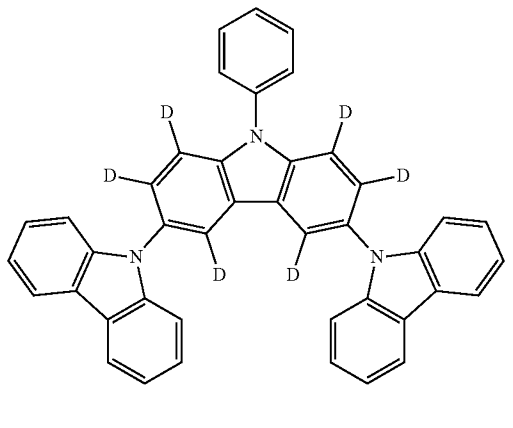

-continued

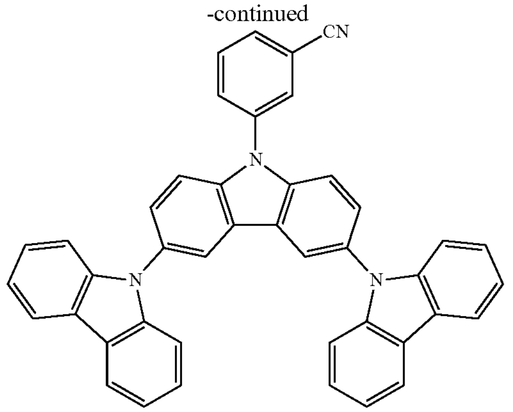

(Charge-Transporting Layer)

A charge-transporting layer means a layer in which charge movement occurs at the time of voltage application to the organic electroluminescence device. Specifically, a hole-injecting layer, a hole-transporting layer, an electron-blocking layer, a light-emitting layer, a hole-blocking layer, an electron-transporting layer and an electron-injecting layer are exemplified. When a charge-transporting layer formed by a coating method is a hole-injecting layer, a hole-transporting layer, an electron-blocking layer, or a light-emitting layer, manufacture of an organic electroluminescence device by low cost and high efficiency becomes possible.

—Hole-Injecting Layer, Hole-Transporting Layer—

A hole-injecting layer and a hole-transporting layer are layers having functions of receiving holes from the anode or anode side and transporting the holes to the cathode side.

In the invention, it is preferred to include a hole-injecting layer and a hole-transporting layer containing an electron-accepting dopant as organic layers.

—Electron-Injecting Layer, Electron-Transporting Layer—

An electron-injecting layer and an electron-transporting layer are layers having functions of receiving electrons from the cathode or cathode side and transporting the electrons to the anode side.

Concerning a hole-injecting layer, a hole-transporting layer, an electron injecting layer and an electron-transporting layer, the items disclosed in JP-A-2008-270736, paragraphs [0165] to [0167] can be applied to the invention.

—Hole-Blocking Layer—

The hole-blocking layer is a layer having a function of preventing the holes transported from the anode side to the light-emitting layer from passing through to the cathode side. In the invention, the hole-blocking layer can be provided as an organic layer contiguous to the light-emitting layer on the cathode side.

As the examples of organic compounds for constituting the hole-blocking layer, aluminum complexes such as aluminum (III)bis(2-methyl-8-quinolinato)-4-phenylphenolate (abbreviated to BAlq), triazole derivatives, and phenanthroline derivatives such as 2,9-dimethyl-4,7-diphenyl-1,10-phenanthroline (abbreviated to BCP) can be exemplified.

The thickness of the hole-blocking layer is preferably 1 nm to 500 nm, more preferably 5 nm to 200 nm, and still more preferably 10 nm to 100 nm.

The hole-blocking layer may have a monolayer structure containing one or two or more kinds of the above materials, or may be a multilayer structure comprising two or more layers of the same composition or different compositions.

—Electron-Blocking Layer—

The electron-blocking layer is a layer having a function of preventing the electrons transported from the cathode side to the light-emitting layer from passing through to the anode side. In the invention, the electron-blocking layer can be provided as an organic layer contiguous to the light-emitting layer on the anode side.

As the examples of organic compounds for constituting the electron-blocking layer, for example, the hole-transporting materials described above can be applied.

The thickness of the electron-blocking layer is preferably 1 nm to 500 nm, more preferably 5 nm to 200 nm, and still more preferably 10 nm to 100 nm.

The electron-blocking layer may have a monolayer structure containing one or two or more kinds of the above materials, or may be a multilayer structure comprising two or more layers of the same composition or different compositions.

<Protective Layer>

In the invention, the organic EL device may be entirely protected with a protective layer.

Concerning the protective layer, the items described in JP-A-2008-270736, paragraphs [0169] to [0170] can be applied to the invention.

<Sealing Case>

The device in the invention may be entirely sealed with a sealing case. Concerning the sealing case, the items described in JP-A-2008-270736, paragraph [0171] can be applied to the invention.

(Driving)

By the application of D.C. (if necessary, A.C. component may be contained) voltage (generally 2 to 15 volts) between the anode and the cathode, or by the application, of D.C. electric current, light emission of the organic electroluminescence device of the invention can be obtained.

With respect to the driving method of the organic electroluminescence device of the invention, the driving methods disclosed in JP-A-2-148687, JP-A-6-301355, JP-A-5-29080, JP-A-7-134558, JP-A-8-234685, JP-A-8-241047, U.S. Pat. No. 2,784,615, U.S. Pat. Nos. 5,828,429 and 6,023,308 can be applied to the invention.

The collecting efficiency of light of the electroluminescence device of the invention can be improved by various known contrivances. For example, it is possible to improve light collecting efficiency and external quantum efficiency by processing the surface shape of a substrate (for example, forming a fine uneven pattern), controlling the refractive indices of a substrate, an ITO layer and an organic layer, and controlling the thicknesses of a substrate, an ITO layer and an organic layer.

The luminescence device of the invention may take what is called a top emission system of collecting light emission from the anode side.

The organic EL device in the invention may have a resonator structure, for example, having multilayer film mirror including plural laminated films different in refractive indices, a transparent or translucent electrode, a light-emitting layer, and a metal electrode superposed on a transparent substrate. The light generated in the light-emitting layer repeats reflection between the multilayer film mirror and the metal electrode as reflectors and resonates.

As another preferred embodiment, a transparent or translucent electrode and a metal electrode function as reflectors on a transparent substrate and the light generated in the light-emitting layer repeats reflection between the reflectors to cause resonance.

For forming a resonator structure, the effective refractive indices of two reflectors and optical path length determined from the refractive index and thickness of each layer between the reflectors are adjusted to an optimal value to obtain desired resonant wavelength. The expression of computation in the case of the first embodiment is described in JP-A-9-180883. The expression of computation in the case of the second embodiment is described in JP-A-2004-127795.

The external quantum efficiency of the organic electroluminescence device in the invention is preferably 5% or more, and more preferably 7% or more. As the value of external quantum efficiency, the maximum value of external quantum efficiency at the time of driving the device at 20° C., alternatively the value of external quantum efficiency near 100 to 300 cd/$m^2$ at the time of driving the device at 20° C., can be used.

The internal quantum efficiency of the organic electroluminescence device in the invention is preferably 30% or more, more preferably 50% or more, and still more preferably 70% or more. The internal quantum efficiency of the device is computed by dividing the external quantum efficiency by the light collecting efficiency. The light collecting efficiency of ordinary organic EL devices is about 20%, but it is possible to make the light collecting efficiency 20% or more by variously designing the shape of substrate, the shape of electrode, the thickness of organic layer, the thickness of inorganic layer, the refractive index of organic layer, the refractive index of inorganic layer, etc.

The organic electroluminescence device in the invention preferably has maximum light emission wavelength (the strongest wavelength of light emission spectrum) of 350 nm or more and 700 nm or less, more preferably 350 nm or more and 600 nm or less, still more preferably 400 nm or more and 520 nm or less, and especially preferably 400 nm or more and 470 nm or less.

(Uses of the Electroluminescence Device of the Invention)

The luminescence device in the invention can be preferably used in light emission apparatus, pixels, display apparatus, displays, backlights, electrophotography, illumination light sources, illumination apparatus, recording light sources, exposure light sources, reading light sources, indicators, signboards, interior designs, optical communications, and the like. The luminescence device in the invention is particularly preferably used in devices driven in the region high in light emission luminance such as a light emission apparatus, an illumination apparatus and display apparatus.

Figure 2:
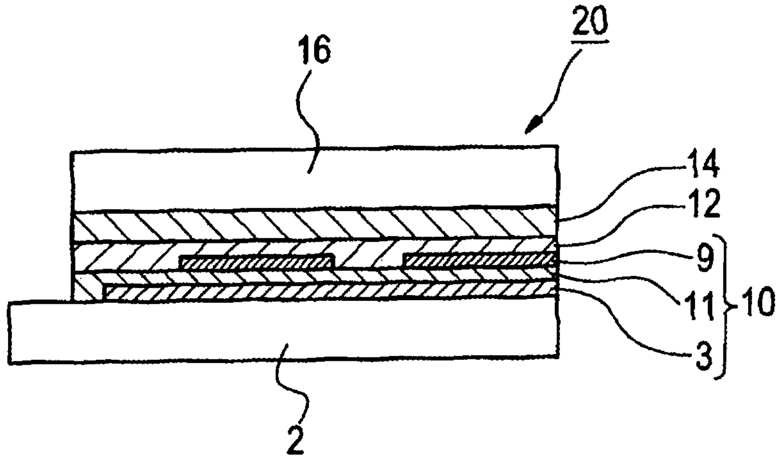
FIG. 2 is a schematic drawing showing an example (a second embodiment) of a light emission apparatus according to the invention.

In the next place, the light emission apparatus in the invention is described with referring to FIG. 2.

The light emission apparatus according to the invention uses the organic electroluminescence device.

FIG. 2 is a cross-sectional view schematically showing an example of the light emission apparatus according to the invention.

Light emission apparatus 20 in FIG. 2 consists of transparent substrate (a supporting substrate) 2, organic electroluminescence device 10, and sealing case 11.

Organic electroluminescence device 10 includes substrate 2 having thereon laminated anode (first electrode) 3, organic layer 11, and cathode (second electrode) 9 in this order. On cathode 9 is laminated protective layer 12, and sealing case 16 is provided on protective layer 12 sandwiching adhesive layer 14 in. Parts of electrodes 3 and 9, bulkhead and insulating layer are omitted.

As adhesive layer 14, photo-curable adhesives such as epoxy resin and the like and thermosetting adhesives can be used and, for example, a thermosetting adhesive sheet can also be used.

The uses of the light emission apparatus in the invention are not especially restricted and, besides illuminating apparatus, the light emission apparatus can be used, for example, as display apparatus such as television, personal computer, portable telephone, electronic paper, and the like.

(Illumination Apparatus)

Figure 3:
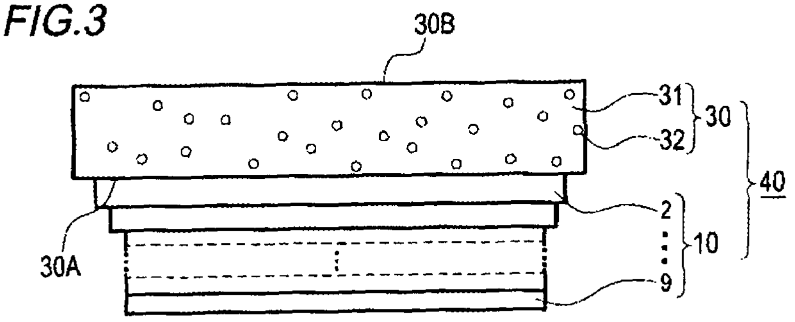
FIG. 3 is a schematic drawing showing an example (a third embodiment) of an illumination apparatus according to the invention.

In the next place, the illumination apparatus of the invention is described with referring to FIG. 3.

FIG. 3 is a cross-sectional view schematically showing an example of the illumination apparatus according to the invention. Illumination apparatus 40 in the invention is equipped with organic EL device 10 and light-scattering member 30, as shown in FIG. 3. More specifically, illumination apparatus 40 is constituted so that substrate 2 of organic EL device 10 is contiguous to light-scattering member 30.

Light-scattering member 30 is not especially restricted so long as it can scatter light, but in FIG. 3, light-scattering member 30 is a member comprising transparent substrate 31 containing particles 32 having been dispersed therein. As transparent substrate 31, e.g., a glass substrate is preferably exemplified. As particles 32, transparent resin particles are preferably exemplified. As the glass substrate and transparent resin particles, known materials can be used. In illumination apparatus 40, when light emission from organic electroluminescence device 10 is incident to plane of incidence of light 30A of light-scattering member 30, the incident light is scattered by light-scattering member 30, and the scattered light is outgoing from plane of outgoing of light 30B as illumination light.

EXAMPLE

The invention will be described in further detail with reference to examples, but the range of the invention is not restricted thereto.

All of the organic materials for use in Examples and Comparative Examples are the materials having been subjected to sublimation purification. The structures of the compounds used in Examples and Comparative Examples are shown below.

1-a

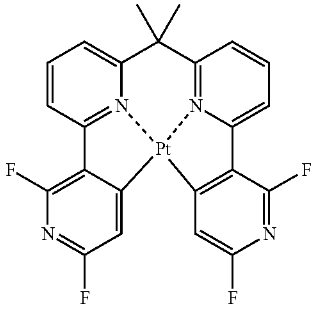

1-b

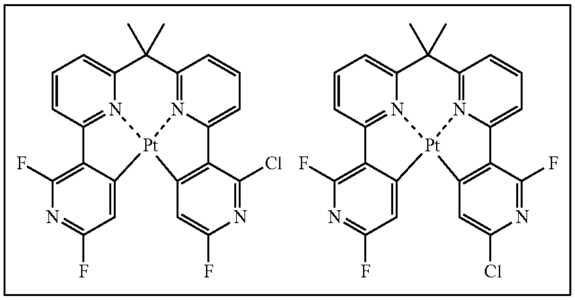

-continued 1-c

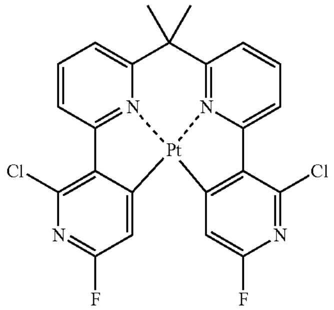

1-d

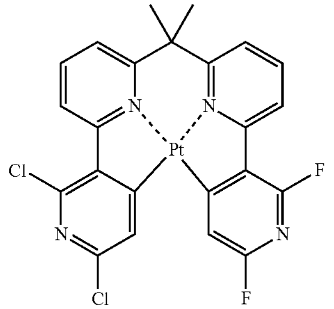

1-e

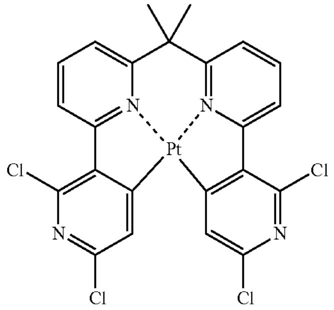

ref-1-b

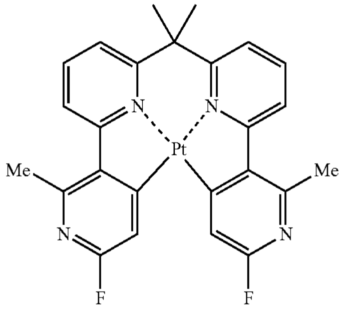

2-a

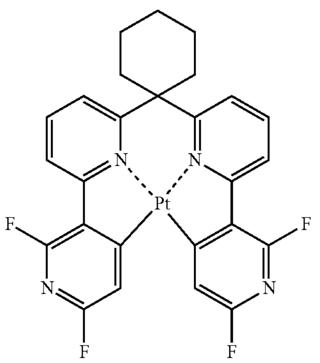

-continued
2-b
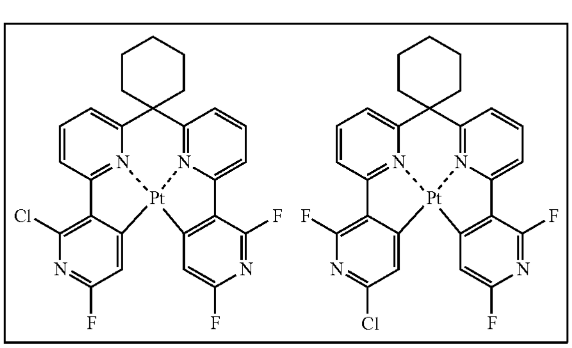
2-c
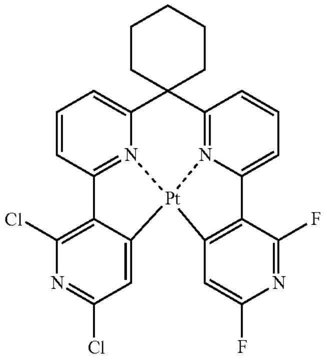
2-d
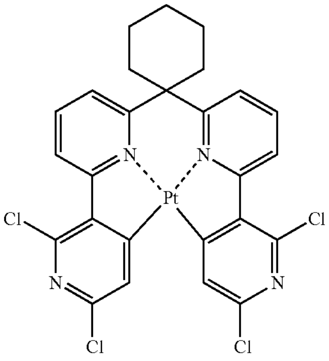
3-a
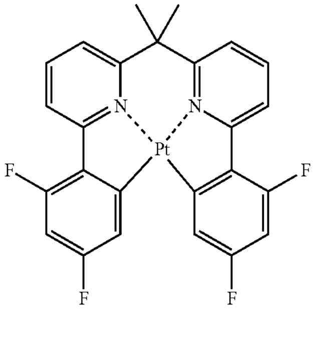
-continued
3-b
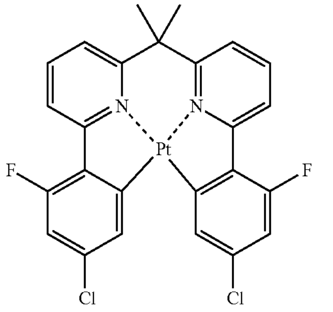
3-c
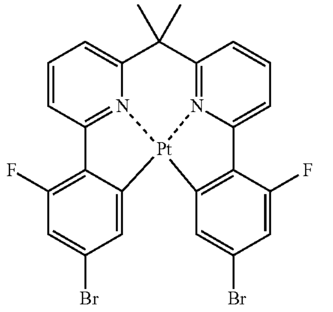
3-d
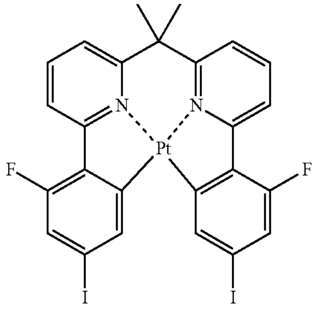
4-a
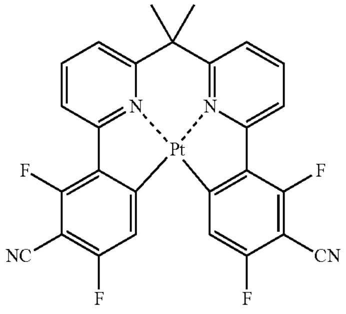
4-b
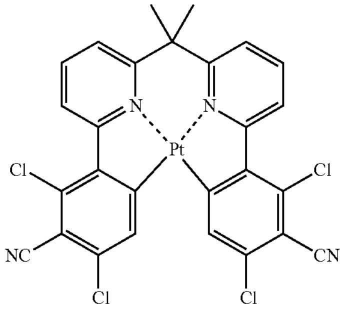

-continued
ref-4-b
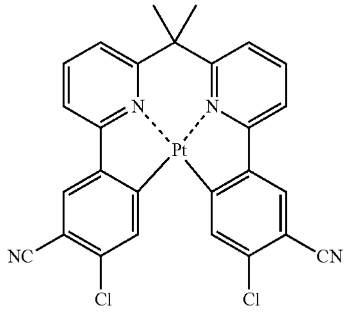
5-a
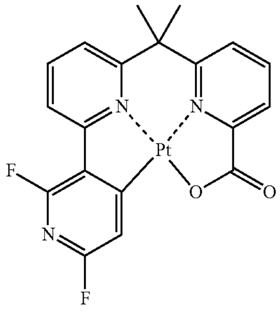
5-b
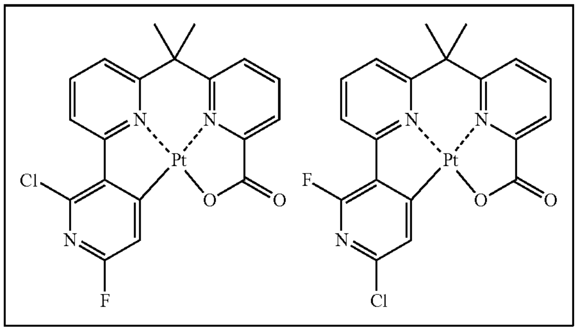
ref-5-b
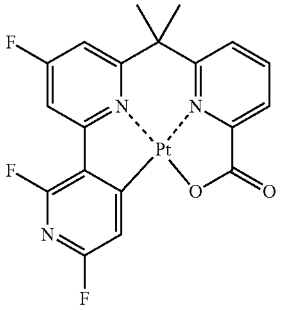
6-a
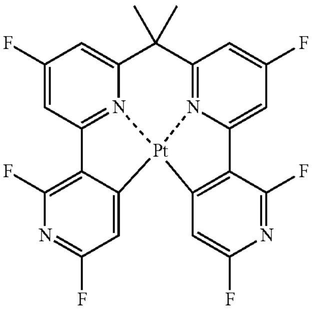
-continued
6-b
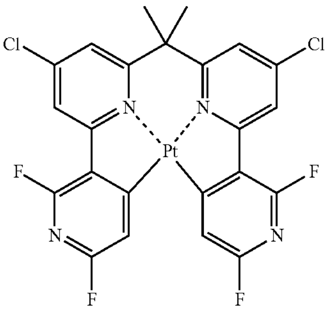
6c
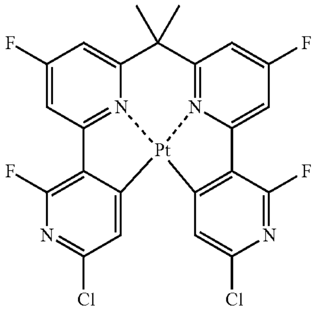
6-d
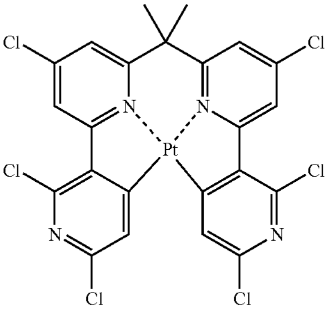
ref-6-b
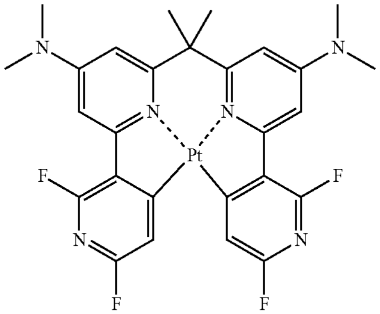
7-a
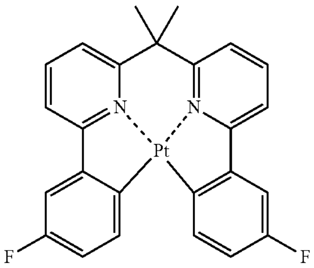

US 8,426,042 B2
215
-continued
7-b
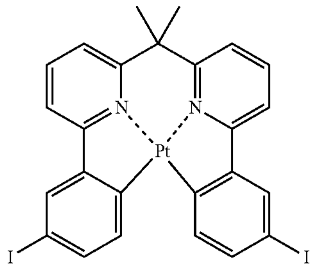
8-a
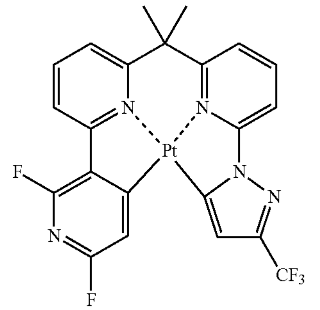
8-b
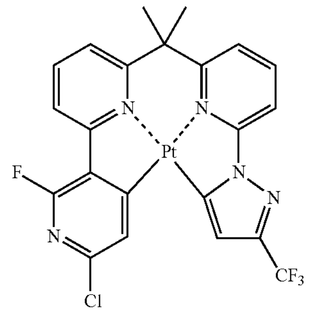
9-a
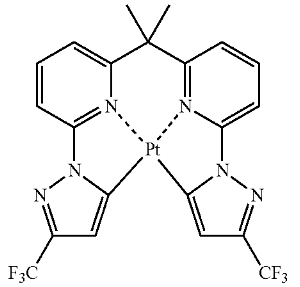
9-b
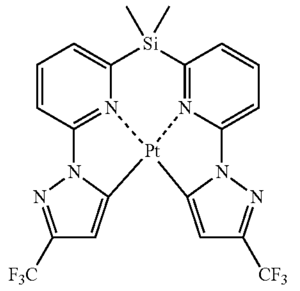
216
-continued
10-a
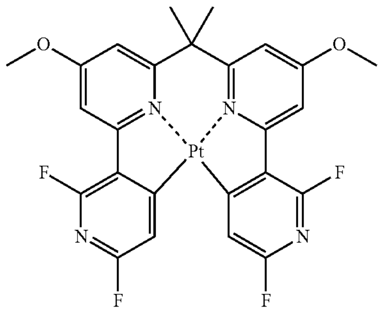
10-b
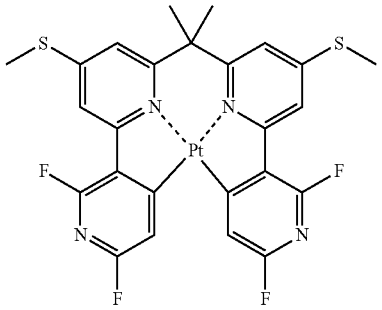
11-a
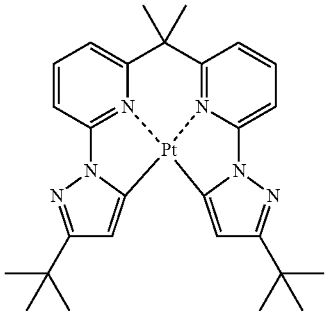
11-b
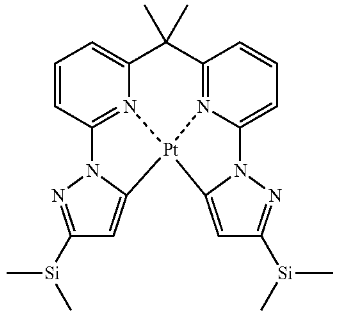
12-a
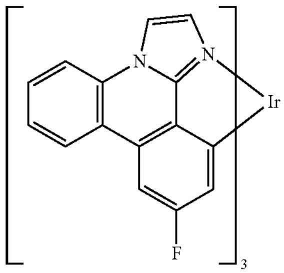

-continued
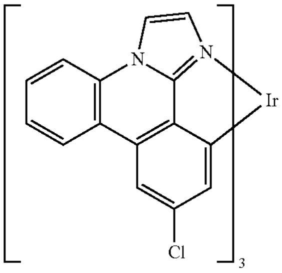
12-b
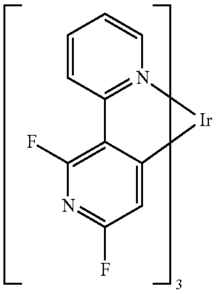
13-a
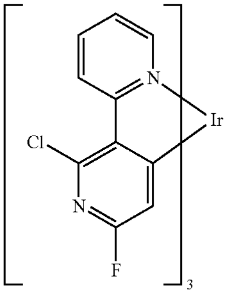
13-b
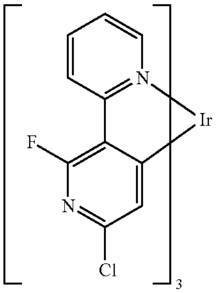
13-c
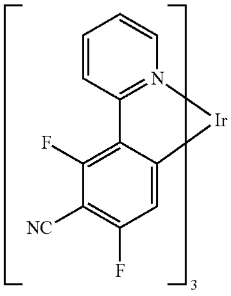
14-a
-continued
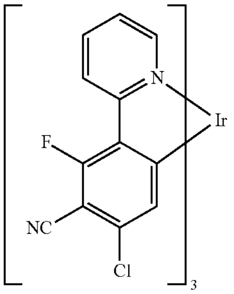
14-b
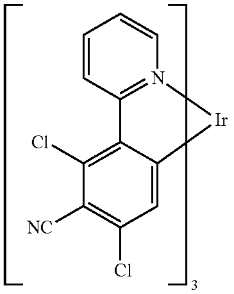
14-c
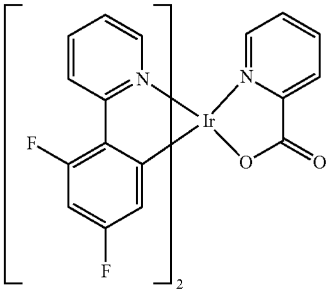
15-a
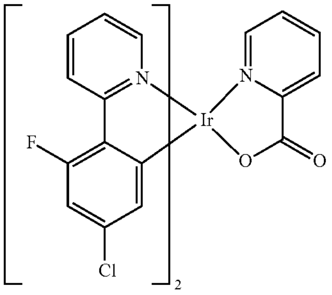
15-b
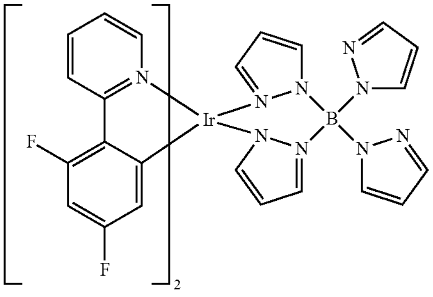
16-a 16-b
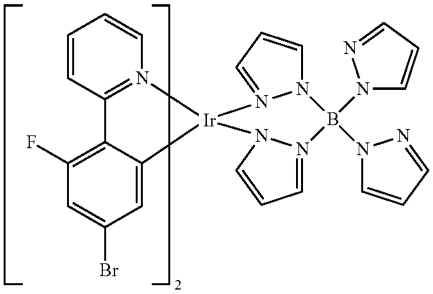
17-a
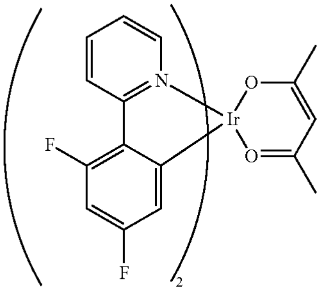
17-b
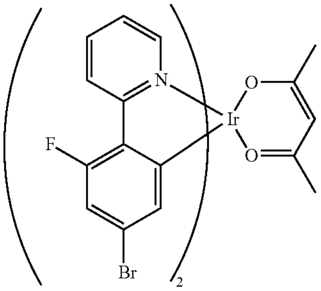
17-c
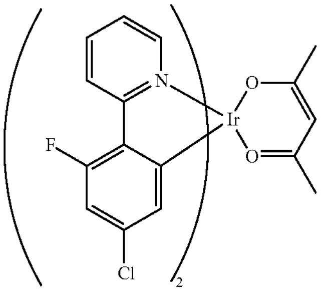
18-a
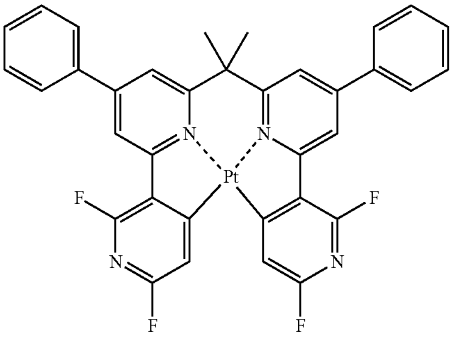
18-b
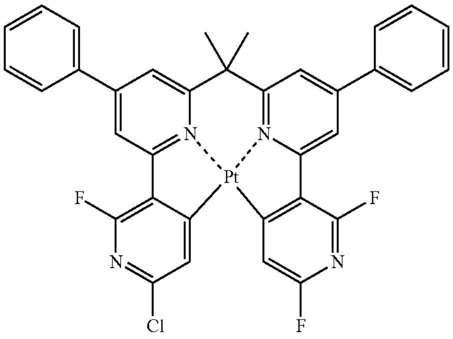
18-c
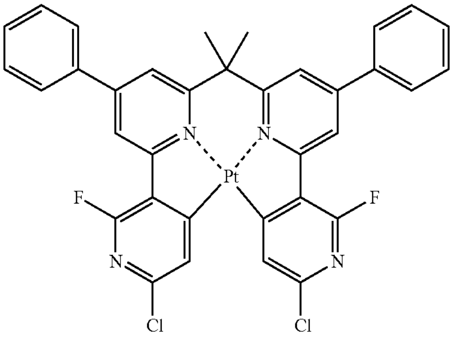
19-a
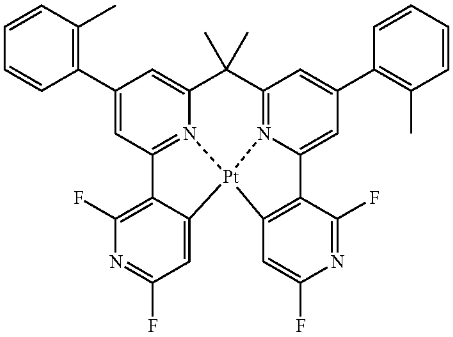
19-b
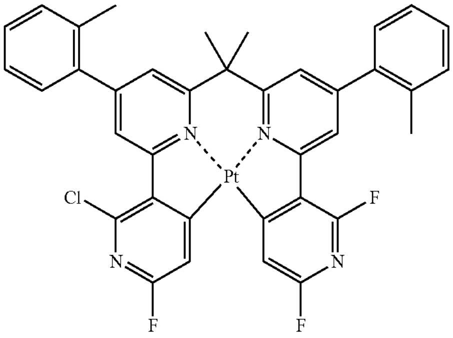

-continued 19-c

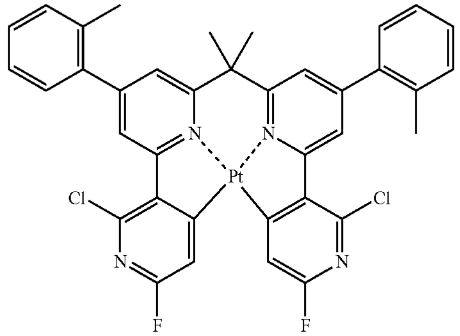

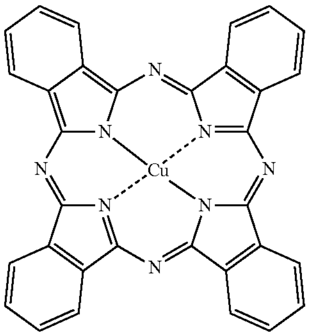

CuPc

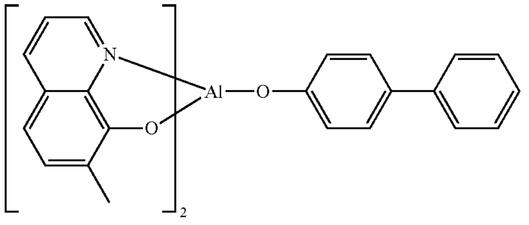

Balq

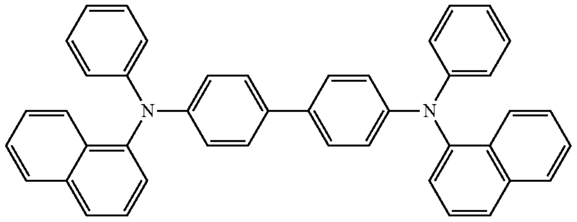

NPD

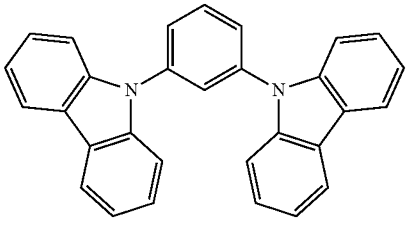

mCP

Compound 12-a is synthesized by referring to the method disclosed in U.S. Patent Publication 2008/297,033, p. 55, on and after paragraph [0129]. Compound 15-a is synthesized according to the method disclosed in WO 02/15645, p. 33. Compound 17-a is synthesized according to the method disclosed in WO 08/140,114, p. 169. Compound 16-a is synthesized by the method described in Polyhedron, No. 23 (2004), on and after page 419. Compounds 13-a and 14-a are synthesized according to the methods described in Inorganic Chemistry, No. 30 (1991), on and after page 1685. Incidentally, concerning each compound, the complex expressed by other than X-a (X indicates Compound Nos. 1 to 19) can be similarly synthesized by changing the material in synthesizing the ligand. For example, Compound 15-b can be synthesized as shown below by using chlorofluorophenylboric acid in place of difluorophenylboric acid as the compound of the ligand. The cases of the following shown platinum complexes are also the same.

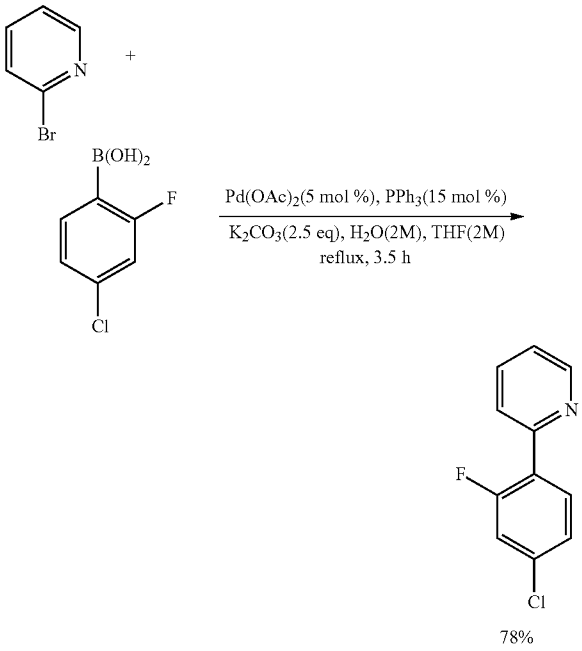

With regard to platinum complexes, Compounds 9-a, 9-b, 11-a, and 11-b are synthesized by referring to JP-A-2006-256999. Compounds 5-a, 5-b, and ref-5-b are synthesized by referring to JP-A-2006-261623. Compounds 3-a to 3-d, 4-a, 4-b, ref-4-b, 7-a, and 7-b are synthesized by referring to JP-A-2006-093542. Compound 2-a is synthesized as shown below. Compounds 2-b to 2-d are also synthesized similarly. Compounds 1-a to 1-e, ref-1-b, 6-a to 6-d, ref-6-b, 8-a, 8-b, 10-a, 10-b, 16-a, 16-b, and 19-a to 19-c are also similarly synthesized by various known methods.

(Synthesis of Compound 2-a)

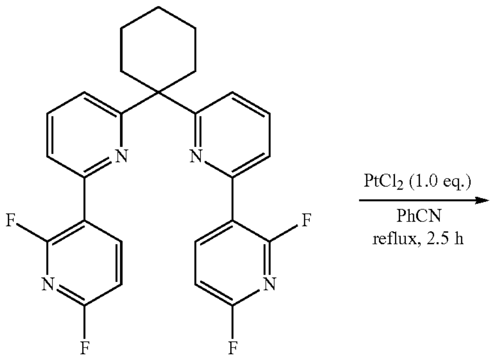

M2

-continued

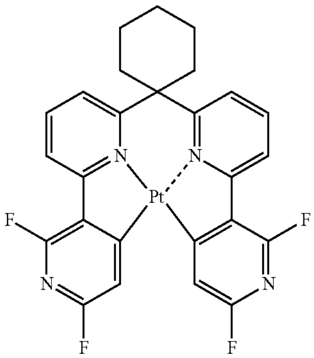

compound 2-a

Platinous chloride (2.66 g, 10.0 mmol) and Compound M2 (3.4 g, 7.3 mmol) are stirred for 2 hours and 30 minutes in benzonitrile (70 mL) on condition of reflux by heating in the nitrogen atmosphere. The reaction solution is allowed to be cooled to room temperature, and the precipitated solid is filtered and washed with methanol to obtain 3.2 g of Compound 2-a as yellow powder. Yield: 75%

Compound 1-b is obtained as a mixture with Compound 1-a when synthesis is performed by the following method, and the composition is confirmed by HPLC and mass spectrometry. Compounds 2-b and 5-b are also the same.

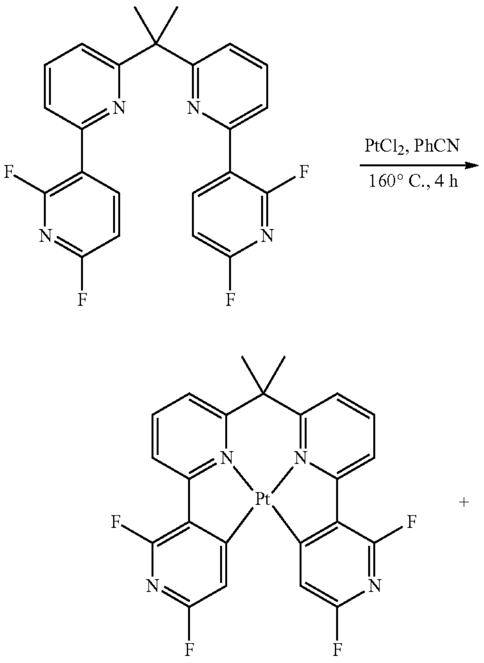

1-a
Chemical Formula: $C_{23}H_{14}F_4N_4Pt$
Exact Mass: 617.08

-continued

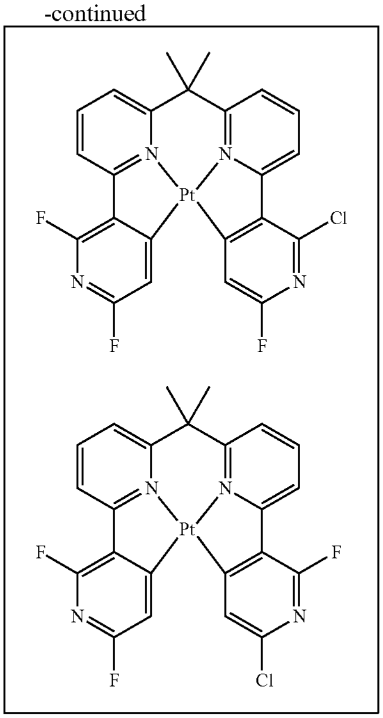

1-b(0.4 mol %)
Chemical Formula: $C_{23}H_{14}ClF_3N_4Pt$
Exact Mass: 633.05

(Synthesis of Compound 18-a)

Compound 18-a is synthesized as follows.

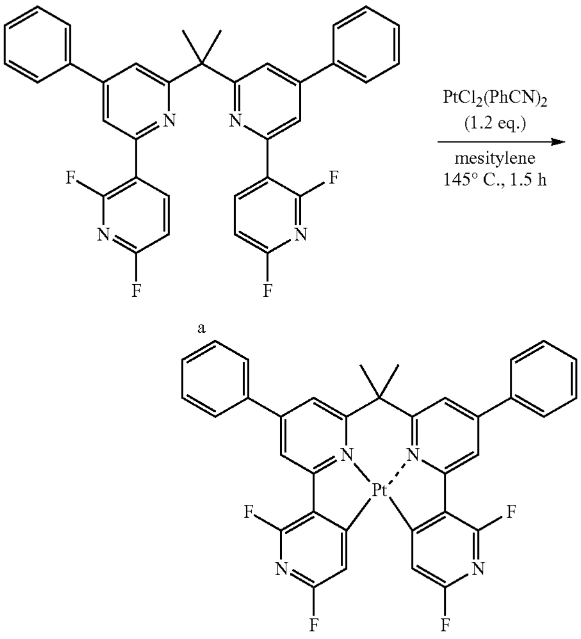

a

>99%
compound 2-a

Platinum(II) chloride (1.96 g, 4.2 mmol, 1.2 equivalent) and Compound a (2.0 g, 3.5 mmol, 1.0 equivalent) are stirred for an hour and a half in mesitylene (15 mL) at 145° C. in the nitrogen atmosphere. The reaction solution is allowed to be cooled to room temperature, and the precipitated solid is filtered and washed with methanol to obtain 2.7 g of a platinum complex as yellow powder. Yield: 99%. Compounds 18-b and 18-c are also similarly synthesized.

$^1$H-NMR (300 MHz, $CDCl_3$) δ: The obtained synthesized product cannot be dissolved in a solvent and analysis is impossible.

The organic materials used in Examples are all subjected to sublimation purification, and purities are computed by analysis with high performance liquid chromatography (TSKgel ODS-100Z, manufactured by Toso Corporation).

Example 1

(Manufacture of Organic Electroluminescence Device)

A glass substrate having an indium tin oxide (ITO) film (manufactured by Geomatec Co., Ltd., surface resistance: 10Ω/□)) having a thickness of 100 μm and a size of 2.5 cm square is put in a washer and subjected to ultrasonic wave washing in 2-propanol, and then UV-ozone treatment for 30 minutes. The organic layers shown below are deposited on the transparent anode (ITO film) in sequence by a vacuum deposition method. At this time the materials are put in the crucible and deposited immediately.

First Layer CuPc (copper phthalocyanine), film thickness: 120 nm

Second Layer: NPD (N,N'-di-α-naphthyl-N,N'-diphenyl) benzidine, film thickness: 10 nm Third Layer (light-emitting layer): light-emitting material (12% by mass), mCP (1,3-bis(N-carbazolyl)benzene), host material (88% by mass), film thickness: 30 nm Fourth Layer: first electron-transporting material (BAlq), film thickness: 30 nm Lithium fluoride in a thickness of 1 nm and metal aluminum in a thickness of 100 nm are deposited thereon in this order to obtain a cathode.

The obtained laminate is put in a glove box replaced with argon gas so as not to be in contact with air, and sealed with a stainless steel sealing can and a UV-curing type adhesive (XNR5516HV, manufactured by Nagase Ciba Corp.) to obtain a device. A device manufactured in this manner by putting materials in a crucible and immediately depositing is taken as “device 1”. A device obtained by putting the same materials with the materials of device 1 in a crucible, being subjected to white light exposure for 3 days in the crucible, and then manufacturing in the same manner as above is taken as “device 2”.

As the light-emitting material in the light-emitting layer, the light-emitting materials 1 and 2 shown in Table 16 below are used in the mixing ratio as shown in Table 16.

Concerning the content of a part of the metal complex of light-emitting material 2 in Table 16, in parallel with the measurement by HPLC-MS, a sample is combusted in oxygen flow, the chlorine component is trapped in aqueous hydrogen peroxide with automatic sample combustion equipment AQF-100 (manufactured by (Mitsubishi Chemical Analytech Co., Ltd.), chlorine, fluorine and bromine in the aqueous hydrogen peroxide containing halogen components are measured with Ion Chromatograph ICS-1500 (manufactured by Dionex Co. Ltd.), and the exact content of the metal complex which is light-emitting material 2 is evaluated from the halogen concentration in the sample. The iodine content in a metal complex is similarly measured with the above apparatus by trapping in aqueous hydrogen peroxide and a sodium carbonate aqueous solution.

From these measurement results, it is confirmed that the absorbance of each material is almost equivalent and the area ratio obtained with HPLC may be used as the content as it is.

(Evaluation of Performance of Organic Electroluminescence Device)

(a) Durability Ratio (Stability Against Visible Light)

Concerning the above-prepared device 1, and device 2 prepared from the same material with the materials of device 1 but subjected to white light exposure for 3days in the crucible and then manufacturing in the same manner, DC voltage is applied to the samples so that each luminance reaches 2,000 cd/m$^2$ to continue light emission and half life time of luminance is measured. The half life time of luminance of device 2 to that of device 1 is computed in percentage and shown in Table 16 as durability ratio. The greater the “durability ratio”, the more stable is the material used in the manufacture of the device against visible light.

(b) Efficiency Ratio (Efficiency at High Luminance Driving Time)

DC voltage is applied to each device 1 for light emission with a source measure unit Model 2400 (manufactured by Toyo Corporation) and the luminance at that time is measured with a luminometer BM-8 (manufactured by Topcon Corporation). The light emission spectrum and emission wavelength are measured with a spectrum analyzer PMA-11 (manufactured by Hamamatsu Photonics K.K.). On the basis of these measurements, external quantum efficiency at the time of current density of 1 mA/cm$^2$ and external quantum efficiency at the time of current density of 250 mA/cm$^2$ are computed according to a luminance conversion method. The ratio is computed by dividing the value of efficiency at 250 mA/cm$^2$ by the value of efficiency at 1 mA/cm$^2$, and shown in Table 16 as “efficiency ratio”. The greater the “efficiency ratio”, the more excellent is the device when the device is driven at high luminance.

TABLE 16

| Device No. | Light Emitting Material 1 | Light Emitting Material 2 | Content of Light-Emitting Material 2 to Light-Emitting Material 1 (% by mass) | Durability Ratio (%) | Efficiency Ratio |
|---|---|---|---|---|---|
| Comparative Device 1-1 | 1-a | — | 0 | 44.6 | 0.53 |
| Comparative Device 1-2 | 1-a | 1-b | 0.0025 | 51.6 | 0.54 |
| Device 1-1 of the invention | 1-a | 1-b | 0.005 | 78.2 | 0.55 |
| Device 1-2 of the invention | 1-a | 1-b | 0.01 | 80.2 | 0.55 |
| Device 1-3 of the invention | 1-a | 1-b | 0.02 | 79.4 | 0.56 |
| Device 1-4 of the invention | 1-a | 1-b | 0.04 | 80.6 | 0.58 |
| Device 1-5 of the invention | 1-a | 1-b | 0.05 | 80.1 | 0.57 |
| Device 1-6 of the invention | 1-a | 1-b | 0.08 | 81.2 | 0.56 |
| Device 1-7 of the invention | 1-a | 1-b | 0.1 | 80.7 | 0.61 |

TABLE 16-continued

| Device No. | Light Emitting Material 1 | Light Emitting Material 2 | Content of Light-Emitting Material 2 to Light-Emitting Material 1 (% by mass) | Durability Ratio (%) | Efficiency Ratio |
|---|---|---|---|---|---|
| Device 1-8 of the invention | 1-a | 1-b | 0.25 | 89.4 | 0.71 |
| Device 1-9 of the invention | 1-a | 1-b | 0.45 | 94.6 | 0.79 |
| Device 1-10 of the invention | 1-a | 1-b | 0.5 | 98.4 | 0.84 |
| Device 1-11 of the invention | 1-a | 1-b | 0.55 | 98 | 0.84 |
| Device 1-12 of the invention | 1-a | 1-b | 0.75 | 93.1 | 0.83 |
| Device 1-13 of the invention | 1-a | 1-b | 1 | 91.3 | 0.85 |
| Device 1-14 of the invention | 1-a | 1-b | 1.25 | 85.7 | 0.84 |
| Device 1-15 of the invention | 1-a | 1-b | 1.5 | 81.9 | 0.86 |
| Device 1-16 of the invention | 1-a | 1-b | 2 | 75.8 | 0.88 |
| Comparative Device 1-3 | 1-a | 1-b | 2.05 | 61.2 | 0.86 |
| Comparative Device 1-4 | 1-a | 1-b | 2.2 | 55.4 | 0.81 |
| Comparative Device 1-5 | 1-a | 1-c | 0.004 | 64.5 | 0.51 |
| Device 1-17 of the invention | 1-a | 1-c | 0.005 | 81.1 | 0.56 |
| Device 1-18 of the invention | 1-a | 1-c | 0.006 | 81.6 | 0.56 |
| Device 1-19 of the invention | 1-a | 1-c | 0.01 | 82.4 | 0.61 |
| Device 1-20 of the invention | 1-a | 1-c | 0.1 | 83.5 | 0.84 |
| Device 1-21 of the invention | 1-a | 1-c | 0.5 | 99.4 | 0.87 |
| Device 1-22 of the invention | 1-a | 1-c | 0.6 | 97.5 | 0.86 |
| Device 1-23 of the invention | 1-a | 1-c | 1 | 93.5 | 0.84 |
| Device 1-24 of the invention | 1-a | 1-c | 1.2 | 93.1 | 0.81 |
| Device 1-25 of the invention | 1-a | 1-c | 1.9 | 84.5 | 0.86 |
| Comparative Device 1-6 | 1-a | 1-c | 2.1 | 71.2 | 0.84 |
| Device 1-26 of the invention | 1-a | 1-d | 0.5 | 97.8 | 0.84 |
| Device 1-27 of the invention | 1-a | 1-e | 0.5 | 99.9 | 0.87 |
| Comparative Device 1-7 | 1-a | ref-1-b | 0.004 | 50.2 | 0.51 |
| Comparative Device 1-8 | 1-a | ref-1-b | 0.005 | 55.8 | 0.59 |
| Comparative Device 1-9 | 1-a | ref-1-b | 0.5 | 56.5 | 0.64 |
| Comparative Device 1-10 | 1-a | ref-1-b | 2.5 | 60.4 | 0.6 |
| Comparative Device 1-11 | 2-a | — | 0 | 61.4 | 0.58 |
| Device 1-28 of the invention | 2-a | 2-b | 0.5 | 65.8 | 0.81 |
| Device 1-29of the invention | 2-a | 2-c | 0.5 | 99.6 | 0.82 |
| Device 1-30 of the invention | 2-a | 2-d | 0.5 | 99.4 | 0.81 |
| Comparative Device 1-12 | 3-a | — | 0 | 69.8 | 0.49 |
| Device 1-31 of the invention | 3-a | 3-b | 0.5 | 97.4 | 0.89 |
| Device 1-32 of the invention | 3-a | 3-c | 0.5 | 96.2 | 0.81 |
| Device 1-33 of the invention | 3-a | 3-d | 0.5 | 94.4 | 0.81 |
| Comparative Device 1-13 | 4-a | — | 0 | 67.8 | 0.51 |
| Device 1-34 of the invention | 4-a | 4-b | 0.5 | 94.4 | 0.83 |
| Comparative Device 1-14 | 4-a | ref-4-b | 0.5 | 71.4 | 0.5 |
| Comparative Device 1-15 | 5-a | — | 0 | 34.4 | 0.4 |
| Device 1-35 of the invention | 5-a | 5-b | 0.5 | 89.8 | 0.76 |
| Comparative Device 1-16 | 5-a | ref-5-b | 0.5 | 51.4 | 0.41 |
| Comparative Device 1-17 | 6-a | — | 0 | 23.5 | 0.43 |
| Device 1-37 of the invention | 6-a | 6-b | 0.5 | 87.8 | 0.78 |
| Device 1-38 of the invention | 6-a | 6-c | 0.5 | 84.5 | 0.8 |
| Device 1-39 of the invention | 6-a | 6-d | 0.5 | 88.4 | 0.76 |
| Comparative Device 1-18 | 6-a | ref-6-b | 0.5 | 21.1 | 0.51 |
| Comparative Device 1-19 | 7-a | — | 0 | 70.1 | 0.46 |
| Device 1-40 of the invention | 7-a | 7-b | 0.5 | 99.5 | 0.76 |
| Comparative Device 1-20 | 8-a | — | 0 | 59.8 | 0.52 |
| Device 1-41 of the invention | 8-a | 8-b | 0.5 | 94.4 | 0.89 |
| Comparative Device 1-21 | 9-a | — | — | 55.4 | 0.6 |
| Device 1-42 of the invention | 9-a | 9-b | 0.5 | 78.7 | 0.71 |
| Comparative Device 1-22 | 10-a | — | 0 | 45.4 | 0.21 |
| Device 1-43 of the invention | 10-a | 10-b | 0.5 | 78.7 | 0.69 |
| Comparative Device 1-23 | 11-a | — | 0 | 44.1 | 0.29 |
| Device 1-44 of the invention | 11-a | 11-b | 0.5 | 80.1 | 0.74 |
| Comparative Device 1-24 | 12-a | — | 0 | 23.1 | 0.34 |
| Device 1-45 of the invention | 12-a | 12-b | 0.5 | 78.4 | 0.51 |
| Comparative Device 1-25 | 13-a | — | 0 | 26.9 | 0.41 |
| Device 1-46 of the invention | 13-a | 13-b | 0.5 | 89.8 | 0.84 |
| Device 1-47 of the invention | 13-a | 13-c | 0.5 | 90.2 | 0.86 |
| Comparative Device 1-26 | 14-a | — | 0 | 59.5 | 0.46 |
| Device 1-48 of the invention | 14-a | 14-b | 0.5 | 90.1 | 0.74 |
| Device 1-49 of the invention | 14-a | 14-c | 0.5 | 89.8 | 0.71 |
| Comparative Device 1-27 | 15-a | — | 0 | 49.8 | 0.47 |
| Device 1-50 of the invention | 15-a | 15-b | 0.005 | 70.1 | 0.51 |
| Device 1-51 of the invention | 15-a | 15-b | 0.05 | 72.4 | 0.54 |
| Device 1-52 of the invention | 15-a | 15-b | 0.5 | 92.5 | 0.68 |
| Device 1-53 of the invention | 15-a | 15-b | 1 | 84.5 | 0.71 |
| Device 1-54 of the invention | 15-a | 15-b | 2 | 68.1 | 0.72 |
| Comparative Device 1-28 | 15-a | 16-a | 0.5 | 51.4 | 0.46 |
| Comparative Device 1-29 | 16-a | — | 0 | 44.4 | 0.69 |

TABLE 16-continued

| Device No. | Light Emitting Material 1 | Light Emitting Material 2 | Content of Light-Emitting Material 2 to Light-Emitting Material 1 (% by mass) | Durability Ratio (%) | Efficiency Ratio |
|---|---|---|---|---|---|
| Device 1-55 of the invention | 16-a | 16-b | 0.5 | 89.7 | 0.78 |
| Comparative Device 1-30 | 17-a | — | 0 | 46.8 | 0.56 |
| Device 1-56 of the invention | 17-a | 17-b | 0.5 | 89.1 | 0.87 |
| Device 1-57 of the invention | 17-a | 17-c | 0.5 | 91.7 | 0.88 |
| Comparative Device 1-31 | 18-a | — | 0 | 65.7 | 0.67 |
| Device 1-58 of the invention | 18-a | 18-b | 0.5 | 94.5 | 0.94 |
| Device 1-59 of the invention | 18-a | 18-c | 0.5 | 95.8 | 0.96 |
| Comparative Device 1-32 | 19-a | — | 0 | 55.7 | 0.64 |
| Device 1-60 of the invention | 19-a | 19-b | 0.5 | 99.4 | 0.91 |
| Device 1-61 of the invention | 19-a | 19-c | 0.5 | 98.6 | 0.9 |

The devices according to the invention are greater in the values of durability ratio and efficiency ratio. From this fact, it can be seen that the devices according to the invention are excellent in stability under visible light and also excellent in efficiency at high luminance.

Figure 4:
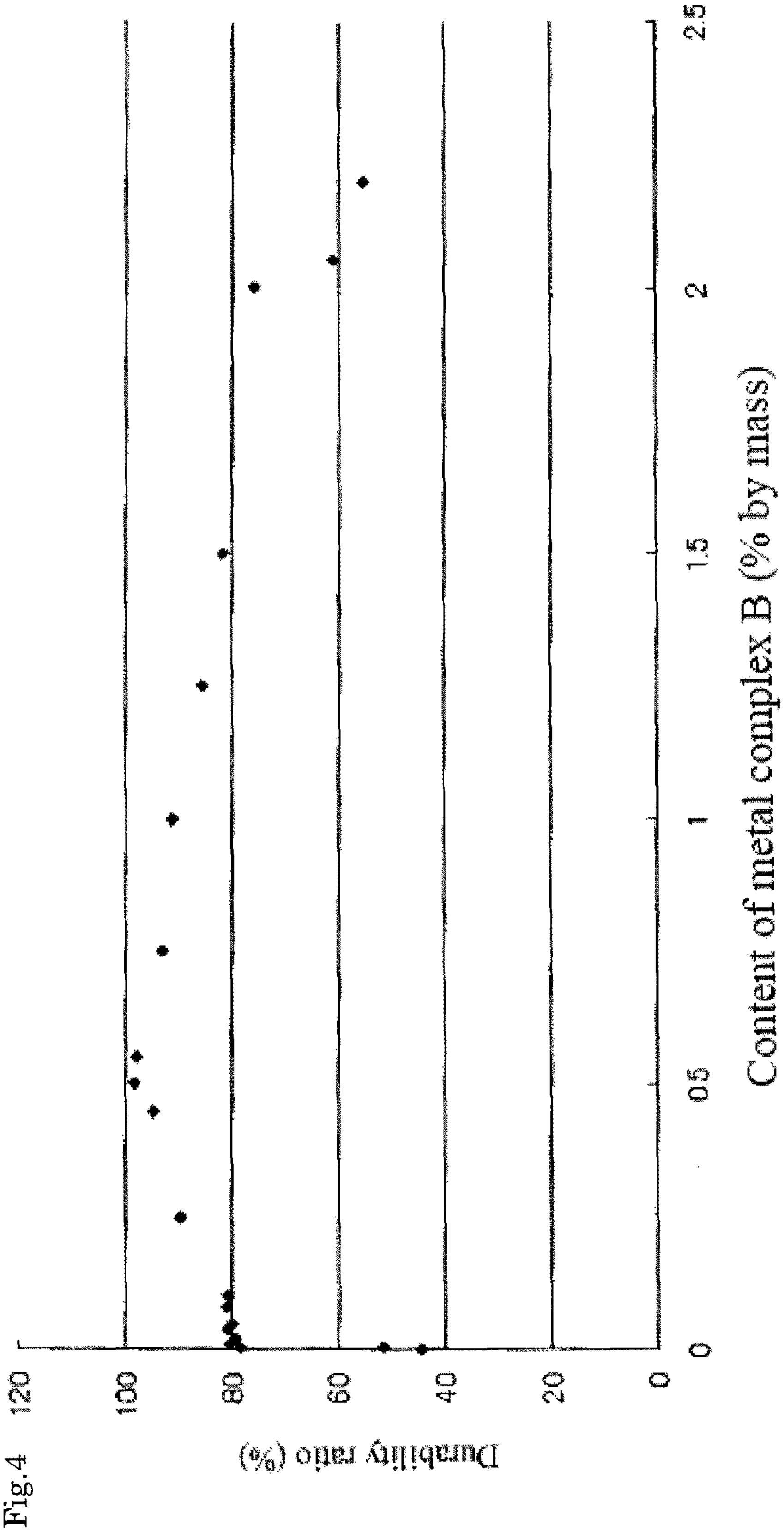
FIG. 4 is a graph plotting the relationship between the ratio (% by mass) of the content of the metal complex B to the content of metal complex A and the ratio of durability (%) in an example.
Figure 5:
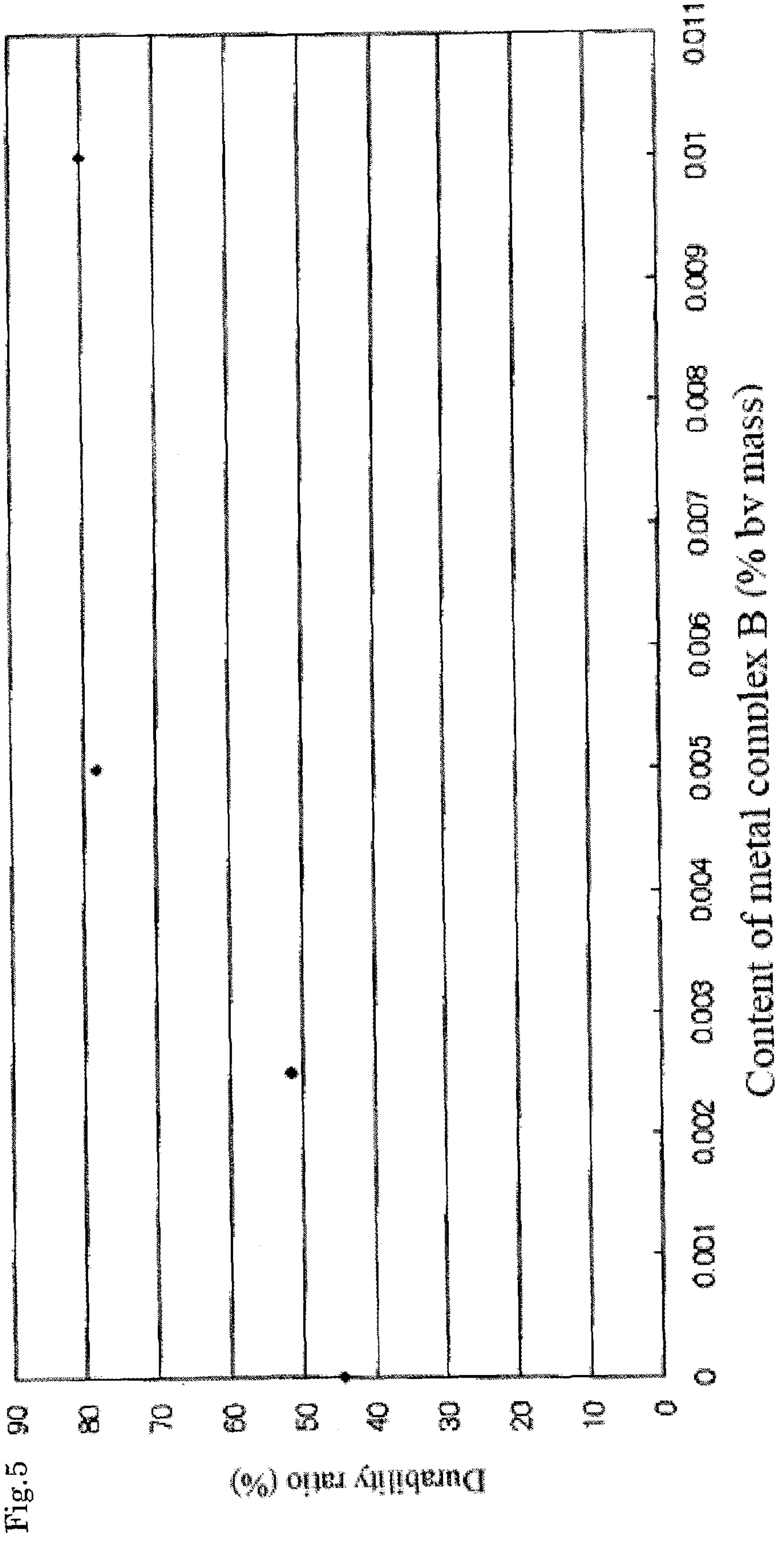
FIG. 5 is a graph plotting the relationship between the ratio (% by mass) of the content of the metal complex B to the content of metal complex A and the ratio of durability (%) in an example.

FIG. 4 is a graph plotting the relationship between the ratio of the content of metal complex B (% by mass) to the content of metal complex A and the ratio of durability (%) in the examples using the devices 1-1 to 1-16 of the invention and comparative devices 1-1 to 1-3 wherein compound 1-a is used as metal complex A and compound 1-b is used as metal complex B. FIG. 5 is a graph plotting the relationship between the ratio of the content of metal complex B (% by mass) to the content of metal complex A and the ratio of durability (%) in connection with the devices 1-1 and 1-2 of the invention and comparative devices 1-1 and 1-2 in the case of containing metal complex B in a small amount for easier understanding.

From FIGS. 4 and 5, it can be seen that durability is excellent when the content of metal complex B to the content of metal complex A is 0.005% by mass or more and 2% by mass or less.

Figure 6:
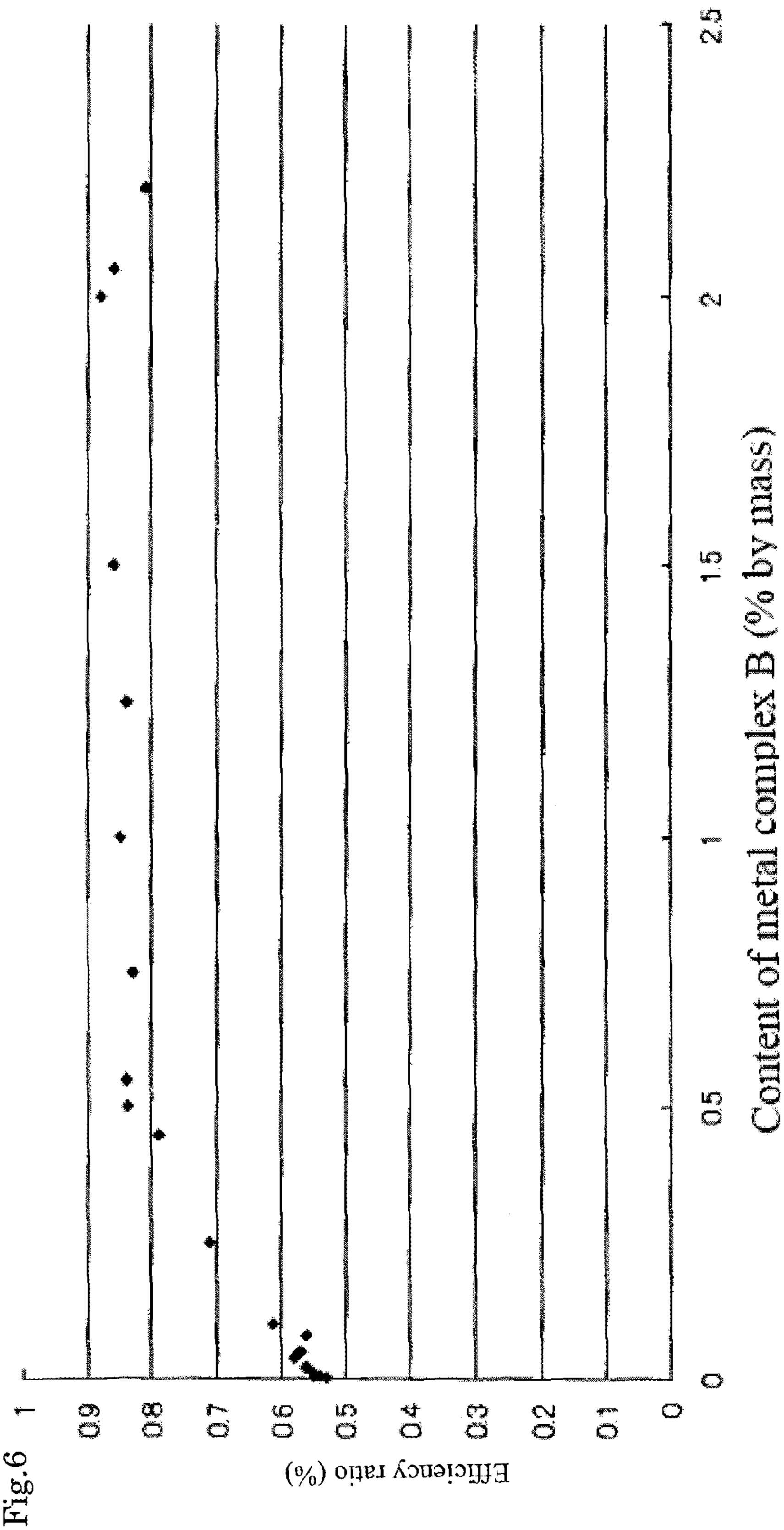
FIG. 6 is a graph plotting the relationship between the ratio (% by mass) of the content of the metal complex B to the content of the metal complex A and the ratio of efficiency in an example.
Figure 7:
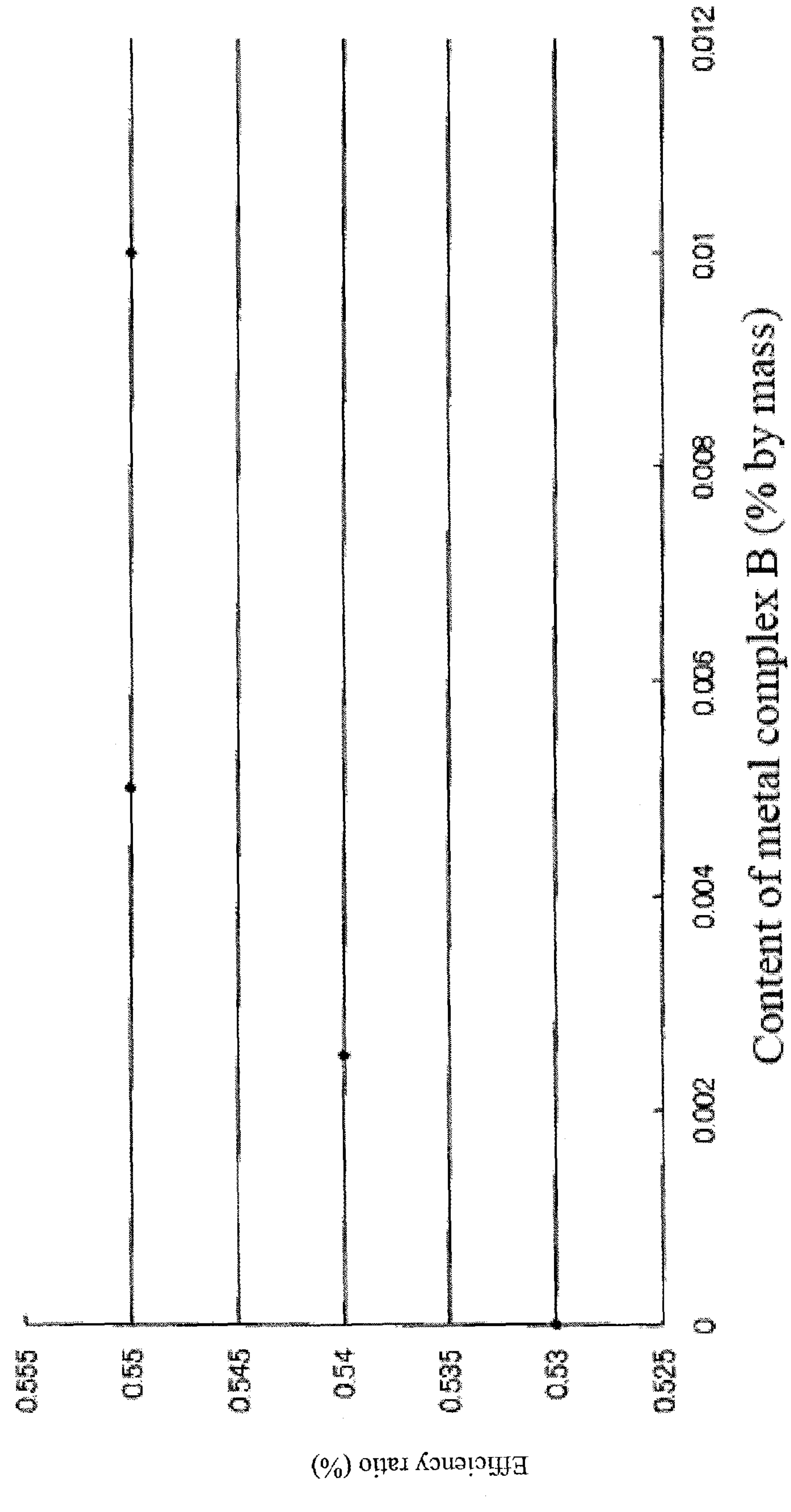
FIG. 7 is a graph plotting the relationship between the ratio (% by mass) of the content of the metal complex B to the content of metal the complex A and the ratio of efficiency in an example.

FIG. 6 is a graph plotting the relationship between the ratio of the content of metal complex B (% by mass) to the content of metal complex A and the ratio of efficiency concerning the devices 1-1 to 1-16 of the invention and comparative devices 1-1 to 1-3 using compound 1-a as metal complex A and compound 1-b as metal complex B. FIG. 7 is a graph plotting the relationship between the ratio of the content of metal complex B (% by mass) to the content of metal complex A and the ratio of efficiency in the examples using devices 1-1 and 1-2 of the invention and comparative devices 1-1 and 1-2 in the case of containing metal complex B in a small amount for easier understanding.

From FIGS. 6 and 7, it can be seen that efficiency ratio is excellent when the content of metal complex B to the content of metal complex A is 0.005% by mass or more and 2% by mass or less.

Example 2

Devices are manufactured in the same manner as in Example 1 except for changing the kinds and contents of light-emitting materials 1 and 2 and using the host materials shown in Table 17 below, and evaluation of durability as shown below is carried out.

(c) Durability

DC voltage is applied to the above-prepared each device so that luminance reaches 2,000 cd/m$^2$ to continue light emission and half life time of luminance is measured. The half life time of luminance of devices 2-1 to 2-7 of the invention as relative values taking the value of half life time of luminance of device 2-1 as 1, and relative values of devices 2-8 to 2-11 of the invention taking the value of device 2-8 of the invention as 1, are shown in Table 17 below.

TABLE 17

| Device No. | Light Emitting Material 1 | Light Emitting Material 2 | Content of Light-Emitting Material 2 to Light-Emitting Material 1 (% by mass) | Host Material | Durability Ratio |
|---|---|---|---|---|---|
| Device 2-1 of the invention | 1-a | 1-b | 0.5 | H-1 | 1 |
| Device 2-2 of the invention | 1-a | 1-b | 0.5 | H-2 | 1.2 |
| Device 2-3 of the invention | 1-a | 1-b | 0.5 | H-3 | 1.26 |
| Device 2-4 of the invention | 1-a | 1-b | 0.5 | H-4 | 0.94 |
| Device 2-5 of the invention | 1-a | 1-b | 0.5 | H-5 | 1.05 |
| Device 2-6 of the invention | 1-a | 1-b | 0.5 | H-6 | 0.87 |
| Device 2-7 of the invention | 1-a | 1-b | 0.5 | H-7 | 0.85 |
| Device 2-8 of the invention | 13-a | 13-b | 0.5 | H-1 | 1 |
| Device 2-9 of the invention | 13-a | 13-b | 0.5 | H-2 | 1.01 |
| Device 2-10 of the invention | 13-a | 13-b | 0.5 | H-3 | 1.2 |
| Device 2-11 of the invention | 13-a | 13-b | 0.5 | H-5 | 1.05 |

As shown in Table 17, when H-1 to H-3 and H-5 are used as the host materials, durability is improved as compared with the cases where other host materials are used.

Example 3

Devices are manufactured in the same manner as in Example 1 except for changing the kinds and contents of light-emitting materials 1 and 2 as shown in Table 18 below, and providing a layer in a thickness of 5 nm including the material shown in Table 18 between the second layer and the third layer, and evaluation of durability is carried out in the same manner as in Example 2. The results are shown as relative values taking the value of half life time of luminance of device 3-1 of the invention as 1.

TABLE 18

| Device No. | Light Emitting Material 1 | Light Emitting Material 2 | Content of Light-Emitting Material 2 to Light-Emitting Material 1 (% by mass) | Material Used between Second Layer and Third Layer | Durability Ratio |
|---|---|---|---|---|---|
| Device 3-1 of the invention | 1-a | 1-b | 0.5 | Nothing | 1 |
| Device 3-2 of the invention | 1-a | 1-b | 0.5 | HT-1 | 1.44 |
| Device 3-3 of the invention | 1-a | 1-b | 0.5 | HT-2 | 1.41 |
| Device 3-4 of the invention | 1-a | 1-b | 0.5 | HT-3 | 1.52 |

As shown in Table 18, when the layer using each of HT-1 to HT-3 of the carbazole material is provided between the second layer and the third layer, it is seen that durability is improved as compared with the case where the layer is not provided.

Example 4

Devices are manufactured in the same manner as in Example 1 except for changing the kinds and contents of light-emitting materials 1 and 2 as shown in Table 19 below, and providing a layer in a thickness of 3 nm including the material shown in Table 19 between the third layer and the fourth layer, and evaluation of efficiency of the device is carried out.

(d) Efficiency

DC voltage is applied to each device for light emission with a source measure unit Model 2400 (manufactured by Toyo Corporation) and the luminance at that time is measured with a luminometer BM-8 (manufactured by Topcon Corporation). The light emission spectrum and emission wavelength are measured with a spectrum analyzer PMA-11 (manufactured by Hamamatsu Photonics K.K.). On the basis of these measurements, external quantum efficiency at the time of current density of 1 mA/cm$^2$ is computed according to a luminance conversion method. The results are shown in Table 19 as a relative value taking the external quantum efficiency of device 4-1 of the invention as 1.

TABLE 19

| Device No. | Light Emitting Material 1 | Light Emitting Material 2 | Content of Light-Emitting Material 2 to Light-Emitting Material 1 (% by mass) | Material Used between Third Layer and Fourth Layer | Efficiency Ratio |
|---|---|---|---|---|---|
| Device 4-1 of the invention | 13-a | 13-b | 0.5 | Nothing | 1 |
| Device 4-2 of the invention | 13-a | 13-b | 0.5 | E-1 | 1.86 |
| Device 4-3 of the invention | 13-a | 13-b | 0.5 | E-2 | 1.82 |
| Device 4-4 of the invention | 13-a | 13-b | 0.5 | E-3 | 1.43 |
| Device 4-5 of the invention | 13-a | 13-b | 0.5 | E-4 | 1.46 |
| Device 4-6 of the invention | 13-a | 13-b | 0.5 | E-5 | 1.55 |

As shown in Table 19, when the layer using each of E-1 to E-5 of the aromatic hydrocarbon compound is provided between the third layer and the fourth layer, efficiency is greatly improved and the effect is especially conspicuous when E-1 and E-2 having a triphenylene structure are used.

Example 5

<Preparation of Coating Solution for Forming Light-Emitting Layer>mCP and a light-emitting material (light-emitting material 1 and light-emitting material 2 shown in Table 20 below are used in a mixing ratio as shown in Table 20) are dissolved in methyl ethyl ketone (MEK) in a mass ratio of mCP/light-emitting material of 95/5 to prepare a coating solution having solid concentration of 1.0% by mass. The obtained solution is filtered through a PTFE filter having a pore size of 0.22 μm to prepare a coating solution for forming each light-emitting layer.

A glass substrate having an ITO film (manufactured by Geomatec Co., Ltd., surface resistance: 10Ω□)) having a thickness of 0.5 mm and a size of 2.5 cm square is put in a washer and subjected to ultrasonic wave washing in 2-propanol, and then UV-ozone treatment for 30 minutes. On the transparent anode (ITO film), an aqueous solution of PEDOT (poly(3,4-ethyenedioxythiophene))/PSS (polystyrene-sulfonic acid) (Baytron P (standard product)) is coated by spin coating (4,000 rpm, for 60 seconds), and dried at 120° C. for 10 minutes to thereby form a hole-transporting buffer layer.

In the next place, the above-prepared coating solution for forming a light-emitting layer is coated on the hole-transporting buffer layer by spin coating (2,000 rpm, for 60 seconds) to form a light-emitting layer. On the light-emitting layer is coated BAlq by vacuum deposition in a thickness of 20 nm as an electron-injecting layer. Further, lithium fluoride in a thickness of 0.1 nm and metal aluminum in a thickness of 100 nm are deposited thereon in this order to obtain a cathode.

The obtained laminate is put in a glove box replaced with nitrogen gas so as not to be in contact with air, and sealed with a glass sealing can and a UV-curing type adhesive (XNR5516HV, manufactured by Nagase Ciba Corp.) to obtain devices 5-1 to 5-8 of the invention and comparative devices 5-1 to 5-5. Each device is evaluated similarly to evaluation of device 1-1 of the invention. The results obtained are shown in Table 20 below.

[Table 25]

TABLE 20

| Device No. | Light Emitting Material 1 | Light Emitting Material 2 | Content of Light-Emitting Material 2 to Light-Emitting Material 1 (% by mass) | Durability Ratio (%) | Efficiency Ratio |
|---|---|---|---|---|---|
| Comparative Device 5-1 | 1-a | — | 0 | 48.7 | 0.49 |
| Device 5-1 of the invention | 1-a | 1-b | 0.005 | 74.5 | 0.51 |
| Device 5-2 of the invention | 1-a | 1-b | 0.5 | 95.4 | 0.8 |
| Device 5-3 of the invention | 1-a | 1-b | 1 | 90.1 | 0.81 |
| Comparative Device 5-2 | 1-a | 1-b | 2.5 | 51.9 | 0.79 |
| Comparative Device 5-3 | 2-a | — | 0 | 57.8 | 0.54 |
| Device 5-4 of the invention | 2-a | 2-b | 0.5 | 94.8 | 0.78 |
| Device 5-5 of the invention | 2-a | 2-d | 0.5 | 96.5 | 0.77 |
| Comparative Device 5-4 | 18-a | — | 0 | 61.8 | 0.61 |
| Device 5-6 of the invention | 18-a | 18-b | 0.5 | 96.8 | 0.94 |
| Comparative Device 5-5 | 15-a | — | 0 | 46.5 | 0.41 |
| Device 5-7 of the invention | 15-a | 15-b | 0.01 | 75.5 | 0.49 |
| Device 5-8 of the invention | 15-a | 15-b | 0.5 | 91.5 | 0.66 |

As shown in Table 20, it can be seen that the same effect can be obtained even in the case of manufacturing the devices with the solution coating method.

Example 6

<Preparation of Coating Solution for Forming Light-Emitting Layer>

Host material H-2 and a light-emitting material (light-emitting material 1 and light-emitting material 2 shown in Table 24 below are used in a mixing ratio as shown in Table 24) are dissolved in methyl ethyl ketone (MEK) in a mass ratio of H-2/light-emitting material of 95/5 to prepare a coating solution having solid concentration of 1.0% by mass. The obtained solution is filtered through a PTFE filter having a pore size of 0.22 μm to prepare a coating solution for forming each light-emitting layer.

<Preparation of Coating Solution a for Forming Hole-Transporting Layer>

Compound A shown below is dissolved in xylene for electronic industrial use to make entire solid concentration 0.4% by mass, and the solution is filtered through a PTFE filter having a pore size of 0.22 μm to prepare coating solution A for forming a hole-transporting layer.

<Manufacture of Device>

On a glass plate having a size of 25 mm×25 mm×0.7 mm is deposited an ITO film in a thickness of 150 nm to prepare a transparent supporting substrate. The transparent supporting substrate is put in a washer and subjected to ultrasonic wave washing in 2-propanol, and then UV-ozone treatment for 30 minutes.

Compound B (0.5 parts by mass) represented by the following formula (described in U.S. Patent 2008/0,220,265) is dissolved in 99.5 parts by mass of cyclohexanone, and coated on the glass plate having the ITO film by spin coating 4,000 rpm, for 30 seconds) in a thickness of 5 nm, and dried at 200° C. for 30 minutes to thereby form a hole-injecting layer.

A

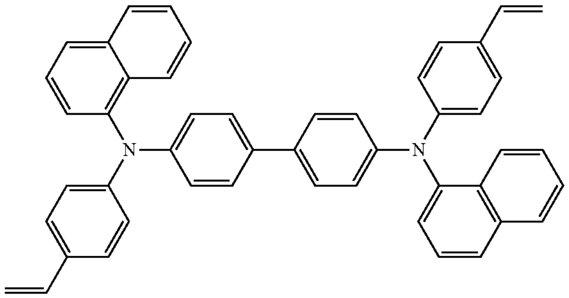

B

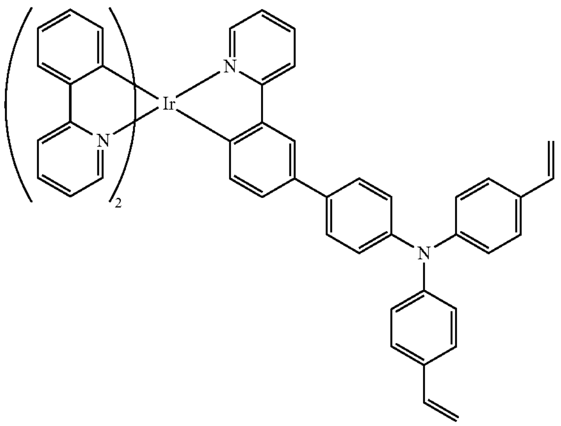

Coating solution A for forming a hole-transporting layer is coated on the above-prepared hole-injecting layer in a thickness of about 10 nm by spin coating (1,500 rpm, for 20 seconds), and dried at 120° C. for 30 minutes to thereby form a hole-transporting layer.

On the hole-transporting layer, the coating solution for forming a light emitting layer is coated by spin coating (1,500 rpm, for 20 seconds) in a thickness of about 30 nm in a glove box (dew point: −68°, oxygen concentration: 10 ppm) to thereby obtained a light-emitting layer.

Subsequently, on the light-emitting layer is coated BAIq by vacuum deposition in a thickness of 20 nm as an electron-transporting layer. Further, lithium fluoride (LiF) in a thickness of 0.1 nm as an electron-injecting layer, and metal aluminum in a thickness of 100 nm as a cathode are deposited thereon in this order to for a film.

The obtained laminate is put in a glove box replaced with argon gas, and sealed with a stainless steel sealing can and a UV-curing type adhesive (XNR5516HV, manufactured by Nagase Ciba Corp.) to obtain organic electroluminescence devices 6-1 to 6-7 of the invention and comparative organic electroluminescence devices 6-1 to 6-5. Each device is evaluated similarly to evaluation of device 1-1 of the invention. The results obtained are shown in Table 24 below.

TABLE 24

| Device No. | Light Emitting Material 1 | Light Emitting Material 2 | Content of Light-Emitting Material 2 to Light-Emitting Material 1 (% by mass) | Durability Ratio (%) | Efficiency Ratio |
|---|---|---|---|---|---|
| Comparative Device 6-1 | 1-a | — | 0 | 61.1 | 0.34 |
| Device 6-1 of the invention | 1-a | 1-b | 0.005 | 76.4 | 0.77 |
| Device 6-2 of the invention | 1-a | 1-b | 0.5 | 99.2 | 0.8 |
| Device 6-3 of the invention | 1-a | 1-b | 1 | 98.6 | 0.81 |
| Comparative Device 6-2 | 1-a | 1-b | 2.5 | 64.1 | 0.79 |
| Comparative Device 6-3 | 12-a | — | 0 | 56.3 | 0.41 |
| Device 6-4 of the invention | 12-a | 12-b | 0.5 | 99.1 | 0.79 |
| Device 6-5 of the invention | 12-a | 12-d | 0.5 | 98.4 | 0.76 |
| Comparative Device 6-5 | 15-a | — | 0 | 64.1 | 0.45 |
| Device 6-6 of the invention | 15-a | 15-b | 0.01 | 78.2 | 0.86 |
| Device 6-7 of the invention | 15-a | 15-b | 0.5 | 98.2 | 0.9 |

The compounds used are shown below.

E-1

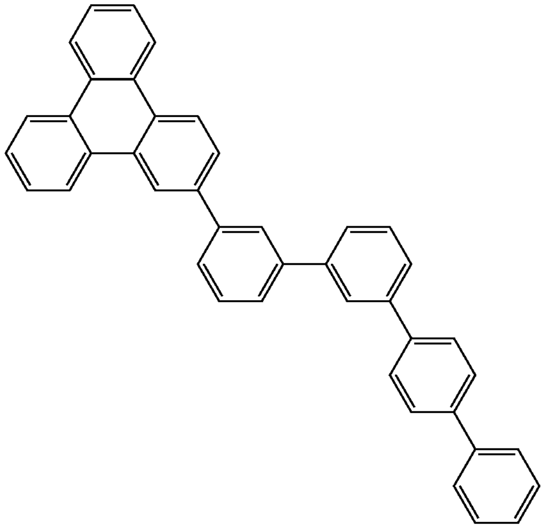

-continued

E-2

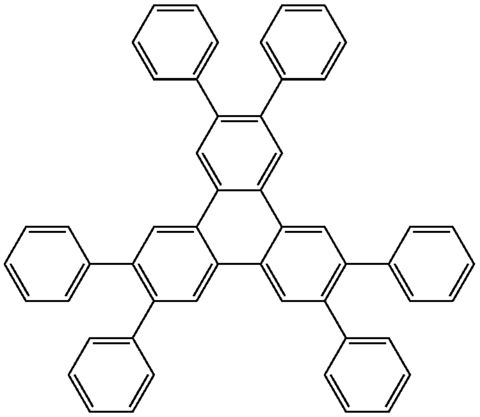

-continued

E-3

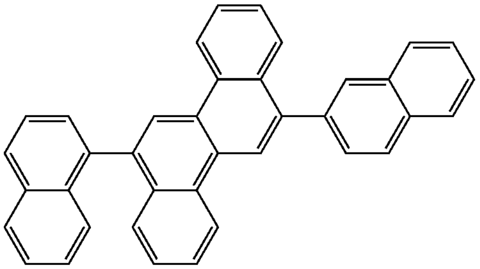

E-4

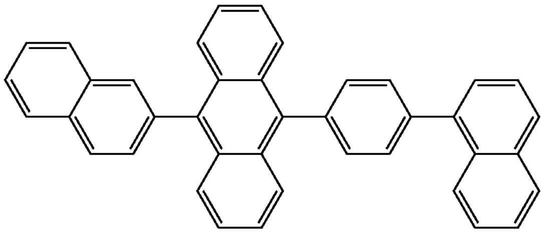

-continued
E-5
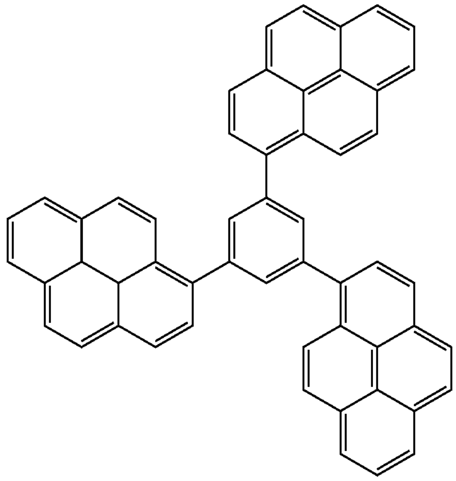
HT-1
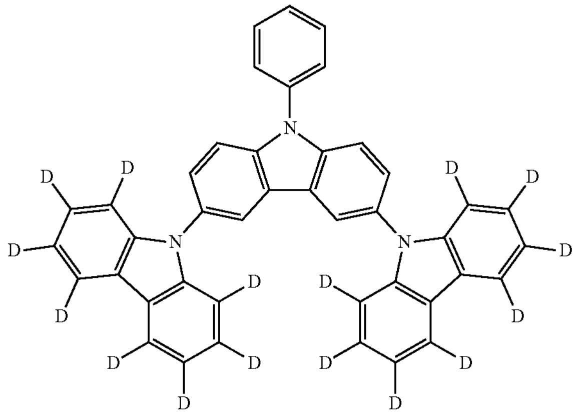
HT-2
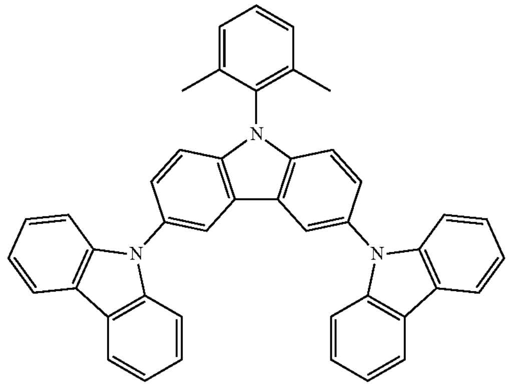
-continued
HT-3
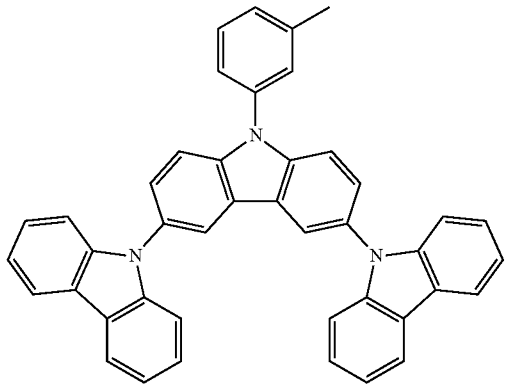
H-1
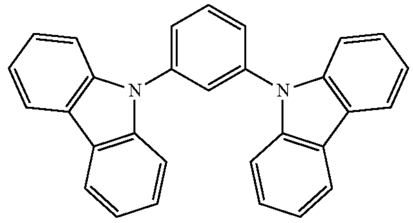
H-2
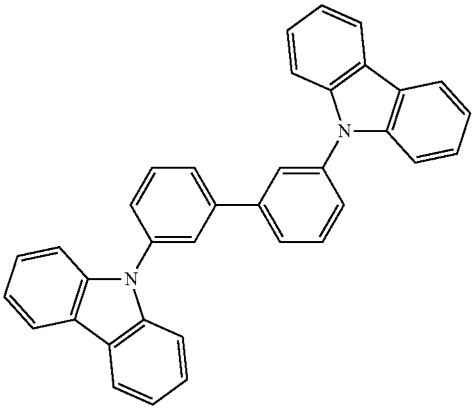
H-3
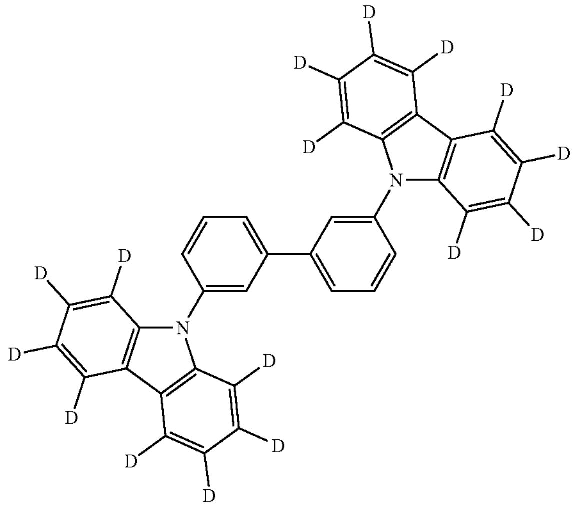

-continued

H-4

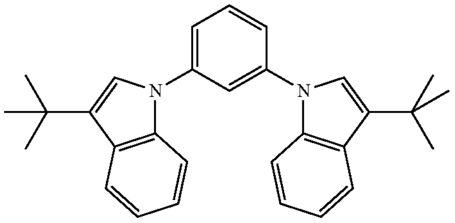

H-5

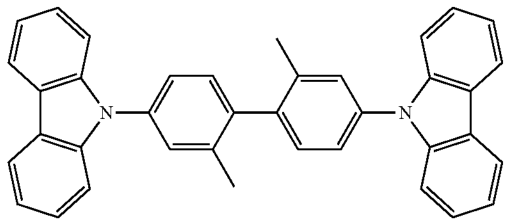

H-6

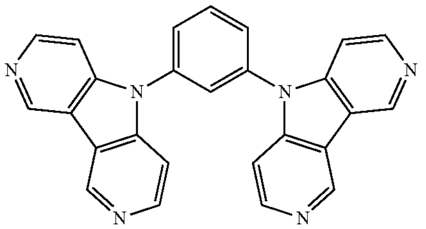

H-7

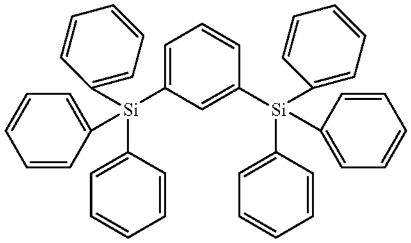

DESCRIPTION OF REFERENCE NUMERALS

2: Substrate
3: Anode
4: Hole-injecting layer
5: Hole-transporting layer
6: Light-emitting layer
7: Hole-blocking layer
8: Electron-transporting layer
9: Cathode
10: Organic electroluminescence device (organic EL device)
11: Organic layer
12: Protective layer
14: Adhesive layer
16: Sealing case
20: Light emission apparatus
30: Light-scattering member
30A: Light incident plane
30B: Light outgoing plane
31: Transparent substrate
32: Particle
40: Illumination apparatus

INDUSTRIAL APPLICABILITY

According to the invention, a material for an organic electroluminescence device which can be used in an organic EL device, stably preserved under visible light, and excellent in efficiency when a device is driven at high luminance, and an organic electroluminescence device using the same material can be provided.

This patent application is based on Japanese patent application filed on Sep. 30, 2009 (Japanese Patent Application No. 2009-228690), Japanese patent application filed on Mar. 30, 2010 (Japanese Patent Application No. 2010-79925), and Japanese patent application filed on Sep. 3, 2010 (Japanese Patent Application No. 2010-198384), and the contents of these patent applications are incorporated in the present patent application as reference.

The invention claimed is:

1. A material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure with the phosphorescent metal complex A except that, in at least one substituent of $R^1$ and $R^2$ in the formula (1), one or more atoms directly bonding to $Q^1$ or $Q^2$ are substituted with an atom belonging to the same group as in the one or more atoms and having a greater atomic weight than the one or more atoms, and a ratio of the content of the phosphorescent metal complex B to a content of the phosphorescent metal complex A is 0.005% by mass or more and 2% by mass or less:

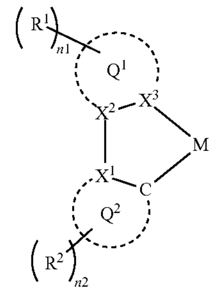

(1)

wherein each of $R^1$ and $R^2$ independently represents a substituent; when a plurality of $R^1$'s are present, the $R^1$'s may be the same with or different from each other; when a plurality of $R^2$'s are present, the $R^2$'s may be the same with or different from each other; and the $R^1$'s and the $R^2$'s may be bonded to each other to form a ring; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

2. The material for an organic electroluminescence device as claimed in claim 1, wherein the metal complex A has at least one fluorine atom as at least one of $R^1$ and $R^2$ in formula (1), and the at least one fluorine atom of the metal complex A is replaced with at least one halogen atom other than the fluorine atom in the metal complex B.

3. The material for an organic electroluminescence device as claimed in claim 2, wherein the halogen atom other than the fluorine atom in the metal complex B is a chlorine atom.

4. The material for an organic electroluminescence device as claimed in claim 1, wherein both of $R^1$ and $R^2$ are fluorine atoms.

5. The material for an organic electroluminescence device as claimed in claim 1, wherein the metal complex A comprises a partial structure represented by the following formula (2):

(2)

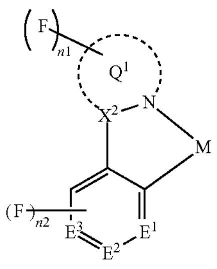

wherein M represents a metal having an atomic weight of 40 or more; $X^2$ represents a carbon atom or a nitrogen atom; $Q^1$ represents a 5- or 6-membered aromatic heterocyclic ring;

each of $E^1$, $E^2$ and $E^3$ independently represents a carbon atom or a nitrogen atom, provided that all of $E^1$, $E^2$ and $E^3$ do not represent a nitrogen atom; each of n1 and n2 independently represents an integer of 0 to 4, but there is no case where the sum of n1 and n2 is 0; and the bidentate ligand including ring $Q^1$ and the ring containing $E^1$, $E^2$ and $E^3$ may form a tridentate or higher multidentate ligand by bonding to other ligands.

6. The material for an organic electroluminescence device as claimed in claim 1, wherein the metal complex A comprising a partial structure represented by the following formula (3):

(3)

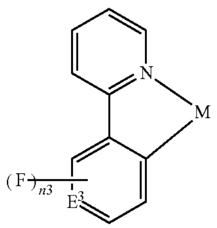

wherein M represents a metal having an atomic weight of 40 or more; $E^3$ represents a carbon atom or a nitrogen atom; n3 represents an integer of 1 to 4; and the bidentate ligand including pyridine and the ring containing $E^3$ may form a tridentate or higher multidentate ligand by bonding to other ligands.

7. The material for an organic electroluminescence device as claimed in claim 1, wherein $E^3$ represents a carbon atom.

8. The material for an organic electroluminescence device as claimed in claim 1, wherein M represents Pt.

9. The material for an organic electroluminescence device as claimed in claim 1, wherein the formula (1) is represented by the following formula (C-2):

formula(C-2)

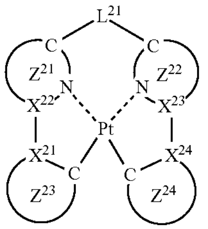

wherein $L^{21}$ represents a single bond or a divalent linking group; each of $Z^{21}$ and $Z^{22}$ independently represents a 5- or 6-membered nitrogen-containing aromatic heterocyclic ring;

each of $Z^{23}$ and $Z^{24}$ independently represents a benzene ring or a 5- or 6-membered aromatic heterocyclic ring; each of $Z^{21}$ and $Z^{23}$ may independently have 1 to 4 substituents, and these substituents may be bonded to each other to form a ring, provided that at least one of $Z^{21}$ and $Z^{23}$ has one or more substituents; each of $Z^{22}$ and $Z^{24}$ may have a substituent and these substituents may be bonded to each other to form a ring; and each of $X^{21}$, $X^{22}$, $X^{23}$ and $X^{24}$ independently represents a carbon atom or a nitrogen atom.

10. The material for an organic electroluminescence device as claimed in claim 1, wherein M represents Ir.

11. The material for an organic electroluminescence device as claimed in claim 1, wherein the formula (1) is represented by the following formula (A10):

(A10)

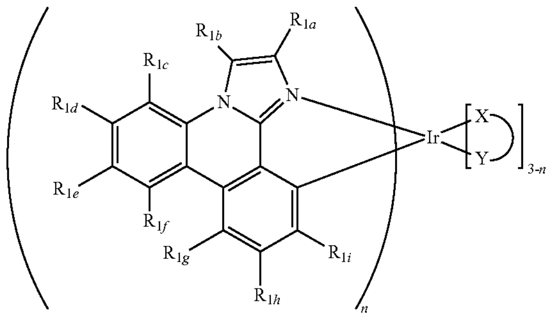

wherein each of $R_{1a}$ to $R_{1i}$ independently represents a hydrogen atom or a substituent; X—Y represents a mono-anionic bidentate ligand; and n represents an integer of 1 to 3, wherein at least one of $R_{1a}$, $R_{1b}$, $R_{1g}R_{1h}$,or $R^{1i}$ is a substituent.

12. The material for an organic electroluminescence device as claimed in claim 1, wherein the formula (1) is represented by the following formula (P-1):

(P-1)

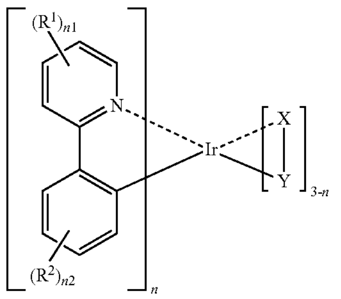

wherein each of $R^1$ and $R^2$ independently represents a substituent, and when a plurality of $R^1$ and $R^2$ are present, these $R^1$ and $R^2$ may be the same with or different from each other; each of n1 and n2 independently represents an integer of 0 to 4, but there is no case where the sum of n1 and n2 is 0; X—Y represents a mono-anionic bidentate ligand; and n represents an integer of 1 to 3.

13. An organic electroluminescence device comprising a substrate having thereon a pair of electrodes and at least one organic layer comprising a light-emitting layer comprising a light-emitting material between the pair of electrodes, wherein the light-emitting layer comprises the material for an organic electroluminescence device as claimed in claim 1.

14. An organic electroluminescence device comprising a substrate having thereon a pair of electrodes and at least one organic layer comprising a light-emitting layer comprising a light-emitting material between the pair of electrodes, wherein at least any layer of the organic layers comprises the material for an organic electroluminescence device as claimed in claim 1.

15. A light emission apparatus comprising the organic electroluminescence device as claimed in claim 14.

16. A display apparatus comprising the organic electroluminescence device as claimed in claim 14.

17. An illumination apparatus comprising the organic electroluminescence device as claimed in claim 14.

18. A composition of a material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure as the phosphorescent metal complex A except that, in at least one substituent of $R^1$ and $R^2$ in the formula (1), one or more atoms directly bonding to $Q^1$ or $Q^2$ are substituted with atoms belonging to the same group of the one or more atoms and having a greater atomic weight than the one or more atoms, and ratio of the content of the phosphorescent metal complex B to the content of phosphorescent the metal complex A is 0.005% by mass or more and 2% by mass or less:

(1)

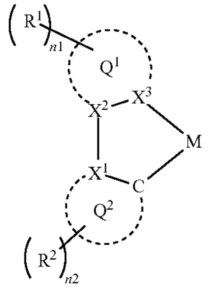

wherein each of $R^1$'s and $R^2$'s independently represents a substituent, when a plurality of $R^1$'s and a plurality of $R^2$'s are present, the plurality of $R^1$ and $R^2$ may be the same with or different from each other, and the plurality of $R^1$ and $R^2$ may be bonded to each other to form a ring; M represents a metal having an atomic weight of 40 or more; each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

19. A light-emitting layer which comprises a material for an organic electroluminescence device comprising at least a phosphorescent metal complex A and a phosphorescent metal complex B, wherein the phosphorescent metal complex A comprises a partial structure represented by the following formula (1), and the phosphorescent metal complex B has the same structure with the phosphorescent metal complex A except that, in at least one substituent of $R^1$ and $R^2$ in the formula (1), one or more atoms directly bonding to $Q^1$ or $Q^2$ are substituted with atoms belonging to the same group of the one or more atoms and having a greater atomic weight than the one or more atoms, and a ratio of the content of the phosphorescent metal complex B to the content of the phosphorescent metal complex A is 0.005% by mass or more and 2% by mass or less:

(1)

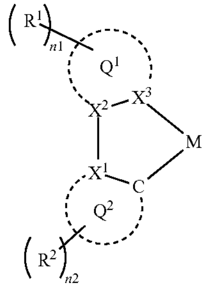

wherein each of $R^1$'s and $R^2$'s independently represents a substituent, and when a plurality of $R^1$'s and a plurality of $R^2$'s are present, the plurality of $R^1$ and $R^2$ may be the same with or different from each other; M represents a metal having an atomic weight of 40 or more;

each of $X^1$, $X^2$ and $X^3$ independently represents a carbon atom or a nitrogen atom, provided that all of $X^1$, $X^2$ and $X^3$ do not represent a nitrogen atom; $Q^1$ represents a 5- or 6-membered aromatic heterocyclic ring; $Q^2$ represents a 5- or 6-membered aromatic hydrocarbon ring or aromatic heterocyclic ring; each of n1 and n2 independently represents an integer of 0 to 4, but there is no case where the sum of n1 and n2 is 0; the bidentate ligand including $Q^1$ and $Q^2$ may form a tridentate or higher multidentate ligand by bonding to other ligands, and $Q^1$ and $Q^2$ may be linked via a linking group to form a ring.

* * * * *